(12) United States Patent
Marron et al.

(10) Patent No.: US 8,357,711 B2
(45) Date of Patent: Jan. 22, 2013

(54) HETEROCYCLIC SULFONAMIDES AS INHIBITORS OF ION CHANNELS

(75) Inventors: Brian Edward Marron, Durham, NC (US); Paul Christopher Fritch, Cary, NC (US); Christopher John Markworth, Durham, NC (US); Andrew Thomas Maynard, Durham, NC (US); Nigel Alan Swain, Sandwich (GB)

(73) Assignees: Pfizer Limited, Sandwich (GB); Icagen, Inc., Durham, NC (US)

( * ) Notice: Subject to any disclaimer, the term of this patent is extended or adjusted under 35 U.S.C. 154(b) by 543 days.

(21) Appl. No.: 12/052,593

(22) Filed: Mar. 20, 2008

(65) Prior Publication Data
US 2009/0143358 A1  Jun. 4, 2009

Related U.S. Application Data

(60) Provisional application No. 60/896,735, filed on Mar. 23, 2007, provisional application No. 61/035,324, filed on Mar. 10, 2008.

(51) Int. Cl.
*A61K 31/427* (2006.01)
(52) U.S. Cl. ........................... 514/370; 548/190
(58) Field of Classification Search ............. 548/190
See application file for complete search history.

(56) References Cited

U.S. PATENT DOCUMENTS

| | | | |
|---|---|---|---|
| 5,514,696 A | 5/1996 | Murugesan et al. | 514/380 |
| 5,786,373 A | 7/1998 | Hartman et al. | 514/326 |
| 6,107,320 A | 8/2000 | Murugesan et al. | 514/379 |
| 6,221,866 B1 | 4/2001 | Brendel et al. | 514/237.8 |
| 6,342,512 B1 | 1/2002 | Kirsch et al. | 514/326 |
| 6,420,567 B1 | 7/2002 | Wu et al. | 548/245 |
| 6,586,475 B1 | 7/2003 | Kato et al. | 514/622 |
| 6,667,342 B1 | 12/2003 | Clarke et al. | 514/603 |
| 6,673,824 B1 | 1/2004 | Murugesan et al. | 514/379 |
| 6,953,857 B2 | 10/2005 | Nazareet et al. | 546/194 |
| 7,105,564 B1 | 9/2006 | Honma et al. | 514/422 |
| 7,538,135 B2 | 5/2009 | Vedananda | 514/407 |
| 7,754,717 B2 | 7/2010 | Dimauro et al. | 514/248 |
| 2001/0049444 A1 | 12/2001 | McNaughton-Smith et al. | 546/268.1 |
| 2004/0186148 A1 | 9/2004 | Shankar et al. | 514/357 |
| 2005/0228020 A1 | 10/2005 | Miyamoto et al. | 514/319 |
| 2007/0191336 A1 | 8/2007 | Flynn et al. | 514/211.01 |
| 2007/0244140 A1 | 10/2007 | Hu et al. | 514/275 |
| 2008/0015223 A1 | 1/2008 | Strah-Pleynet et al. | 514/314 |
| 2009/0023710 A1 | 1/2009 | Vicker et al. | 514/217.11 |
| 2009/0291965 A1 | 11/2009 | Close et al. | 514/253.09 |
| 2010/0004284 A1 | 1/2010 | Farina et al. | 514/318 |

FOREIGN PATENT DOCUMENTS

| | | |
|---|---|---|
| EP | 1132376 | 9/2001 |
| EP | 1217000 | 6/2002 |
| WO | WO 9408577 | 4/1994 |
| WO | WO 9427979 | 12/1994 |
| WO | WO 9740017 | 10/1997 |
| WO | WO 9813366 | 4/1998 |
| WO | WO 9849162 | 11/1998 |
| WO | WO 9947508 | 9/1999 |
| WO | WO 0031021 | 6/2000 |
| WO | WO 0116094 | 3/2001 |
| WO | WO 0149289 | 7/2001 |
| WO | WO 0149685 | 7/2001 |
| WO | WO 0170734 | 9/2001 |
| WO | WO 0187293 | 11/2001 |
| WO | WO 0190090 | 11/2001 |
| WO | WO 0198264 | 12/2001 |
| WO | WO 03043999 | 5/2003 |
| WO | WO 03044009 | 5/2003 |
| WO | WO 2004048319 | 6/2004 |
| WO | WO 2004098518 | 11/2004 |
| WO | WO 2004098528 | 11/2004 |
| WO | WO 2004112779 | 12/2004 |
| WO | WO 2004113310 | 12/2004 |
| WO | WO 2004113782 | 12/2004 |
| WO | WO 2005000309 | 1/2005 |
| WO | WO 2005005421 | 1/2005 |
| WO | WO 2006060762 | 6/2006 |
| WO | WO 2006129199 | 12/2006 |
| WO | WO 2007003934 | 1/2007 |
| WO | WO 2007022380 | 2/2007 |
| WO | WO 2007055941 | 5/2007 |

OTHER PUBLICATIONS

West, Anthony R., Solid State Chemistry and its Applications, Wiley, New York, 1988, pp. 358 and 365.*
Morissette et al. "High-throughput crystallization: polymorphs, salts, co-crystals and solvates of pharmaceutical solids." 2004, Advanced Drug Delivery Reviews, 56, 275-300.*
Chemical Abstracts Registry No. 612540-88-2.
Compound 51. Chemical Abstracts Services (CAS): American Chemical Society, Columbus, OH, Jul. 25, 2006. Registry No. 895731-05-2, (3-[ [(5-methy1-1,3,4-thiadiazol-2-y1)amino]sulfonyl]-N-phenyl-Benzamide).
Compound 52. Chemical Abstracts Services (CAS): American Chemical Society, Columbus, OH, Jul. 25, 2006. Registry No. 895731-13-2, (N-(4-methylphenyl)-3-[[ (5-methyl-1,3,4-thiadiazol-2-y1)amino]sulfonyl]-Benzamide).
Compound 53. Chemical Abstracts Services (CAS): American Chemical Society, Columbus, OH, Apr. 2007. Registry No. 936824-15-6, (N-1,3-benzodioxo1-5-y1-2-[[ (3-methyl-5isoxazolypamino]sulfonyl]-Benzamide).

(Continued)

*Primary Examiner* — Brian McDowell
(74) *Attorney, Agent, or Firm* — J. Michael Dixon

(57) ABSTRACT

The invention is directed to compounds of the formula

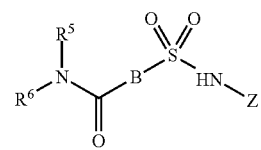

in which $R^5$, $R^6$ B and Z are defined supra.

39 Claims, No Drawings

OTHER PUBLICATIONS

Compound 54. Chemical Abstracts Services (CAS): American Chemical Society, Columbus, OH, Apr. 2007. Registry No. 936824-16-7, (N-1,3-benzodioxo1-5-y1-2-[[ (3,4-dimethyl-5isoxazolypamino]sulfonyl]-Benzamide).
Compound 55. Chemical Abstracts Services (CAS): American Chemical Society, Columbus, OH, Apr. 2007. Registry No. 936824-17-8, (N-(3,4-dimethoxyphenyl)-2-[ [(3,4-dimethyl-5-isoxazolyl)amino]sulfonyl]-Benzamide).
Compound 56. Chemical Abstracts Services (CAS): American Chemical Society, Columbus, OH, Apr. 2007. Registry No. 936824-18-9, (2-[ [(3,4-dimethy1-5-isoxazolypamino]sulfonyl]-N-(4methoxypheny1)-Benzamide).
Compound 57. Chemical Abstracts Services (CAS): American Chemical Society, Columbus, OH, Apr. 2007. Registry No. 936824-19-0, (2-[ [(3,4-dimethy1-5-isoxazolypamino]sulfonyl]-N-(4-methylpheny1)-Benzamide).
Compound 58. Chemical Abstracts Services (CAS): American Chemical Society, Columbus, OH, Apr. 2007. Registry No. 936824-20-3, (N-1,3-benzodioxo1-5-y1-2-[[ (4-chloro-3-methyl-5-isoxazolyl)amino]sulfonyl]-Benzamide).
Compound 59. Chemical Abstracts Services (CAS): American Chemical Society, Columbus, OH, Apr. 2007. Registry No. 936824-21-4, (2-[ [(4-chloro-3-methy1-5-isoxazolypamino]sulfonyl]-N-(3,4-dimethoxypheny1)-Benzamide).
Compound 60. Chemical Abstracts Services (CAS): American Chemical Society, Columbus, OH, Apr. 2007. Registry No. 936824-23-6, (2-[ [(4-chloro-3-methy1-5-isoxazolypamino]sulfonyl]-N-(4methoxypheny1)—Benzamide).
Compound 61. Chemical Abstracts Services (CAS): American Chemical Society, Columbus, OH, Apr. 2007. Registry No. 936824-24-7, (2-[ [(4-chloro-3-methy1-5-isoxazolypamino]sulfonyl]-N-(4-methylpheny1)-Benzamide).
Compound 62. Chemical Abstracts Services (CAS): American Chemical Society, Columbus, OH, Apr. 2007. Registry No. 936824-25-8, (2-[ [(4-chloro-3-methyl-5-isoxazolypamino]sulfonyl]-N-(2,4,6-trimethylpheny1)-Benzamide).
Compound 1. Chemical Abstracts Services (CAS): American Chemical Society, Columbus, OH, Aug. 29, 2001. Registry No. 353467-66-0. (N-(5-methyl-3-isoxazolyl)-3-[[ (5-methyl-3isoxazolyl) amino]sulfonyl]-Benzamide.
Compound 2. Chemical Abstracts Services (CAS): American Chemical Society, Columbus, OH, Nov. 29, 2001. Registry No. 376636-52-1, (4-Thiazoleacetic acid, 2-[ [[3-[[ [4-(2-ethoxy-2-oxoethyl)-2thiazolyl]amino]carbonyl]phenyl] sulfonyl]amino]-ethyl ester).
Compound 3. Chemical Abstracts Services (CAS): American Chemical Society, Columbus, OH, Nov. 29, 2001. Registry No. 376636-54-3, (4-Thiazoleacetic acid, 2-[ [[4-[[ [4-(2-ethoxy-2-oxoethyl)-2thiazolyl]amino]carbonyl]phenyl] sulfonyl]amino]-ethyl ester).
Compound 4. Chemical Abstracts Services (CAS): American Chemical Society, Columbus, OH, Mar. 26, 2004. Registry No. 667902-47-8, (3-[ [(5-methyl-3-isoxazolypamino]sulfonyl]-N-I,3,4-thiadiazol-2y1-)-Benzamide).
Compound 5. Chemical Abstracts Services (CAS): American Chemical Society, Columbus, OH, Jul. 25, 2006. Registry No. 895730-98-0, (N-(5-ethyl-I,3,4-thiadiazol-2-yl)-3-(4morpholinylcarbonyl)-Benzenesulfonamide).
Compound 6. Chemical Abstracts Services (CAS): American Chemical Society, Columbus, OH, Sep. 1, 2003. Registry No. 607356-33-2, (3-[ [[5-(aminosulfony1)-1,3,4-thiadiazol-2-yl]amino]sulfonyl]-N[2-(diethylamino)ethyl]-Benzamide).
Compound 7. Chemical Abstracts Services (CAS): American Chemical Society, Columbus, OH, Sep. 1, 2003. Registry No. 607356-42-3, (4-[ [[5-(aminosulfony1)-1,3,4-thiadiazol-2-yl]amino]sulfonyl]-N[2-(diethylamino)ethyl]Benzamide).
Compound 8. Chemical Abstracts Services (CAS): American Chemical Society, Columbus, OH, Sep. 1, 2003. Registry No. 607356-62-7, (3-[ [[5-(aminosulfony1)-1,3,4-thiadiazol-2-yl]amino]sulfonyl]-N[2-(diethylamino)ethyl]-, hydrochloride (9CI)-Benzamide).
Compound 9. Chemical Abstracts Services (CAS): American Chemical Society, Columbus, OH, Sep. 1, 2003. Registry No. 607356-66-1, (4-[ [[5-(aminosulfony1)-I,3,4-thiadiazol-2-yl]amino]sulfonyl]-N[2-(diethylamino)ethyl]-, hydrochloride (9CI)-Benzamide).
Compound 10. Chemical Abstracts Services (CAS): American Chemical Society, Columbus, OH, Oct. 15, 2003. Registry No. 612540-88-2, (1-[3-[ [[5-(1,1-dimethylethyl)-4-methyl-2thiazolyl]aminolsulfonyl]benzoyll-(9CI)-Piperidine).
Compound 11. Chemical Abstracts Services (CAS): American Chemical Society, Columbus, OH, Jan. 15, 2004. Registry No. 655241-20-6, (5-[ [(4-butyl-4H-1,2,4-triazol-3-yl)amino]su1fony1]-2-ch1Or0-4-mercapto-N-(phenyl methyl)-Benzamide).
Compound 12. Chemical Abstracts Services (CAS): American Chemical Society, Columbus, OH, Jul. 25, 2006. Registry No. 895731-21-2, (N-(5-methyl-1,3,4-thiadiazol-2-y1)-3-(4morpho1iny1carbonyl)-Benzenesulfonamide).
Compound 13. Chemical Abstracts Services (CAS): American Chemical Society, Columbus, OH, Mar. 2, 2007. Registry No. 924259-07-4, (2-Thiophenecarboxylic acid, 3-[[ [4-[ (methyl amino) carbonyl]phenyl]sulfonyl]amino]-, methyl ester).
Compound 14. Chemical Abstracts Services (CAS): American Chemical Society, Columbus, OH, Mar. 2, 2007. Registry No. 924435-62-1, (Index Name Not Yet Assigned).
Compound 15. Chemical Abstracts Services (CAS): American Chemical Society, Columbus, OH, Dec. 5, 2007. Registry No. 956809-14-6, (N-methyl-4-[[ (I-methyl-Ih-pyrazol-3-yl)amino]sulfonyl]-Benzamide).
Compound 16. Chemical Abstracts Services (CAS): American Chemical Society, Columbus, OH, Mar.-Apr. 1995. Registry No. 170747-29-2, (5-[ [(5-amino-Ih-I,2,4-triazol-3-yl)amino]sulfonyl]-2-chloro-N(4-chlorophenyl)-4-mercapto-(9CI)-Benzamide).
Compound 17. Chemical Abstracts Services (CAS): American Chemical Society, Columbus, OH Jul. 12, 2001. Registry No. 349453-88-9, (N-(2-acetyl-4,6-dimethylphenyl)-2-[[(4-chloro-3-methyl-5isoxazolypamino]sulfonyl]Benzamide).
Compound 18. Chemical Abstracts Services (CAS): American Chemical Society, Columbus, OH, Aug. 29, 2001. Registry No. 353465-15-3, (2-chloro-5-[[(5-methyl-3-isoxazolyl) amino]sulfonyl]-N-phenyl-Benzamide).
Compound 19. Chemical Abstracts Services (CAS): American Chemical Society, Columbus, OH, Oct. 14, 2001. Registry No. 361989-46-0, (4-bromo-3-[[(5-methyl-3-isoxazolyl)amino]sulfonyl]-N-phenyl-Benzamide).
Compound 20. Chemical Abstracts Services (CAS): American Chemical Society, Columbus, OH, Dec. 27, 2001. Registry No. 382593-29-5, (5-bromo-2-[[(5-chloro-2-thienyl)amino]sulfony1]-N-[3(trifluoromethy1)phenyl]Benzamide).
Compound 21. Chemical Abstracts Services (CAS): American Chemical Society, Columbus, OH, Dec. 27, 2001. Registry No. 382593-30-8, (5-chloro-N-(4-chlorophenyl)-2-[[(5-chloro-2-thienyl)amino]sulfonyl]-Benzamide).
Compound 22. Chemical Abstracts Services (CAS): American Chemical Society, Columbus, OH, Dec. 27, 2001. Registry No. 382593-45-5, (5-bromo-2-[[(5-chloro-2-thienyl)amino]sulfonyl]-N-pheny-Benzamide).
Compound 23. Chemical Abstracts Services (CAS): American Chemical Society, Columbus, OH, Dec. 27, 2001. Registry No. 382593-46-6, (5-bromo-N-(4-chlorophenyl)-2-[[(5-chloro-2thienyl)amino]sulfonyl]-Benzamide).
Compound 24. Chemical Abstracts Services (CAS): American Chemical Society, Columbus, OH, Jan. 14, 2002. Registry No. 382651-44-7, (N-phenyl-4-[ (2-thiazolylamino)sulfonyl-Benzamide).
Compound 25. Chemical Abstracts Services (CAS): American Chemical Society, Columbus, OH, Jan. 15, 2002. Registry No. 383161-03-3, (4-[ [(5-ethyl-I,3,4-thiadiazol-2-yl)amino]sulfonyl]-N-phenyl-Benzamide).
Compound 26. Chemical Abstracts Services (CAS): American Chemical Society, Columbus, OH, Jun. 2003. Registry No. 628710-44-1, (2-chloro-5-[[(4,5-dihydro-5-oxo-4-phenyl-1H-1,2,4-triazol-3-yl)amino]sulfonyl]-4-mercapto-Nphenyl-Benzamide).
Compound 27. Chemical Abstracts Services (CAS): American Chemical Society, Columbus, OH, Jun. 2003. Registry No. 628710-45-2, (2-chloro-5-[[ (4,5-dihydro-5-oxo-4-phenyl-1H-1,2,4-triazol-3-yl)amino]sulfonyl]-4-mercapto-N-(4- methylpheny1)-Benzamide).

Compound 28. Chemical Abstracts Services (CAS): American Chemical Society, Columbus, OH, Jun. 2003. Registry No. 628710-46-3, (2-chloro-N-(4-chlorophenyl)-5-[[ (4,5-dihydro-5-oxo-4-phenyl-1H-12,4-triazol-3-yl)amino] sulfonyl]-4-mercapto-Benzamide).

Compound 29. Chemical Abstracts Services (CAS): American Chemical Society, Columbus, OH, Jun. 2003. Registry No. 628710-47-4, (2-chloro-N-(2-chlorophenyl)-5-[[ (4,5-dihydro-5-oxo-4-phenyl-1H-1,2,4- triazol-3-yl)amino]sulfonyl]-4-mercapto-Benzamide).

Compound 30. Chemical Abstracts Services (CAS): American Chemical Society, Columbus, OH, Jan. 15, 2004. Registry No. 655241-13-7, (2-chloro-5-[[ [4-(4-chlorophenyl)-4H-I,2,4-triazol-3yl]amino]sulfonyl]-4-mercapto-Nphenyl-Benzamide).

Compound 31. Chemical Abstracts Services (CAS): American Chemical Society, Columbus, OH, Jan. 15, 2004. Registry No. 655241-14-8, (2-chloro-4-mercapto-5-[ [[4-(4-methylphenyl)-4H-I,2,4-triazol-3yl]aminolsulfonyl]-Nphenyl-Benzamide).

Compound 32. Chemical Abstracts Services (CAS): American Chemical Society, Columbus, OH, Jan. 15, 2004. Registry No. 655241-15-9, (2-chloro-N-(4-fluorophenyl)-5-[[ [4-(4-fluorophenyl)-4H-1,2,4triazol-3-yl]amino] sulfonyl]-4-mercapto-Benzamide).

Compound 33. Chemical Abstracts Services (CAS): American Chemical Society, Columbus, OH, Jan. 15, 2004. Registry No. 655241-16-0, (2-chloro-N-(4-chlorophenyl)-5-[[ [4-(4-fluorophenyl)-4H-1,2,4triazol-3-yl]amino] sulfonyl]-4-mercapto-Benzamide).

Compound 34. Chemical Abstracts Services (CAS): American Chemical Society, Columbus, OH, Jan. 15, 2004. Registry No. 655241-17-1, (2-chloro-4-mercapto-N-(4-methylphenyl)-5-[ [(4-propyl-4H-1,2,4triazol-3-yl)amino] sulfonyl]-Benzamide).

Compound 35. Chemical Abstracts Services (CAS): American Chemical Society, Columbus, OH, Jan. 15, 2004. Registry No. 655241-18-2, (5-[ [(4-butyl-4H-1,2,4-triazol-3-yl)amino]sulfonyl]-2-chloro-N-(4-chlorophenyl)-4-mercapto-Benzamide).

Compound 36. Chemical Abstracts Services (CAS): American Chemical Society, Columbus, OH, Jan. 15, 2004. Registry No. 655241-19-3, (5-[ [(4-butyl-4H-1,2,4-triazol-3-yl)amino]sulfonyl]-2-chloro-4-mercapto-N-(4-methylphenyl)-Benzamide).

Compound 37. Chemical Abstracts Services (CAS): American Chemical Society, Columbus, OH, Jan. 15, 2004. Registry No. 655241-21-7, (2-chloro-N-(4-chlorophenyl)-4-mercapto-5-[ [[4-(2-methylpropyl)-4H-1,2,4-triazol-3-yl] amino]sulfonyl]-Benzamide).

Compound 38. Chemical Abstracts Services (CAS): American Chemical Society, Columbus, OH, Jan. 15, 2004. Registry No. 655241-22-8, (2-chloro-4-mercapto-N-(4-methoxyphenyl)-5-[[ [4-(2-methylpropyl)-4H-1,2,4-triazol-3-yl]amino]sulfonyl]—Benzamide).

Compound 39. Chemical Abstracts Services (CAS): American Chemical Society, Columbus, OH, Jan. 15, 2004. Registry No. 655241-23-9, (2-chloro-4-mercapto-N-(4-methylphenyl)-5-[ [[4-(1-methylpropyl)-4H-1,2,4-triazol-3-yl] amino]sulfonyl]-Benzamide).

Compound 40. Chemical Abstracts Services (CAS): American Chemical Society, Columbus, OH, Jan. 15, 2004. Registry No. 655241-24-0, (2-chloro-4-mercapto-N-(4-methylphenyl)-5-[ [[4-(phenylmethyl)-4H-1,2,4-triazol-3-yl] amino]sulfonyl]—Benzamide).

Compound 41. Chemical Abstracts Services (CAS): American Chemical Society, Columbus, OH, Jan. 15, 2004. Registry No. 655241-25-1, (2-chloro-5-[[ [4-(4-fluorophenyl)-4H-1,2,4-triazol-3-yl]amino]sulfonyl]-4-mercapto-Nphenyl-Benzamide).

Compound 42. Chemical Abstracts Services (CAS): American Chemical Society, Columbus, OH, Jan. 15, 2004. Registry No. 655241-26-2, (2-chloro-N-(4-chlorophenyl)-4-mercapto-5-[ [[4-(4-methylphenyl)-4H-I,2,4-triazol-3-yl) amino]sulfonyl]-Benzamide).

Compound 43. Chemical Abstracts Services (CAS): American Chemical Society, Columbus, OH, Jan. 15, 2004. Registry No. 655241-29-5, ([[5-chloro-4-[[ (4-methylphenyl)amino]carbonyl]-2-[ [(4-propyl-4H-1,2,4-triazol-3-yl) amino]sulfonyl]phenyl]thio]-(9C1)-Acetic acid).

Compound 44. Chemical Abstracts Services (CAS): American Chemical Society, Columbus, OH, Mar. 26, 2004. Registry No. 667901-49-7, (4-methyl-N-phenyl-3-[ (1,3,4-thiadiazol-2-ylamino)sulfonyl]-Benzamide).

Compound 45. Chemical Abstracts Services (CAS): American Chemical Society, Columbus, OH, Mar. 4, 2004 Registry No. 668268-03-9, (5-bromo-2-[[4-[ (1H-1,2,4-triazol-3-ylamino) sulfonyl]benzoyl]amino]-(9CI))-Benzoic acid).

Compound 46. Chemical Abstracts Services (CAS): American Chemical Society, Columbus, OH, Nov. 20, 1978. Registry No. 69519-30-8, (2-[ (phenylamino)carbonyl]-4-[ (2-thiazolylamino)sulfonyl]-Benzoic acid).

Compound 47. Chemical Abstracts Services (CAS): American Chemical Society, Columbus, OH, Jun. 25, 2009.

Compound 48. Chemical Abstracts Services (CAS): American Chemical Society, Columbus, OH, Apr. 15, 2005. Registry No. 848583-90-4, (2,4-dichloro-5-[ [[ (2-methoxyphenyl)methyl]amino]sulfonyl]-,2-[4-[ (2-thienylsulfonyl) amino]benzoyl]hydrazide) Benzoic acid.

Compound 49. Chemical Abstracts Services (CAS): American Chemical Society, Columbus, OH, Jul. 25, 2006. Registry No. 895730-82-2, (2,4-dichloro-5-[ [[ (2-methoxyphenyl)methyl]amino]sulfonyl]-,2-[4-[ (2-thienylsulfonyl) amino]benzoyl]hydrazide)-Benzamide).

Compound 50. Chemical Abstracts Services (CAS): American Chemical Society, Columbus, OH, Jul. 25, 2006. Registry No. 895730-90-2, (3-[ [(5-ethyl-1,3,4-thiadiazol-2-yl)amino]sulfonyll-N-(4methylphenyl)-Benzamide).

* cited by examiner

HETEROCYCLIC SULFONAMIDES AS INHIBITORS OF ION CHANNELS

CROSS-REFERENCE TO RELATED APPLICATIONS

This application claims priority to U.S. Provisional Patent Application Ser. No. 61/035,324 filed on Mar. 10, 2008 and 60/896,735, filed on Mar. 23, 2007, each of which is herein incorporated by reference in their entirety for all purposes.

FIELD OF THE INVENTION

This invention relates to the use of certain compounds as sodium channel blockers and to the treatment of pain by the inhibition of sodium channels. Additionally, this invention relates to novel compounds that are useful as sodium channel blockers.

BACKGROUND OF THE INVENTION

Voltage-gated sodium channels are found in all excitable cells including myocytes of muscle and neurons of the central and peripheral nervous system. In neuronal cells sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (See Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)). See Table A, below.

duction disorders (Liu H, et al., *Am. J. Pharmacogenomics*, 3(3): 173-9 (2003)). Consequently, blockers of Nav1.5 have found clinical utility in treatment of such disorders (Srivatsa U, et al., *Curr. Cardiol. Rep.*, 4(5): 401-10 (2002)). The remaining TTX-resistant sodium channels, Nav1.8 (SCN10A, PN3, SNS) and Nav1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of Nav1.8 has been found in the CNS of human multiple sclerosis (MS) patients and also in a rodent model of MS (Black, J A, et al., *Proc. Natl. Acad. Sci. USA*, 97(21): 11598-602 (2000)). Evidence for involvement in nociception is both associative (preferential expression in nociceptive neurons) and direct (genetic knockout). Nav1.8-null mice exhibited typical nociceptive behavior in response to acute noxious stimulation but had significant deficits in referred pain and hyperalgesia (Laird J M, et al., *J. Neurosci.*, 22(19): 8352-6 (2002)).

The TTX-sensitive subset of voltage-gated sodium channels is expressed in a broader range of tissues than the TTX-resistant channels and has been associated with a variety of human disorders. The $Na_V1.1$ channel well exemplifies this general pattern, as it is expressed in both the central and peripheral nervous system and has been associated with several seizure disorders including Generalized Epilepsy with Febrile Seizures Plus, types 1 and 2 (GEFS+1, GEFS+2), Severe Myoclonic Epilepsy of Infancy (SMEI), and others (Claes, L, et al., *Am. J. Hum. Genet.*, 68: 1327-1332 (2001); Escayg, A., *Am. J. Hum. Genet.*, 68: 866-873 (2001); Lossin, C, *Neuron*, 34: 877-884 (2002)). The Nav1.2 channel is largely, if not exclusively, expressed in the central nervous system and quantitative studies indicate it is the most abundant VGSC of the CNS. Mutations of Nav1.2 are also associated with seizure disorders (Berkovic, S. F., et al., *Ann. Neurol.*, 55: 550-557 (2004)) and Nav1.2-null "knockout" mice exhibit perinatal lethality (Planells-Cases R et al., *Bio-*

TABLE A

| Type | Gene Symbol | Primary tissue | TTX IC-50 | Disease association | Indications |
|---|---|---|---|---|---|
| $Na_v1.1$ | SCN1A | CNS/PNS | 10 | Epilepsy | Pain, seizures, neurodegeneration |
| $Na_v1.2$ | SCN2A | CNS | 10 | Epilepsy | Epilepsy, neurodegeneration |
| $Na_v1.3$ | SCN3A | CNS | 15 | — | Pain |
| $Na_v1.4$ | SCN4A | Sk. muscle | 25 | Myotonia | Myotonia |
| $Na_v1.5$ | SCN5A | Heart | 2000 | Arrhythmia | Arrhythmia |
| $Na_v1.6$ | SCN8A | CNS/PNS | 6 | — | Pain, movement disorders |
| $Na_v1.7$ | SCN9A | PNS | 25 | Erythermalgia | Pain |
| $Na_v1.8$ | SCN10A | PNS | 50000 | — | Pain |
| $Na_v1.9$ | SCN11A | PNS | 1000 | — | Pain |

There are currently at least nine known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v1.5$, H1) is almost exclusively expressed in cardiac tissue and has been shown to underlie a variety of cardiac arrhythmias and con-

*phys. J.*, 78(6):2878-91 (2000)). Expression of the Nav1.4 gene is largely restricted to skeletal muscle and, accordingly, mutations of this gene are associated with a variety of movement disorders (Ptacek, L. J., *Am. J. Hum. Genet.*, 49: 851-854 (1991); Hudson A J, *Brain*, 118(2): 547-63 (1995)). The majority of these disorders are related to hyperactivity or "gain-of-function" and have been found to respond to treatment with sodium channel blockers (Desaphy J F, et al., *J. Physiol.*, 554(2): 321-34 (2004)).

Neither the SCN3A nor the SCN8A VGSC genes have been conclusively linked to heritable disorders in humans. Loss-of-function mutations of the SCN8A gene are known in mice and yield increasingly debilitating phenotypes, dependent upon the remaining functionality of the gene products (Meisler M H, *Genetica*, 122(1): 37-45 (2004)). Homozygous null mutations cause progressive motor neuron failure leading to paralysis and death, while heterozygous null animals are asymptomatic. Homozygous med$^j$ mice have nearly 90% reduction in functional Nav1.6 current and exhibit dystonia and muscle weakness but are still viable. Evidence for Nav1.6 being important for nociception is largely associative as Nav1.6 is expressed at high levels in dorsal root ganglia and can be found in spinal sensory tracts (Tzoumaka E, *J. Neurosci. Res.*, 60(1): 37-44 (2000)). It should be noted however that expression of Nav1.6 is not restricted to sensory neurons of the periphery. Like the Nav1.6 channel, expression of the Nav1.3 VGSC can also be detected in both the central and peripheral nervous system, though levels in the adult CNS are generally much higher than PNS. During development and the early postnatal period Nav1.3 is expressed in peripheral neurons but this expression wanes as the animal matures (Shah B S, *J. Physiol.*, 534(3): 763-76 (2001); Schaller K L, *Cerebellum*, 2(1): 2-9 (2003)). Following neuronal insult Nav1.3 expression is upregulated, more closely mimicking the developmental expression patterns (Hains B C, *J. Neurosci.*, 23(26): 8881-92 (2003)). Coincident with the recurrence of Nav1.3 expression is the emergence of a rapidly re-priming sodium current in the injured axons with a biophysical profile similar to Nav1.3 (Leffler A, et al., *J. Neurophysiol.*, 88(2): 650-8 (2002)). Treatment of injured axons with high levels of GDNF has been shown to diminish the rapidly repriming sodium current and reverses thermal and mechanical pain-related behaviors in a rat model of nerve injury, presumably by down-regulating the expression of Nav1.3 (Boucher T J, *Curr. Opin. Pharmacol.*, 1(1): 66-72 (2001)). Specific down-regulation of Nav1.3 via treatment with antisense oligonucleotides has also been shown to reverse pain-related behaviors following spinal cord injury (Hains B C, *J. Neurosci.*, 23(26): 8881-92 (2003)).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows 90% amino acid identity between the human and rat genes (Toledo-Aral et al., *Proc. Natl. Acad. Sci. USA*, 94(4): 1527-1532 (1997)).

An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir. (Wien)*, 144(8): 803-10 (2002)). Mutations of $Na_v1.7$, both familial and sporadic, have also been linked to primary erythermalgia, a disease characterized by burning pain and inflammation of the extremities (Yang et al., *J. Med. Genet.*, 41(3): 171-4 (2004)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433).

Sodium channel-blocking agents have been reported to be effective in the treatment of various disease states, and have found particular use as local anesthetics and in the treatment of cardiac arrhythmias. It has also been reported that sodium channel-blocking agents may be useful in the treatment of pain, including acute, chronic, inflammatory and/or neuropathic pain; see, for example, Wood, J N et al., *J. Neurobiol.*, 61(1): 55-71 (2004). Preclinical evidence demonstrates that sodium channel-blocking agents can suppress neuronal firing in peripheral and central sensory neurons, and it is via this mechanism that they may be useful for relieving pain. In some instances abnormal or ectopic firing can originate from injured or otherwise sensitized neurons. For example, it has been shown that sodium channels can accumulate in peripheral nerves at sites of axonal injury and may function as generators of ectopic firing (Devor et al. *J. Neurosci.*, 132: 1976 (1993)). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., *Brain Res.*, 824(2): 296-9 (1999); Black et al., *Pain*, 108(3): 237-47 (2004)). Alterations in either the level of expression or distribution of sodium channels, therefore, may have a major influence on neuronal excitability and pain-related behaviors.

Many patients with either acute or chronic pain disorders respond poorly to current pain therapies and resistance or insensitivity to opiates is common. In addition, many of the currently available treatments have undesirable side effects. It has been reported that there is no treatment to prevent the development of neuropathic pain or to control established neuropathic pain. Mannion et al., *Lancet*, 353: 1959-1964 (1999).

Ohkawa et al. have described a class of cyclic ethers that are of use as sodium channel blockers (U.S. Pat. No. 6,172, 085).

In view of the limited number of agents presently available and the low levels of efficacy of the available agents, there is a pressing need for compounds that are potent, specific inhibitors of ion channels implicated in neuropathic pain. The present invention provides such compounds, methods of using them, and compositions that include the compounds.

SUMMARY OF THE INVENTION

It has now been discovered that various substituted pyridinyl and substituted aryl sulfonamides are potent modulators of sodium channels. In the discussion that follows, the invention is exemplified by reference to the inhibition of sodium channels that are localized in the peripheral nervous system, and in particular those compounds that are selective inhibitors of TTX-s sodium channels, and are useful for treating pain through the inhibition of sodium ion flux through channels that include a TTX-s sodium channel subunit. The compounds, compositions and methods of the present invention are useful for treating diseases in which modulating one or more TTX-s sodium channels provides relief from the disease. Of particular interest is the use of the compounds, compositions and methods of the invention for treating pain and central or peripheral nervous system disorders, preferably peripheral nervous system disorders. The present invention is of use for treating acute, chronic, inflammatory, and/or neuropathic pain.

The present invention provides compounds that are useful in the treatment of diseases through the modulation of sodium ion flux through voltage-dependent sodium channels. More particularly, the invention provides compounds, compositions and methods that are useful in ameliorating or alleviating conditions susceptible to such ion channel modulation as more fully described below.

Additional aspects, advantages and objects of the present invention will be apparent from the detailed description that follows.

DETAILED DESCRIPTION OF THE INVENTION

Abbreviations

The abbreviations used herein generally have their conventional meaning within the chemical and biological arts. Unless otherwise provided herein: CHO means Chinese hamster ovary; HEK means human embryonic kidney; EBSS means Earl's Balanced Salt Solution; SDS means sodium dodecyl sulfate; $Et_3N$ means triethylamine; CDI means N,N'-carbonyldiimidazole; WSCDI or EDCI HCl means 1-(3-dimethylaminopropyl)-3-ethylcarbodiimide hydrochloride; DCC means N,N'-dicyclohexylcarbodiimide; HOAT means 1-hydroxy-7-azabenzotriazole; HOBT means 1-hydroxybenzotriazole hydrate; HBTU means O-benzotriazol-1-yl-N,N,N',N'-tetramethyluronium hexafluorophosphate; TBTU means O-(Benzotriazol-1-yl)-N,N,N',N'-tetramethyluronium tetrafluoroborate; HATU means 2-(1H-7-Azabenzotriazol-1-yl)-1,1,3,3-tetramethyl uronium hexafluorophosphate methanaminium; Hünig's base means N-ethyldiisopropylamine; $Et_3N$ means triethylamine; DMAP means 4-dimethylaminopyridine; LiHMDS means lithium bis(trimethylsilyl)amide; Boc means tert-butoxycarbonyl; CBz means benzyloxycarbonyl; THF means tetrahydrofuran; DMSO means dimethyl sulphoxide; DCM means dichloromethane; DMF means N,N-dimethylformamide; AcOH means acetic acid; MeOH means methanol; TFA means trifluoroacetic acid; HCl means hydrochloric acid; DABCO means 1,4-diazabicyclo[2.2.2]octane; TLC means thin layer chromatography; and NaH means sodium hydride.

Definitions

The symbol , whether utilized as a bond or displayed perpendicular to a bond, indicates the point at which the displayed moiety is attached to the remainder of the molecule.

The symbol , whether utilized as a bond or displayed perpendicular to a bond, indicates the point at which the displayed moiety is attached to the carbon atom of a carbonyl moiety.

The symbol , whether utilized as a bond or displayed perpendicular to a bond, indicates the point at which the displayed moiety is attached to the sulfur atom on a sulfonamidyl moiety.

The symbol , indicates the point at which the displayed moiety is attached to the remainder of the molecule, such as for the connection of the R and Z substituents in the Tables.

"Compound of the invention," as used herein refers to the compounds discussed herein, pharmaceutically acceptable salts and prodrugs of these compounds.

"Biological medium," as used herein refers to both in vitro and in vivo biological milieus. Exemplary in vitro "biological media" include, but are not limited to, cell culture or extracts thereof, tissue culture or extracts thereof, homogenates or extracts thereof, biopsied material obtained from a mammal or extracts thereof, and blood, saliva, urine, feces, semen, tears, or other body fluids or extracts thereof. In vivo applications are generally performed in mammals, preferably humans.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Inhibiting" and "blocking," are used interchangeably herein to refer to the partial or full blockade of a voltage sodium gated channel by a compound of the invention, which leads to a decrease in ion flux either into or out of a cell in which a voltage-gated sodium channel is found.

The compounds of the invention and/or formula (I), being sodium channel modulators, are potentially useful in the treatment of a range of disorders. The treatment of pain, particularly neuropathic pain and/or inflammatory pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, *Prog. Neurobiol.*, 57, 1-164 for a review). These sensory fibres are known as nociceptors and are characteristically small diameter axons with slow conduction velocities. Nociceptors encode the intensity, duration and quality of noxious stimulus and by virtue of their topographically organized projection to the spinal cord, the location of the stimuli. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain these mechanisms can be useful, in promoting protective behaviors which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumor related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
  pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
  heart and vascular pain, including pain caused by angina, myocardical infarction, mitral stenosis, pericarditis, Raynaud's phenomenon, scleredoma and skeletal muscle ischemia;
  head pain, such as migraine (including migraine with aura and migraine without aura), cluster headache, tension-type headache mixed headache and headache associated with vascular disorders; and
  orofacial pain, including dental pain, otic pain, burning mouth syndrome and temporomandibular myofascial pain.

Where substituent groups are specified by their conventional chemical formulae, written from left to right, they equally encompass the chemically identical substituents, which would result from writing the structure from right to left, e.g., —$CH_2O$— is preferably intended to also recite —$OCH_2$—.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more group referred to hereinbelow as an "alkyl group substituent."

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Two or more heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent refers to a substituted or unsubstituted divalent heteroalkyl radical, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents-$C(O)_2$R'— and, preferably, —R'$C(O)_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) preferably includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR""—C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl in a number ranging from zero to (2m'+1), where m' is the total number of carbon atoms in such radical. R', R", R''', R'''' and R''''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''', R'''' and R''''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR'''''—C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', R'''' and R''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''', R'''' and R''''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE—A HANDBOOK, Verlag Helvetica Chimica Acta (2002)

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise NO, NO₂, —ONO, or —ONO₂ moieties. The term "prodrug" is accorded a meaning herein such that prodrugs do not encompass the parent compound of the prodrug. When used to describe a compound of the invention, the term "prodrug" may also to be interpreted to exclude other compounds of the invention.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

I. The Compounds

In a first aspect, the invention is a compound described herein. In an exemplary embodiment, the invention is according to a formula described herein. In an exemplary embodiment, the compound has a formula according to Formula I:

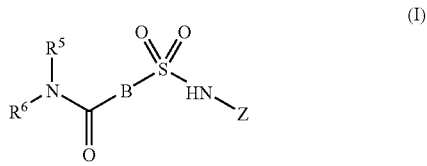

or a pharmaceutically acceptable salt or solvate thereof, wherein $R^5$ and $R^6$ are each members independently selected from H, substituted or unsubstituted alkyl, substituted or unsubstituted heteroalkyl, substituted or unsubstituted heterocycloalkyl, substituted or unsubstituted cycloalkyl, substituted or unsubstituted heteroaryl and substituted or unsubstituted aryl; with the proviso that $R^5$ and $R^6$ are not both hydrogen; with the further proviso that $R^5$ and $R^6$, when taken together with the nitrogen to which they are attached, are optionally joined to form a substituted or unsubstituted 4- to 8-membered heterocycloalkyl ring; B is a member selected from substituted or unsubstituted aryl and substituted or unsubstituted 6-membered heteroaryl; and Z is a substituted or unsubstituted 5-membered heteroaryl.

In an exemplary embodiment, there is a proviso that the compound of formula (I) is not one of the following: N-(5-methyl-3-isoxazolyl)-3-[[(5-methyl-3-isoxazolyl)amino] sulfonyl]-benzamide; 3-[[(5-methyl-3-isoxazolyl)amino] sulfonyl]-N-1,3,4-thiadiazol-2-yl-benzamide; N-(5-ethyl-1,3,4-thiadiazol-2-yl)-3-(4-morpholinylcarbonyl)-benzenesulfonamide; 1-[3-[[[5-(1,1-dimethylethyl)-4-methyl-2-thiazolyl]amino]sulfonyl]benzoyl]piperidine; N-(5-methyl-1,3,4-thiadiazol-2-yl)-3-(4-morpholinylcarbonyl)-benzenesulfonamide; and N-methyl-4-[[(1-methyl-1H-pyrazol-3-yl)amino]sulfonyl]-benzamide.

In an exemplary embodiment, $R^5$ and $R^6$ are each members independently selected from H, substituted or unsubstituted arylalkyl, substituted or unsubstituted (heteroaryl)alkyl, substituted or unsubstituted (heterocycloalkyl)alkyl and substituted or unsubstituted (cycloalkyl)alkyl. In an exemplary embodiment, $R^5$ and $R^6$ are each members independently selected from H, substituted or unsubstituted aryl($C_1$-$C_4$) alkyl, substituted or unsubstituted heteroaryl($C_1$-$C_4$)alkyl, substituted or unsubstituted heterocycloalkyl($C_1$-$C_4$)alkyl and substituted or unsubstituted cycloalkyl($C_1$-$C_4$)alkyl. In an exemplary embodiment, $R^5$ and $R^6$ are each members independently selected from H, substituted or unsubstituted aryl($C_1$-$C_2$)alkyl, substituted or unsubstituted heteroaryl($C_1$-$C_2$)alkyl, substituted or unsubstituted heterocycloalkyl($C_1$-$C_2$)alkyl and substituted or unsubstituted cycloalkyl($C_1$-$C_2$) alkyl.

In an exemplary embodiment, $R^5$ and $R^6$ are each members independently selected from H, substituted or unsubstituted aryloxy, substituted or unsubstituted heteroaryloxy, substituted or unsubstituted (heterocycloalkyl)oxy and substituted or unsubstituted (cycloalkyl)oxy.

In an exemplary embodiment, $R^5$ and $R^6$ are each members independently selected from H, substituted or unsubstituted aryloxyalkyl, substituted or unsubstituted heteroaryloxyalkyl, substituted or unsubstituted heterocycloalkyloxyalkyl and substituted or unsubstituted cycloalkyloxyalkyl. In an exemplary embodiment, $R^5$ and $R^6$ are each members independently selected from H, substituted or unsubstituted aryloxy($C_1$-$C_4$)alkyl, substituted or unsubstituted heteroaryloxy($C_1$-$C_4$)alkyl, substituted or unsubstituted heterocycloalkyloxy($C_1$-$C_4$)alkyl and substituted or unsubstituted cycloalkyloxy($C_1$-$C_4$)alkyl. In an exemplary embodiment, $R^5$ and $R^6$ are each members independently selected from H, substituted or unsubstituted aryloxy($C_1$-$C_2$)alkyl, substituted or unsubstituted heteroaryloxy($C_1$-$C_2$)alkyl, substituted or unsubstituted heterocycloalkyloxy($C_1$-$C_2$)alkyl and substituted or unsubstituted cycloalkyloxy($C_1$-$C_2$)alkyl.

In an exemplary embodiment, $R^5$ and $R^6$ are each members independently selected from H, substituted or unsubstituted arylaminoalkyl and substituted or unsubstituted heteroarylaminoalkyl. In an exemplary embodiment, $R^5$ and $R^6$ are each members independently selected from H, substituted or unsubstituted arylamino($C_1$-$C_4$)alkyl and substituted or unsubstituted heteroarylamino($C_1$-$C_4$)alkyl. In an exemplary embodiment, $R^5$ and $R^6$ are each members independently selected from H, substituted or unsubstituted arylamino($C_1$-$C_2$)alkyl and substituted or unsubstituted heteroarylamino($C_1$-$C_2$)alkyl.

In an exemplary embodiment, $R^5$ is a member selected from H, substituted or unsubstituted ($C_1$-$C_{10}$)alkyl and substituted or unsubstituted ($C_3$-$C_8$)cycloalkyl. In an exemplary embodiment, $R^5$ is H. In an exemplary embodiment, $R^5$ is a member selected from substituted or unsubstituted ($C_1$-$C_{10}$) alkyl and substituted or unsubstituted ($C_3$-$C_8$)cycloalkyl. In an exemplary embodiment, $R^5$ is a member selected from ($C_1$-$C_4$)alkyl, hydroxy ($C_1$-$C_4$)alkyl, cyano ($C_1$-$C_4$)alkyl, ($C_3$-$C_8$)cycloalkyl, phenyl($C_1$-$C_4$)alkyl, hydroxycyclohexyl and hydroxyalkylcyclohexyl. In an exemplary embodiment, $R^5$ is a member selected from methyl, ethyl, isopropyl, propyl, n-butyl, t-butyl, hydroxymethyl, hydroxypropyl, hydroxybutyl, hydroxyethyl, cyanomethyl, cyanoethyl, cyanopropyl, cyanoisopropyl, cyanobutyl, 2-hydroxy-1-phenylethyl, cyclopropyl, cyclopentyl, cyclohexyl, (1R, 2R) 2-hydroxycyclohexyl, (1R, 2R) 2-hydroxycyclohexyl, (1R, 2S) (2-hydroxymethyl)cyclohexyl and (1S, 2R) (2-hydroxymethyl)cyclohexyl. In an exemplary embodiment, $R^5$ is a member selected from methyl, ethyl, isopropyl, hydroxyethyl, cyanoethyl, 2-hydroxy-1-phenylethyl, cyclopropyl, cyclohexyl, (1R, 2R) 2-hydroxycyclohexyl, (1R, 2R) 2-hydroxycyclohexyl, (1R, 2S) (2-hydroxymethyl)cyclohexyl and (1S, 2R) (2-hydroxymethyl)cyclohexyl.

In an exemplary embodiment, $R^6$ is H, and $R^5$ is a member selected from substituted or unsubstituted ($C_1$-$C_{10}$)alkyl and substituted or unsubstituted ($C_3$-$C_8$)cycloalkyl. In an exemplary embodiment, $R^6$ is H, and $R^5$ is a member selected from ($C_1$-$C_4$)alkyl, hydroxy ($C_1$-$C_4$)alkyl, cyano ($C_1$-$C_4$)alkyl, ($C_3$-$C_8$)cycloalkyl, phenyl($C_1$-$C_4$)alkyl and hydroxycyclohexyl and hydroxyalkylcyclohexyl. In an exemplary embodiment, $R^6$ is H, $R^5$ is a member selected from methyl, ethyl, isopropyl, propyl, n-butyl, t-butyl, hydroxymethyl, hydroxypropyl, hydroxybutyl, hydroxyethyl, cyanomethyl, cyanoethyl, cyanopropyl, cyanoisopropyl, cyanobutyl, 2-hydroxy-1-phenylethyl, cyclopropyl, cyclopentyl, cyclohexyl, (1R, 2R) 2-hydroxycyclohexyl, (1R, 2R) 2-hydroxycyclohexyl, (1R, 2S) (2-hydroxymethyl)cyclohexyl and (1S, 2R) (2-hydroxymethyl)cyclohexyl. In an exemplary embodiment, $R^6$ is H, and $R^5$ is a member selected from methyl, ethyl, isopropyl, hydroxyethyl, cyanoethyl, 2-hydroxy-1-phenylethyl, cyclopropyl, cyclohexyl, (1R, 2R) 2-hydroxycyclohexyl, (1R, 2R) 2-hydroxycyclohexyl, (1R, 2S) (2-hydroxymethyl)cyclohexyl, (1S, 2R) (2-hydroxymethyl)cyclohexyl.

In an exemplary embodiment, $R^6$ is not H, and $R^5$ is a member selected from substituted or unsubstituted ($C_1$-$C_{10}$) alkyl and substituted or unsubstituted ($C_3$-$C_8$)cycloalkyl. In an exemplary embodiment, $R^6$ is not H, and $R^5$ is a member selected from ($C_1$-$C_4$)alkyl, hydroxy ($C_1$-$C_4$)alkyl, cyano ($C_1$-$C_4$)alkyl, ($C_3$-$C_8$)cycloalkyl, phenyl($C_1$-$C_4$)alkyl and hydroxycyclohexyl and hydroxyalkylcyclohexyl. In an exemplary embodiment, $R^6$ is not H, and $R^5$ is a member selected from methyl, ethyl, isopropyl, propyl, n-butyl, t-butyl, hydroxymethyl, hydroxypropyl, hydroxybutyl, hydroxyethyl, cyanomethyl, cyanoethyl, cyanopropyl, cyanoisopropyl, cyanobutyl, 2-hydroxy-1-phenylethyl, cyclopropyl, cyclopentyl, cyclohexyl, (1R, 2R) 2-hydroxycyclohexyl, (1R, 2R) 2-hydroxycyclohexyl, (1R, 2S) (2-hydroxymethyl)cyclohexyl and (1S, 2R) (2-hydroxymethyl)cyclohexyl. In an exemplary embodiment, $R^6$ is not H, and $R^5$ is a member selected from methyl, ethyl, isopropyl, hydroxyethyl, cyanoethyl, 2-hydroxy-1-phenylethyl, cyclopropyl, cyclohexyl, (1R, 2R) 2-hydroxycyclohexyl, (1R, 2R) 2-hydroxycyclohexyl, (1R, 2S) (2-hydroxymethyl)cyclohexyl and (1S, 2R) (2-hydroxymethyl)cyclohexyl.

In an exemplary embodiment, $R^6$ is substituted or unsubstituted benzyl, and $R^5$ is a member selected from substituted or unsubstituted ($C_1$-$C_{10}$)alkyl and substituted or unsubstituted ($C_3$-$C_8$)cycloalkyl. In an exemplary embodiment, $R^6$ is substituted or unsubstituted benzyl, and $R^5$ is a member selected from ($C_1$-$C_4$)alkyl, hydroxy($C_1$-$C_4$)alkyl, cyano ($C_1$-$C_4$)alkyl, ($C_3$-$C_8$)cycloalkyl, phenyl($C_1$-$C_4$)alkyl, hydroxycyclohexyl and hydroxyalkylcyclohexyl. In an exemplary embodiment, $R^6$ is substituted or unsubstituted benzyl, and $R^5$ is a member selected from methyl, ethyl, isopropyl, propyl, n-butyl, t-butyl, hydroxymethyl, hydroxypropyl, hydroxybutyl, hydroxyethyl, cyanomethyl, cyanoethyl, cyanopropyl, cyanoisopropyl, cyanobutyl, 2-hydroxy-1-phenylethyl, cyclopropyl, cyclopentyl, cyclohexyl, (1R, 2R) 2-hydroxycyclohexyl, (1R, 2R) 2-hydroxycyclohexyl, (1R, 2S) (2-hydroxymethyl)cyclohexyl and (1S, 2R) (2-hydroxymethyl)cyclohexyl. In an exemplary embodiment, $R^6$ is substituted or unsubstituted benzyl, and $R^5$ is a member selected from methyl, ethyl, isopropyl, hydroxyethyl, cyanoethyl, 2-hydroxy-1-phenylethyl, cyclopropyl, cyclohexyl, (1R, 2R) 2-hydroxycyclohexyl, (1R, 2R) 2-hydroxycyclohexyl, (1R, 2S) (2-hydroxymethyl)cyclohexyl and (1S, 2R) (2-hydroxymethyl)cyclohexyl.

In an exemplary embodiment, $R^5$ is methyl, and $R^6$ is substituted or unsubstituted benzyl. In an exemplary embodiment, $R^5$ is methyl, and $R^6$ is a member selected from (halo)benzyl and (trihalo($C_1$-$C_4$)alkyl)benzyl. In an exemplary embodiment, $R^5$ is methyl, and $R^6$ is a member selected from (halo)benzyl and (trihalo($C_1$-$C_4$)alkyl)benzyl. In an exemplary embodiment, $R^5$ is methyl, and $R^6$ is a member selected from (fluoro)benzyl, chlorobenzyl and (trifluoro($C_1$-$C_4$) alkyl)benzyl. In an exemplary embodiment, $R^5$ is methyl, and $R^6$ is a member selected from (trifluoromethyl)benzyl, (trifluoroethyl)benzyl and (trifluoropropyl)benzyl. In an exemplary embodiment, $R^5$ is methyl, and $R^6$ is a member selected from (4-halo)benzyl, (3-trihalo($C_1$-$C_4$)alkyl)benzyl and (4-trihalo($C_1$-$C_4$)alkyl)benzyl. In an exemplary embodiment, $R^5$ is methyl, and $R^6$ is a member selected from (4-fluoro) benzyl, (3-trifluoro($C_1$-$C_4$)alkyl)benzyl and (4-trifluoro($C_1$-$C_4$)alkyl)benzyl. In an exemplary embodiment, $R^5$ is methyl, and $R^6$ is a member selected from (4-fluoro)benzyl, (3-trifluoromethyl)benzyl and (4-trifluoromethyl)benzyl.

In an exemplary embodiment, $R^5$ is methyl, and $R^6$ is substituted or unsubstituted phenylpropyl. In an exemplary embodiment, $R^5$ is methyl, and $R^6$ is hydroxyphenylpropyl. In an exemplary embodiment, $R^5$ is methyl, and $R^6$ is 3-hydroxy-3-phenylpropyl.

In an exemplary embodiment, $R^5$ is a member selected from ethyl and methyl, and $R^6$ is a member selected from substituted or unsubstituted 1-phenylethyl and substituted or unsubstituted 2-phenylethyl. In an exemplary embodiment, $R^5$ is a member selected from ethyl and methyl, and $R^6$ is a member selected from hydroxy-2-phenylethyl, diphenylethyl and (hydroxy($C_1$-$C_4$)alkyl)-2-phenylethyl. In an exemplary embodiment, $R^5$ is a member selected from ethyl and methyl, and $R^6$ is a member selected from 1,2-diphenylethyl, 2-hydroxy-2-phenylethyl, (1S)-1-phenylethyl, 2-oxo-1-methyl-2-phenylethyl and 2-hydroxy-1-methyl-2-phenylethyl. In an exemplary embodiment, $R^5$ is methyl, and $R^6$ is a member selected from ((1S,2R)-2-hydroxy-1-methyl-2-phenylethyl and (1S)-1-phenylethyl. In an exemplary embodiment, $R^5$ is ethyl, and $R^6$ is 1-methyl-2-oxo-2-phenylethyl. In an exemplary embodiment, $R^5$ is ethyl, and $R^6$ is 2-hydroxy-1-phenylethyl. In an exemplary embodiment, $R^5$ is ethyl, and $R^6$ is a member selected from 1,2-diphenylethyl, 2-hydroxy-2-phenylethyl and (1S)-2-hydroxy-1-phenylethyl.

In an exemplary embodiment, $R^5$ is a member selected from (1R, 2R) 2-hydroxycyclohexyl, (1R, 2R) 2-hydroxycyclohexyl, (1R, 2S) (2-hydroxymethyl)cyclohexyl, (1S, 2R) (2-hydroxymethyl)cyclohexyl, and $R^6$ is substituted or unsubstituted benzyl.

In an exemplary embodiment, $R^5$ is isopropyl, and $R^6$ is substituted or unsubstituted benzyl. In an exemplary embodiment, $R^5$ is isopropyl, and $R^6$ is unsubstituted benzyl.

In an exemplary embodiment, $R^5$ is cyclopropyl, and $R^6$ is substituted or unsubstituted benzyl. In an exemplary embodiment, $R^5$ is cyclopropyl, and $R^6$ is (halo)benzyl. In an exemplary embodiment, $R^5$ is cyclopropyl, and $R^6$ is (4-halo)benzyl. In an exemplary embodiment, $R^5$ is cyclopropyl, and $R^6$ is (4-fluoro)benzyl.

In an exemplary embodiment, $R^5$ and $R^6$, along with the nitrogen atom to which they are both attached, are joined to form a substituted or unsubstituted 5 to 8 membered ring.

In an exemplary embodiment, $R^5$ and $R^6$, along with the nitrogen atom to which they are both attached, have a structure according to the following formula:

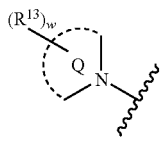

wherein the dotted line encircling Q comprises the atoms necessary for the formation of one ring to three fused rings having 4 to 9 atoms in each ring. The symbol w is an integer selected from 0 to the number of atoms necessary for the formation of Q. Each $R^{13}$ is a member independently selected from H, cyano, hydroxyl, substituted or unsubstituted aryl, substituted or unsubstituted arylalkyl, substituted or unsubstituted heteroaryl, substituted or unsubstituted heteroarylalkyl, substituted or unsubstituted ($C_1$-$C_{10}$)alkyl, substituted or unsubstituted ($C_1$-$C_{10}$)alkoxy and substituted or unsubstituted ($C_3$-$C_8$)cycloalkyl. Each $R^{13}$ is a member independently selected from H, cyano, hydroxyl, substituted or unsubstituted phenyl, substituted or unsubstituted benzyl, substituted or unsubstituted ($C_1$-$C_4$)alkyl and substituted or unsubstituted ($C_1$-$C_4$)alkoxy. In an exemplary embodiment, each $R^{13}$ is a member independently selected from H, cyano, hydroxyl, halophenyl, (alkyl)phenyl, dialkylphenyl, (alkoxy)phenyl, halobenzyl, hydroxyl, pyrazolyl, phenoxy, (alkyl)phenoxy, (halo)phenoxy, (halo)(alkyl)phenoxy, methyl, cyano(halo)phenoxy, (halo)alkylphenyl, (alkoxy)benzyl, benzyl, (halo)(alkoxy)benzyl, (alkoxy)phenoxy, substituted or unsubstituted isoindolyl, 1,3 dihydroisoindolyl, benzyloxy, substituted or unsubstituted cycloalkyl, substituted or unsubstituted pyrimidinyl, (alkyl)pyridimidinyl, (substituted or unsubstituted pyrimidinyl)alkyl, substituted or unsubstituted pyridinyl, (substituted or unsubstituted pyridinyl)alkyl, substituted or unsubstituted benzoyl, (substituted or unsubstituted cycloalkyl)methoxy and oxo.

In another exemplary embodiment, each $R^{13}$ is a member selected from 2-chlorophenyl, 3-fluorobenzyl, phenyl, methyl, phenoxymethyl, hydroxy, fluorobenzyl, 3-methylphenoxy, 3-methylphenyl, 1H-pyrazolyl, cyano(fluoro)phenoxy, fluoro(methyl)phenyl, chlorophenyl, 2-methoxybenzyl, benzyl, 2-methylphenoxy, 3-fluoro-4-methoxybenzyl, 2-chlorophenoxy, 3-methoxyphenyl, 2,5-dimethylphenyl, 4-methoxyphenoxy, 2-methylphenoxy, 4-methoxybenzyl, 4-methylphenyl, 1-oxo-1,3-dihydro-2H-isoindol-2-yl, 3-benzyloxy, 2-methylpyrimidin-4-yl, 5-fluoropyridin-2-yl, 3-methoxyphenyl, 3-fluorophenyl, 4-fluorobenzyl, 4-fluorophenyl, phenoxymethyl, 6-methylpyridinyl, 2-phenylethyl, 3-methylphenyl, 2-cyclopropyl, 2-methoxyphenyl, 2-fluorobenzyl, 3-chlorophenoxy, 4-chlorophenyl, pyrimidinylmethyl, 3-methoxybenzyl, 6-methylpyridin-2-yl, 2-methylpyridin-3-yloxy, pyridin-2-ylmethyl, 4,6-dimethylpyridin-2-yl, 2-chlorophenoxy, 4-methylpyridin-2-yl, 4-methylphenoxy, 4-methylphenyl, benzoyl, 3-methoxypropoxy, 3,5-difluorophenoxy, 3-methoxybenzyl, 4-fluorophenoxy, 3-cyanophenoxy, 3-phenoxymethyl, cyclopropylmethoxy, 4-methoxybenzyl, pyrimidin-5-ylmethyl, 3-methoxyphenyl, oxo, 3-methylbenzyl, phenoxy, 3-cyanophenoxy, 3-chlorobenzyl, hydroxymethyl, 4-methoxyphenyl and 2-fluorophenyl.

In an exemplary embodiment, Q is a member selected from (4aR,9aS)-2,3,9,9a-tetrahydroindeno[2,1-b][1,4]oxazin-4(4aH)yl, (4aS,9aR)-2,3,9,9a-tetrahydroindeno[2,1-b][1,4]oxazin-4(4aH)yl, (5-chloro)3,4-dihydroisoquinolinyl, dihydroisoquinolinyl, (5-chloro)-1,3-dihydro-2H-isoindolyl, (4-chloro)-1,3-dihydro-2H-isoindolyl and (3S, 3aR, 6R, 7aS)-8-oxo-2-phenyloctahydro-1H-3,6-methanoindolyl.

In an exemplary embodiment, said $R^5$ and $R^6$, along with the nitrogen atom to which they are both attached, is a member selected from substituted or unsubstituted thiomorpholinyl, substituted or unsubstituted piperidinyl, substituted or unsubstituted morpholinyl, substituted or unsubstituted pyrrolidinyl, substituted or unsubstituted oxazepanyl, substituted or unsubstituted oxazinanyl, substituted or unsubstituted azepanyl and substituted or unsubstituted piperazinyl.

In an exemplary embodiment, said $R^5$ and $R^6$, along with the nitrogen atom to which they are both attached, is a member selected from substituted or unsubstituted 1,4 oxazepanyl and substituted or unsubstituted 1,3 oxazinanyl.

In an exemplary embodiment, said $R^5$ and $R^6$, along with the nitrogen atom to which they are both attached, is a member selected from unsubstituted thiomorpholinyl, (2-chlorophenyl)thiomorpholinyl, (3-fluorobenzyl)piperidinyl, (3-phenyl)morpholinyl, methyl(phenoxymethyl)pyrrolidinyl), hydroxy(fluorobenzyl)1,4-oxazepanyl, (3-methylphenoxy)piperidinyl, methyl(3-methylphenyl)morpholinyl, (1H-pyrazolyl)ethyl, (phenyl)pyrrolidinyl, (cyano(fluoro)phenoxy)piperidinyl, (fluoro(methyl)phenyl)piperidinyl, methyl(chlorophenyl)piperidinyl, (2-methoxybenzyl)piperidinyl, (2-benzyl)pyrrolidinyl, (2-methylphenoxy)pyrrolidinyl, (3-fluoro-4-methoxybenzyl)-1,4-oxazepanyl, (2-chlorophenoxy)pyrrolidinyl, (3-methoxyphenyl)piperidinyl, (2,5-dimethylphenyl)pyrrolidinyl, (4-methoxyphenoxy)piperidinyl, (2-methylphenoxy)pyrrolidinyl, phenylpyrrolidinyl, (4-methoxybenzyl)pyrrolidinyl, (4-methylphenyl)piperidinyl, (1-oxo-1,3-dihydro-2H-isoindol-2-yl)methylmorpholinyl, (3-benzyloxy)piperidinyl, (2-methylpyrimidin-4-yl)pyrrolidinyl, 2-benzyl-1,3-oxazinanyl, (2-chlorophenyl)pyrrolidinyl, (5-fluoropyridin-2-yl)methyl-1,4-oxazepanyl, (3-methoxyphenyl)piperidinyl, (3-fluorophenyl)(hydroxy)piperidinyl, (3-fluorophenyl)piperidinyl, (4-fluorobenzyl)piperidinyl, (4-fluorophenyl)thiomorpholinyl, (phenoxymethyl)piperidinyl, (6-methylpyridinyl)methyl-1,4-oxazepanyl, (2-phenylethyl)pyrrolidinyl, (3-methylphenyl)pyrrolidinyl, (2-cyclopropyl)morpholinyl, (2-methoxyphenyl)morpholinyl, (2-fluorobenzyl)pyrrolindinyl, (3-chlorophenoxy)methylmorpholinyl, (4-chlorophenyl)(hydroxy)piperidinyl, (pyrimidinylmethyl)piperidinyl, (2-pyridin-2-yl)piperidinyl, (2-phenyl)piperidinyl, (3-methoxybenzyl)pyrrolidinyl, (6-methylpyridin-2-yl)methylpiperidinyl, [(2-methylpyridin-3-yl)oxy]methylmorpholinyl, (pyridin-2-ylmethyl)piperidinyl, [(4,6-dimethylpyridin-2-yl)methyl]azepanyl, (2-chlorophenoxy)pyrrolidinyl, (4-methylpyridin-2-yl)methylpyrroldinyl, (4-methylphenoxy)piperidinyl, hydroxy(4-methylphenyl)piperidinyl, benzoylpiperidinyl, (2-methoxyphenyl)pyrrolidinyl, (pyridin-2-yl)azepanyl, (benzyl)hydroxy-1,4-oxazepanyl, (benzyl)1,4-oxazepanyl, (3-methoxypropoxy)piperidinyl, (pyridin-2-yl)piperidinyl, (3,5-difluorophenoxy)methylmorpholinyl, (3-methoxybenzyl)piperidinyl, (4-fluorophenoxy)methylpiperidinyl, (3-cyanophenoxy)piperidinyl, (2-chloro-4-fluorophenoxy)methylmorpholinyl, (3-phenoxymethyl)piperidinyl, 2-phenylazepanyl, (cyclopropylmethoxy)methylpyrrolidinyl, (4-methoxybenzyl)piperidinyl, (3,5-difluorophenoxy)methylpiperidinyl, (pyrimidin-5-ylmethyl)piperidinyl, (3-methoxyphenyl)pyrrolidinyl, (2-methoxyphenyl)azepanyl, (oxo)(3-methylbenzyl)piperazinyl, 3-phenoxypiperidinyl, (3-cyanophenoxy)methylpiperidinyl, (3-chlorobenzyl)pyrrolidinyl, (hydroxymethyl)(4-methoxyphenyl)pyrrolidinyl, (2-fluorophenyl)pyrrolidinyl, (3-benzyl)pyrrolidinyl and (pyridin-2-yl)pyrrolidinyl.

In an exemplary embodiment, $R^6$ is a member selected from

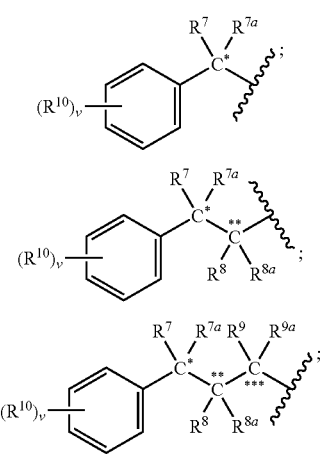

wherein
v is an integer selected from 0 to 3;
w is an integer selected from 0 to 2;
X is a member selected from O and N;
each $R^{10}$ is a member independently selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, substituted or unsubstituted phenyl, substituted or unsubstituted heteroaryl and trifluoromethylthio;
$R^{10a}$ is a member selected from H, ($C_1$-$C_4$)alkyl, substituted or unsubstituted $C_3$-$C_8$ cycloalkyl, substituted or unsubstituted phenyl, substituted or unsubstituted heteroaryl, and substituted or unsubstituted benzyl;
$R^7$, $R^{7a}$, $R^8$, $R^{8a}$, $R^9$ and $R^{9a}$ are each members independently selected from H, halogen, cyano, hydroxyl, substituted or unsubstituted $C_1$-$C_4$ alkyl, substituted or unsubstituted $C_3$-$C_8$ cycloalkyl, substituted or unsubstituted $C_3$-$C_8$ heterocycloalkyl, substituted or unsubstituted $C_1$-$C_4$ alkyloxy, substituted or unsubstituted phenyloxy, trifluoromethylthio, substituted or unsubstituted pyrazolyl, substituted or unsubstituted heteroaryl $C_1$-$C_4$ alkyl;
with the proviso that $R^7$ and $R^{7a}$ are optionally joined with C* to form a member selected from a carbonyl and substituted and unsubstituted 3- to 7-membered ring;
with the further proviso that $R^8$ and $R^{8a}$ are optionally joined with C** to form a member selected from a carbonyl and substituted and unsubstituted 3- to 7-membered ring;
with the further proviso that $R^9$ and $R^{9a}$ are optionally joined with C*** to form a member selected from a carbonyl and substituted and unsubstituted 3- to 7-membered ring;

with the further proviso that $R^7$ and $R^8$ are optionally joined, along with the atoms to which they are attached, to form a 3- to 7-membered ring;
with the further proviso that $R^8$ and $R^9$ are optionally joined, along with the atoms to which they are attached, to form a 3- to 7-membered ring;
with the further proviso that $R^7$ and $R^9$ are optionally joined, along with the atoms to which they are attached, to form a 3- to 7-membered ring;
with the further proviso that $R^7$ and $R^{10}$ are optionally joined, along with the atoms to which they are attached, to form a 3- to 7-membered ring;
with the further proviso that $R^8$ and $R^{10}$ are optionally joined, along with the atoms to which they are attached, to form a 3- to 7-membered ring.
with the further proviso that $R^9$ and $R^{10}$ are optionally joined, along with the atoms to which they are attached, to form a 3- to 7-membered ring.

with the further proviso that when v is 2 or 3, each $R^{10}$ are optionally joined, along with the atoms to which they are attached, to form a 3- to 7-membered ring. In an exemplary embodiment, $R^{10}$ is substituted or unsubstituted pyrazolyl.

In an exemplary embodiment, $R^7$, $R^{7a}$, $R^8$, $R^{8a}$, $R^9$ and $R^{9a}$ are each members independently selected from H, hydroxy, 2-hydroxyethyl, methyl, (S)-methyl, (R)-methyl, cyclopropyl, substituted or unsubstituted isoxazol-5-yl, (substituted or unsubstituted $C_1$-$C_4$ alkyl) isoxazol-5-yl, methyl isoxazol-5-yl, 3-methyl isoxazol-5-yl, halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl.

In an exemplary embodiment, $R^6$ is a member selected from

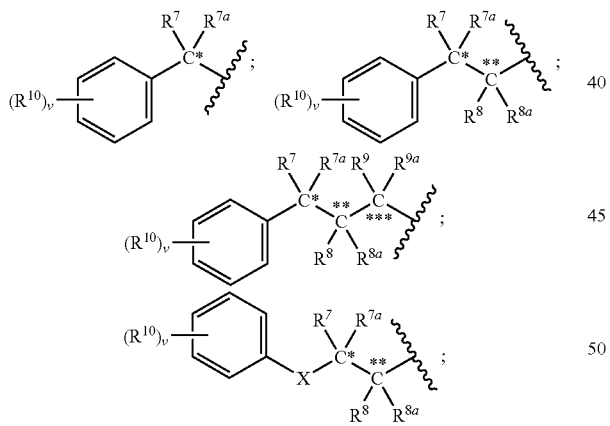

$R^7$ and $R^{7a}$ are joined with C* to form a carbonyl. $R^7$ and $R^{7a}$ are joined with C* to form a member selected from substituted or unsubstituted cyclopropyl and substituted or unsubstituted cyclopentyl, and wherein C* has a configuration which is a member selected from R and S. $R^8$ and $R^{8a}$ are joined with C to form a member selected from substituted or unsubstituted cyclopropyl and wherein C has a configuration which is a member selected from R and S. $R^7$ and $R^8$, along with the atoms to which they are attached, are joined to form substituted or unsubstituted cyclopropyl and substituted or unsubstituted tetrahydrofuran. $R^9$ and $R^{9a}$ are each members independently selected from H, 2-hydroxyethyl, methyl, (S)-methyl, (R)-methyl, halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl.

In an exemplary embodiment, $R^6$ is a member selected from

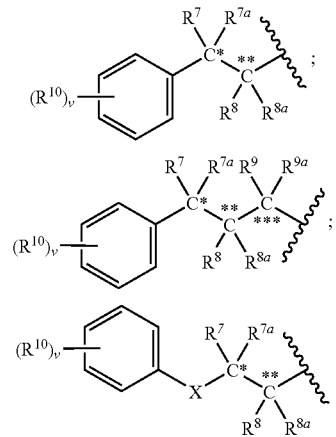

wherein $R^8$, $R^{8a}$, $R^9$ and $R^{9a}$ are each H. In an exemplary embodiment, $R^6$ is a member selected from

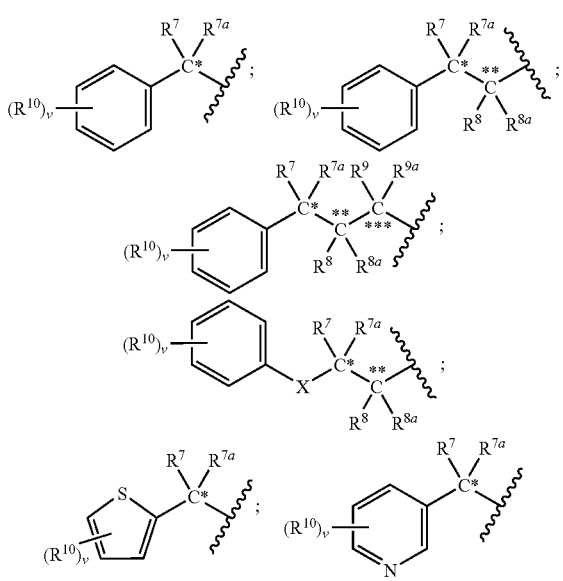

wherein $R^7$ and $R^{7a}$ are each independently selected from H, methyl and hydroxy.

In an exemplary embodiment, $R^6$ is a member selected from

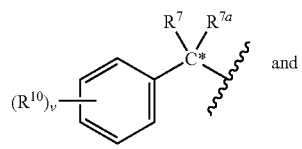

and

-continued

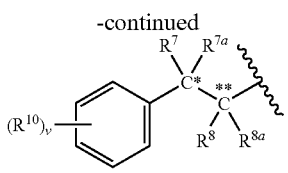

wherein $R^7$ is a member selected from hydroxy, methyl, ethyl and hydroxymethyl, and C* is in a configuration which is a member selected from R and S. $R^8$ is a member selected from hydroxy, methyl, ethyl and hydroxymethyl, and C** is in a configuration which is a member selected from R and S. $R^7$ and $R^8$, along with C* and C**, are joined to form a member selected from substituted or unsubstituted cyclopropyl, substituted or unsubstituted tetrahydrofuran and substituted or unsubstituted cyclopentyl and wherein C* and C** are each independently in a configuration which is a member selected from R and S.

In an exemplary embodiment, $R^6$ is a member selected from

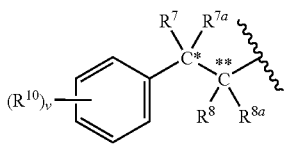

wherein $R^7$ and $R^{7a}$ are joined with C* to form a carbonyl; and $R^8$ is methyl.

In an exemplary embodiment, v is 1 and $R^{10}$ is a member selected from halogen, cyano, hydroxyl, substituted or unsubstituted methyl, substituted or unsubstituted methoxy, substituted or unsubstituted methylthio, substituted or unsubstituted ethoxy, substituted or unsubstituted isopropyloxy, cyclopropyl, pyrazol-1-yl, substituted or unsubstituted phenyl, substituted or unsubstituted benzyl. In an exemplary embodiment, v is 1 and $R^{10}$ is a member selected from fluoro, chloro, cyano, hydroxyl, methyl, trifluoromethyl, methoxy, trifluoromethoxy, difluoromethoxy, isopropyloxy, cyclopropyl, ethoxy, pyrazol-1-yl, phenyl, chlorophenyl and chlorobenzyl.

In an exemplary embodiment, $R^6$ is

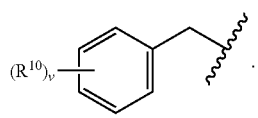

In an exemplary embodiment, v is 1. In an exemplary embodiment, $R^6$ is

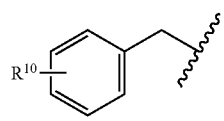

and $R^{10}$ is a member selected from halogen, cyano, hydroxyl, substituted or unsubstituted methyl, substituted or unsubstituted methoxy, substituted or unsubstituted methylthio, substituted or unsubstituted ethoxy, substituted or unsubstituted isopropyloxy, cyclopropyl, t-butyl, pyrazol-1-yl, substituted or unsubstituted phenyl, substituted or unsubstituted benzyl. In an exemplary embodiment, $R^6$ is

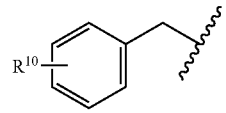

and $R^{10}$ is a member selected from trifluoromethoxy, trifluoromethyl, chloro and fluoro. In an exemplary embodiment, $R^6$ is a member selected from

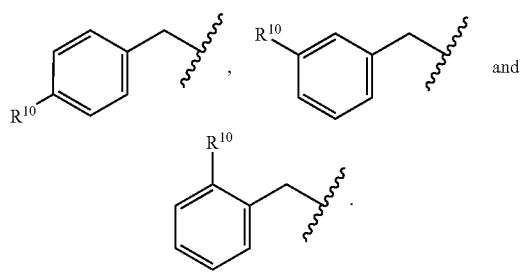

In an exemplary embodiment, $R^6$ is a member selected from

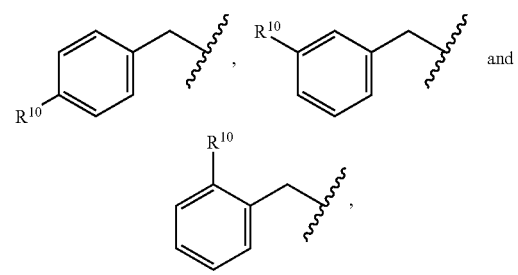

and $R^{10}$ is a member selected from trifluoromethoxy, trifluoromethyl, chloro and fluoro, $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl. In an exemplary embodiment, $R^6$ is a member selected from

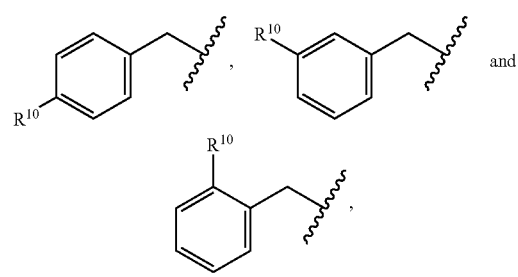

and $R^{10}$ is a member selected from trifluoromethoxy, trifluoromethyl, chloro and fluoro. In an exemplary embodiment, $R^5$ is H, and $R^6$ is a member selected from

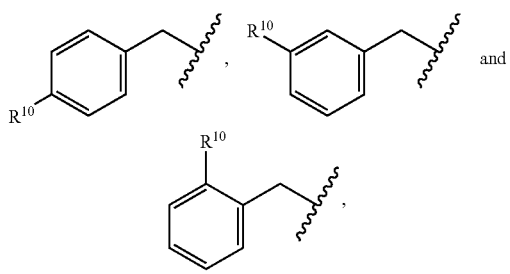

and $R^{10}$ is a member selected from trifluoromethoxy, trifluoromethyl, chloro and fluoro. In an exemplary embodiment, $R^5$ is H, and $R^6$ is a member selected from (4-trifluoromethyl)benzyl, (3-trifluoromethyl)benzyl, (2-trifluoromethyl)benzyl, (4-trifluoromethoxy)benzyl, (3-trifluoromethoxy)benzyl, (2-trifluoromethoxy)benzyl, (4-fluoro)benzyl, (4-chloro)benzyl, (3-fluoro)benzyl, (3-chloro)benzyl, (2-fluoro)benzyl, (2-chloro)benzyl, (4-methyl)benzyl, (3-methyl)benzyl, (2-methyl)benzyl, (4-t-butyl)benzyl, (4-phenyl)benzyl, (3-phenyl)benzyl, (2-phenyl)benzyl, (cyclopropyl)benzyl, (4-phenoxy)benzyl, (3-phenoxy)benzyl, (3-[1H-pyrazol-1-yl])benzyl, (4-[1H-pyrazol-1-yl])benzyl, (3-difluoromethoxy)benzyl, (2-difluoromethoxy)benzyl, (2-ethoxy)benzyl, (2-trifluoromethylthio)benzyl, (2-methoxy)benzyl, (3-methoxy)benzyl, (4-methoxy)benzyl, (4-cyano) benzyl, (3-cyano)benzyl and (4-isopropoxy)benzyl.

In an exemplary embodiment, $R^6$ is

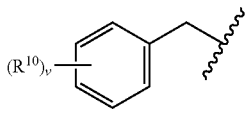

wherein v is 2. In an exemplary embodiment, $R^6$ is a member selected from

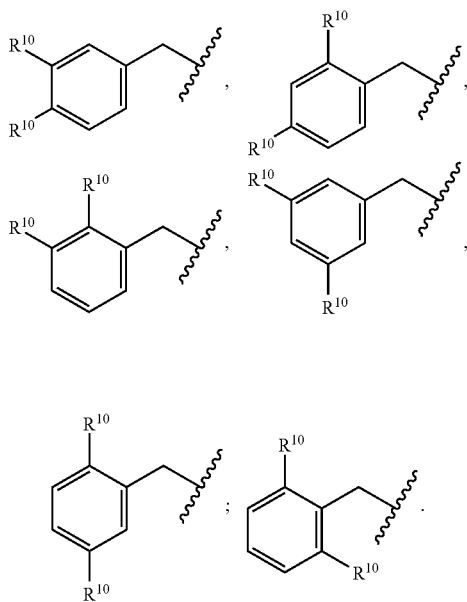

In an exemplary embodiment, $R^6$ is a member selected from

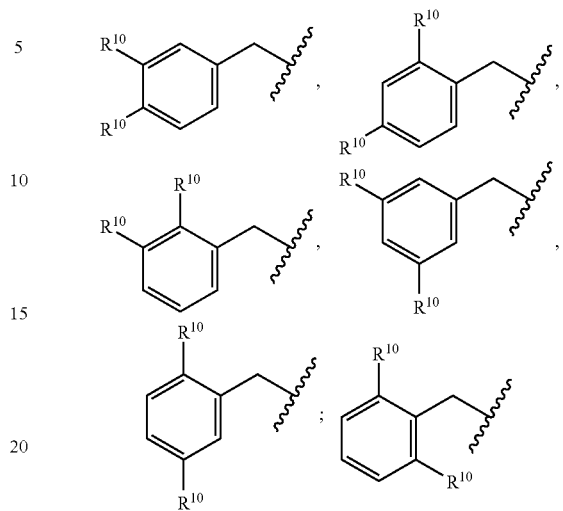

and each $R^{10}$ is a member independently selected from halogen, cyano, hydroxyl, substituted or unsubstituted methyl, substituted or unsubstituted methoxy, substituted or unsubstituted methylthio, substituted or unsubstituted ethoxy, substituted or unsubstituted isopropyloxy, cyclopropyl, t-butyl, pyrazol-1-yl, substituted or unsubstituted phenyl, substituted or unsubstituted benzyl. In an exemplary embodiment, $R^5$ is H, $R^6$ is a member selected from

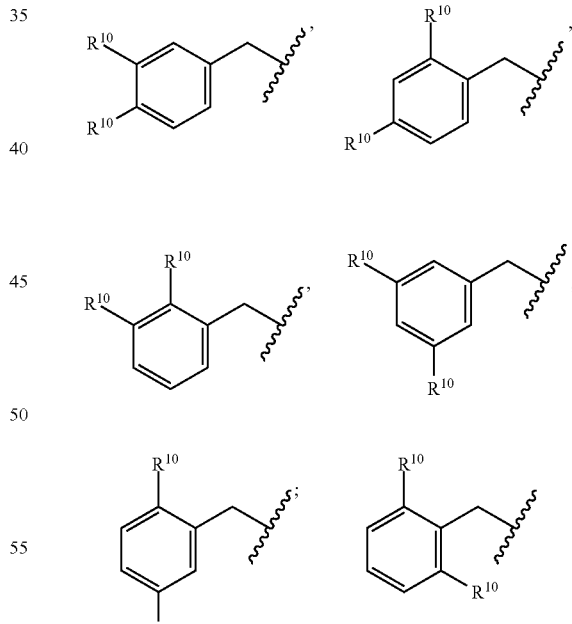

and each $R^{10}$ is a member independently selected from halogen, cyano, hydroxyl, substituted or unsubstituted methyl, substituted or unsubstituted methoxy, substituted or unsubstituted methylthio, substituted or unsubstituted ethoxy, substituted or unsubstituted isopropyloxy, cyclopropyl, t-butyl, pyrazol-1-yl, substituted or unsubstituted phenyl, substituted or unsubstituted benzyl.

In an exemplary embodiment, $R^6$ is

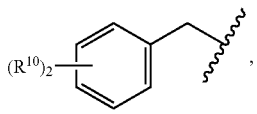

wherein each $R^{10}$ is a member independently selected from trifluoromethoxy, trifluoromethyl, chloro and fluoro. In an exemplary embodiment, $R^6$ is a member selected from

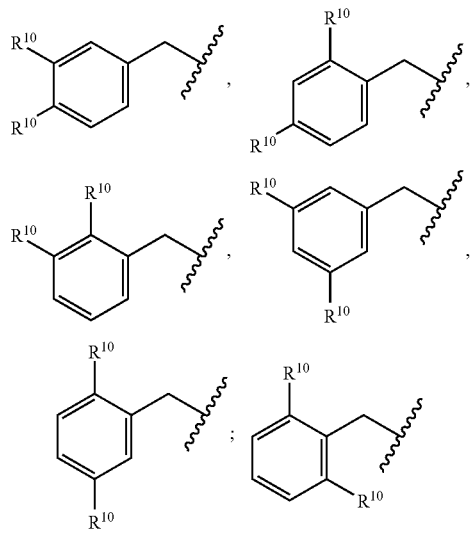

wherein each $R^{10}$ is a member independently selected from trifluoromethoxy, trifluoromethyl, chloro and fluoro. In an exemplary embodiment, $R^5$ is H and $R^6$ is a member selected from

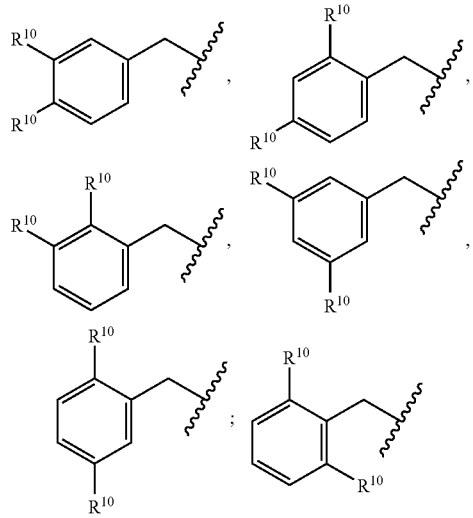

wherein each $R^{10}$ is a member independently selected from trifluoromethoxy, trifluoromethyl, chloro and fluoro.

In an exemplary embodiment, $R^6$ is

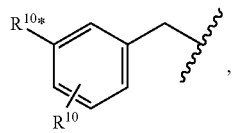

wherein $R^{10*}$ is a member selected from trifluoromethoxy, trifluoromethyl, chloro and fluoro, $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl. In an exemplary embodiment, $R^5$ is H, $R^6$ is

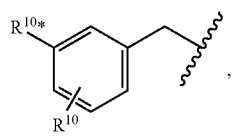

wherein $R^{10*}$ is a member selected from cyclopropyl, trifluoromethoxy, trifluoromethyl, chloro and fluoro, $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl. In an exemplary embodiment, $R^6$ is

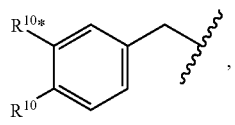

wherein $R^{10*}$ is a member selected from chloro and fluoro, and $R^{10}$ is a member selected from trifluoromethoxy, trifluoromethyl, chloro and fluoro.

In an exemplary embodiment, $R^6$ is

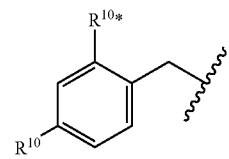

wherein $R^{10*}$ is a member selected from cyclopropyl, trifluoromethoxy, trifluoromethyl, chloro and fluoro, and $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy and trifluoromethylthio. In an exemplary embodiment, $R^5$ is H, $R^6$ is

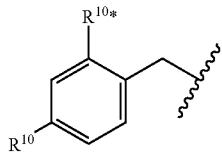

wherein $R^{10*}$ is a member selected from chloro and fluoro, and $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl.

In an exemplary embodiment, $R^6$ is

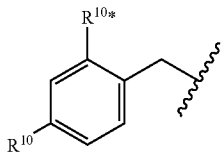

wherein $R^{10*}$ is a member selected from substituted or unsubstituted $C_1$-$C_4$ alkoxy and substituted or unsubstituted $C_1$-$C_4$ alkyl, and $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl. In an exemplary embodiment, $R^5$ is H and $R^6$ is

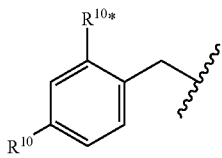

wherein $R^{10*}$ is a member selected from substituted or unsubstituted $C_1$-$C_6$ alkoxy and substituted or unsubstituted $C_1$-$C_4$ alkyl, and $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl. In an exemplary embodiment, $R^5$ is H and $R^6$ is

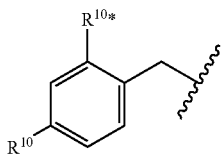

wherein $R^{10*}$ is a member selected from methyl and methoxy, and $R^{10}$ is a member selected from halogen, cyano, hydroxyl, substituted or unsubstituted $C_1$-$C_4$ alkyl, substituted or unsubstituted $C_3$-$C_8$ cycloalkyl, substituted or unsubstituted $C_1$-$C_4$ alkyloxy, substituted or unsubstituted phenyloxy, trifluoromethylthio and substituted or unsubstituted pyrazolyl. In an exemplary embodiment, $R^5$ is H and $R^6$ is

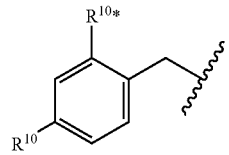

wherein $R^{10*}$ is a member selected from methyl and methoxy, and $R^{10}$ is a member selected from chloro, fluoro, trifluoromethyl and trifluoromethoxy.

In an exemplary embodiment, $R^6$ is a member selected from 2,3-dichlorobenzyl, 2,3 dimethylbenzyl, 2-methyl-3-chlorobenzyl, 2-trifluoromethyl-4-fluorobenzyl, 2-trifluoromethyl-4-chlorobenzyl, 4-trifluoromethyl-2-fluorobenzyl, 4-trifluoromethoxy-2-methoxybenzyl, 2-fluoro-4-chlorobenzyl, 2-chloro-4-fluorobenzyl, 2,4-difluorobenzyl, 2-methyl-4-chlorobenzyl, 2-fluoro-4-methylbenzyl, 2-methyl-5-fluorobenzyl, 2-methyl-5-chlorobenzyl, 2,5-dichlorobenzyl, 2,5-difluorobenzyl, 2-fluoro-5-trifluoromethyl benzyl, 2-trifluoromethyl-5-fluorobenzyl, 2-chloro-6-fluoro benzyl, 2,6-difluorobenzyl, 2-fluoro-6-trifluoromethylbenzyl, 3,5-difluorobenzyl, 4-fluoro-3-cyanobenzyl, 4-methyl-3-chlorobenzyl, 3-chloro-4-methylbenzyl, 3-chloro-4-methoxybenzyl, 3-trifluoromethyl-4-methoxybenzyl, 4-trifluoromethoxy-3-fluorobenzyl, 4-fluoro-3-cyanobenzyl, 3-trifluoromethoxy-4-fluorobenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl. In an exemplary embodiment, $R^5$ is H, and $R^6$ is a member selected from 2,3-dichlorobenzyl, 2,3 dimethylbenzyl, 2-methyl-3-chlorobenzyl, 2-trifluoromethyl-4-fluorobenzyl, 2-trifluoromethyl-4-chlorobenzyl, 4-trifluoromethyl-2-fluorobenzyl, 4-trifluoromethoxy-2-methoxybenzyl, 2-fluoro-4-chlorobenzyl, 2-chloro-4-fluorobenzyl, 2,4-difluorobenzyl, 2-methyl-4-chlorobenzyl, 2-fluoro-4-methylbenzyl, 2-methyl-5-fluorobenzyl, 2-methyl-5-chlorobenzyl, 2,5-dichlorobenzyl, 2,5-difluorobenzyl, 2-fluoro-5-trifluoromethyl benzyl, 2-trifluoromethyl-5-fluorobenzyl, 2-chloro-6-fluoro benzyl, 2,6-difluorobenzyl, 2-fluoro-6-trifluoromethylbenzyl, 3,5-difluorobenzyl, 4-fluoro-3-cyanobenzyl, 4-methyl-3-chlorobenzyl, 3-chloro-4-methylbenzyl, 3-chloro-4-methoxybenzyl, 3-trifluoromethyl-4-methoxybenzyl, 4-trifluoromethoxy-3-fluorobenzyl, 4-fluoro-3-cyanobenzyl, 3-trifluoromethoxy-4-fluorobenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl.

In an exemplary embodiment, $R^6$ is a member selected from 2-chloro-4-trifluoromethylbenzyl, 2-methoxy-4-trifluoromethoxybenzyl, (1-(4-chlorophenyl)cyclopropyl)methyl, 2-methyl-3-chlorobenzyl, 2-fluoro-3-trifluoromethylbenzyl, 1-(4-trifluoromethylbenzyl)ethyl, 2,5-dichlorobenzyl and 2-fluoromethoxy-2-methyl-propyl.

In an exemplary embodiment, $R^6$ is

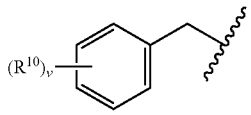

wherein v is 3. In an exemplary embodiment, $R^6$ is

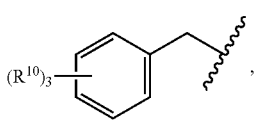

wherein each $R^{10}$ is a member independently selected from trifluoromethoxy, trifluoromethyl, chloro and fluoro. In an exemplary embodiment, $R^6$ is a member selected from

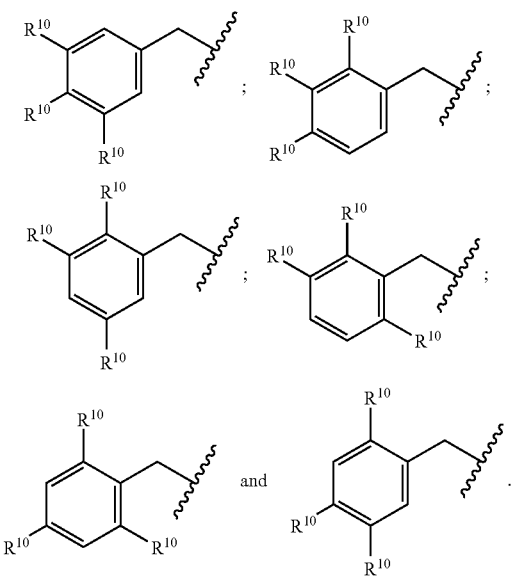

In an exemplary embodiment, $R^6$ is a member selected from

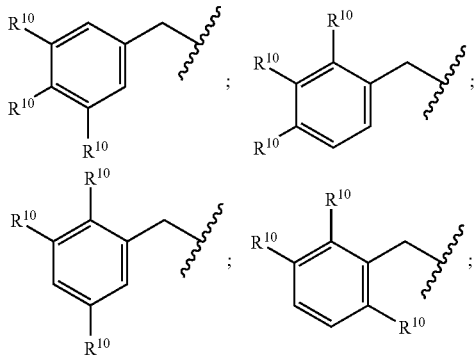

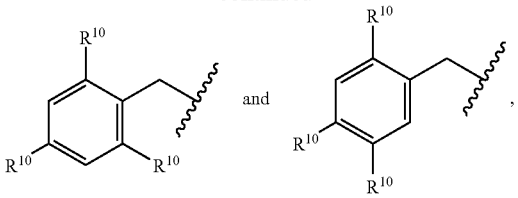

and $R^{10}$, wherein each $R^{10}$ is a member independently selected from trifluoromethoxy, trifluoromethyl, chloro and fluoro. In an exemplary embodiment, $R^5$ is H, $R^6$ is a member selected from

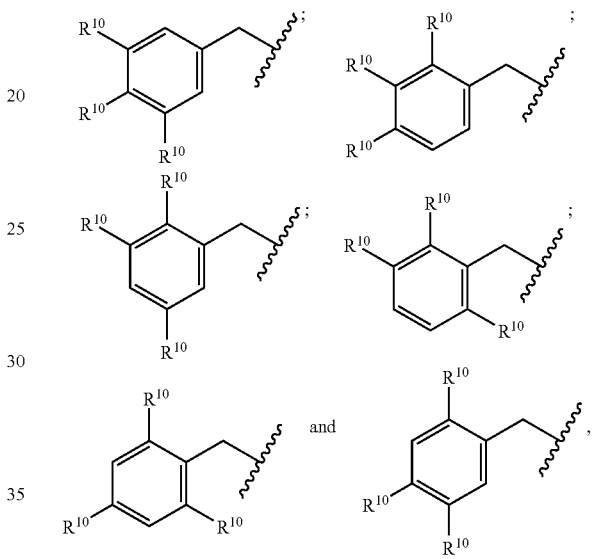

wherein each $R^{10}$ is a member independently selected from trifluoromethoxy, trifluoromethyl, chloro and fluoro. In an exemplary embodiment, $R^6$ is a member selected from 2,3,5-trifluorobenzyl, 3,4,5-trifluorobenzyl and 2,3,6-trifluorobenzyl. In an exemplary embodiment, $R^5$ is H and $R^6$ is a member selected from 2,3,5-trifluorobenzyl, 3,4,5-trifluorobenzyl and 2,3,6-trifluorobenzyl.

In an exemplary embodiment, $R^6$ is a member selected from

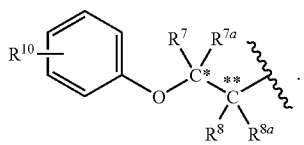

In an exemplary embodiment, $R^6$ is a member selected from 2-(halophenoxy)ethyl, 2-(halophenoxy)propyl, 2-(phenoxy)ethyl, 2-(phenoxy)propyl, 2-(($C_1$-$C_4$)alkylphenoxy)ethyl, 2-(($C_1$-$C_4$)alkylphenoxy)propyl. In an exemplary embodiment, $R^6$ is a member selected from 2-(fluorophenoxy)ethyl, 2-(chlorophenoxy)ethyl, 2-(fluorophenoxy)propyl, 2-(chlorophenoxy)propyl, 2-(phenoxy)ethyl, 2-(phenoxy)propyl, 2-(ethylphenoxy)ethyl, 2-(ethylphenoxy)propyl, 2-(methylphenoxy)ethyl, 2-(methylphenoxy)propyl. In an exemplary embodiment, $R^6$ is a member selected from 2-(2-fluorophenoxy)ethyl, 2-(2-chlorophenoxy)ethyl, 2-(2-fluorophenoxy)

propyl, 2-(2-chlorophenoxy)propyl, 2-(3-fluorophenoxy)ethyl, 2-(3-chlorophenoxy)ethyl, 2-(3-fluorophenoxy)propyl, 2-(3-chlorophenoxy)propyl, 2-(4-fluorophenoxy)ethyl, 2-(4-chlorophenoxy)ethyl, 2-(4-fluorophenoxy)propyl, 2-(4-chlorophenoxy)propyl. In an exemplary embodiment, $R^6$ is a member selected from 2-(4-methylphenoxy)ethyl, 2-(4-methylphenoxy)propyl, 2-(3-methylphenoxy)ethyl, 2-(3-methylphenoxy)propyl, 2-(2-methylphenoxy)ethyl, 2-(2-methylphenoxy)propyl. In an exemplary embodiment, $R^6$ is a member selected from 2-(3-chlorophenoxy)ethyl, 2-(2-chlorophenoxy)propyl, 2-(2-chlorophenoxy)ethyl, 2-(4-methylphenoxy)ethyl, 2-phenoxypropyl, 2-(2-fluorophenoxy)ethyl, 2-phenoxyethyl, 2-(4-chlorophenoxy)ethyl and 2-(4-fluorophenoxy)-2-methylpropyl.

In an exemplary embodiment, $R^6$ is

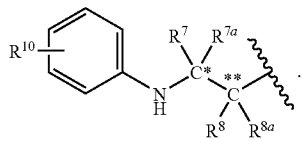

In an exemplary embodiment, $R^6$ is 2-[(halophenyl)amino]ethyl. In an exemplary embodiment, $R^6$ is a member selected from 2-[(chlorophenyl)amino]ethyl and 2-[(fluorophenyl)amino]ethyl. In an exemplary embodiment, $R^6$ is a member selected from 2-[(4-halophenyl)amino]ethyl, 2-[(3-halophenyl)amino]ethyl and 2-[(2-halophenyl)amino]ethyl. In an exemplary embodiment, $R^6$ is 2-[(4-chlorophenyl)amino]ethyl.

In an exemplary embodiment, $R^6$ is

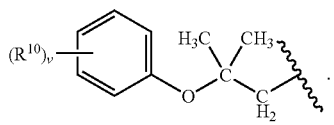

In an exemplary embodiment, $R^6$ is a member selected from 1-(substituted or unsubstituted phenyl)ethyl and 2-methyl-2-halophenoxypropyl. In an exemplary embodiment, $R^6$ is a member selected from 1-(4-trifluorophenyl)ethyl and 2-methyl-2-(4-fluorophenoxy)propyl.

In an exemplary embodiment, $R^6$ is a member selected from

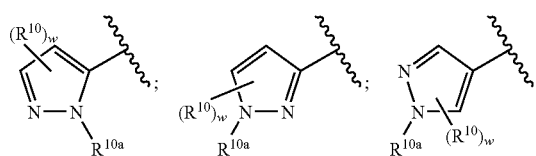

wherein $R^{10a}$ is a member selected from H, substituted or unsubstituted $(C_1-C_{10})$alkyl, substituted or unsubstituted phenyl, substituted or unsubstituted benzyl and substituted or unsubstituted heteroaryl. In an exemplary embodiment, $R^{10a}$ is a member selected from H, $(C_1-C_4)$alkyl, phenyl and halobenzyl. In an exemplary embodiment, $R^{10a}$ is a member selected from methyl, phenyl and 4-chlorobenzyl. In an exemplary embodiment, w is 1, $R^{10}$ is a member selected from substituted or unsubstituted $(C_1-C_4)$alkyl, substituted or unsubstituted phenyl and substituted or unsubstituted benzyl, and $R^{10a}$ is a member selected from $(C_1-C_4)$alkyl, substituted or unsubstituted phenyl and substituted or unsubstituted benzyl. In an exemplary embodiment, w is 1, $R^{10}$ is a member selected from $(C_1-C_4)$alkyl and halobenzyl, and $R^{10a}$ is a member selected from $(C_1-C_4)$alkyl, phenyl and halobenzyl. In an exemplary embodiment, w is 1, $R^{10}$ is a member selected from methyl and chlorobenzyl, and $R^{10a}$ is a member selected from methyl, phenyl and chlorobenzyl. In an exemplary embodiment, w is 1, $R^{10}$ is a member selected from methyl and 4-chlorobenzyl, and $R^{10a}$ is a member selected from methyl, phenyl and 4-chlorobenzyl. In an exemplary embodiment, $R^6$ is a member selected from

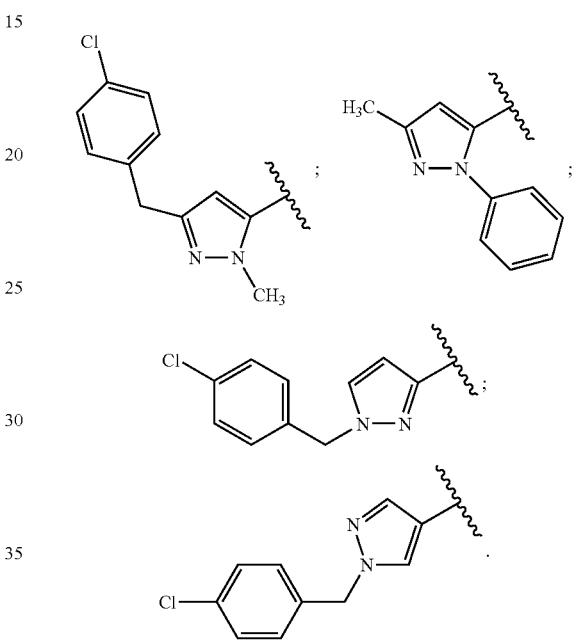

In an exemplary embodiment, $R^6$ is

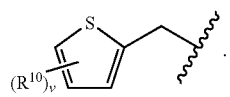

In an exemplary embodiment, $R^6$ is

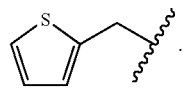 [SMILES: *Cc1cccs1]

In an exemplary embodiment, $R^6$ is a member selected from

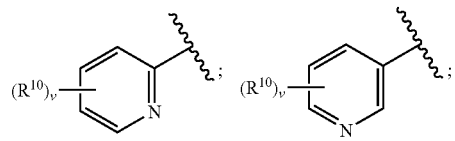

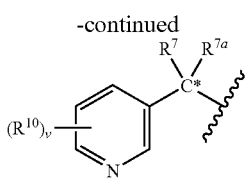

In another exemplary embodiment, $R^6$ is substituted or unsubstituted pyridin-2-yl. In another exemplary embodiment, $R^6$ is a member selected from $(C_1-C_4)$alkylpyridin-2-yl and di$(C_1-C_4)$alkylpyridin-2-yl. In another exemplary embodiment, $R^6$ is a member selected from 4-$(C_1-C_4)$alkylpyridin-2-yl, 3-$(C_1-C_4)$alkyl-5-$(C_1-C_4)$alkylpyridin-2-yl and 3-$(C_1-C_4)$alkyl-6-$(C_1-C_4)$alkylpyridin-2-yl. In another exemplary embodiment, $R^6$ is a member selected from 4-methylpyridin-2-yl, 3,5-dimethylpyridin-2-yl and 3-ethyl-6-methylpyridin-2-yl.

In another exemplary embodiment, $R^6$ is substituted or unsubstituted pyridin-3-yl. In another exemplary embodiment, $R^6$ is a member selected from pyridin-3-yl, $(C_1-C_4)$alkoxypyridin-3-yl, (substituted or unsubstituted$(C_1-C_4)$alkyl)pyridin-3-yl and di$(C_1-C_4)$alkylpyridin-3-yl. In another exemplary embodiment, $R^6$ is a member selected from 5,6-dimethylpyridin-3-yl and 6-methoxypyridin-3-yl.

In another exemplary embodiment, $R^6$ is a member selected from 6-halopyridin-3-ylmethyl and (6-halomethyl)pyridin-3-ylmethyl. In another exemplary embodiment, $R^6$ is a member selected from 6-chloropyridin-3-ylmethyl and 6-(trifluoromethyl)pyridin-3-ylmethyl.

In an exemplary embodiment, $R^6$ is a member selected from 1,7 naphthylpyridine, isoquinolinyl and 6,7 dihydrocyclopentapyridinyl. In another exemplary embodiment, $R^6$ is a member selected from

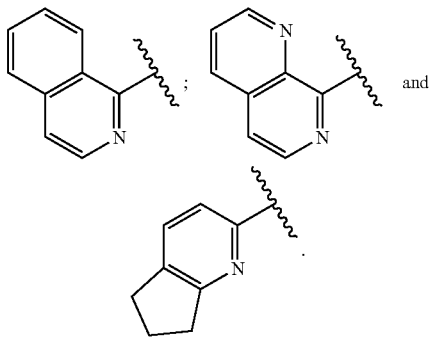

In an exemplary embodiment, $R^6$ is a member selected from 1,7 naphthylpyridine, isoquinolinyl and 6,7 dihydrocyclopentapyridinyl.

In another exemplary embodiment, $R^5$ is methyl and $R^6$ is 2,3-dihydro-1-benzofuran-2-ylmethyl.

In another exemplary embodiment, $R^6$ is substituted or unsubstituted pyridin-3-yl. In another exemplary embodiment, $R^6$ is a member selected from pyridin-3-yl, $(C_1-C_4)$alkoxypyridin-3-yl, (substituted or unsubstituted$(C_1-C_4)$alkyl)pyridin-3-yl and di$(C_1-C_4)$alkylpyridin-3-yl. In another exemplary embodiment, $R^6$ is a member selected from 5,6-dimethylpyridin-3-yl and 6-methoxypyridin-3-yl.

In an exemplary embodiment, B is a member selected from substituted or unsubstituted 6-membered aryl and substituted or unsubstituted 6-membered heteroaryl. In another exemplary embodiment, B is a member selected from 6-membered aryl, halo 6-membered aryl, cyano 6-membered aryl, $(C_1-C_4$ alkyl) 6-membered aryl, $(C_1-C_4$ haloalkyl) 6-membered aryl, $(C_1-C_4$ alkoxy) 6-membered aryl, $(C_1-C_4$ haloalkoxy) 6-membered aryl. In another exemplary embodiment, B is a member selected from 6-membered heteroaryl, halo 6-membered heteroaryl, cyano 6-membered heteroaryl, $(C_1-C_4$ alkyl) 6-membered heteroaryl, $(C_1-C_4$ haloalkyl) 6-membered heteroaryl, $(C_1-C_4$ alkoxy) 6-membered heteroaryl, $(C_1-C_4$ haloalkoxy) 6-membered heteroaryl.

In an exemplary embodiment, B has a formula which is a member selected from

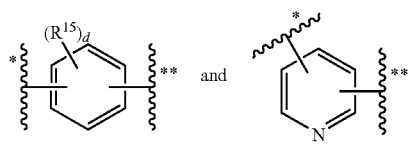

wherein ⁓⌇— represents a bond covalently attached to said carbon of said carbonyl. The symbol —⌇⁓ represents a bond covalently attached to said sulfur of said sulfonamide. The index d is an integer from 0 to 2. $R^{15}$ is a member selected from halogen, cyano, $(C_1-C_4)$alkyl, halo$(C_1-C_4)$alkyl, $(C_1-C_4)$alkoxy, halo$(C_1-C_4)$alkoxy.

In an exemplary embodiment, B is a member selected from

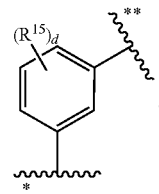

In another exemplary embodiment, B is

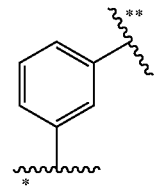

In an exemplary embodiment, B is a member selected from

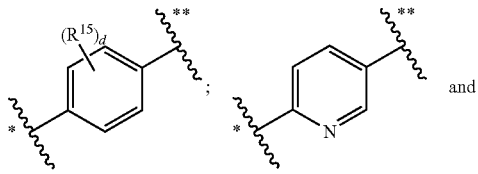

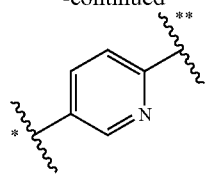
In an exemplary embodiment, B is a member selected from
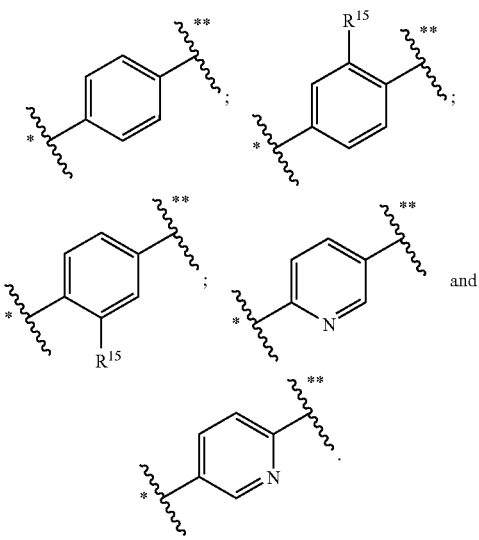
In an exemplary embodiment, B is a member selected from
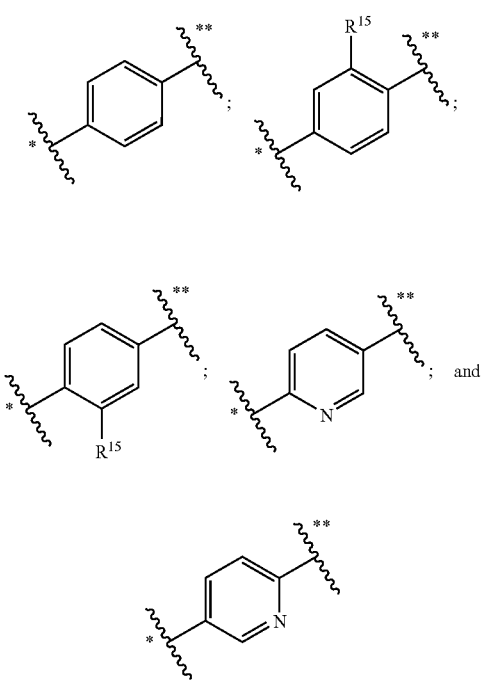
wherein $R^{15}$ is a member selected from fluoro, chloro and cyano. In an exemplary embodiment, B is a member selected from
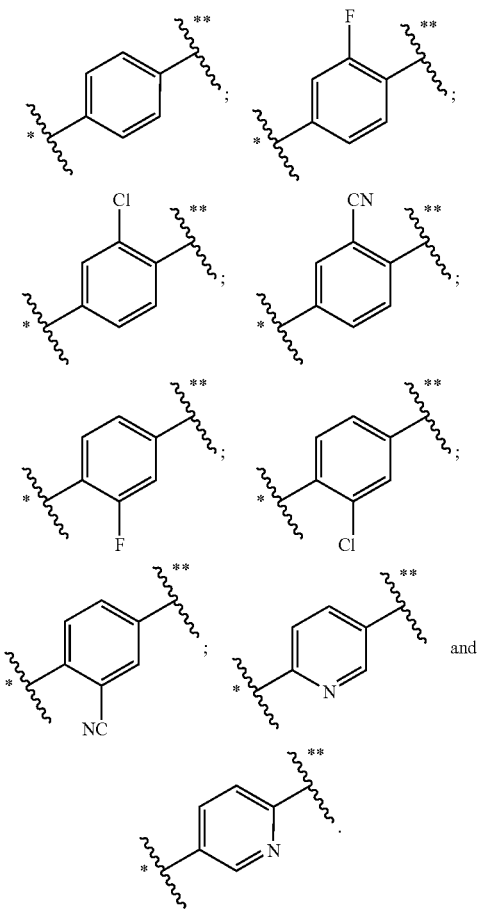
In an exemplary embodiment, B is a member selected from In an exemplary embodiment, B is a member selected from

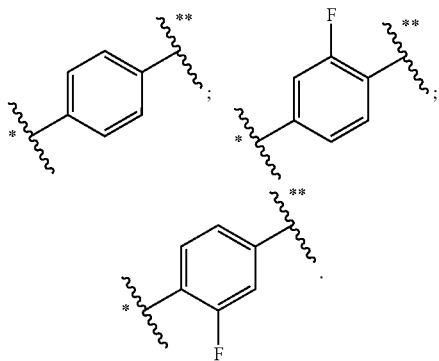

In an exemplary embodiment, B is

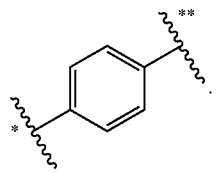 [SMILES: *c1ccc(*)cc1]

In an exemplary embodiment, B is

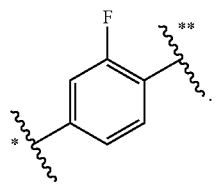

In an exemplary embodiment, B is

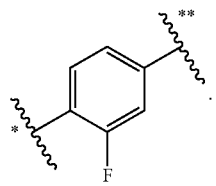 [SMILES: *c1ccc(*)c(F)c1]

In an exemplary embodiment, Z is a member selected from substituted or unsubstituted thiazolyl, substituted or unsubstituted thiadiazolyl, substituted or unsubstituted isoxazolyl, substituted or unsubstituted tetrazolyl, substituted or unsubstituted triazolyl and substituted or unsubstituted pyrazolyl. In an exemplary embodiment, Z is substituted or unsubstituted thiazolyl. In an exemplary embodiment, Z is substituted or unsubstituted thiadiazolyl. In an exemplary embodiment, Z is a member selected from substituted or unsubstituted thiazol-2-yl, substituted or unsubstituted thiazol-4-yl, substituted or unsubstituted thiazol-5-yl, substituted or unsubstituted thiadiazol-2-yl, substituted or unsubstituted thiadiazol-5-yl, substituted or unsubstituted pyrazol-3-yl, substituted or unsubstituted pyrazol-4-yl, substituted or unsubstituted pyrazol-5-yl, substituted or unsubstituted isoxazol-5-yl, substituted or unsubstituted isoxazol-4-yl, substituted or unsubstituted isoxazol-3-yl, substituted or unsubstituted tetrazol-5-yl, substituted or unsubstituted triazol-3-yl and substituted or unsubstituted triazol-4-yl. In an exemplary embodiment, Z is a member selected from substituted or unsubstituted 1,3 thiazolyl, substituted or unsubstituted 1,2,4 thiadiazolyl, substituted or unsubstituted 1,3,4 thiadiazolyl, substituted or unsubstituted isoxazolyl, substituted or unsubstituted 2H-tetrazolyl, substituted or unsubstituted 2H-1,2,3 triazolyl, substituted or unsubstituted 2H-1,2,4 triazolyl and substituted or unsubstituted 1H-pyrazolyl. In an exemplary embodiment, Z is a member selected from substituted or unsubstituted 1,3 thiazol-2-yl, substituted or unsubstituted 1,3 thiazol-4-yl, substituted or unsubstituted 1,3 thiazol-5-yl, substituted or unsubstituted 1,3,4 thiadiazol-2-yl, substituted or unsubstituted 1,2,4 thiadiazol-5-yl, substituted or unsubstituted 1H-pyrazol-3-yl, substituted or unsubstituted 1H-pyrazol-4-yl, substituted or unsubstituted 1H-pyrazol-5-yl, substituted or unsubstituted isoxazol-5-yl, substituted or unsubstituted isoxazol-4-yl, substituted or unsubstituted isoxazol-3-yl, substituted or unsubstituted 2H-tetrazol-5-yl, substituted or unsubstituted 1H-1,2,4 triazol-3-yl and substituted or unsubstituted-2H-1,2,3 triazol-4-yl. In an exemplary embodiment, Z is a member selected from 1,3 thiazol-2-yl, (halo)1,3 thiazol-2-yl, (substituted or unsubstituted $(C_1-C_{10})$alkyl)1,3 thiazol-2-yl, 1,3 thiazol-4-yl, (substituted or unsubstituted $(C_1-C_{10})$alkyl)1,3 thiazol-4-yl, 1,3 thiazol-5-yl, (substituted or unsubstituted $(C_1-C_{10})$alkyl)1,3 thiazol-5-yl, (substituted or unsubstituted $(C_1-C_{10})$alkyl) 1,3,4 thiadiazol-2-yl, 1,3,4 thiadiazol-2-yl, (substituted or unsubstituted $(C_1-C_{10})$alkyl) 1,2,4 thiadiazol-5-yl, 1,2,4 thiadiazol-5-yl, (substituted or unsubstituted $(C_1-C_{10})$alkyl)1H-pyrazol-3-yl, (substituted or unsubstituted $(C_1-C_{10})$alkyl) 1H-pyrazol-4-yl, 1H-pyrazol-5-yl, (substituted or unsubstituted $(C_1-C_{10})$alkyl)isoxazol-5-yl, isoxazol-4-yl, (substituted or unsubstituted $(C_1-C_{10})$alkyl) isoxazol-4-yl, isoxazol-3-yl, (substituted or unsubstituted $(C_1-C_{10})$alkyl)isoxazol-3-yl, (substituted or unsubstituted $(C_1-C_{10})$alkyl) 2H-tetrazol-5-yl, (substituted or unsubstituted $(C_1-C_{10})$alkyl) 1H-1,2,4 triazol-3-yl, 1H-1,2,4 triazol-3-yl and (substituted or unsubstituted $(C_1-C_{10})$alkyl) 2H-1,2,3 triazol-4-yl. In an exemplary embodiment, Z is a member selected from 1,3 thiazol-2-yl, (halo)1,3 thiazol-2-yl, (substituted or unsubstituted $(C_1-C_4)$alkyl)1,3 thiazol-2-yl, 1,3 thiazol-4-yl, (substituted or unsubstituted $(C_1-C_4)$alkyl)1,3 thiazol-4-yl, 1,3 thiazol-5-yl, (substituted or unsubstituted $(C_1-C_4)$alkyl)1,3 thiazol-5-yl, (substituted or unsubstituted $(C_1-C_4)$alkyl) 1,3,4 thiadiazol-2-yl, 1,3,4 thiadiazol-2-yl, (substituted or unsubstituted $(C_1-C_4)$alkyl) 1,2,4 thiadiazol-5-yl, 1,2,4 thiadiazol-5-yl, (substituted or unsubstituted $(C_1-C_4)$alkyl) 1H-pyrazol-3-yl, (substituted or unsubstituted $(C_1-C_4)$alkyl) 1H-pyrazol-4-yl, 1H-pyrazol-5-yl, (substituted or unsubstituted $(C_1-C_4)$alkyl)isoxazol-5-yl, isoxazol-4-yl, (substituted or unsubstituted $(C_1-C_4)$alkyl)isoxazol-4-yl, isoxazol-3-yl, (substituted or unsubstituted $(C_1-C_4)$alkyl) isoxazol-3-yl, (substituted or unsubstituted $(C_1-C_4)$alkyl) 2H-tetrazol-5-yl, (substituted or unsubstituted $(C_1-C_4)$alkyl) 1H-1,2,4 triazol-3-yl, 1H-1,2,4 triazol-3-yl and (substituted or unsubstituted $(C_1-C_4)$alkyl) 2H-1,2,3 triazol-4-yl. In an exemplary embodiment, Z is a member selected from 1,3 thiazol-2-yl, (5-chloro)1,3 thiazol-2-yl, (4-methyl)1,3 thiazol-2-yl, (5-methyl)1,3 thiazol-2-yl, 4(methoxycarbonyl)(1,3 thiazol-2-yl), 4-trifluoromethyl 1,3 thiazol-2-yl, 1,3 thiazol-4-yl, 2-methyl 1,3 thiazol-4-yl, 1,3 thiazol-5-yl, 2-methyl 1,3 thiazol-5-yl, 4-trifluoromethyl 1,3,4 thiadiazol-2-yl, 5-methyl 1,3,4 thiadiazol-2-yl, 1,3,4 thiadiazol-2-yl, 3-methyl 1,2,4 thiadiazol-5-yl, 3-ethyl 1,2,4 thiadiazol-5-yl, 1,2,4 thiadiazol-5-yl, 1-methyl 1H-pyrazol-3-yl, 1-methyl 1H-pyrazol-4-yl, 1,3,5 trimethyl 1H-pyrazol-4-yl, 1H-pyrazol-5-yl, 3-methyl isoxazol-5-yl, 3,4-dimethyl isoxazol-5-yl, isoxazol-4-yl, 3,5-dimethylisoxazol-4-yl, isoxazol-3-yl, 5-methyl isoxazol-3-yl, 2-methyl 2H-tetrazol-5-yl, 1-methyl 1H-1,2,4 triazol-3-yl, 1H-1,2,4 triazol-3-yl and 2-ethyl 2H-1, 2,3 triazol-4-yl. In an exemplary embodiment, Z is a member selected from 1,3 thiazol-2-yl, 5-chloro(1,3 thiazol-2-yl), 4-methyl(1,3 thiazol-2-yl), 5-methyl(1,3 thiazol-2-yl), 4(methoxycarbonyl)(1,3 thiazol-2-yl), 4-trifluoromethyl 1,3 thiazol-2-yl, 1,3 thiazol-4-yl, 2-methyl 1,3 thiazol-4-yl, 3-methyl 1,2,4 thiadiazol-5-yl, 3-ethyl 1,2,4 thiadiazol-5-yl, unsubstituted 1,2,4 thiadiazol-5-yl. In an exemplary embodiment, Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl. In an exemplary embodiment, Z is a member selected from 1,3 thiazol-2-yl, 1,3 thiazol-4-yl, 5-chloro(1,3 thiazol-2-yl), 5-methyl(1,3 thiazol-2-yl) and 1,2,4 thiadiazol-5-yl. In an exemplary embodiment, Z is a member selected from 1,3 thiazol-2-yl, 5-chloro(1,3 thiazol-2-yl) and 1,2,4 thiadiazol-5-yl. In an exemplary embodiment, Z is 1,3 thiazol-2-yl. In an exemplary embodiment, Z is 5-chloro(1,3 thiazol-2-yl). In an exemplary embodiment, Z is 1,2,4 thiadiazol-5-yl.

In an exemplary embodiment, B is

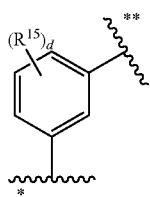

and Z is a member selected from substituted or unsubstituted thiazolyl, substituted or unsubstituted thiadiazolyl, substituted or unsubstituted isoxazolyl, substituted or unsubstituted tetrazolyl, substituted or unsubstituted triazolyl and substituted or unsubstituted pyrazolyl. In an exemplary embodiment, B is

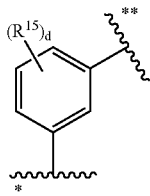

and Z is a member selected from 1,3 thiazol-2-yl, (halo) 1,3 thiazol-2-yl, (substituted or unsubstituted $(C_1-C_4)$alkyl)1,3 thiazol-2-yl, 1,3 thiazol-4-yl, (substituted or unsubstituted $(C_1-C_4)$alkyl)1,3 thiazol-4-yl, 1,3 thiazol-5-yl, (substituted or unsubstituted $(C_1-C_4)$alkyl)1,3 thiazol-5-yl, (substituted or unsubstituted $(C_1-C_4)$alkyl) 1,3,4 thiadiazol-2-yl, 1,3,4 thiadiazol-2-yl, (substituted or unsubstituted $(C_1-C_4)$alkyl) 1,2,4 thiadiazol-5-yl, 1,2,4 thiadiazol-5-yl, (substituted or unsubstituted $(C_1-C_4)$alkyl)1H-pyrazol-3-yl, (substituted or unsubstituted $(C_1-C_4)$alkyl) 1H-pyrazol-4-yl, 1H-pyrazol-5-yl, (substituted or unsubstituted $(C_1-C_4)$alkyl)isoxazol-5-yl, isoxazol-4-yl, (substituted or unsubstituted $(C_1-C_4)$alkyl) isoxazol-4-yl, isoxazol-3-yl, (substituted or unsubstituted $(C_1-C_4)$alkyl)isoxazol-3-yl, (substituted or unsubstituted $(C_1-C_4)$alkyl) 2H-tetrazol-5-yl, (substituted or unsubstituted $(C_1-C_4)$alkyl) 1H-1,2,4 triazol-3-yl, 1H-1,2,4 triazol-3-yl and (substituted or unsubstituted $(C_1-C_4)$alkyl) 2H-1,2,3 triazol-4-yl. In an exemplary embodiment, B is

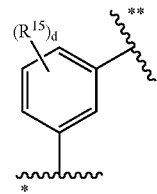

and Z is 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl. In another exemplary embodiment, B is

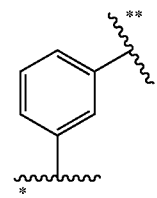 [SMILES: *c1cccc(*)c1]

and Z is 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, $R^5$ is H, $R^6$ is a member selected from 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl; and B is a member selected from

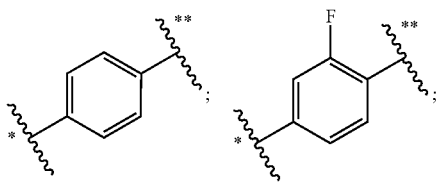

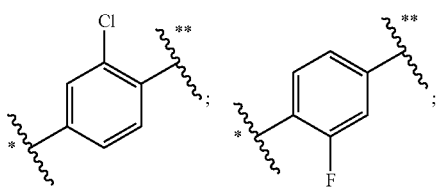

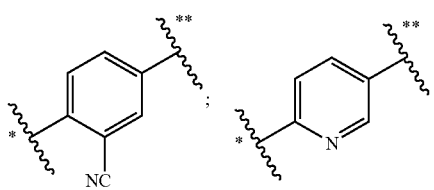

wherein $\xi\text{—}$, represents a bond covalently attached to said carbon of said carbonyl, and $\text{—}\xi^{**}$, represents a bond covalently attached to said sulfur of said sulfonamide.

In an exemplary embodiment, $R^5$ is H, $R^6$ is a member selected from 1-(substituted or unsubstituted phenyl)ethyl and 2-methyl-2-halophenoxypropyl; and B is a member selected from

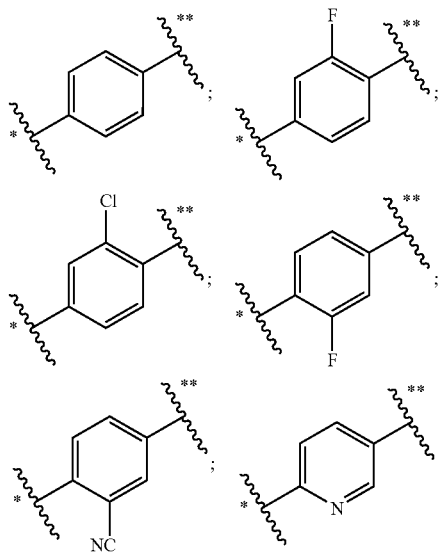

wherein $\xi\text{—}$, represents a bond covalently attached to said carbon of said carbonyl, and $\text{—}\xi^{**}$, represents a bond covalently attached to said sulfur of said sulfonamide.

In an exemplary embodiment, $R^5$ is H, $R^6$ is a member selected from 1-(4-trifluorophenyl)ethyl, 2-methyl-2-(4-fluorophenoxy)propyl, 2-chloro-4-trifluoromethylbenzyl, 2-methoxy-4-trifluoromethoxybenzyl, (1-(4-chlorophenyl)cyclopropyl)methyl, 2-methyl-3-chlorobenzyl, 2-fluoro-3-trifluoromethylbenzyl, 1-(4-trifluoromethylbenzyl)ethyl, 2,5-dichlorobenzyl and 2-fluoromethoxy-2-methyl-propyl; and B is a member selected from

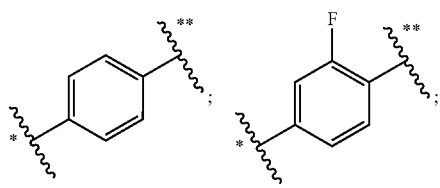

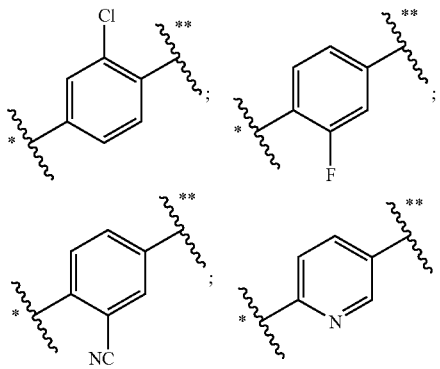

wherein $\xi\text{—}$, represents a bond covalently attached to said carbon of said carbonyl, and $\text{—}\xi^{**}$, represents a bond covalently attached to said sulfur of said sulfonamide.

In an exemplary embodiment, $R^5$ is H, $R^6$ is a member selected from 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl; and Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, $R^5$ is H, $R^6$ is a member selected from 1-(substituted or unsubstituted phenyl)ethyl and 2-methyl-2-halophenoxypropyl; and Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, $R^5$ is H, $R^6$ is a member selected from 1-(4-trifluorophenyl)ethyl, 2-methyl-2-(4-fluorophenoxy)propyl, 2-chloro-4-trifluoromethylbenzyl, 2-methoxy-4-trifluoromethoxybenzyl, (1-(4-chlorophenyl)cyclopropyl)methyl, 2-methyl-3-chlorobenzyl, 2-fluoro-3-trifluoromethylbenzyl, 1-(4-trifluoromethylbenzyl)ethyl, 2,5-dichlorobenzyl and 2-fluoromethoxy-2-methyl-propyl; and Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, B is a member selected from

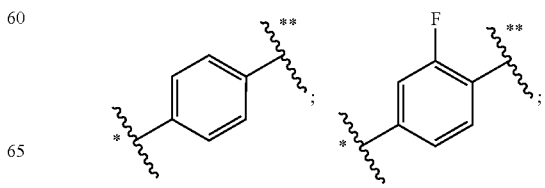

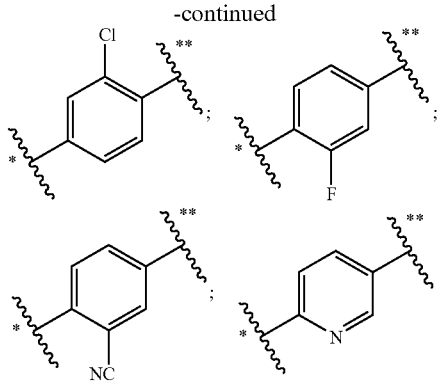

wherein $\xi$—, represents a bond covalently attached to said carbon of said carbonyl; —$\xi$**, represents a bond covalently attached to said sulfur of said sulfonamide; and Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, $R^5$ is H; $R^6$ is a member selected from 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl; B is a member selected from

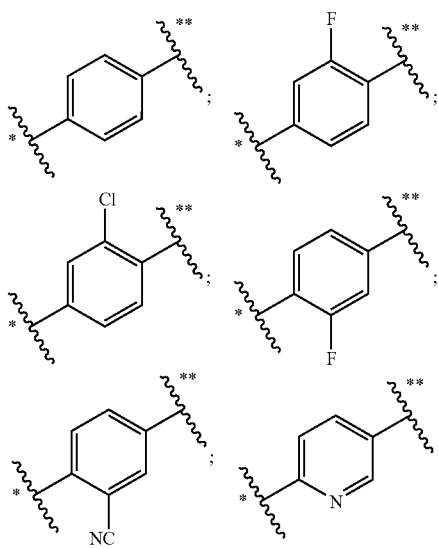

wherein $\xi$—, represents a bond covalently attached to said carbon of said carbonyl; —$\xi$**, represents a bond covalently attached to said sulfur of said sulfonamide; Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, $R^5$ is H; $R^6$ is a member selected from 1-(substituted or unsubstituted phenyl)ethyl and 2-methyl-2-halophenoxypropyl; B is a member selected from

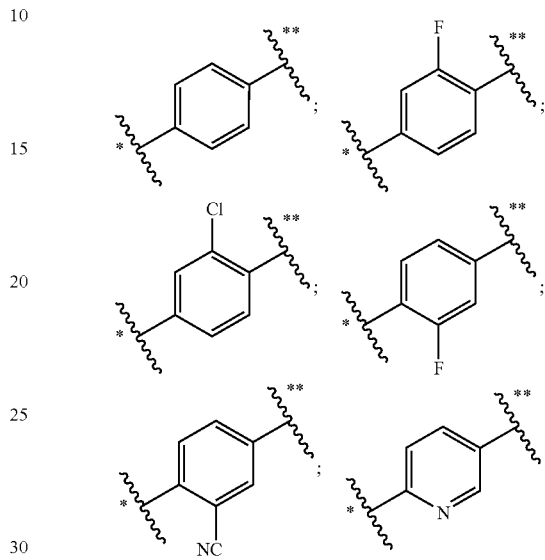

wherein $\xi$—, represents a bond covalently attached to said carbon of said carbonyl; —$\xi$**, represents a bond covalently attached to said sulfur of said sulfonamide; Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, $R^5$ is H; $R^6$ is a member selected from 1-(4-trifluorophenyl)ethyl, 2-methyl-2-(4-fluorophenoxy)propyl, 2-chloro-4-trifluoromethylbenzyl, 2-methoxy-4-trifluoromethoxybenzyl, (1-(4-chlorophenyl)cyclopropyl)methyl, 2-methyl-3-chlorobenzyl, 2-fluoro-3-trifluoromethylbenzyl, 1-(4-trifluoromethylbenzyl)ethyl, 2,5-dichlorobenzyl and 2-fluoromethoxy-2-methyl-propyl; and Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl; B is a member selected from

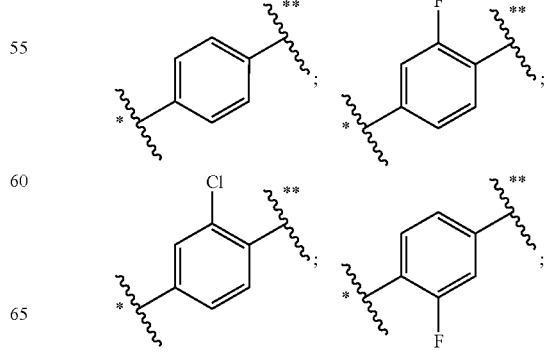

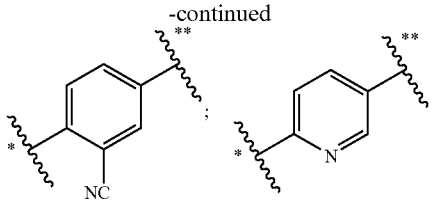

wherein ⁂, represents a bond covalently attached to said carbon of said carbonyl; ⁂, represents a bond covalently attached to said sulfur of said sulfonamide; Z is a member selected from 1,3 thiazol-2-yl, 1,3 thiazol-4-yl, 5-halo(1,3 thiazol-2-yl), 5-alkyl(1,3 thiazol-2-yl) and 1,2,4 thiadiazol-5-yl.

In an exemplary embodiment, B is

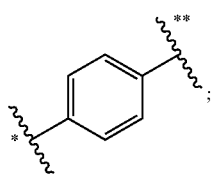 [SMILES: *c1ccc(*)cc1]

Z is a member selected from 1,3 thiazol-2-yl, 5-chloro(1,3 thiazol-2-yl) and 1,2,4 thiadiazol-5-yl; $R^5$ is H, $R^6$ is a member selected from 3-chloro-4-trifluoromethoxybenzyl, 3-chloro-4-trifluoromethylbenzyl, 3-fluoro-4-trifluoromethoxybenzyl, 3,4 dichlorobenzyl, 3-fluoro-4-trifluoromethylbenzyl, 3-trifluoromethoxy-4-fluorobenzyl, 4-trifluoromethoxybenzyl, 4-trifluoromethylbenzyl, 3-fluoro-4-chlorobenzyl, 3-chloro-4-fluorobenzyl, 3-trifluoromethoxy-4-fluorobenzyl, 3-cyclopropyl-4-fluorobenzyl, 2-methoxy-4-trifluoromethoxybenzyl, 3,4-difluorobenzyl, 2-methyl-3-chlorobenzyl, 3-trifluoromethoxybenzyl, 2-fluoro-4-trifluoromethylbenzyl and 2-fluoro-3-trifluoromethylbenzyl.

In an exemplary embodiment, B is

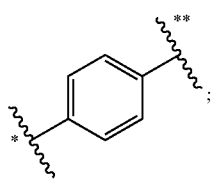 [SMILES: *c1ccc(*)cc1]

Z is 1,3 thiazol-2-yl; $R^5$ is H; $R^6$ is a member selected from 3-chloro-4-trifluoromethylbenzyl, 3-fluoro-4-trifluoromethoxybenzyl, 3-fluoro-4-trifluoromethylbenzyl, 3-trifluoromethoxy-4-fluorobenzyl, 3-cyclopropyl-4-fluorobenzyl, 3-trifluoromethyl-4-fluorobenzyl, 2-methoxy-4-trifluoromethoxybenzyl, 2-methyl-3-chlorobenzyl, 3-trifluoromethoxybenzyl, 3-fluoro-4-trifluoromethylbenzyl, 2-fluoro-3-trifluoromethylbenzyl and 3-trifluoromethylbenzyl.

In an exemplary embodiment, B is

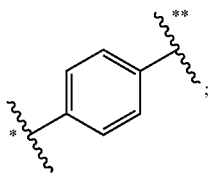 [SMILES: *c1ccc(*)cc1]

Z is 5-chloro(1,3 thiazol-2-yl); $R^5$ is H; $R^6$ is a member selected from 3,4 dichlorobenzyl, 3-fluoro-4-trifluoromethoxybenzyl, 3-chloro-4-fluorobenzyl, 3-fluoro-4-trifluoromethylbenzyl, 3-trifluoromethoxy-4-fluorobenzyl, 4-trifluoromethoxybenzyl, 4-trifluoromethylbenzyl, 3-fluoro-4-chlorobenzyl, 3-trifluoromethyl-4-fluorobenzyl, 2-fluoro-3-trifluoromethylbenzyl, 3,4-difluorobenzyl, 3-trifluoromethoxybenzyl and 3-trifluoromethylbenzyl.

In an exemplary embodiment, B is

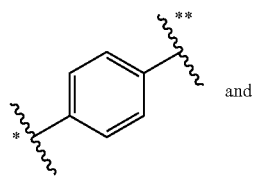 [SMILES: *c1ccc(*)cc1]

Z is 1,2,4 thiadiazol-5-yl; $R^5$ is H; $R^6$ is a member selected from 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl and 4-trifluoromethylbenzyl.

In an exemplary embodiment, B is

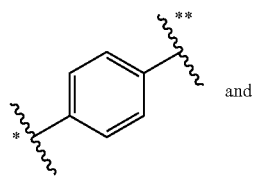 [SMILES: *c1ccc(*)cc1] and

Z is (1,3 thiazol-4-yl).

In an exemplary embodiment, B is

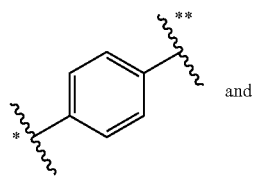 [SMILES: *c1ccc(*)cc1];

Z is (1,3 thiazol-4-yl); $R^5$ is H; and $R^6$ is a member selected from 3,4 dichlorobenzyl, 3-fluoro-4-trifluoromethoxybenzyl, 3-chloro-4-fluorobenzyl, 3-fluoro-4-trifluoromethylbenzyl, 3-trifluoromethoxy-4-fluorobenzyl, 4-trifluoromethoxybenzyl, 4-trifluoromethylbenzyl, 3-fluoro-4-chlorobenzyl, 3-trifluoromethyl-4-fluorobenzyl, 2-fluoro-3-trifluoromethylbenzyl, 3,4-difluorobenzyl, 3-trifluoromethoxybenzyl and 3-trifluoromethylbenzyl.

In an exemplary embodiment, Z is (1,3 thiazol-4-yl), $R^5$ is H and $R^6$ is 4-trifluoromethylbenzyl. In an exemplary embodiment, B is

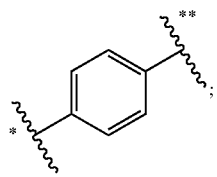 [SMILES: *c1ccc(*)cc1]

R⁵ is H, R⁶ is 4-trifluoromethylbenzyl. In an exemplary embodiment, B is

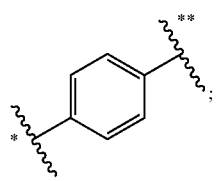 [SMILES: *c1ccc(*)cc1]

Z is (1,3 thiazol-4-yl), R⁵ is H, R⁶ is 4-trifluoromethylbenzyl.

In an exemplary embodiment, B is

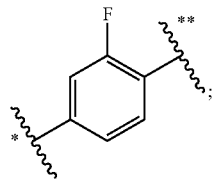 [SMILES: *c1ccc(*)c(F)c1]

Z is a member selected from 1,3 thiazol-2-yl, 5-chloro(1,3 thiazol-2-yl) and 1,2,4 thiadiazol-5-yl; R⁵ is H; and R⁶ is a member selected from 3-chloro-4-trifluoromethoxybenzyl, 3-chloro-4-trifluoromethylbenzyl, 3-fluoro-4-trifluoromethylbenzyl, 3-fluoro-4-trifluoromethoxybenzyl, 3,4 dichlorobenzyl, 4-trifluoromethoxybenzyl, 4-trifluoromethylbenzyl, 3-chloro-4-fluorobenzyl, 3-fluoro-4-chlorobenzyl, 3-trifluoromethoxy-4-fluorobenzyl, 3,4-difluorobenzyl, 3-trifluoromethyl-4-fluorobenzyl, 3-trifluoromethoxybenzyl and 3-trifluoromethylbenzyl.

In an exemplary embodiment, B is

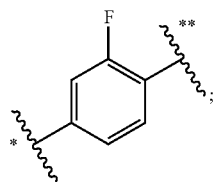 [SMILES: *c1ccc(*)c(F)c1]

Z is 1,3 thiazol-2-yl; R⁵ is H; R⁶ is a member selected from 3-chloro-4-trifluoromethylbenzyl, 3,4 dichlorobenzyl, 3-fluoro-4-trifluoromethoxybenzyl, 3-fluoro-4-trifluoromethylbenzyl, 3-chloro-4-fluorobenzyl, 3-trifluoromethoxy-4-fluorobenzyl, 3,4-difluorobenzyl, 4-trifluoromethoxybenzyl, 3-trifluoromethoxybenzyl, 3-fluoro-4-chlorobenzyl and 3-trifluoromethylbenzyl.

In an exemplary embodiment, B is

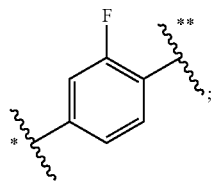 [SMILES: *c1ccc(*)c(F)c1]

Z is 5-chloro(1,3 thiazol-2-yl); R⁵ is H; R⁶ is a member selected from 3-fluoro-4-trifluoromethylbenzyl, 3,4 dichlorobenzyl, 4-trifluoromethoxybenzyl, 3-fluoro-4-trifluoromethoxybenzyl, 4-trifluoromethylbenzyl, 3-fluoro-4-chlorobenzyl, 3,4-difluorobenzyl, 3-trifluoromethyl-4-fluorobenzyl and 3-fluoro-4-trifluoromethoxybenzyl.

In an exemplary embodiment, B is

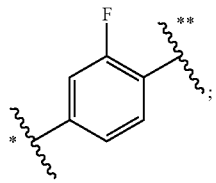 [SMILES: *c1ccc(*)c(F)c1]

Z is 1,2,4 thiadiazol-5-yl; R⁵ is H; R⁶ is a member selected from 3-chloro-4-trifluoromethoxybenzyl, 3-chloro-4-trifluoromethylbenzyl, 3-fluoro-4-trifluoromethylbenzyl and 3-fluoro-4-trifluoromethoxybenzyl.

In an exemplary embodiment, B is

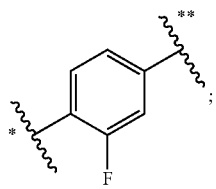 [SMILES: *c1ccc(*)c(F)c1]

Z is a member selected from 1,3 thiazol-2-yl, 5-chloro(1,3 thiazol-2-yl) and 1,2,4 thiadiazol-5-yl; R⁵ is H; R⁶ is a member selected from 3,4 dichlorobenzyl, 3-fluoro-4-trifluoromethoxybenzyl, 3-chloro-4-fluorobenzyl, 4-trifluoromethoxybenzyl, 3-fluoro-4-chlorobenzyl, 4-trifluoromethylbenzyl, 3-trifluoromethoxybenzyl, 3-trifluoromethylbenzyl, 3-fluoro-4-trifluoromethylbenzyl, 3-trifluoromethyl-4-fluorobenzyl, 3,4-difluorobenzyl and 3-trifluoromethoxy-4-fluorobenzyl.

In an exemplary embodiment, B is

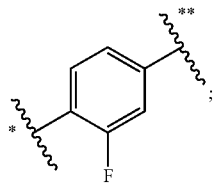 [SMILES: *c1ccc(*)c(F)c1]

Z is 1,3 thiazol-2-yl; R⁵ is H; R⁶ is a member selected from 3,4 dichlorobenzyl, 3-fluoro-4-trifluoromethoxybenzyl, 4-trifluoromethoxybenzyl, 3-fluoro-4-trifluoromethylbenzyl, 3-trifluoromethyl-4-fluorobenzyl, 3-trifluoromethylbenzyl, 3-fluoro-4-chlorobenzyl, 3,4-difluorobenzyl, 3-chloro-4-fluorobenzyl and 4-trifluoromethylbenzyl.

In an exemplary embodiment, B is

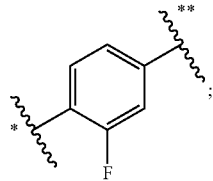 [SMILES: *c1ccc(*)c(F)c1]

Z is 5-chloro(1,3 thiazol-2-yl); $R^5$ is H; $R^6$ is a member selected from 3,4 dichlorobenzyl, 3-chloro-4-fluorobenzyl, 3-fluoro-4-chlorobenzyl, 4-trifluoromethoxybenzyl, 3-fluoro-4-trifluoromethoxybenzyl, 4-trifluoromethylbenzyl, 3-trifluoromethoxybenzyl, 3-trifluoromethylbenzyl, 3-fluoro-4-trifluoromethylbenzyl, 3-trifluoromethyl-4-fluorobenzyl, 3,4-difluorobenzyl and 3-trifluoromethoxy-4-fluorobenzyl.

In an exemplary embodiment, B is

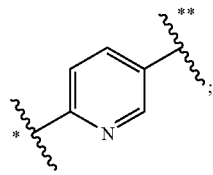 [SMILES: *c1ccc(*)nc1]

Z is a member selected from 1,3 thiazol-2-yl, 5-chloro(1,3 thiazol-2-yl) and 1,2,4 thiadiazol-5-yl; $R^5$ is H; $R^6$ is a member selected from 3-chloro-4-trifluoromethylbenzyl, 3-fluoro-4-trifluoromethylbenzyl, 3-fluoro-4-trifluoromethoxybenzyl and 4-trifluoromethylbenzyl.

In an exemplary embodiment, B is

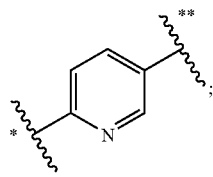 [SMILES: *c1ccc(*)nc1]

Z is 1,3 thiazol-2-yl; $R^5$ is H; $R^6$ is a member selected from 3-chloro-4-trifluoromethylbenzyl, 3-fluoro-4-trifluoromethylbenzyl and 3-fluoro-4-trifluoromethoxybenzyl.

In an exemplary embodiment, B is

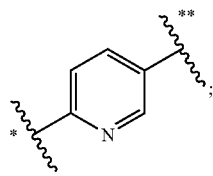 [SMILES: *c1ccc(*)nc1]

Z is 5-chloro(1,3 thiazol-2-yl); $R^5$ is H; $R^6$ is a member selected from 3-chloro-4-trifluoromethylbenzyl and 3-fluoro-4-trifluoromethylbenzyl.

In an exemplary embodiment, B is

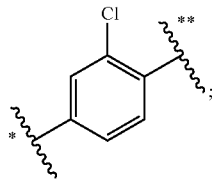 [SMILES: *c1ccc(*)c(Cl)c1]

Z is a member selected from 1,3 thiazol-2-yl, 5-chloro(1,3 thiazol-2-yl) and 1,2,4 thiadiazol-5-yl; $R^5$ is H; $R^6$ is a member selected from 3-fluoro-4-trifluoromethoxybenzyl, 4-trifluoromethylbenzyl, 3-chloro-4-trifluoromethylbenzyl and 3,4 dichlorobenzyl.

In an exemplary embodiment, B is

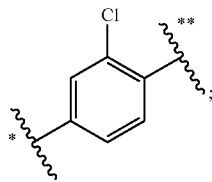 [SMILES: *c1ccc(*)c(Cl)c1]

Z is 1,3 thiazol-2-yl; $R^5$ is H; $R^6$ is a member selected from 3-fluoro-4-trifluoromethoxybenzyl and 4-trifluoromethylbenzyl.

In an exemplary embodiment, B is

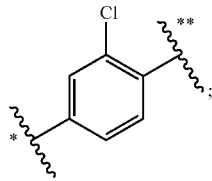 [SMILES: *c1ccc(*)c(Cl)c1]

Z is 5-chloro(1,3 thiazol-2-yl); $R^5$ is H; $R^6$ is 3,4 dichlorobenzyl.

In an exemplary embodiment, B is

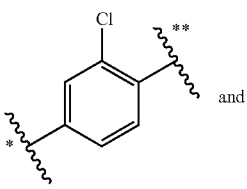 [SMILES: *c1ccc(*)c(Cl)c1]

and

Z is a member selected from 1,3 thiazol-2-yl, 5-chloro(1,3 thiazol-2-yl) and 1,2,4 thiadiazol-5-yl; $R^5$ is H; $R^6$ is a member selected from 3-fluoro-4-trifluoromethoxybenzyl, 3-chloro-4-trifluoromethylbenzyl and 3-fluoro-4-trifluoromethylbenzyl.

In an exemplary embodiment, B is

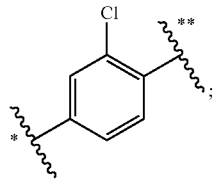 [SMILES: *c1ccc(*)c(Cl)c1]

Z is 5-chloro(1,3 thiazol-2-yl), $R^6$ is 3-fluoro-4-trifluoromethoxybenzyl.

In an exemplary embodiment, B is

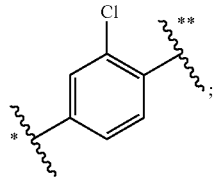 [SMILES: *c1ccc(*)c(Cl)c1]

Z is 1,2,4 thiadiazol-5-yl; $R^5$ is H; $R^6$ is a member selected from 3-chloro-4-trifluoromethoxybenzyl, 3-chloro-4-trifluoromethylbenzyl and 3-fluoro-4-trifluoromethylbenzyl.

In an exemplary embodiment, the invention is a compound of formula (I):

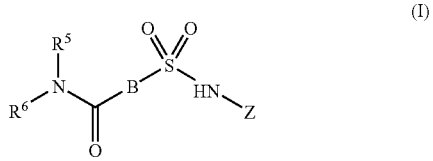

(I)

or a pharmaceutically acceptable salt or solvate thereof. In this invention, $R^5$ and $R^6$ are each members independently selected from H and a group which is a member selected from $(C_1-C_{10})$alkyl, heteroalkyl, heterocycloalkyl, heterocycloalkyl($C_1-C_2$)alkyl, $(C_3-C_8)$cycloalkyl, $(C_3-C_8)$cycloalkyl$(C_1-C_2)$alkyl, aryl$(C_1-C_3)$alkyl, aryloxy$(C_1-C_2)$alkyl, arylamino$(C_1-C_2)$alkyl, heteroaryl, heteroarylamino$(C_1-C_2)$alkyl, heteroaryloxy$(C_1-C_2)$alkyl and heteroaryl$(C_1-C_2)$alkyl. Each group is optionally substituted at any suitable point with one or more substituents selected from the group consisting of oxo, halogen, cyano, hydroxy, $(C_1-C_4)$alkyl, halo$(C_1-C_4)$alkyl, $(C_1-C_4)$alkoxy, $(C_1-C_4)$alkoxy$(C_1-C_4)$alkoxy, hydroxy$(C_1-C_4)$alkyl, hydroxy$(C_1-C_4)$alkoxy, halo$(C_1-C_4)$alkoxy, $(C_3-C_8)$cycloalkyl$(C_1-C_4)$alkoxy, amino, $(C_1-C_4)$alkylamino, di$(C_1-C_4)$alkylamino, trifluoromethylthio, $(C_3-C_8)$cycloalkyl, pyrazolyl, pyrazolylmethyl, pyrazolylethyl, phenyl, benzyl, phenethyl, pyridyl, pyridylmethyl, phenoxy, phenoxymethyl, pyridyloxy and pyridyloxymethyl. Each pyrazolyl, pyrazolylmethyl, pyrazolylethyl, phenyl, benzyl, phenethyl, pyridyl, pyridylmethyl, phenoxy, phenoxymethyl, pyridyloxy or pyridyloxymethyl is optionally substituted with halogen, cyano, hydroxy, methyl, methoxy, trifluoromethyl or trifluoromethoxy. There is a proviso that $R^5$ and $R^6$ are not both hydrogen. $R^5$ and $R^6$, when taken together with the nitrogen to which they are attached, are optionally joined to form a 4- to 8-membered heterocycloalkyl ring. The 4- to 8-membered heterocycloalkyl ring is optionally substituted with one or more substituents selected from the group consisting of oxo, halogen, cyano, hydroxy, $(C_1-C_4)$alkyl, halo$(C_1-C_4)$alkyl, $(C_1-C_4)$alkoxy, $(C_1-C_4)$alkoxy$(C_1-C_4)$alkoxy, hydroxy$(C_1-C_4)$alkoxy, halo$(C_1-C_4)$alkoxy, $(C_3-C_8)$cycloalkyl$(C_1-C_4)$alkoxy, $(C_3-C_8)$cycloalkyl$(C_1-C_4)$alkoxy$(C_1-C_4)$alkyl, amino, $(C_1-C_4)$alkylamino, di$(C_1-C_4)$alkylamino, trifluoromethylthio, $(C_3-C_8)$cycloalkyl, pyrazolyl, pyrazolylmethyl, pyrazolylethyl, phenyl, benzyl, phenethyl, pyridyl, pyridylmethyl, phenoxy, phenoxymethyl, pyridyloxy and pyridyloxymethyl. Each pyrazolyl, pyrazolylmethyl, pyrazolylethyl, phenyl, benzyl, phenethyl, pyridyl, pyridylmethyl, phenoxy, phenoxymethyl, pyridyloxy or pyridyloxymethyl is optionally substituted with halogen, cyano, hydroxy, methyl, methoxy, trifluoromethyl or trifluoromethoxy. B is a member selected from the group consisting of aryl and 6-membered heteroaryl. Each B is optionally substituted with one or more substituents selected from the group consisting of halogen, cyano, $(C_1-C_4)$alkyl, halo$(C_1-C_4)$alkyl, $(C_1-C_4)$alkoxy and halo$(C_1-C_4)$alkoxy. Z is a 5-membered heteroaryl, which is optionally substituted with one or more substituents selected from the group consisting of halogen, cyano, $(C_1-C_4)$alkyl, halo$(C_1-C_4)$alkyl, $(C_1-C_4)$alkoxycarbonyl, $(C_1-C_4)$alkoxy, halo$(C_1-C_4)$alkoxy, $(C_3-C_8)$cycloalkyl, amino, $(C_1-C_4)$alkylamino and di$(C_1-C_4)$alkylamino.

In an exemplary embodiment, an embodiment described herein has a proviso that the compound of formula (I) is not one of the following compounds: N-(5-methyl-3-isoxazolyl)-3-[[(5-methyl-3-isoxazolyl)amino]sulfonyl]-benzamide; 3-[[(5-methyl-3-isoxazolyl)amino]sulfonyl]-N-1,3,4-thiadiazol-2-yl-benzamide; N-(5-ethyl-1,3,4-thiadiazol-2-yl)-3-(4-morpholinylcarbonyl)-benzenesulfonamide; 1-[3-[[[5-(1,1-dimethylethyl)-4-methyl-2-thiazolyl]amino]sulfonyl]benzoyl]piperidine; N-(5-methyl-1,3,4-thiadiazol-2-yl)-3-(4-morpholinylcarbonyl)-benzenesulfonamide; and N-methyl-4-[[(1-methyl-1H-pyrazol-3-yl)amino]sulfonyl]-benzamide.

In another exemplary embodiment, $R^5$, in any of the embodiments of the previous paragraphs, is $(C_1-C_{10})$alkyl or $(C_3-C_8)$cycloalkyl. This $R^5$ can be optionally substituted with one or more substituents such as oxo, halogen, cyano, hydroxy, hydroxy$(C_1-C_4)$alkyl, hydroxy$(C_1-C_4)$alkoxy, $(C_1-C_4)$alkyl, halo$(C_1-C_4)$alkyl, $(C_1-C_4)$alkoxy, halo$(C_1-C_4)$alkoxy or phenyl.

In another exemplary embodiment, $R^5$, in any of the embodiments of the previous paragraphs, $(C_1-C_4)$alkyl, hydroxy$(C_1-C_4)$alkyl, cyano$(C_1-C_4)$alkyl, $(C_3-C_8)$cycloalkyl, phenyl$(C_1-C_4)$alkyl, hydroxycyclohexyl or hydroxy$(C_1-C_4)$alkylcyclohexyl.

In another exemplary embodiment, $R^5$, in any of the embodiments of the previous paragraphs, is methyl, ethyl, isopropyl, hydroxyethyl, cyanoethyl, 2-hydroxy-1-phenylethyl, cyclopropyl, cyclohexyl, (1R, 2R) 2-hydroxycyclohexyl, (1R, 2R) 2-hydroxycyclohexyl, (1R, 2S) (2-hydroxymethyl)cyclohexyl or (1S, 2R) (2-hydroxymethyl)cyclohexyl.

In another exemplary embodiment, $R^6$ in any of the embodiments of the previous paragraphs, is either H or it is not H.

In another exemplary embodiment, $R^6$, in any of the embodiments of the previous paragraphs, is heteroaryl, aryl $(C_1-C_3)$alkyl, heteroaryl$(C_1-C_2)$alkyl, aryloxy$(C_1-C_2)$alkyl, heteroaryloxy$(C_1-C_2)$alkyl, arylamino$(C_1-C_2)$alkyl or heteroarylamino$(C_1-C_2)$alkyl. Each of these groups is optionally substituted with one or more substituents such as halogen, cyano, hydroxy, $(C_1-C_4)$alkyl, halo$(C_1-C_4)$alkyl, $(C_1-C_4)$alkoxy, $(C_1-C_4)$alkoxy$(C_1-C_4)$alkoxy, hydroxy$(C_1-C_4)$alkoxy, halo$(C_1-C_4)$alkoxy, $(C_3-C_8)$cycloalkyl$(C_1-C_4)$ alkoxy, amino, (C₁-C₄)alkylamino, di(C₁-C₄)alkylamino, trifluoromethylthio, (C₃-C₈)cycloalkyl, pyrazolyl, pyrazolylmethyl, pyrazolylethyl, phenyl, benzyl, phenethyl, pyridyl, pyridylmethyl, phenoxy, phenoxymethyl, pyridyloxy and pyridyloxymethyl. Each pyrazolyl, pyrazolylmethyl, pyrazolylethyl, phenyl, benzyl, phenethyl, pyridyl, pyridylmethyl, phenoxy, phenoxymethyl, pyridyloxy or pyridyloxymethyl is optionally substituted at any suitable point with one or more substituents such as halogen, cyano, hydroxy, methyl, methoxy, trifluoromethyl or trifluoromethoxy.

In another exemplary embodiment, $R^6$, in any of the embodiments of the previous paragraphs, is:

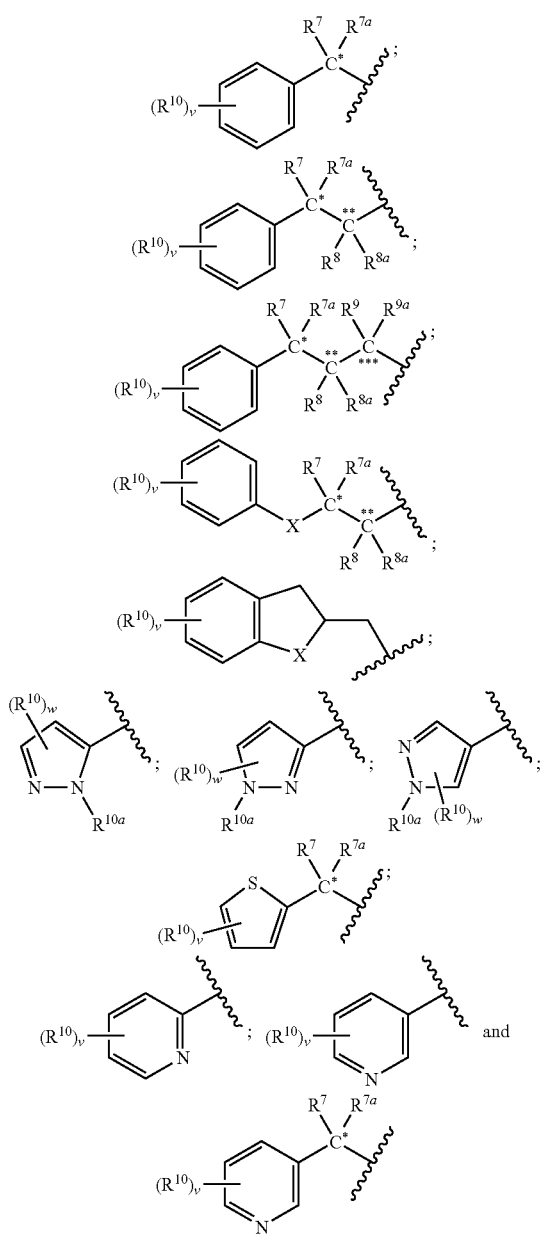

wherein the index v is an integer selected from 0 to 3. The index w is an integer selected from 0 to 2. X is a member selected from O and N. Each $R^{10}$ is a member independently selected from halogen, cyano, hydroxyl and a group which is a member selected from (C₁-C₄)alkyl, halo(C₁-C₄)alkyl, (C₃-C₈)cycloalkyl, (C₁-C₄)alkoxy, trifluoromethylthio, phenyl, benzyl, phenethyl, phenoxy, and pyrazolyl, wherein each phenyl, benzyl, phenethyl, phenoxy, and pyrazolyl group is optionally substituted at any suitable point with one or more halogen moieties. $R^{10a}$ is a member selected from H and a group which is a member selected from (C₁-C₄)alkyl, halo(C₁-C₄)alkyl, phenyl, benzyl and phenethyl, wherein each phenyl, benzyl or phenethyl group is optionally substituted at any suitable point with one or more halogen moieties. $R^7$, $R^{7a}$, $R^8$, $R^{8a}$, $R^9$ and $R^{9a}$ are each members independently selected from H, halogen, cyano, hydroxyl, (C₁-C₄)alkyl, hydroxy(C₁-C₄)alkyl, (C₃-C₈)cycloalkyl, (C₁-C₄)alkoxy, phenoxy, trifluoromethylthio or pyrazolyl wherein each group is optionally substituted at any suitable point with (C₁-C₄)alkyl. This embodiment has the proviso that $R^7$ and $R^{7a}$ are optionally joined with C* to form a member selected from a carbonyl and substituted and unsubstituted 3- to 7-membered ring. This embodiment has the further proviso that $R^8$ and $R^{8a}$ are optionally joined with C to form a member selected from a carbonyl and substituted and unsubstituted 3- to 7-membered ring. This embodiment has the further proviso that $R^9$ and $R^{9a}$ are optionally joined with C* to form a member selected from a carbonyl and substituted and unsubstituted 3- to 7-membered ring. This embodiment has the further proviso that $R^7$ and $R^8$ are optionally joined, along with the atoms to which they are attached, to form a 3- to 7-membered ring. This embodiment has the further proviso that $R^8$ and $R^9$ are optionally joined, along with the atoms to which they are attached, to form a 3- to 7-membered ring. This embodiment has the further proviso that $R^7$ and $R^9$ are optionally joined, along with the atoms to which they are attached, to form a 3- to 7-membered ring. This embodiment has the further proviso that $R^7$ and $R^{10}$ are optionally joined, along with the atoms to which they are attached, to form a 3- to 7-membered ring. This embodiment has the further proviso that $R^8$ and $R^{10}$ are optionally joined, along with the atoms to which they are attached, to form a 3- to 7-membered ring. This embodiment has the further proviso that $R^9$ and $R^{10}$ are optionally joined, along with the atoms to which they are attached, to form a 3- to 7-membered ring. This embodiment has the further proviso that when v is 2 or 3, each $R^{10}$ are optionally joined, along with the atoms to which they are attached, to form a 3- to 7-membered ring.

In another exemplary embodiment, $R^7$, $R^{7a}$, $R^8$, $R^{8a}$, $R^9$ and $R^{9a}$, in any of the embodiments of the previous paragraphs, are each independently selected from H, hydroxy, halogen, cyano, 2-hydroxyethyl, (S)-methyl, (R)-methyl or cyclopropyl.

In another exemplary embodiment, in any of the embodiments of the previous paragraphs, $R^7$ is H and $R^{7a}$ is hydroxy, cyano, 2-hydroxyethyl, (S)-methyl, (R)-methyl or cyclopropyl.

In another exemplary embodiment, in any of the embodiments of the previous paragraphs, $R^6$ is

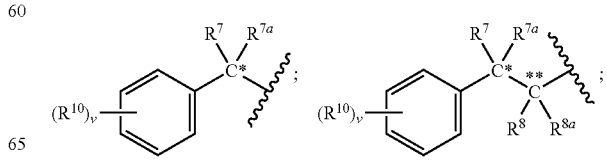

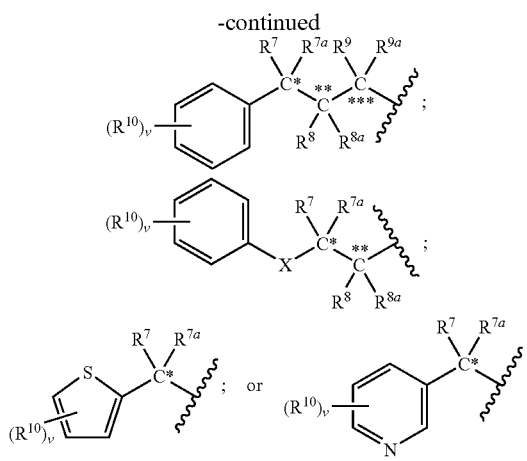

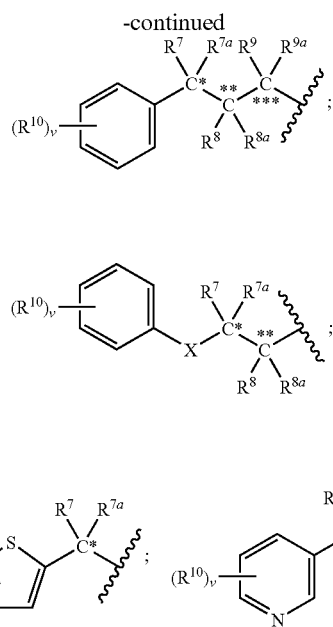

in which $R^7$ and $R^{7a}$ are optionally joined with C* to form a carbonyl. Alternatively $R^7$ and $R^{7a}$ are optionally joined with C* to form a member selected from cyclopropyl and cyclopentyl. In this embodiment, C* can have an R or S configuration. $R^8$ and $R^{8a}$ are optionally joined with C to form cyclopropyl and wherein C has a configuration which is a member selected from R and S. $R^7$ and $R^8$, along with the atoms to which they are attached, are optionally joined to form a member selected from cyclopropyl and tetrahydrofuran. $R^9$ and $R^{9a}$ are each members independently selected from H, 2-hydroxyethyl, (S)-methyl, (R)-methyl, halogen, cyano, hydroxyl, $(C_3$-$C_8)$cycloalkyl, $(C_1$-$C_4)$alkoxy, phenoxy, trifluoromethylthio and pyrazolyl.

In another exemplary embodiment, in any of the embodiments of the previous paragraphs, $R^6$ is a member selected from

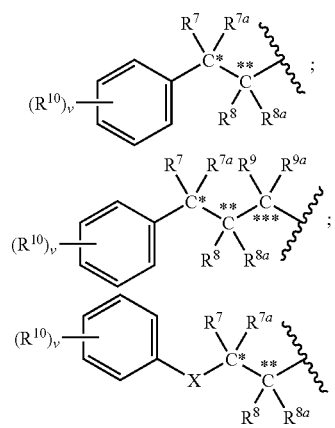

wherein $R^8$, $R^{8a}$, $R^9$ and $R^{9a}$ are each H.

In another exemplary embodiment, in any of the embodiments of the previous paragraphs, $R^6$ is a member selected from

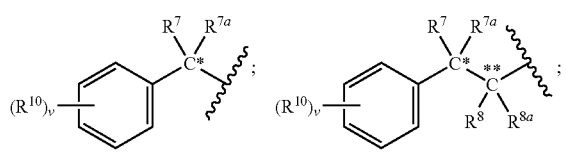

wherein each $R^7$ and $R^{7a}$ are members independently selected from H, methyl and hydroxy.

In another exemplary embodiment, in any of the embodiments of the previous paragraphs, $R^6$ is

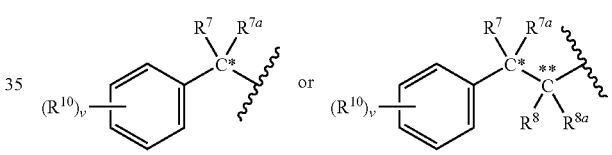

wherein $R^7$ is hydroxy, methyl, ethyl or hydroxymethyl, and C* is in a configuration which is a member selected from R and S. $R^8$ is a member selected from hydroxy, methyl, ethyl and hydroxymethyl, and C** is in a configuration which is a member selected from R and S. $R^7$ and $R^8$, along with C* and C**, are optionally joined to form a member selected from cyclopropyl, tetrahydrofuran and cyclopentyl and wherein C* and C** are each independently in a configuration which is a member selected from R and S.

In another exemplary embodiment, in any of the embodiments of the previous paragraphs, $R^6$ is

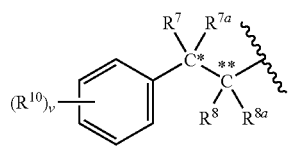

wherein $R^7$ and $R^{7a}$ are joined with C* to form a carbonyl; and $R^8$ is methyl.

In another exemplary embodiment, in any of the embodiments of the previous paragraphs, $R^{10}$ is fluoro, chloro, cyano, hydroxyl, methyl, trifluoromethyl, methoxy, trifluoromethoxy, difluoromethoxy, isopropyloxy, cyclopropyl, ethoxy, pyrazol-1-yl, phenyl, chlorophenyl or chlorobenzyl.

In another exemplary embodiment, in any of the embodiments of the previous paragraphs, $R^6$ is

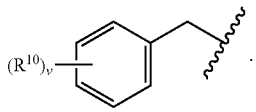

In another exemplary embodiment, in any of the embodiments of the previous paragraphs, v is 1.

In another exemplary embodiment, in any of the embodiments of the previous paragraphs, $R^{10}$ is trifluoromethoxy, trifluoromethyl, chloro or fluoro.

In another exemplary embodiment, in any of the embodiments of the previous paragraphs, $R^6$ is

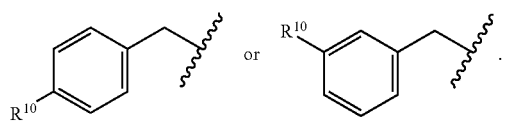

In another exemplary embodiment, in any of the embodiments of the previous paragraphs, $R^{10}$ is trifluoromethoxy, trifluoromethyl, chloro or fluoro.

In another exemplary embodiment, in any of the embodiments of the previous paragraphs, v is 2.

In another exemplary embodiment, in any of the embodiments of the previous paragraphs, each $R^{10}$ is a member independently selected from trifluoromethoxy, trifluoromethyl, chloro and fluoro.

In another exemplary embodiment, in any of the embodiments of the previous paragraphs, $R^6$ is

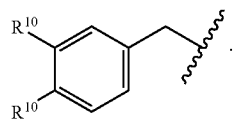

In another exemplary embodiment, in any of the embodiments of the previous paragraphs, $R^6$ is 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl or 3-trifluoromethyl-4-fluorobenzyl.

In another exemplary embodiment, in any of the embodiments of the previous paragraphs, $R^5$ is H.

In another exemplary embodiment, in any of the embodiments of the previous paragraphs, $R^6$ is

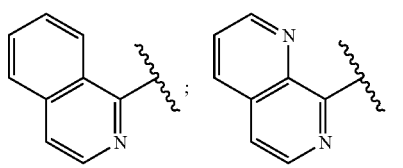

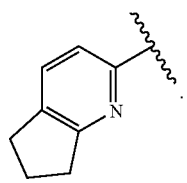

In another exemplary embodiment, in any of the embodiments of the previous paragraphs, B has a formula which is

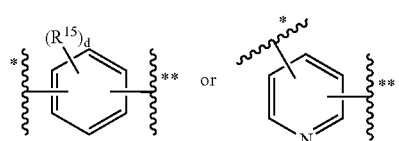

wherein ⁎, represents a bond covalently attached to said carbon of said carbonyl. ⁎⁎, represents a bond covalently attached to said sulfur of said sulfonamide. The index d is an integer from 0 to 2. $R^{15}$ is halogen, cyano, $(C_1-C_4)$alkyl, halo$(C_1-C_4)$alkyl, $(C_1-C_4)$alkoxy or halo$(C_1-C_4)$alkoxy.

In another exemplary embodiment, in any of the embodiments of the previous paragraphs, B is

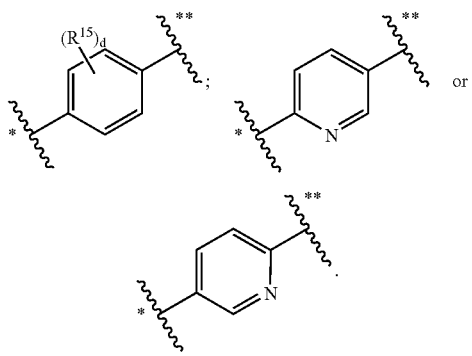

In another exemplary embodiment, in any of the embodiments of the previous paragraphs, B is

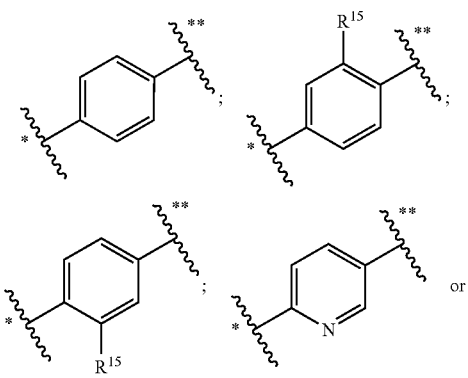

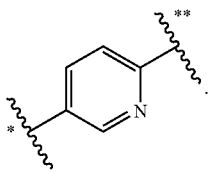

In another exemplary embodiment, in any of the embodiments of the previous paragraphs, R¹⁵ is fluoro, chloro or cyano.

In another exemplary embodiment, in any of the embodiments of the previous paragraphs, B is

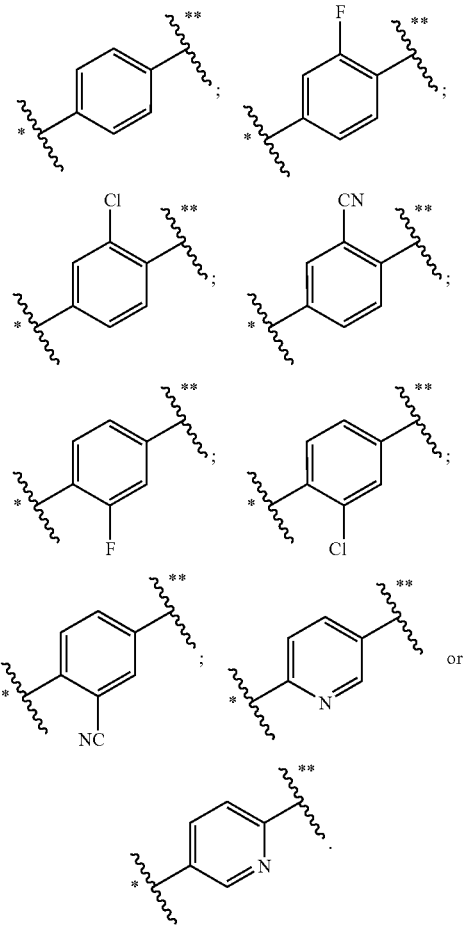

In another exemplary embodiment, in any of the embodiments of the previous paragraphs, B is a member selected from

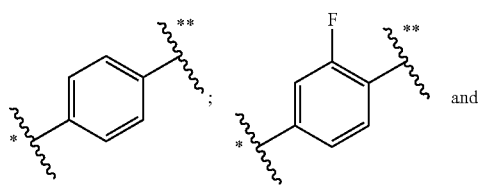 and

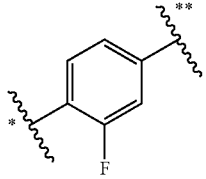

In another exemplary embodiment, in any of the embodiments of the previous paragraphs, Z is thiazolyl, thiadiazolyl, isoxazolyl, tetrazolyl, triazolyl and pyrazolyl, wherein each group is optionally substituted at any suitable point with one or more substituents selected from halogen, $(C_1\text{-}C_4)$alkyl, halo$(C_1\text{-}C_4)$alkyl or $(C_1\text{-}C_4)$alkoxycarbonyl.

In another exemplary embodiment, in any of the embodiments of the previous paragraphs, Z is thiazolyl, thiadiazolyl, isoxazolyl, tetrazolyl, triazolyl and pyrazolyl, wherein each group is optionally substituted at any suitable point with one or more substituents selected from fluorine, chlorine, methyl, trifluoromethyl or methoxycarbonyl.

In another exemplary embodiment, in any of the embodiments of the previous paragraphs, Z is thiazol-2-yl, thiazol-4-yl, thiazol-5-yl, thiadiazol-2-yl, thiadiazol-5-yl, pyrazol-3-yl, pyrazol-4-yl, pyrazol-5-yl, isoxazol-5-yl, isoxazol-4-yl, isoxazol-3-yl, tetrazol-5-yl, triazol-3-yl or triazol-4-yl, wherein each group is optionally substituted at any suitable point with one or more substituents selected from halogen, $(C_1\text{-}C_4)$alkyl, halo$(C_1\text{-}C_4)$alkyl or $(C_1\text{-}C_4)$alkoxycarbonyl.

In another exemplary embodiment, in any of the embodiments of the previous paragraphs, Z is 1,3 thiazolyl, 1,2,4 thiadiazolyl, 1,3,4 thiadiazolyl, isoxazolyl, 2H-tetrazolyl, 2H-1,2,3 triazolyl, 2H-1,2,4 triazolyl and 1H-pyrazolyl wherein each group is optionally substituted at any suitable point with one or more substituents selected from halogen, $(C_1\text{-}C_4)$alkyl, halo$(C_1\text{-}C_4)$alkyl or $(C_1\text{-}C_4)$alkoxycarbonyl.

In another exemplary embodiment, in any of the embodiments of the previous paragraphs, Z is 1,3 thiazol-2-yl, 1,3 thiazol-4-yl, 1,3 thiazol-5-yl, 1,3,4 thiadiazol-2-yl, 1,2,4 thiadiazol-5-yl, 1H-pyrazol-3-yl, 1H-pyrazol-4-yl, 1H-pyrazol-5-yl, isoxazol-5-yl, isoxazol-4-yl, isoxazol-3-yl, 2H-tetrazol-5-yl, 1H-1,2,4 triazol-3-yl and -2H-1,2,3 triazol-4-yl wherein each group is optionally substituted at any suitable point with one or more substituents selected from halogen, $(C_1\text{-}C_4)$ alkyl, halo$(C_1\text{-}C_4)$alkyl or $(C_1\text{-}C_4)$alkoxycarbonyl.

In another exemplary embodiment, in any of the embodiments of the previous paragraphs, Z is 1,3 thiazol-2-yl, (5-chloro)1,3 thiazol-2-yl, (4-methyl)1,3 thiazol-2-yl, (5-methyl)1,3 thiazol-2-yl, 4(methoxycarbonyl)(1,3 thiazol-2-yl), 4-trifluoromethyl 1,3 thiazol-2-yl, 1,3 thiazol-4-yl, 2-methyl 1,3 thiazol-4-yl, 1,3 thiazol-5-yl, 2-methyl 1,3 thiazol-5-yl, 4-trifluoromethyl 1,3,4 thiadiazol-2-yl, 5-methyl 1,3,4 thiadiazol-2-yl, 1,3,4 thiadiazol-2-yl, 3-methyl 1,2,4 thiadiazol-5-yl, 3-ethyl 1,2,4 thiadiazol-5-yl, 1,2,4 thiadiazol-5-yl, 1-methyl 1H-pyrazol-3-yl, 1-methyl 1H-pyrazol-4-yl, 1,3,5 trimethyl 1H-pyrazol-4-yl, 1H-pyrazol-5-yl, 3-methyl isoxazol-5-yl, 3,4-dimethyl isoxazol-5-yl, isoxazol-4-yl, 3,5-dimethylisoxazol-4-yl, isoxazol-3-yl, 5-methyl isoxazol-3-yl, 2-methyl 2H-tetrazol-5-yl, 1-methyl 1H-1,2,4 triazol-3-yl, 1H-1,2,4 triazol-3-yl or 2-ethyl 2H-1,2,3 triazol-4-yl.

In another exemplary embodiment, in any of the embodiments of the previous paragraphs, Z is 1,3 thiazol-2-yl, 5-chloro(1,3 thiazol-2-yl), 4-methyl(1,3 thiazol-2-yl), 5-methyl(1,3 thiazol-2-yl), 4(methoxycarbonyl)(1,3 thiazol-2-yl), 4-trifluoromethyl 1,3 thiazol-2-yl, 1,3 thiazol-4-yl, 2-methyl 1,3 thiazol-4-yl, 3-methyl 1,2,4 thiadiazol-5-yl, 3-ethyl 1,2,4 thiadiazol-5-yl or 1,2,4 thiadiazol-5-yl.

In another exemplary embodiment, in any of the embodiments of the previous paragraphs, Z is 1,3 thiazol-2-yl, 1,3 thiazol-4-yl, 5-halo(1,3 thiazol-2-yl), 5-($C_1$-$C_4$)alkyl(1,3 thiazol-2-yl) or 1,2,4 thiadiazol-5-yl.

In another exemplary embodiment, in any of the embodiments of the previous paragraphs, Z is 1,3 thiazol-2-yl, 1,3 thiazol-4-yl, 5-chloro(1,3 thiazol-2-yl), 5-methyl(1,3 thiazol-2-yl) or 1,2,4 thiadiazol-5-yl.

In another exemplary embodiment, in any of the embodiments of the previous paragraphs, $R^5$ is H. $R^6$ is 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl or 3-trifluoromethyl-4-fluorobenzyl. B is

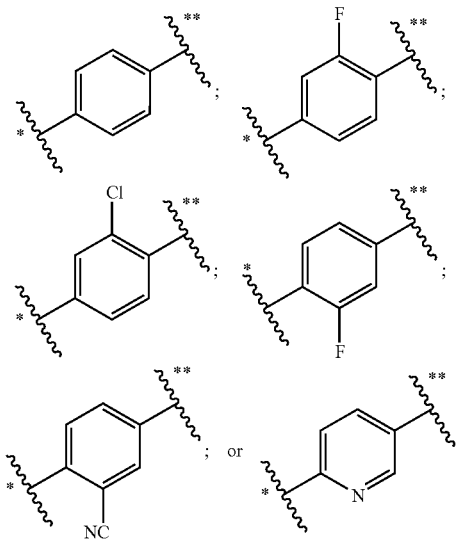

wherein ⁓ⁱ⎯, represents a bond covalently attached to said carbon of said carbonyl, and —⎯ⁱⁱ, represents a bond covalently attached to said sulfur of said sulfonamide.

In another exemplary embodiment, in any of the embodiments of the previous paragraphs, $R^5$ is H, and $R^6$ is 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl or 3-trifluoromethyl-4-fluorobenzyl. Z is 1,3 thiazol-2-yl, 1,3 thiazol-4-yl, 5-halo(1,3 thiazol-2-yl), 5-($C_1$-$C_4$)alkyl(1,3 thiazol-2-yl) or 1,2,4 thiadiazol-5-yl.

In another exemplary embodiment, in any of the embodiments of the previous paragraphs, B is

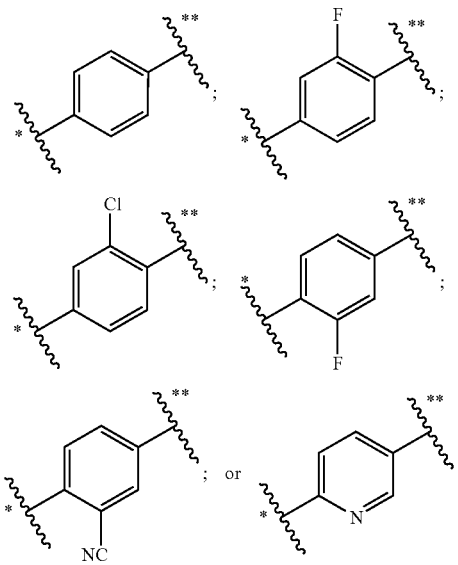

wherein ⁓ⁱ⎯, represents a bond covalently attached to said carbon of said carbonyl, and —⎯ⁱⁱ, represents a bond covalently attached to said sulfur of said sulfonamide. Z is 1,3 thiazol-2-yl, 1,3 thiazol-4-yl, 5-halo(1,3 thiazol-2-yl), 5-($C_1$-$C_4$)alkyl(1,3 thiazol-2-yl) or 1,2,4 thiadiazol-5-yl.

In another exemplary embodiment, in any of the embodiments of the previous paragraphs, $R^5$ is H. $R^6$ is 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl or 3-trifluoromethyl-4-fluorobenzyl. B is

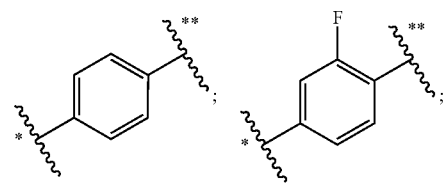

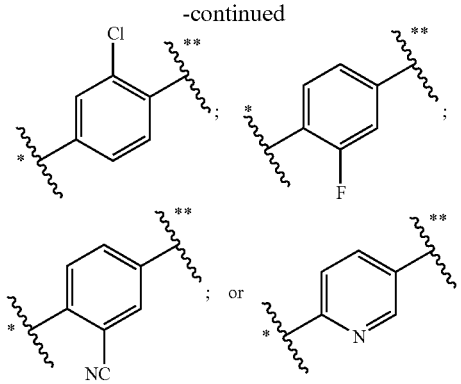

wherein ⸗, represents a bond covalently attached to said carbon of said carbonyl, and ⸗**, represents a bond covalently attached to said sulfur of said sulfonamide. Z is 1,3 thiazol-2-yl, 1,3 thiazol-4-yl, 5-halo(1,3 thiazol-2-yl), 5-($C_1$-$C_4$)alkyl(1,3 thiazol-2-yl) or 1,2,4 thiadiazol-5-yl.

In another exemplary embodiment, in any of the embodiments of the previous paragraphs, B is

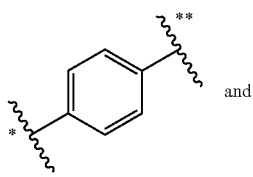 [SMILES: *c1ccc(*)cc1]

Z is 1,3 thiazol-2-yl, 5-chloro(1,3 thiazol-2-yl) or 1,2,4 thiadiazol-5-yl.

In another exemplary embodiment, in any of the embodiments of the previous paragraphs, $R^6$ is 3-chloro-4-trifluoromethoxybenzyl, 3-chloro-4-trifluoromethylbenzyl, 3-fluoro-4-trifluoromethoxybenzyl, 3,4 dichlorobenzyl, 3-fluoro-4-trifluoromethylbenzyl, 3-trifluoromethoxy-4-fluorobenzyl, 4-trifluoromethoxybenzyl, 4-trifluoromethylbenzyl, 3-fluoro-4-chlorobenzyl, 3-chloro-4-fluorobenzyl, 3-trifluoromethoxy-4-fluorobenzyl, 3-cyclopropyl-4-fluorobenzyl, 2-methoxy-4-trifluoromethoxybenzyl, 3,4-difluorobenzyl, 2-methyl-3-chlorobenzyl, 3-trifluoromethoxybenzyl, 2-fluoro-4-trifluoromethylbenzyl or 2-fluoro-3-trifluoromethylbenzyl.

In another exemplary embodiment, in any of the embodiments of the previous paragraphs, when Z is 1,3 thiazol-2-yl, $R^6$ is 3-chloro-4-trifluoromethylbenzyl, 3-fluoro-4-trifluoromethoxybenzyl, 3-fluoro-4-trifluoromethylbenzyl, 3-trifluoromethoxy-4-fluorobenzyl, 3-cyclopropyl-4-fluorobenzyl, 3-trifluoromethyl-4-fluorobenzyl, 2-methoxy-4-trifluoromethoxybenzyl, 2-methyl-3-chlorobenzyl, 3-trifluoromethoxybenzyl, 3-fluoro-4-trifluoromethylbenzyl, 2-fluoro-3-trifluoromethylbenzyl or 3-trifluoromethylbenzyl.

In another exemplary embodiment, in any of the embodiments of the previous paragraphs, when Z is 5-chloro(1,3 thiazol-2-yl), $R^6$ is 3,4 dichlorobenzyl, 3-fluoro-4-trifluoromethoxybenzyl, 3-chloro-4-fluorobenzyl, 3-fluoro-4-trifluoromethylbenzyl, 3-trifluoromethoxy-4-fluorobenzyl, 4-trifluoromethoxybenzyl, 4-trifluoromethylbenzyl, 3-fluoro-4-chlorobenzyl, 3-trifluoromethyl-4-fluorobenzyl, 2-fluoro-3-trifluoromethylbenzyl, 3,4-difluorobenzyl, 3-trifluoromethoxybenzyl or 3-trifluoromethylbenzyl.

In another exemplary embodiment, in any of the embodiments of the previous paragraphs, when Z is 1,2,4 thiadiazol-5-yl, $R^6$ is 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl or 4-trifluoromethylbenzyl.

In another exemplary embodiment, in any of the embodiments of the previous paragraphs, B is

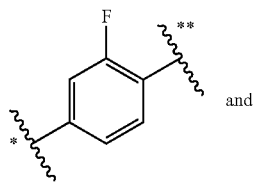 [SMILES: *c1ccc(*)c(F)c1]

Z is 1,3 thiazol-2-yl, 5-chloro(1,3 thiazol-2-yl) or 1,2,4 thiadiazol-5-yl.

In another exemplary embodiment, in any of the embodiments of the previous paragraphs, $R^6$ is 3-chloro-4-trifluoromethoxybenzyl, 3-chloro-4-trifluoromethylbenzyl, 3-fluoro-4-trifluoromethylbenzyl, 3-fluoro-4-trifluoromethoxybenzyl, 3,4 dichlorobenzyl, 4-trifluoromethoxybenzyl, 4-trifluoromethylbenzyl, 3-chloro-4-fluorobenzyl, 3-fluoro-4-chlorobenzyl, 3-trifluoromethoxy-4-fluorobenzyl, 3,4-difluorobenzyl, 3-trifluoromethyl-4-fluorobenzyl, 3-trifluoromethoxybenzyl or 3-trifluoromethylbenzyl.

In another exemplary embodiment, in any of the embodiments of the previous paragraphs, when Z is 1,3 thiazol-2-yl, $R^6$ is 3-chloro-4-trifluoromethylbenzyl, 3,4 dichlorobenzyl, 3-fluoro-4-trifluoromethoxybenzyl, 3-fluoro-4-trifluoromethylbenzyl, 3-chloro-4-fluorobenzyl, 3-trifluoromethoxy-4-fluorobenzyl, 3,4-difluorobenzyl, 4-trifluoromethoxybenzyl, 3-trifluoromethoxybenzyl, 3-fluoro-4-chlorobenzyl or 3-trifluoromethylbenzyl.

In another exemplary embodiment, in any of the embodiments of the previous paragraphs, when Z is 5-chloro(1,3 thiazol-2-yl), $R^6$ is 3-fluoro-4-trifluoromethylbenzyl, 3,4 dichlorobenzyl, 4-trifluoromethoxybenzyl, 3-fluoro-4-trifluoromethoxybenzyl, 4-trifluoromethylbenzyl, 3-fluoro-4-chlorobenzyl, 3,4-difluorobenzyl, 3-trifluoromethyl-4-fluorobenzyl or 3-fluoro-4-trifluoromethoxybenzyl.

In another exemplary embodiment, in any of the embodiments of the previous paragraphs, when Z is 1,2,4 thiadiazol-5-yl, $R^6$ is 3-chloro-4-trifluoromethoxybenzyl, 3-chloro-4-trifluoromethylbenzyl, 3-fluoro-4-trifluoromethylbenzyl or 3-fluoro-4-trifluoromethoxybenzyl.

In another exemplary embodiment, in any of the embodiments of the previous paragraphs, B is

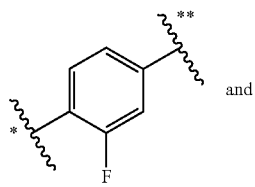 [SMILES: *c1ccc(*)c(F)c1]

Z is 1,3 thiazol-2-yl, 5-chloro(1,3 thiazol-2-yl) or 1,2,4 thiadiazol-5-yl.

In another exemplary embodiment, in any of the embodiments of the previous paragraphs, R⁶ is 3,4 dichlorobenzyl, 3-fluoro-4-trifluoromethoxybenzyl, 3-chloro-4-fluorobenzyl, 4-trifluoromethoxybenzyl, 3-fluoro-4-chlorobenzyl, 4-trifluoromethylbenzyl, 3-trifluoromethoxybenzyl, 3-trifluoromethylbenzyl, 3-fluoro-4-trifluoromethylbenzyl, 3-trifluoromethyl-4-fluorobenzyl, 3,4-difluorobenzyl or 3-trifluoromethoxy-4-fluorobenzyl.

In another exemplary embodiment, in any of the embodiments of the previous paragraphs, when Z is 1,3 thiazol-2-yl, R⁶ is 3,4 dichlorobenzyl, 3-fluoro-4-trifluoromethoxybenzyl, 4-trifluoromethoxybenzyl, 3-fluoro-4-trifluoromethylbenzyl, 3-trifluoromethyl-4-fluorobenzyl, 3-trifluoromethylbenzyl, 3-fluoro-4-chlorobenzyl, 3,4-difluorobenzyl, 3-chloro-4-fluorobenzyl or 4-trifluoromethylbenzyl.

In another exemplary embodiment, in any of the embodiments of the previous paragraphs, when Z is 5-chloro(1,3 thiazol-2-yl), R⁶ is 3,4 dichlorobenzyl, 3-chloro-4-fluorobenzyl, 3-fluoro-4-chlorobenzyl, 4-trifluoromethoxybenzyl, 3-fluoro-4-trifluoromethoxybenzyl, 4-trifluoromethylbenzyl, 3-trifluoromethoxybenzyl, 3-trifluoromethylbenzyl, 3-fluoro-4-trifluoromethylbenzyl, 3-trifluoromethyl-4-fluorobenzyl, 3,4-difluorobenzyl or 3-trifluoromethoxy-4-fluorobenzyl.

In another exemplary embodiment, in any of the embodiments of the previous paragraphs, B is

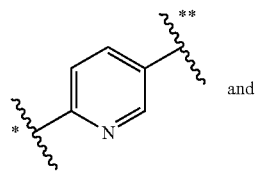 [SMILES: *c1ccc(*)nc1]

and

Z is 1,3 thiazol-2-yl, (5-chloro)1,3 thiazol-2-yl or 1,2,4 thiadiazol-5-yl.

In another exemplary embodiment, in any of the embodiments of the previous paragraphs, R⁶ is 3-chloro-4-trifluoromethylbenzyl, 3-fluoro-4-trifluoromethylbenzyl, 3-fluoro-4-trifluoromethoxybenzyl or 4-trifluoromethylbenzyl.

In another exemplary embodiment, in any of the embodiments of the previous paragraphs, when Z is 1,3 thiazol-2-yl, R⁶ is 3-chloro-4-trifluoromethylbenzyl, 3-fluoro-4-trifluoromethylbenzyl or 3-fluoro-4-trifluoromethoxybenzyl.

In another exemplary embodiment, in any of the embodiments of the previous paragraphs, when Z is (5-chloro)1,3 thiazol-2-yl, R⁶ is 3-chloro-4-trifluoromethylbenzyl or 3-fluoro-4-trifluoromethylbenzyl.

In another exemplary embodiment, in any of the embodiments of the previous paragraphs, B is

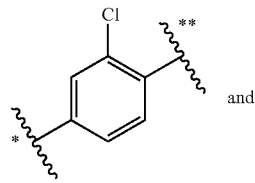 [SMILES: *c1ccc(*)c(Cl)c1]

and

Z is 1,3 thiazol-2-yl, (5-chloro)1,3 thiazol-2-yl or 1,2,4 thiadiazol-5-yl.

In another exemplary embodiment, in any of the embodiments of the previous paragraphs, R⁶ is 3-fluoro-4-trifluoromethoxybenzyl, 4-trifluoromethylbenzyl, 3-chloro-4-trifluoromethylbenzyl or 3,4 dichlorobenzyl.

In another exemplary embodiment, in any of the embodiments of the previous paragraphs, when Z is 1,3 thiazol-2-yl, R⁶ is 3-fluoro-4-trifluoromethoxybenzyl or 4-trifluoromethylbenzyl.

In another exemplary embodiment, in any of the embodiments of the previous paragraphs, when Z is 5-chloro(1,3 thiazol-2-yl), R⁶ is 3,4 dichlorobenzyl.

In another exemplary embodiment, in any of the embodiments of the previous paragraphs, B is

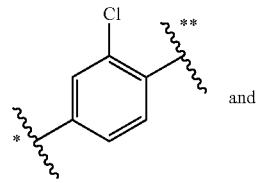 [SMILES: *c1ccc(*)c(Cl)c1]

and

Z is 1,3 thiazol-2-yl, (5-chloro)1,3 thiazol-2-yl or 1,2,4 thiadiazol-5-yl.

In another exemplary embodiment, in any of the embodiments of the previous paragraphs, R⁶ is 3-fluoro-4-trifluoromethoxybenzyl, 3-chloro-4-trifluoromethylbenzyl or 3-fluoro-4-trifluoromethylbenzyl.

In another exemplary embodiment, in any of the embodiments of the previous paragraphs, when Z is 5-chloro(1,3 thiazol-2-yl), R⁶ is 3-fluoro-4-trifluoromethoxybenzyl.

In another exemplary embodiment, in any of the embodiments of the previous paragraphs, when Z is 1,2,4 thiadiazol-5-yl, R⁶ is 3-chloro-4-trifluoromethoxybenzyl, 3-chloro-4-trifluoromethylbenzyl or 3-fluoro-4-trifluoromethylbenzyl.

In another exemplary embodiment, the invention is a compound of formula (I):

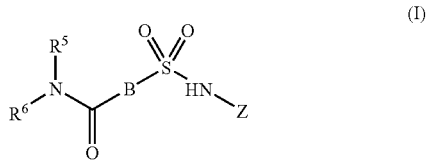

or a pharmaceutically acceptable salt or solvate thereof, wherein: R⁵ and R⁶, when taken together with the nitrogen to which they are attached, are joined to form a fused ring system comprising more than one ring, which is a member selected from tetrahydroindenooxazinyl, dihydroisoquinolinyl, dihydroisoindolyl and octahydromethanoindolyl. This fused ring system is optionally substituted with one or more substituents selected from the group consisting of oxo, halogen, (C₁-C₄)alkyl and aryl. B is aryl or 6-membered heteroaryl, each optionally substituted with one or more substituents selected from the group consisting of halogen, cyano, (C₁-C₄)alkyl, halo(C₁-C₄)alkyl, (C₁-C₄)alkoxy and halo(C₁-C₄)alkoxy. Z is a 5-membered heteroaryl, which is optionally substituted with one or more substituents selected from the group consisting of halogen, cyano, (C₁-C₄)alkyl, halo(C₁-C₄)alkyl, (C₁-C₄)alkoxycarbonyl, (C₁-C₄)alkoxy, halo(C₁-C₄)alkoxy, (C₃-C₈)cycloalkyl, amino, (C₁-C₄)alkylamino and di(C₁-C₄)alkylamino.

In another exemplary embodiment, in any of the embodiments of the previous paragraphs, R⁵ and R⁶, when taken together with the nitrogen to which they are attached, are members selected from (4aR,9aS)-2,3,9,9a-tetrahydroindeno[2,1-b][1,4]oxazin-4(4aH)-yl, (4aS,9aR)-2,3,9,9a-tetrahydroindeno[2,1-b][1,4]oxazin-4(4aH)-yl, 3,4-dihydroisoquinolin-2(1H)-yl, 3,4-dihydroisoquinolin-2(1H)-yl, 5-chloro-1,3-dihydro-2H-isoindol-2-yl, 4-chloro-1,3-dihydro-2H-isoindol-2-yl and (3S,3aR,6R,7aS)-8-oxo-2-phenyloctahydro-1H-3,6-methanoindol-1-yl.

In another exemplary embodiment, the invention is a compound of formula (I):

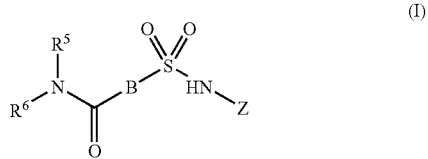

(I)

or a pharmaceutically acceptable salt or solvate thereof, wherein $R^5$ is H. $R^6$ forms a fused ring system which is naphthpyridinyl, isoquinolinyl, 2,3-dihydroindenyl, 6,7-dihydrocyclopenta[b]pyridinyl or 2,3-dihydro-1-benzofuranylmethyl. B is aryl or 6-membered heteroaryl, each optionally substituted with one or more substituents selected from halogen, cyano, $(C_1-C_4)$alkyl, halo$(C_1-C_4)$alkyl, $(C_1-C_4)$alkoxy or halo$(C_1-C_4)$alkoxy. Z is a 5-membered heteroaryl, optionally substituted with one or more substituents selected from halogen, cyano, $(C_1-C_4)$alkyl, halo$(C_1-C_4)$alkyl, $(C_1-C_4)$alkoxycarbonyl, $(C_1-C_4)$alkoxy, halo$(C_1-C_4)$alkoxy, $(C_3-C_8)$cycloalkyl, amino, $(C_1-C_4)$alkylamino or di$(C_1-C_4)$alkylamino.

In another exemplary embodiment, in any of the embodiments of the previous paragraphs, $R^6$ is 1,7-naphthpyridin-8-yl, isoquinolin-1-yl, 2,3-dihydro-1H-inden-1-yl, 6,7-dihydro-5H-cyclopenta[b]pyridin-2-yl, 2,3-dihydro-1H-inden-2-yl or 2,3-dihydro-1-benzofuran-2-ylmethyl.

In another exemplary embodiment, the invention is a compound of formula (I):

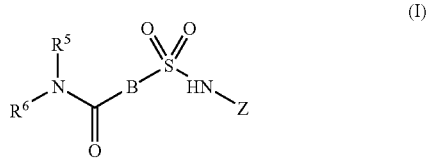

(I)

or a pharmaceutically acceptable salt or solvate thereof, wherein $R^5$ and $R^6$, when taken together with the nitrogen to which they are attached, are joined to form morpholinyl, which is substituted with dihydroisoindolyl$(C_1-C_4)$alkyl, wherein said dihydroisoindolyl$(C_1-C_4)$alkyl is optionally substituted with one or more substituents selected from oxo, halogen, $(C_1-C_4)$alkyl or aryl. B is a member selected from the group consisting of aryl and 6-membered heteroaryl, each optionally substituted with one or more substituents selected from halogen, cyano, $(C_1-C_4)$alkyl, halo$(C_1-C_4)$alkyl, $(C_1-C_4)$alkoxy or halo$(C_1-C_4)$alkoxy. Z is a 5-membered heteroaryl, optionally substituted with one or more substituents selected from halogen, cyano, $(C_1-C_4)$alkyl, halo$(C_1-C_4)$alkyl, $(C_1-C_4)$alkoxycarbonyl, $(C_1-C_4)$alkoxy, halo$(C_1-C_4)$alkoxy, $(C_3-C_8)$cycloalkyl, amino, $(C_1-C_4)$alkylamino or di$(C_1-C_4)$alkylamino.

In another exemplary embodiment, in any of the embodiments of the previous paragraphs, dihydroisoindolyl$(C_1-C_4)$alkyl is 1-oxo-1,3-dihydro-2H-isoindol-2-ylmethyl.

In another exemplary embodiment, in any of the embodiments of the previous paragraphs, halo$(C_1-C_4)$alkyl is monohalo$(C_1-C_4)$alkyl, dihalo$(C_1-C_4)$alkyl or trihalo$(C_1-C_4)$alkyl.

In another exemplary embodiment, in any of the embodiments of the previous paragraphs, halo$(C_1-C_4)$alkoxy is monohalo$(C_1-C_4)$alkoxy, dihalo$(C_1-C_4)$alkoxy or trihalo$(C_1-C_4)$alkoxy.

In another exemplary embodiment, in any of the embodiments of the previous paragraphs, $R^5$ and $R^6$ are each members independently selected from H and a group which is a member selected from $(C_1-C_{10})$alkyl, heteroalkyl, heterocycloalkyl, heterocycloalkyl$(C_1-C_2)$alkyl, $(C_3-C_8)$cycloalkyl, $(C_3-C_8)$cycloalkyl$(C_1-C_2)$alkyl, aryl$(C_1-C_2)$alkyl, aryloxy$(C_1-C_2)$alkyl, arylamino$(C_1-C_2)$alkyl, heteroaryl, heteroarylamino$(C_1-C_2)$alkyl, heteroaryloxy$(C_1-C_2)$alkyl and heteroaryl$(C_1-C_2)$alkyl. Each group is optionally substituted at any suitable point with one or more substituents selected from the group consisting of oxo, halogen, cyano, hydroxy, $(C_1-C_4)$alkyl, halo$(C_1-C_4)$alkyl, $(C_1-C_4)$alkoxy, $(C_1-C_4)$alkoxy$(C_1-C_4)$alkoxy, hydroxy$(C_1-C_4)$alkyl, hydroxy$(C_1-C_4)$alkoxy, halo$(C_1-C_4)$alkoxy, $(C_3-C_8)$cycloalkyl$(C_1-C_4)$alkoxy, amino, $(C_1-C_4)$alkylamino, di$(C_1-C_4)$alkylamino, trifluoromethylthio, $(C_3-C_8)$cycloalkyl, pyrazolyl, pyrazolylmethyl, pyrazolylethyl, phenyl, benzyl, phenethyl, pyridyl, pyridylmethyl, phenoxy, phenoxymethyl, pyridyloxy and pyridyloxymethyl. Each pyrazolyl, pyrazolylmethyl, pyrazolylethyl, phenyl, benzyl, phenethyl, pyridyl, pyridylmethyl, phenoxy, phenoxymethyl, pyridyloxy or pyridyloxymethyl is optionally substituted with halogen, cyano, hydroxy, methyl, methoxy, trifluoromethyl or trifluoromethoxy.

In another exemplary embodiment, any of the compounds in the previous paragraphs, or pharmaceutically acceptable salts or solvates thereof, can be used as a medicament.

In another exemplary embodiment, the invention is a pharmaceutical formulation which includes one or more pharmaceutically acceptable excipients and a compound encompassed by any of the embodiments of the previous paragraphs.

In another exemplary embodiment, the invention is the use of a compound encompassed by any of the embodiments of the previous paragraphs, in the manufacture of a medicament for the treatment of a disease or condition for which a sodium channel modulator is indicated. Exemplary diseases or conditions to be treated include pain, irritable bowel syndrome, Crohn's disease and tachyarrhythmia.

In another exemplary embodiment, a compound encompassed by any of the embodiments of the previous paragraphs, is used in the treatment of pain, irritable bowel syndrome, Crohn's disease and tachyarrhythmia.

In another exemplary embodiment, the invention is the use of a compound encompassed by any of the embodiments of the previous paragraphs, or a pharmaceutically acceptable salt or solvate thereof, in the preparation of a medicament for the treatment of pain, irritable bowel syndrome, Crohn's disease and tachyarrhythmia.

In another exemplary embodiment, the invention provides a method of ameliorating or alleviating a condition in a subject. This condition is pain, irritable bowel syndrome, Crohn's disease and/or tachyarrhythmia. This method includes administering to a subject an amount of a compound encompassed by any of the embodiments of the previous paragraphs, in an amount sufficient to ameliorate or alleviate the condition.

In an exemplary embodiment, the invention is a compound described herein. In an exemplary embodiment, the invention is a compound described in the Examples.

It is understood that the compound of the invention can have a structure as described in Formula I, wherein any Z described herein is independently and optionally combined with any B and $R^5$ and $R^6$ described herein.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within a motif described herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. *Polymeric Drugs and Drug Delivery Systems*, ACS Symposium Series Vol. 469, American Chemical Society, Washington, D.C. 1991.

II. Preparation of the Compounds

Compounds of the present invention can be prepared using readily available starting materials or known intermediates. The synthetic schemes set forth below provide exemplary synthetic pathways for the preparation of compounds of the invention.

II.a. General Procedure for Synthesizing Sulfonamide-Containing Compounds

A general route to sulfamide-containing compounds of the invention can be synthesized as shown in Scheme A.

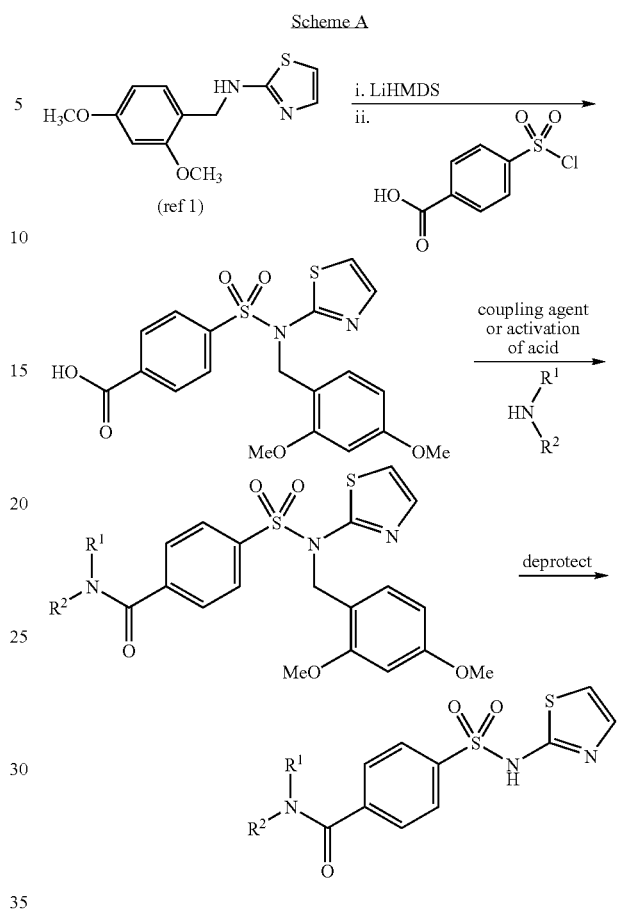

See, (1) Gutierrez et al., *Tetrahedron Letters*, 46(20), 3595-3597 (2005).

An alternate route to sulfonamides of the invention is provided in Scheme B.

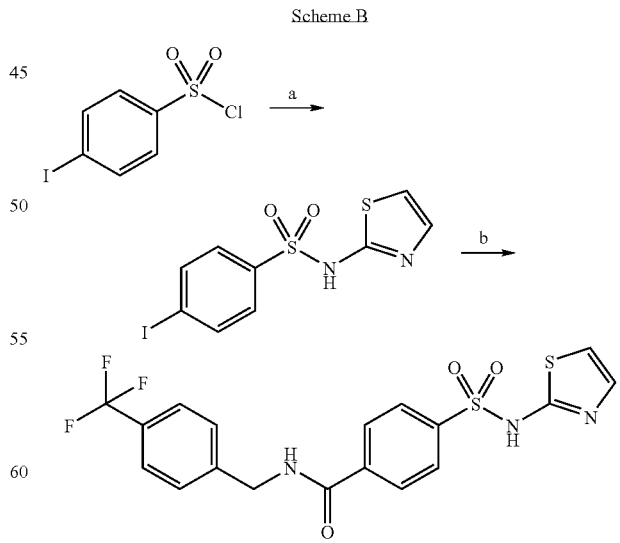

a) 2-aminothiazole (1.1 eq), pyridine; b) 4-(trifluoromethyl)benzylamine (5.0 equiv), hexacarbonylmolybdenum (0.5 equiv), palladium(II) acetate (0.05 equiv), and sodium carbonate (3.0 equiv), water was heated 110° C. via microwave irradiation. Wu et al., *Organometallics* 25, 1434 (2006)

Another route to compounds of the invention is set forth in Scheme C:

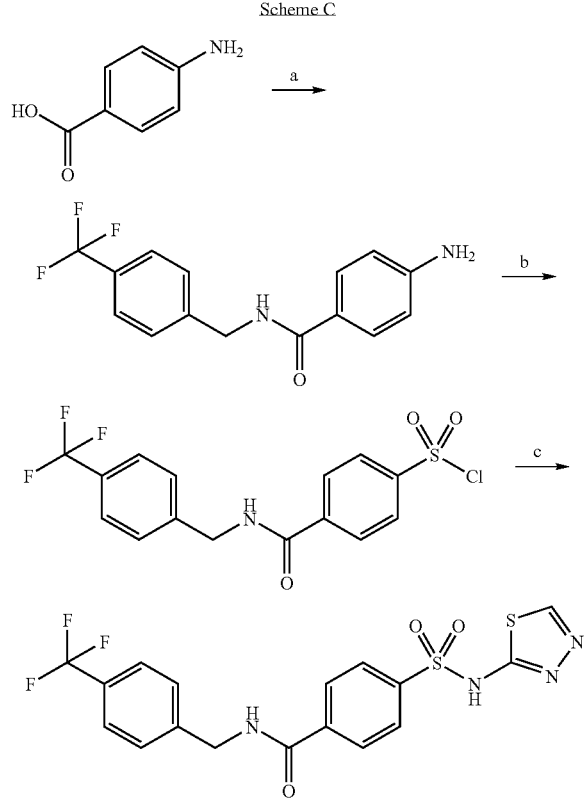

a) i. HBTU (1.0 equiv) anhydrous DMF, 0° C.; ii. N,N-diisopropylethylamine (3.0 equiv); iii. 4-(trifluoromethyl)benzyl-amine (1.2 equiv); b) i. acetonitrile, −5° C., conc. HCl; ii. sodium nitrite (1.1 equiv), H₂O, 0° C.; iii. 0° C. solution of sulfur dioxide (g) in AcOH, copper(II) chloride dihydrate (1.0 equiv); c) CH₂Cl₂, 0° C., 2-amino-1,3,4-thiadiazole (1.1 equiv) in 1.0 mL of anhydrous pyridine.

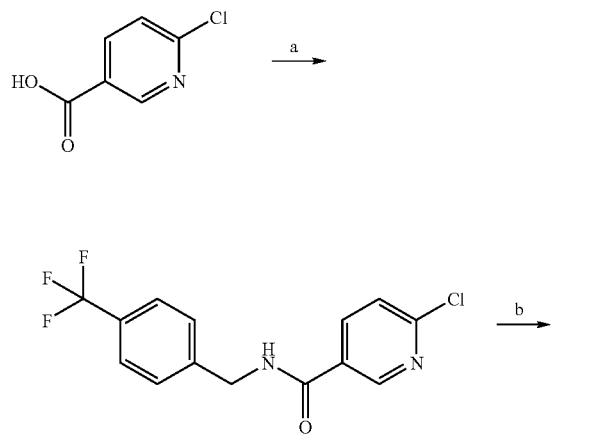

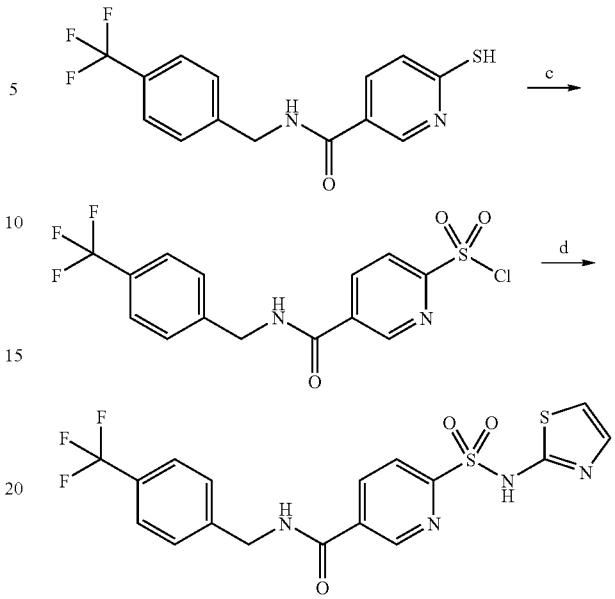

(a) i. DMF at 0° C., HBTU (1.0 equiv); ii. N,N-diisopropylethylamine (3.0 equiv); iii. -(trifluoromethyl)benzylamine (1.2 equiv); b) anhydrous ethanol, thiourea (1.04 equiv.), reflux; ii. cooled to ambient temperature, and an additional thiourea (1 equiv.) was added, reflux; iii. concentrated in vacuo, water, sodium carbonate (0.80 equiv); iv. sodium hydroxide (3.2 equiv, 6 mL H₂O); c) methylene chloride, water, 37% HCl, 10% aqueous solution of sodium hypochlorite (7.9 equiv) added dropwise over 15 min; d) as a solution in methylene chloride add to a 0° C. solution of 2-aminothiazole (1.1 equiv) in anhydrous pyridine.

A further route to compounds of the invention is set forth in Scheme E.

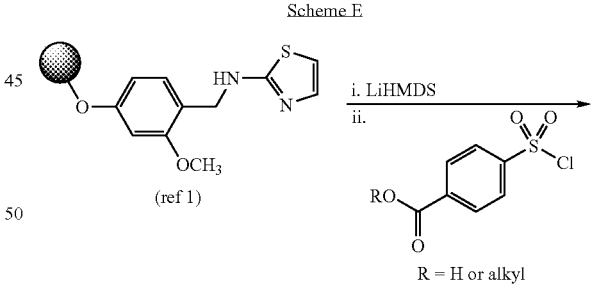

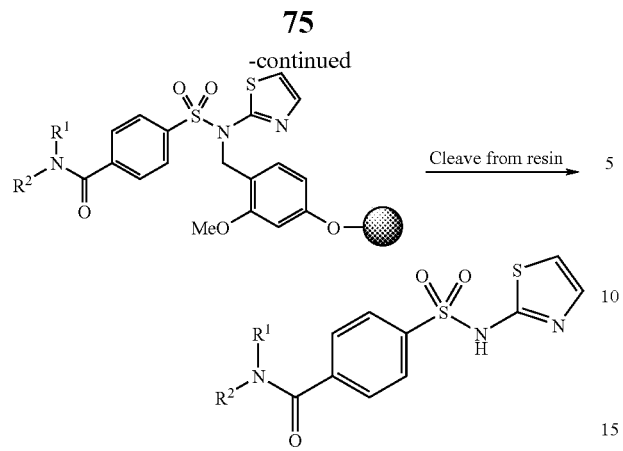

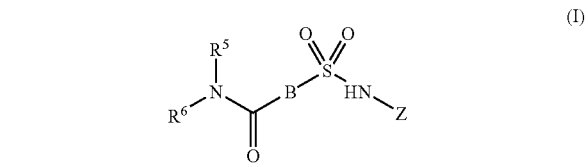

See, (1) Gutierrez et al., *Tetrahedron Letters*, 46(20), 3595-3597 (2005).

The routes below, including those mentioned in the Examples and Preparations, illustrate methods of synthesising the compounds of the invention and/or formula (I). The skilled person will appreciate that the compounds of the invention, and intermediates thereof, could be made by methods other than those specifically described herein, for example by adaptation of the described methods or by modification of methods known in the art. Examples of suitable guides to synthesis, functional group interconversions, use of protecting groups, etc., are: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); "Protecting Groups" by P J, Kocienski, Georg Thieme Verlag (1994); and any updated versions of said standard works.

In the general synthetic methods below, unless otherwise specified, the substituents $R^5$, $R^6$, B and Z are as defined with reference to the compounds of formula (I) above.

Compounds of formula (I) may be prepared from compounds of formula (IV) or (III) by the process illustrated in Scheme 1.

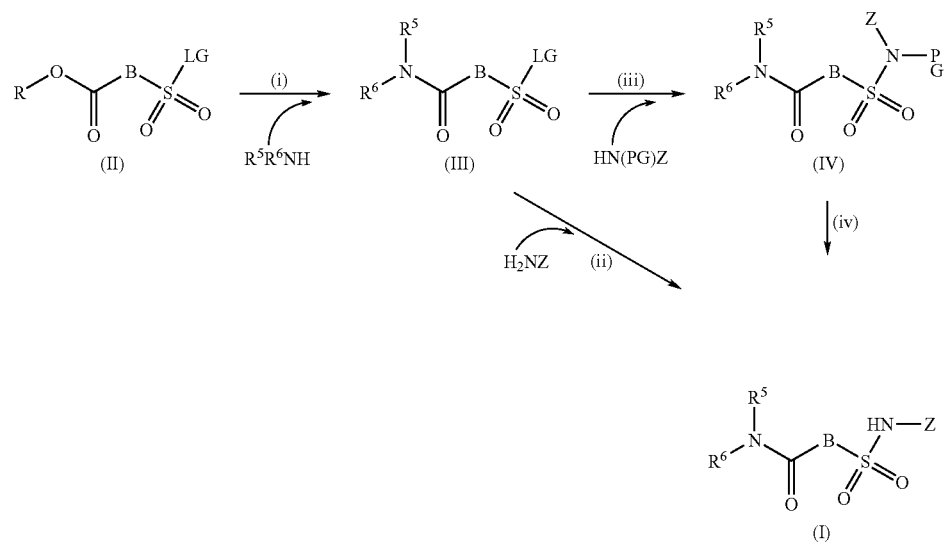

PG=a suitable nitrogen protecting group, preferably 2,4-dimethoxybenzyl
R=H, ($C_1$-$C_{10}$)alkyl, aryl, aryl($C_1$-$C_2$)alkyl
LG=a suitable leaving group for example Cl or OR" where R"=($C_1$-$C_{10}$)alkyl, aryl, aryl($C_1$-$C_2$)alkyl When R is H, compounds of formula (III) may be prepared from compounds of formula (II) according to reaction step (i), an amide coupling between $R^5R^6$NH and the acid chloride formed from compounds of formula (II) in the presence of excess organic base such as triethylamine, pyridine, 2,6-lutidine or Hunig's base, in a suitable solvent, at temperatures of −78° C. to room temperature. The acid chloride may be prepared by reaction of a compound of formula (II) with a suitable agent such as oxalyl chloride-catalytic DMF or thionyl chloride. Typical conditions comprise oxalyl chloride-catalytic DMF in DCM at 0° C.

When LG is OR" a subsequent reaction with the appropriate alcohol R"OH under basic conditions is required. Typical conditions comprise pentafluorophenol in the presence of Et₃N in DCM at room temperature.

Alternatively compounds of formula (III) may be prepared from compounds of formula (XVII), as shown in Scheme 4 illustrated below.

Compounds of formula (I) may be prepared from compounds of formula (III) according to reaction step (ii), displacement of a leaving group with H₂NZ under basic reaction conditions, for example, pyridine, Et₃N, DABCO or Hunig's base, optionally in the presence of a co-solvent such as DCM, at temperatures of 0 to 60° C. Typical conditions comprise reaction in pyridine at room temperature for 16 hours.

able catalyst, or by treatment with 1-chloroethyl chloroformate). Step (iii) is carried out in the presence of a strong base, for example LiHMDS or NaH in a suitable solvent such as THF. Typical conditions comprise LiHMDS in THF at temperatures of −78 to 0° C. Typically PG is 2,4-dimethoxybenzyl.

Compounds of the formula (I) may be prepared from compounds of the formula (IV) according to reaction step (iv), deprotection of the N-protecting group (PG). For example if PG is a benzyl group, it can be readily removed by hydrogenation in the presence of a suitable catalyst or by treatment with 1-chloroethyl chloroformate. When PG=2,4-dimethoxybenzyl typical deprotection conditions comprise HCl in an appropriate solvent such as dioxane, ether, water or TFA in DCM at room temperature.

Compounds of formula (I) may be prepared from compounds of formula (IV) or (VIII) by the process illustrated in Scheme 2.

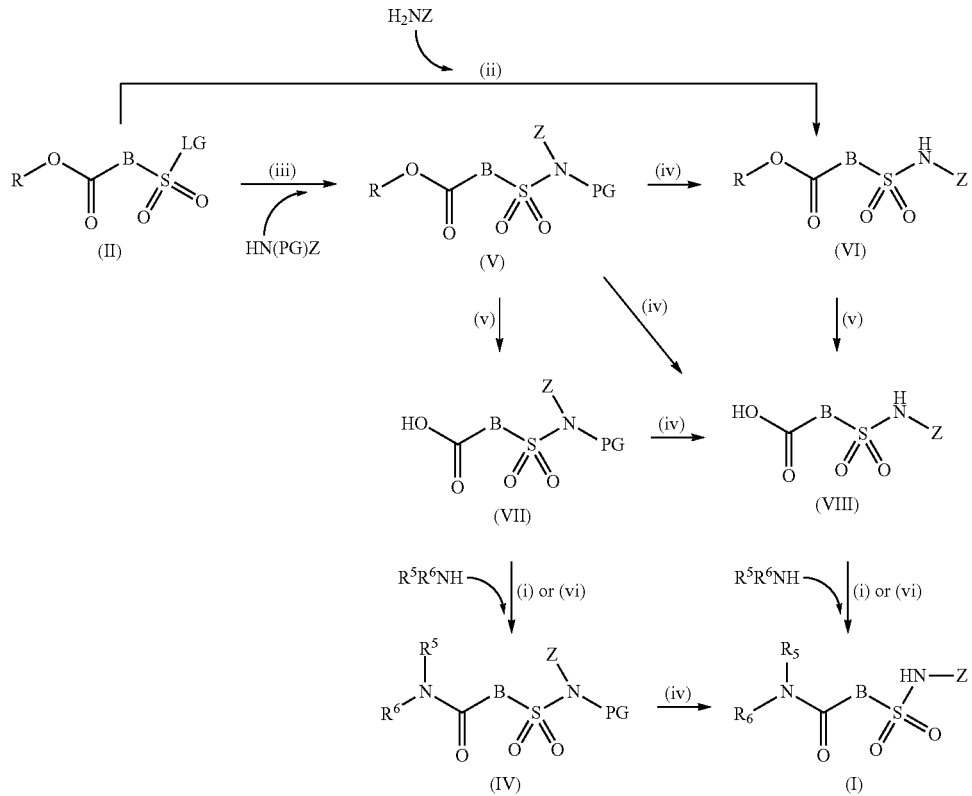

Scheme 2

Compounds of the formula (IV) may be prepared from compounds of the formula (III) according to reaction step (iii), displacement of a leaving group with PG(H)NZ, wherein PG is a suitable N-protecting group. Any suitable nitrogen protecting group may be used (as described in "Protecting Groups in Organic Synthesis" 3rd edition T. W. Greene and P. G. Wuts, Wiley-Interscience, 1999). Common nitrogen protecting groups (PG) suitable for use include tert-butoxycarbonyl (t-Boc) (which is readily removed by treatment with an acid such as TFA or hydrogen chloride in an organic solvent such as DCM or 1,4-dioxane), and benzyl (which is readily removed by hydrogenation in the presence of a suit- PG=a suitable nitrogen protecting group, preferably 2,4-dimethoxybenzyl
R=H, ($C_1$-$C_{10}$)alkyl, aryl, aryl($C_1$-$C_2$)alkyl
LG=a suitable leaving group for example Cl or OR" where R"=H, ($C_1$-$C_{10}$)alkyl, aryl($C_1$-$C_2$)alkyl Compounds of formula (V) can be prepared from compounds of formula (II) according to reaction step (iii) as previously described. Compounds of formula (VI) may be prepared from compounds of formula (V) according to reaction step (iv) as previously described. When R is not H compounds of formula (VI) may be prepared from compounds of formula (II) according to reaction step (ii) as previously described. When R is H compounds of formula (V)=compounds of formula (VII). When R is not H compounds of formula (VII) may be prepared from compounds of formula (V) according to reaction step (v), ester hydrolysis using conventional procedures, typically under aqueous basic conditions, for example in the presence of sodium hydroxide, potassium hydroxide or lithium hydroxide in an inert solvent such as MeOH, EtOH, ethylene glycol, THF, DME, and 1,4-dioxane. Preferred conditions comprise aqueous sodium or lithium hydroxide in dioxane or MeOH at room temperature. When R is H compounds of formula (VIII) can be prepared from compounds of formula (V) according to reaction step (iv) as previously described. When R is H compounds of formula (VI)=compounds of formula (VIII). When R is not H compounds of formula (VIII) can be prepared from compounds of formula (VI) according to reaction step (v) as previously described. Compounds of formula (VIII) can be prepared from compounds of formula (VII) according to reaction step (iv) as previously described.

Compounds of formula (IV) may be prepared from compounds of formula (VII) according to reaction step (i), as previously described, or by reaction step (vi) an amide coupling with $R^5R^6NH$ via activation of the carboxylic acid by a suitable agent such as HBTU, WSCDI or DCC, optionally in the presence of a catalyst for example HOBT or HOAT, and optionally in the presence of a tertiary amine base for example N-methylmorpholine, $Et_3N$ or N,N-diisopropylethylamine in a suitable solvent such as DMF, THF, DMSO, DMA, at 10-40° C. for 0.5-48 hours. Typical conditions comprise activation through TBTU in DCM or DMF in the presence of $Et_3N$ at room temperature for 0.5-16 hours.

Compounds of formula (I) may be prepared from compounds of formula (VIII) according to reaction steps (i) or (vi), as previously described. Compounds of formula (I) may be prepared from compounds of formula (IV) according to reaction step (iv), as previously described.

Compounds of formula (II) may be prepared from compounds of formula (XIV) or (XIII) by the process illustrated in Scheme 3.

LG and LG' are independently a suitable leaving group, for example F, Cl, Br or OR" where
R"=$(C_1-C_{10})$alkyl, aryl, aryl$(C_1-C_2)$alkyl
R H, $(C_1-C_{10})$alkyl, aryl, aryl$(C_1-C_2)$alkyl
G=a group capable of a functional group interconversion to an acid for example $CH_3$, CN Compounds of formula (II) where B=phenyl, 2-chlorophenyl or 3-chlorophenyl are commercially available.

Compounds of the formula (X) are commercially available.

Compounds of formula (XI) may be prepared from compounds of formula (X) according to reaction step (vii), displacement of a leaving group with a sulphur nucleophile for example benzylmercaptan, under basic reaction conditions for example in the presence of potassium carbonate, cesium carbonate or $Et_3N$, in a suitable solvent, for example DMSO, DMF. Typical conditions comprise benzylmercaptan in the presence of cesium carbonate in DMSO at 70-80° C. for 3 hours.

Compounds of formula (XII) may be prepared from compounds of formula (X) according to reaction step (viii) a functional group interconversion to afford an acid. When G is $CH_3$, an oxidation reaction is carried out using an appropriate oxidising agent, for example ceric ammonium nitrate or chromyl chloride. Typical conditions comprise excess potassium permanganate in the presence of excess aqueous KOH at 90° C. for 3-4 hours. When G is CN, a hydrolysis reaction is carried out using conventional procedures, under basic or acidic conditions, for example in the presence of sodium hydroxide and hydrogen peroxide or sulphuric acid. Typical conditions comprise refluxing in concentrated HCl or in NaOH. Alternatively, compounds of formula (XII) may be commercially available.

Compounds of the formula (XIII) may be prepared from compounds of the formula (XII) according to reaction step (vii) or from compounds of the formula (XI) according to reaction step (viii) as previously described.

Compounds of the formula (XIV) may be prepared from compounds of the formula (XII), preferably when R=H,

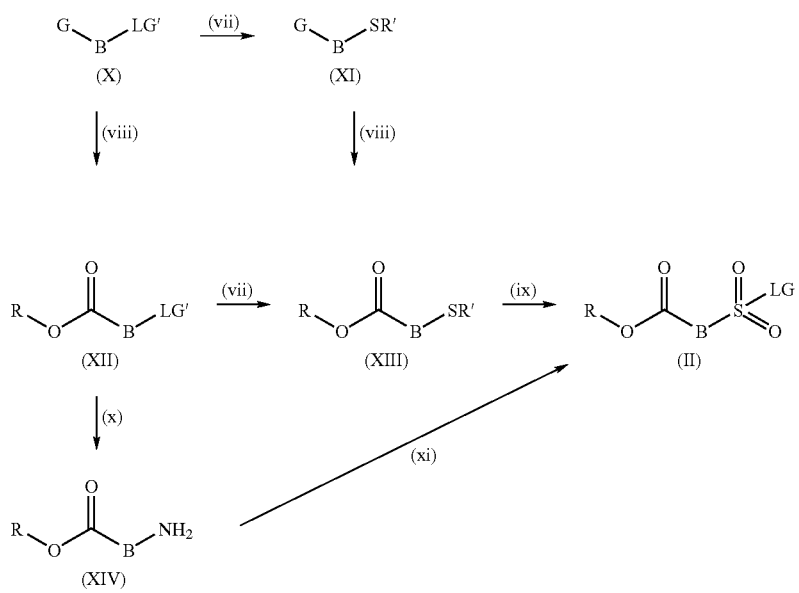

Scheme 3 according to reaction step (x), displacement of LG' with an ammonia source, often at elevated temperatures and pressure. Typical conditions comprise ammonia in MeOH at 180° C. in an autoclave for 3-4 hours.

Compounds of formula (XIV) may be prepared by the skilled person from alternate starting materials for example reduction of the corresponding nitro compound.

Compounds of the formula (II) may be prepared from compounds of the formula (XIV) according to reaction step (xi), a diazotisation using an appropriate source of nitrous acid, for example $H_2SO_4/HNO_3$, followed by displacement of the intermediate diazonium salt with sulphur dioxide in the presence of a copper catalyst and chloride source. Typical conditions comprise sodium nitrite in HCl followed by sulphur dioxide in the presence of copper (I) chloride in AcOH.

When LG is OR", a subsequent reaction with the appropriate alcohol R"OH under basic conditions is required. Typical conditions comprise pentafluorophenol in the presence of $Et_3N$ in DCM at room temperature.

Compounds of formula (II) may be prepared from compounds of formula (XIII) according to reaction step (ix), an oxidation to the sulfonyl chloride using an appropriate agent such as AcOH/chlorine or aq bleach/HCl. Typical conditions comprise aq bleach/HCl at 0° C.

When LG is OR", a subsequent reaction with the appropriate alcohol R"OH under basic conditions is required. Typical conditions comprise pentafluorophenol in the presence of $Et_3N$ in DCM at room temperature.

Compounds of formula (III) may be prepared from compounds of formula (XVII) by the process illustrated in Scheme 4.

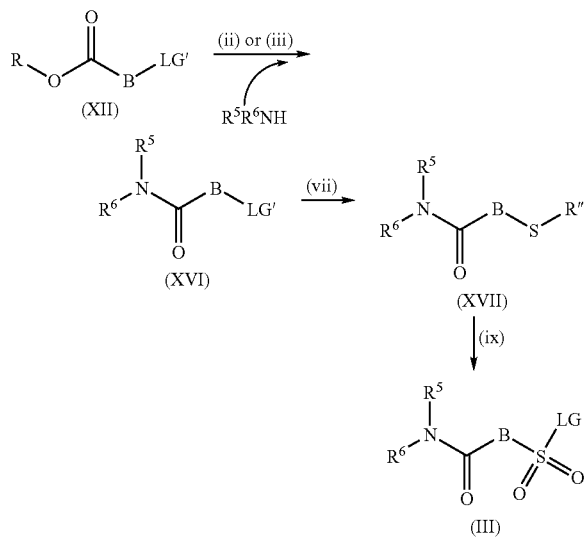

LG'=a suitable leaving group for example F, Cl, Br or OR" where R"=alkyl
R=H, $(C_1-C_{10})$alkyl, aryl, aryl$(C_1-C_2)$alkyl Compounds of the formula (XII) are commercially available or are prepared as described for step (viii) of Scheme 3.

Compounds of the formula (XVI) may be prepared from compounds of the formula (XII) according to reaction step (ii) or (iii) as previously described.

Compounds of the formula (XVII) may be prepared from compounds of the formula (XVI) according to reaction step (vii) as previously described.

Compounds of the formula (III) may be prepared according to reaction step (ix), an oxidation to the sulfonyl chloride using an appropriate agent such as AcOH/chlorine or aqueous bleach/HCl. Typical conditions comprise aqueous bleach/HCl at 0° C. When LG is OR", a subsequent reaction with the appropriate alcohol R" OH under basic conditions is required. Typical conditions comprise pentafluorophenol in the presence of $Et_3N$ in DCM at room temperature.

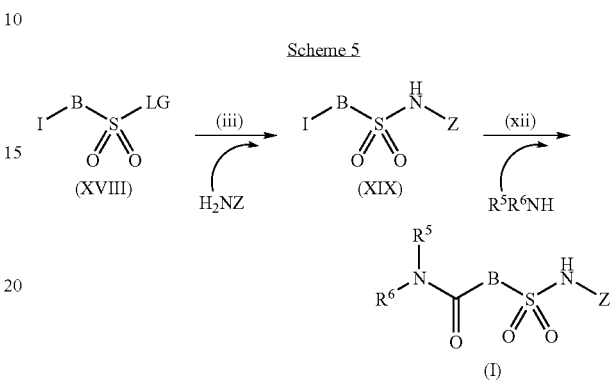

LG=a suitable leaving group for example Cl or OR" where R"=H, $(C_1-C_{10})$alkyl, aryl$(C_1-C_2)$alkyl Compounds of the formula (I) may be prepared from formula (XVIII) according to the process shown in Scheme 5.

Compounds of formula (XIX) may be prepared from compounds of formula (XVIII) using the conditions of step (ii) as previously described.

Compounds of formula (I) may be prepared from compounds of formula (XIX) according to reaction step (xii), a metal-catalyzed carbonyl-insertion amide forming reaction using palladium acetate, hexacarbonylmolybdenum, sodium carbonate, a solvent such as water or dioxane, and microwave irradiation (Wu et al., *Organometallics* 25, 1434 (2006)).

The skilled person will appreciate that many of the aforementioned intermediates could be made by methods other than those specifically described herein, for example by alternate order of reaction steps. For example, compounds of formula (VIII) could be accessed from compounds of the formula (X), by conversion to a sulfonyl chloride and subsequently sulfonamide prior to functional group interconversion to an acid, using the chemical steps already described.

III. Assays for Blockers of Voltage-Dependent TTX-Sensitive Sodium Channels

The activity of sodium channels can be assessed using a variety of in vitro assays, including but not limited to, measuring ion flux, measuring transmembrane potential, and/or measuring ionic current. Measurement of ionic fluxes can be accomplished by measuring changes in the concentration of the permeant species or by tracking the movement of small amounts of an appropriately permeant radioactive tracer. Transmembrane potential can be assessed with voltage-sensitive fluorescent dyes or, more sensitively, with electrophysiological methods.

Determination of the effectiveness of compounds as ex vivo blockers of sodium channels can be assessed by the inhibition of compound action potential propagation in isolated nerve preparations (Kourtney and Stricharz, LOCAL ANESTHETICS, Springer-Verlag, New York, 1987). A number of experimental models in the rat are appropriate for assessing the in vivo efficacy of the compounds of the invention. For example, the neuropathic pain model produced by the tight ligation of spinal nerves, described by Kim et al., *Pain*, 50:

355-363 (1992), can be used to experimentally determine the effect of the compounds of the invention in an in vivo model of pain. Mechanical sensitivity can also be assessed using a procedure described by Chaplan et al., *J. Neurosci. Methods*, 53: 55-63 (1994). Other assays of use are known to those of skill in the art.

Modulators of TTX-sensitive sodium channels can be tested using biologically active recombinant channels, or naturally occurring TTX-sensitive sodium channels, or by using native cells, like neurons expressing a TTX-sensitive sodium current. TTX-sensitive sodium channels can be isolated, co-expressed or expressed in a cell, or expressed in a membrane derived from a cell. In such assays, TTX-sensitive sodium channels are generally expressed alone to form a homomeric sodium channel or may be co-expressed with a second subunit (e.g., an auxiliary beta subunit) so as to form a heteromeric sodium channel. The TTX-sensitive sodium channels are stably expressed in HEK-293 cells, an example of an effective mammalian expression system.

Modulation can be tested using one of the in vitro or in vivo assays described above. Samples or assays that are treated with a potential sodium channel inhibitor are compared to control samples without the test compound, to examine the extent of modulation. Control samples (untreated with inhibitors) are assigned a relative sodium channel activity value of 100. Inhibition of TTX-sensitive sodium channels is achieved when the sodium channel activity value relative to the control is less than 70%, preferably less than 40% and still more preferably, less than 30%. Compounds that decrease the flux of ions will cause a detectable decrease in the ion current density by decreasing the probability of a TTX-sensitive sodium channel being open, by decreasing conductance through the channel, decreasing the number of channels, or decreasing the expression of channels.

Changes in ion flux may be assesed by determining changes in polarization (i.e., electrical potential) of the cell or membrane expressing the sodium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated patch" mode, the "whole cell" mode or other means of controlling or measuring changes in transmembrane potential (see, e.g., Ackerman et al., *New Engl. J. Med.*, 336: 1575-1595 (1997)). Whole cell currents are conveniently determined using the standard methodology (see, e.g., Hamill et al., *Pflugers. Archiv.* 391: 85 (1981). Other known assays include: radiotracer flux assays and fluorescence assays using voltage-sensitive dyes (see, e.g., Vestergarrd-Bogind et al., *J. Membrane Biol.* 88: 67-75 (1988); Daniel et al., *J. Pharmacol. Meth.* 25: 185-193 (1991); Holevinsky et al., *J. Membrane Biology* 137: 59-70 (1994)). Assays for compounds capable of inhibiting or increasing sodium flux through the channel proteins can be performed by application of the compounds to a bath solution in contact with and comprising cells having a channel of the present invention (see, e.g., Blatz et al., *Nature* 323: 718-720 (1986); Park, *J. Physiol.* 481: 555-570 (1994)). Generally, the compounds to be tested are present in the range from about 1 nM to about 100 mM, preferably from about 1 nM to about 30 µM. In an exemplary embodiment, the compounds to be tested are present in the range from about 1 nM to about 3 µM.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or guanidinium ions (see U.S. Pat. No. 5,688,830). The cations can be measured in a variety of standard ways. They can be measured directly by concentration changes of the ions or indirectly by membrane potential or by using radioactive ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is of use in identifying promising candidate compounds of the invention. Physiologically, sodium channels open and close on a millisecond timescale. To overcome the short time in which channels are open the HTS assay can be run in the presence of an agent that modifies the gating of the channel, (e.g., pyrethroids, alpha-scorpion toxins, beta-scorpion toxins, batrachotoxin, etc). These agents modify the gating of sodium channels and keep the pore open for extended periods of time. In addition, while sodium channels are primarily selective for sodium, other ionic species can permeate the channel.

The specificity and effect of the TTX-sensitive sodium channel blocking agents of the invention can also be assayed against non-specific blockers of sodium channels, such as tetracaine, mexilitine, and flecamide.

IV. Pharmaceutical Compositions of VGSC Inhibitors

In another aspect, the present invention provides pharmaceutical compositions comprising a pharmaceutically acceptable excipient and a compound of the invention described herein. In an exemplary embodiment, the invention provides a pharmaceutical formulation comprising a pharmaceutically acceptable excipient and a compound according to a formula described herein. In an exemplary embodiment, the invention provides a pharmaceutical formulation comprising a pharmaceutically acceptable excipient and a compound according to Formula I.

In an exemplary embodiment, a compound of the invention described herein, or a pharmaceutically acceptable salt or solvate thereof, for use as a medicament. In an exemplary embodiment, a compound according to a formula described herein, or a pharmaceutically acceptable salt or solvate thereof, for use as a medicament. In an exemplary embodiment, a compound according to formula I, or a pharmaceutically acceptable salt or solvate thereof, for use as a medicament.

In an exemplary embodiment, the invention provides a pharmaceutical formulation including a compound of the invention described herein, and one or more pharmaceutically acceptable excipients. In an exemplary embodiment, the invention provides a pharmaceutical formulation including a compound according to a formula described herein, and one or more pharmaceutically acceptable excipients. In an exemplary embodiment, the invention provides a pharmaceutical formulation including a compound according to formula I, and one or more pharmaceutically acceptable excipients.

In an exemplary embodiment, the invention provides the use of the compound of the invention described herein, in the manufacture of a medicament for the treatment of a disease or condition for which a sodium channel modulator is indicated, preferably pain, irritable bowel syndrome, Crohn's disease and tachyarrhythmia. In an exemplary embodiment, the invention provides the use of the compound according to a formula described herein, in the manufacture of a medicament for the treatment of a disease or condition for which a sodium channel modulator is indicated, preferably pain, irritable bowel syndrome, Crohn's disease and tachyarrhythmia. In an exemplary embodiment, the invention provides the use of the compound according to formula I, in the manufacture of a medicament for the treatment of a disease or condition for which a sodium channel modulator is indicated, preferably pain, irritable bowel syndrome, Crohn's disease and tachyarrhythmia.

In an exemplary embodiment, the invention provides a compound of the invention described herein, for use in the treatment of pain, irritable bowel syndrome, Crohn's disease and tachyarrhythmia. In an exemplary embodiment, the invention provides a compound according to a formula described herein, for use in the treatment of pain, irritable bowel syndrome, Crohn's disease and tachyarrhythmia. In an exemplary embodiment, the invention provides a compound according to formula I, for use in the treatment of pain, irritable bowel syndrome, Crohn's disease and tachyarrhythmia.

In an exemplary embodiment, the invention provides the use of a compound of the invention described herein, or a pharmaceutically acceptable salt or solvate thereof, in the preparation of a medicament for the treatment of pain, irritable bowel syndrome, Crohn's disease and tachyarrhythmia. In an exemplary embodiment, the invention provides the use of a compound according to a formula described herein, or a pharmaceutically acceptable salt or solvate thereof, in the preparation of a medicament for the treatment of pain, irritable bowel syndrome, Crohn's disease and tachyarrhythmia. In an exemplary embodiment, the invention provides the use of a compound according to formula I, or a pharmaceutically acceptable salt or solvate thereof, in the preparation of a medicament for the treatment of pain, irritable bowel syndrome, Crohn's disease and tachyarrhythmia.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, subdural, epidural, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound described herein, or a pharmaceutically acceptable salt of a compound described herein.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Inhibiting Ion Flow in VGSC

In a third aspect, the invention provides a method of modulating the activity of a voltage-gated sodium channel in a subject or a biological media. This method comprises administering to a subject or biological media an amount of a compound according a formula described herein sufficient to modulate said activity. In an exemplary embodiment, the method comprises administering to a subject or a biological media an amount of a compound described herein sufficient to modulate said activity. This method comprises administering to a subject or a biological media an amount of a compound according a formula described herein sufficient to modulate said activity. In an exemplary embodiment, the method comprises administering to a subject or a biological media an amount of a compound according to Formula I sufficient to modulate said activity. Methods of detecting and amplifying modulation of a sodium channel are generally known in the art. A representative method is set forth herein.

In an exemplary embodiment, the present invention provides methods for decreasing ion flow through voltage gated sodium channels in a cell, comprising contacting a cell containing the target ion channels with a sodium channel-inhibiting amount of a compound described herein.

In an exemplary embodiment, the voltage-gated sodium channel which is substantially inhibited is NaV1.3.

The methods provided in this aspect of the invention are useful for the diagnosis of conditions that can be treated by inhibiting ion flux through voltage gated sodium channels, or for determining if a patient will be responsive to therapeutic agents, which act by inhibiting sodium channels.

Inhibition of NaV.1, NaV1.2, NaV1.3, NaV1.4, NaV1.5, NaV1.6, NaV1.7, NaV1.8 or NaV1.9 activity in a biological media is useful for a variety of purposes that are known to one of skill in the art. Examples of such purposes include, but are not limited to, the study of sodium ion channels in biological and pathological phenomena; and the comparative evaluation of new sodium ion channel inhibitors.

VI. Methods for Treating Conditions Mediated by VGSC

In a fourth aspect, the invention provides a method of ameliorating or alleviating a condition in a subject. The condition can be a member selected from pain, irritable bowel syndrome, Crohn's disease and tachyarrhythmia. In an exemplary embodiment, the method includes administering to the subject an effective amount of a compound described herein and/or according to a formula described herein (for example, formula I) sufficient to ameliorate or alleviate the condition. In a preferred embodiment, the compounds provided herein are used to treat a disorder or condition by inhibiting an ion channel of the VGSC family. In another preferred embodiment, the compounds provided herein are used to treat a disorder or condition by inhibiting NaV1.1 or NaV1.3.

In an exemplary embodiment, the invention provides a method of ameliorating or alleviating a condition in a subject, wherein said condition is a member selected from pain, irritable bowel syndrome, Crohn's disease and tachyarrhythmia, said method including administering to said subject an amount of a compound of the invention described herein, sufficient to ameliorate or alleviate said condition. In an exemplary embodiment, the invention provides a method of ameliorating or alleviating a condition in a subject, wherein said condition is a member selected from pain, irritable bowel syndrome, Crohn's disease and tachyarrhythmia, said method including administering to said subject an amount of a compound of a formula described herein, sufficient to ameliorate or alleviate said condition. In an exemplary embodiment, the invention provides a method of ameliorating or alleviating a condition in a subject, wherein said condition is a member selected from pain, irritable bowel syndrome, Crohn's disease and tachyarrhythmia, said method including administering to said subject an amount of a compound of formula I, sufficient to ameliorate or alleviate said condition.

In an exemplary embodiment, the invention provides a method of ameliorating or alleviating a condition in a subject, wherein said condition is a member selected from pain, irritable bowel syndrome, Crohn's disease and tachyarrhythmia, said method including administering to said subject an amount of a compound of the invention described herein, sufficient to ameliorate or alleviate said condition. In an exemplary embodiment, the invention provides a method of ameliorating or alleviating a condition in a subject, wherein said condition is a member selected from pain, irritable bowel syndrome, Crohn's disease and tachyarrhythmia, said method including administering to said subject an amount of a compound of a formula described herein, sufficient to ameliorate or alleviate said condition. In an exemplary embodiment, the invention provides a method of ameliorating or alleviating a condition in a subject, wherein said condition is a member selected from pain, irritable bowel syndrome, Crohn's disease and tachyarrhythmia, said method including administering to said subject an amount of a compound of Formula I, sufficient to ameliorate or alleviate said condition.

In an exemplary embodiment, the condition is pain, and the pain can be a member selected from acute pain, chronic pain, visceral pain, inflammatory pain and neuropathic pain. Exemplary aspects of this method are described in greater detail herein.

The compounds of the invention are particularly preferred for use in the treating, preventing or ameliorating pain. The method includes administering to a patient in need of such treatment, a therapeutically effective amount of a compound described herein and/or according to a formula described herein, or a pharmaceutically acceptable salt thereof.

The compounds, compositions and methods of the present invention are of particular use in treating pain, including both inflammatory and neuropathic pain. Exemplary forms of pain treated by a compound of the invention include, postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic and idiopathic pain syndromes.

Idiopathic pain is pain of unknown origin, for example, phantom limb pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation and vasculitis. Neuropathic pain is also caused by nerve damage from chronic alcoholism, human immunodeficiency virus infection, hypothyroidism, uremia, or vitamin deficiencies.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound.

Thereafter, the dosage is increased by small increments until the optimum effect under the circumstances is reached. For convenience, the total daily dosage may be divided and administered in portions during the day, if desired.

EXAMPLES

The following examples are offered to illustrate, but not to limit the claimed invention. In the examples below, unless otherwise stated, temperatures are given in degrees Celsius ° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected. The following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIE (diisopropylethylamine). $^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (MS) were recorded using either electrospray ionization (ESI) or atmospheric pressure chemical ionization (APCI). The following abbreviations have been used for common solvents: $CDCl_3$, deuterochloroform; $d_6$-DMSO, deuterodimethylsulphoxide; $CD_3OD$, deuteromethanol; $D_2O$ deuterated water; THF, tetrahydrofuran. LCMS indicates liquid chromatography mass spectrometry (Rt=retention time). Six methods are used, these are shown below:

System 1: LCMS 6 min Run
Basic Run:
A: 0.1% ammonium hydroxide in water
B: 0.1% ammonium hydroxide in acetonitrile
Column: C18 phase Fortis 50×4.6 mm with 5 micron particle size
Gradient: 95-5% A over 3 min, 1 min hold, 1 mL/min
UV: 210 nm-450 nm DAD
Temperature: 50° C.
System 2: 2 minute Run
Acid Run:
A: 0.1% formic acid in water
B: 0.1% formic acid in acetonitrile
Column: C18 phase Fortis Pace 20×2.1 mm with 3 micron particle size
Gradient: 70-2% A over 1.8 min, 0.2 min hold, 1.8 mL/min
UV: 210 nm-450 nm DAD
Temperature: 75° C.
System 3: (Mass Spec)
ESCi: MS
Solvent 20 mM Ammonia 1 minute run
System 4: 6 min Run
Acid Run:
A: 0.1% formic acid in water
B: 0.1% formic acid in acetonitrile
Column: C18 phase Phenomenex Luna 50×4.6 mm with 5 micron particle size
Gradient: 95-5% A over 3 min, 1 min hold, 1 mL/min
UV: 210 nm-450 nm DAD
Temperature: 50° C.
System 5: 5 min Run
Acid Run:
A 0.0375% TFA in water
B 0.01875% TFA in acetonitrile
Column Ymc ODS-AQ 50 mm×2 mm with 5 micron particle size
Gradient: 90-10% A over 4.7 min, 1 min hold, 0.8 mL/min
Temperature: 50° C.
System 6: 5 min Run
Acid Run:
A 0.0375% TFA in water
B 0.01875% TFA in acetonitrile
Column Ymc ODS-AQ 50 mm×2 mm with 5 micron particle size
Gradient: 99-0% A over 4.7 min, 1 min hold, 0.8 mL/min
Temperature: 50° C.
Mass Spectrometer Model: Agilent 1956A
Ionization Mode: API-ES
Polarity: Positive Certain compounds of the Examples and Preparations were purified using Automated Preparative High Performance Liquid Chromatography (HPLC). Samples were submitted dissolved in 1 mL of DMSO. Depending on the nature of the compounds and the results of a pre-analysis, the purification was performed under a number of conditions, these are listed below:

|  | Method a | Method b |
|---|---|---|
| Column | Sunfire C18 | Xterra |
|  | 4.6 × 50 mm id | 4.6 × 50 mm id |
| Temperature | Ambient | Ambient |
| Mobile Phase A | 0.05% formic acid in water | 0.05% ammonia in water |
| Mobile Phase B | 0.05% formic acid in acetonitrile | 0.05% ammonia in acetonitrile |
| Gradient - Initial | 5% B | 5% B |
| Time 0 mins | 5% B | 5% B |
| Time 3 mins | 98% B | 98% B |
| Time 4 mins | 98% B | 98% B |
| Time 4.1 mins | 5% B | 5% B |
| Time 5 mins | 5% B | 5% B |
| Flow rate | 1.5 mL/min | 1.5 mL/min |
| Injection volume | 5 μL | 5 μL |

|  | Method c | Method d |
|---|---|---|
| Column | Ymc ODS-AQ | Luna 5u C18 |
|  | 75 × 30 mm id | 100 × 21.2 mm id |
| Temperature | Ambient | Ambient |
| Mobile Phase A | 0.075% TFA in water (v/v) | 0.075% TFA in water (v/v) |
| Mobile Phase B | 0.075% TFA in acetonitrile (v/v) | 0.075% TFA in acetonitrile (v/v) |
| Gradient - Initial |  |  |
| Time 0 mins |  |  |
| Time 3 mins |  |  |
| Time 4 mins |  |  |
| Time 4.1 mins |  |  |
| Time 5 mins |  |  |
| Flow rate | 30 ml/min | 25 ml/min |
| Injection volume |  |  |

|  | Method e | Method f |
|---|---|---|
| Column | Synergi Hydro-RP | Ymc ODS-AQ |
|  | 100 × 30 mm id | 150 × 30 mm id |
| Temperature | Ambient | Ambient |
| Mobile Phase A | 0.075% TFA in water (v/v) | 0.075% TFA in water (v/v) |
| Mobile Phase B | 0.075% TFA in acetonitrile (v/v) | 0.075% TFA in acetonitrile (v/v) |
| Gradient - Initial |  |  |
| Time 0 mins |  |  |
| Time 3 mins |  |  |
| Time 4 mins |  |  |
| Time 4.1 mins |  |  |
| Time 5 mins |  |  |
| Flow rate | 25 ml/min | 25 ml/min |
| Injection volume |  |  |

|  | Method g | Method h |
|---|---|---|
| Column | Ymc ODS-AQ | Gemini 5u C18 |
|  | 250 × 20 mm 5 um id | 100 × 21.2 mm id |
| Temperature | Ambient | Ambient |
| Mobile Phase A | 0.075% TFA in water (v/v) | 0.05% $NH_4OH$ in water (v/v) |

-continued

| Mobile Phase B | 0.075% TFA in acetonitrile (v/v) | acetonitrile |
|---|---|---|
| Gradient - Initial |  |  |
| Time 0 mins |  |  |
| Time 3 mins |  |  |
| Time 4 mins |  |  |
| Time 4.1 mins |  |  |
| Time 5 mins |  |  |
| Flow rate | 15 ml/min | 25 ml/min |
| Injection volume |  |  |

Example 1

4-{[(5-Chloro-1,3-thiazol-2-yl)amino]sulfonyl}-N-[4-(trifluoromethyl)benzyl]benzamide

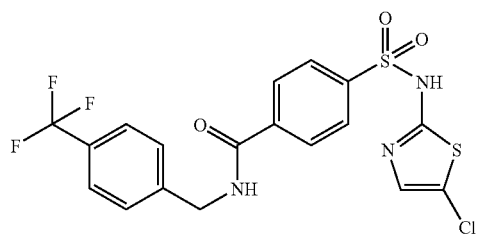 [SMILES: O=C(NCc1ccc(C(F)(F)F)cc1)c1ccc(S(=O)(=O)Nc2ncc(Cl)s2)cc1]

Method A

A solution of 2-amino-5-chlorothiazole hydrochloride (193 mg, 1.1 mmol, 2.1 eq) in pyridine (5 ml) was heated at 50° C. for 10 minutes before the addition of 4-({[4-(trifluoromethyl)benzyl]amino}carbonyl)benzenesulfonyl chloride (Preparation 1, 196 mg, 0.52 mmol, 1 eq) portionwise. The reaction mixture was heated for a further 30 minutes. The solution was added dropwise to a solution of 2M HCl and the resulting precipitate sonicated for 1 hour before being collected by filtration. The crude material was purified by chromatography using an Isco silica cartridge eluting with ethyl acetate then purified further by preparative HPLC to afford the title compound.

Method B 4-({[4-(Trifluoromethyl)benzyl]amino}carbonyl)benzenesulfonyl chloride (Preparation 1, 400 mg, 1 mmol, 1 eq) was added portionwise to a solution of 2-amino-5-chlorothiazole hydrochloride (543 mg, 3.18 mmol, 3 eq) in pyridine (1 ml) and the reaction mixture stirred at room temperature for 18 hours. The solution was added dropwise to a stirred solution 6N HCl and the resulting precipitate sonicated then collected by filtration. The material was purified by chromatography using an Isco silica cartridge eluting with 90:10 DCM:MeOH then further purified by trituration with diethyl ether and ethyl acetate. The title compound was obtained as a pink solid (55 mg, 0.115 mmol, 11%).

$^1$HNMR ($d_6$-DMSO): 4.5 (m, 2H), 7.5 (m, 2H), 7.5 (m, 1H), 7.65 (m, 2H), 7.9 (m, 2H), 8.0 (m, 2H), 9.3 (m, 1H). LCMS Rt=1.51 min. MS m/z 477 [MH]+.

Method C

4-Trifluoromethyl)benzylamine (24 mg, 0.138 mmol, 1.1 eq), Et$_3$N (31 mg, 0.313 mmol, 2.5 eq), 2-(1H-benzotriazol-1-yl)-1,1,1,3,3-tetramethyluronium tetrafluoroborate (TBTU, 48 mg, 0.15 mmol, 1.2 eq) and 4-{[(5-chloro-1,3-thiazol-2-yl)amino]sulfonyl}benzoic acid (Preparation 4, 40 mg, 0.12 mmol, 1 eq) were combined in dimethylformamide (0.5 ml) and the reaction mixture stirred at room temperature for 1 hour. 4M HCl (4 ml) and DCM (1 ml) were added and the mixture stirred for 5 minutes before filtering through a phase separation cartridge. The solvent was removed in vacuo and the residue purified by preparative HPLC to yield the title compound.

Example 2

4-{[(1-Methyl-1H-pyrazol-3-yl)amino]sulfonyl}-N-[4-(trifluoromethyl)benzyl]benzamide

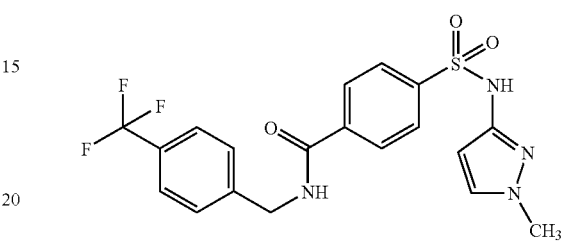

Method D

To an ice cooled solution of 1-methyl-1H-pyrazol-3-amine (14 mg, 0.145 mmol, 1.1 eq) in pyridine (1 ml) was added a solution of 4-({[4-(trifluoromethyl)benzyl]amino}carbonyl)benzenesulfonyl chloride (Preparation 1, 50 mg, 0.13 mmol, 1 eq) in DCM (1 ml) dropwise and the resulting reaction mixture stirred at room temperature for 72 hours. The reaction mixture was diluted with DCM then acidified to pH 3 with a 10% aqueous solution of citric acid. The organic phase was collected by filtration through a phase separation cartridge and the solvent evaporated in vacuo. The crude material was purified by preparative HPLC to afford the title compound.

LCMS Rt=2.45 min. MS m/z 439 [MH]+.

Example 3

4-{[(3-Methylisoxazol-5-yl)amino]sulfonyl}-N-[4-(trifluoromethyl)benzyl]benzamide

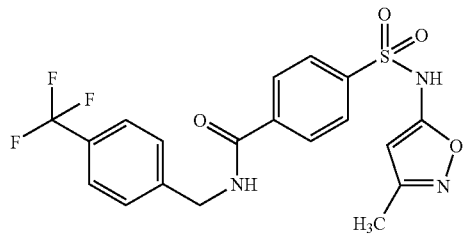 [SMILES: Cc1cc(NS(=O)(=O)c2ccc(C(=O)NCc3ccc(C(F)(F)F)cc3)cc2)on1]

Method E

To a solution of 5-amino-3-methylisoxazole (15 mg, 0.159 mmol, 1 eq) in pyridine (0.5 ml) stirring at 40° C. was added a solution of 4-({[4-(trifluoromethyl)benzyl]amino}carbonyl)benzenesulfonyl chloride (Preparation 1, 60 mg, 0.16 mmol, 1 eq) in DCM (0.5 ml) and the reaction mixture heated for 2 hours. The mixture was added to a stirred solution of 6M HCl, extracted into ethyl acetate, passed through a phase separation cartridge and evaporated. The crude residue was purified by preparative HPLC to yield the title compound.

LCMS Rt=3.89. MS m/z 440 [MH]+.

Example 4

N-[4-(Trifluoromethyl)benzyl]-4-([[4-(trifluoromethyl)-1,3-thiazol-2-yl]amino]sulfonyl)benzamide

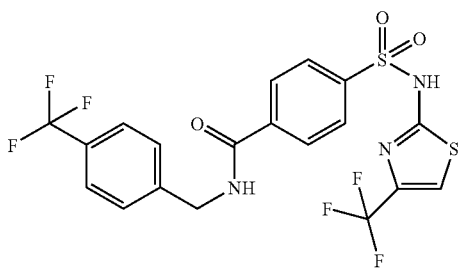 [SMILES: O=C(NCc1ccc(C(F)(F)F)cc1)c1ccc(S(=O)(=O)Nc2nc(C(F)(F)F)cs2)cc1]

Method F

A solution of 2-amino-4-(trifluoromethyl)thiazole (280 mg, 1.665 mmol, 2.5 eq) in pyridine (5 ml) was heated at 65° C. for 10 minutes before the addition of 4-({[4-((trifluoromethyl)benzyl]amino}carbonyl)benzenesulfonyl chloride (Preparation 1, 250 mg, 0.662 mmol, 1 eq). The reaction mixture was heated for 30 minutes then slowly added to a 2M solution of HCl. The resultant precipitate was collected by filtration then further purified by preparative HPLC to yield the title compound.

LCMS Rt=2.37-2.43 min. MS m/z 510 [MH]+.

Example 5

N-[4-(trifluoromethyl)benzyl]-4-({[5-(trifluoromethyl)-1,3,4-thiadiazol-2-yl]amino}sulfonyl)benzamide

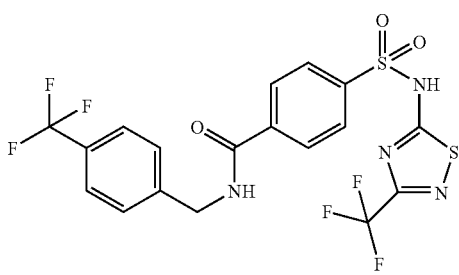 [SMILES: O=C(NCc1ccc(C(F)(F)F)cc1)c1ccc(S(=O)(=O)Nc2nc(C(F)(F)F)ns2)cc1]

Method G

To a solution of 5-amino-5-trifluoromethyl-1,3,4-thiadiazole (168 mg, 0.995 mmol, 5 eq) and 4-dimethylaminopyridine (26.8 mg, 0.219 mmol, 1.1 eq) in pyridine (1 ml) was added 4-({[4-((trifluoromethyl)benzyl]amino}carbonyl)benzenesulfonyl chloride (Preparation 1, 75 mg, 0.2 mmol, 1 eq) portionwise and the reaction mixture stirred at room temperature for 1 hour. 2N HCl was added and the reaction mixture extracted into ethyl acetate. A precipitate formed which was collected by filtration. The crude material was purified by preparative HPLC to yield the title compound.

LCMS Rt=4.58 min. MS m/z 511 [MH]+.

Example 6

4-{[(3-Methyl-1,2,4-thiadiazol-5-yl)amino]sulfonyl}-N-[4-(trifluoromethyl)benzyl]benzamide

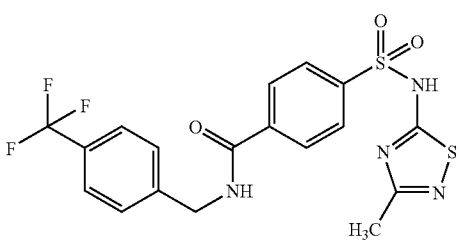 [SMILES: Cc1nsc(NS(=O)(=O)c2ccc(C(=O)NCc3ccc(C(F)(F)F)cc3)cc2)n1]

Method H

3-Methyl-1,2,4-thiadiazol-5-amine (153 mg, 1.3 mmol, 2.5 eq) was dissolved in dioxane (3 ml), a solution of sodium hydroxide (53 mg, 1.32 mmol, 2.5 eq) in water (1 ml) was added and the reaction mixture stirred at room temperature for 10 minutes. 4-({[4-((Trifluoromethyl)benzyl]amino}carbonyl)benzenesulfonyl chloride (Preparation 1, 200 mg, 0.529 mmol, 1 eq) was added portionwise and the reaction mixture stirred at room temperature for 2 hours. The mixture was dropped into 2M HCl (10 ml) and the resultant precipitate collected by filtration and washed with water to yield the title compound as a white solid (65 mg, 0.142 mmol, 26%).

$^1$HNMR (d$_6$-DMSO): 2.15 (s, 3H), 4.55 (d, 2H), 7.55 (d, 2H), 7.70 (d, 2H), 7.90 (d, 2H), 8.05 (d, 2H), 9.25 (t, 1H). LCMS Rt=1.51 min. MS m/z 456 [M−H]−.

The following examples of the general formula

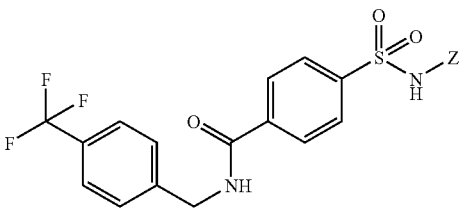

were prepared by Method D, E, F, G or H as described for Examples 2, 3, 4, 5 and 6 above. Unless otherwise noted, preparation details are as described for the method referred to.

TABLE 1

| Example | Name | Z | Data | Preparation Information |
|---|---|---|---|---|
| 7 | 4-[(Isoxazol-3-ylamino)sulfonyl]-N-[4-(trifluoromethyl)benzyl]benzamide | 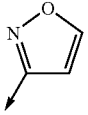 | LCMS Rt = 2.14 min MS m/z 426 [MH]+ | Method D, using 3-amino isoxazole |
| 8 | 4-{[(2-Methyl-2H-tetrazol-5-yl)amino]sulfonyl}-N-[4-(trifluoromethyl)benzyl]benzamide | 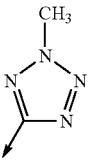 | LCMS Rt = 2.08 min MS m/z 441 [MH]+ | Method D, using 2-methyl-5-amino-2H-tetrazole. Stirred at room temperature for 1 hour. Reaction worked up with water. |
| 9 | 4-{[(1-Methyl-1H-1,2,4-triazol-3-yl)amino]sulfonyl}-N-[4-(trifluoromethyl)benzyl]benzamide | 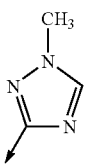 | LCMS Rt = 2.97 min MS m/z 440 [MH]+ | Method D, using 1-methyl-1H-1-methyl-1H-[1,2,4]triazol-3-ylamine. Stirred at room temperature for 1 hour. Reaction worked up with water. |
| 10 | 4-{[(1-Methyl-1H-pyrazol-4-yl)amino]sulfonyl}-N-[4-(trifluoromethyl)benzyl]benzamide | 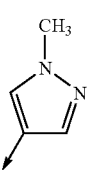 | LCMS Rt = 3.13 min MS m/z 439 [MH]+ | Method D using 1-methyl-1H-pyrazol-4-ylamine dihydrochloride. Stirred at room temperature for 1 hour. Reaction worked up with water. |
| 11 | 4-{[(5-Methyl-1,3,4-thiadiazol-2-yl)amino]sulfonyl}-N-[4-(trifluoromethyl)benzyl]benzamide | 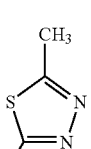 | LCMS Rt = 3.20 min MS m/z 457 [MH]+ | Method D, using 2-amino-5-methyl-1,3,4-thiadiazole. 1.2 eq of 1,1,1,3,3,3-hexanemethyl-disilazane lithium salt (LiHMDS, 1 M in THF) was added. Stirred at room temperature for 1 hour. Reaction worked up with water. |
| 12 | 4-{[(3,4-Dimethylisoxazol-5-yl)amino]sulfonyl}-N-[4-(trifluoromethyl)benzyl]benzamide | 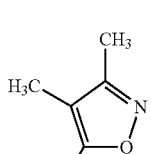 | LCMS Rt = 2.16 min (ELSD) MS m/z 454 [MH]+ | Method D, using 5-amino-3,4-dimethylisoxazole. Reaction was stirred for 18 hours. Reaction was worked up with 6 M HCl resulting in a precipitate which was collected by filtration and further purified by preparative HPLC |

TABLE 1-continued

| Example | Name | Z | Data | Preparation Information |
|---|---|---|---|---|
| 13 | 4-[(1,3-Thiazol-4-yl amino)sulfonyl]-N-[4-(trifluoromethyl)benzyl] benzamide | 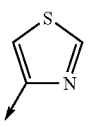 | LCMS Rt = 3.35-3.40 MS m/z 442 [MH]+ | Method F, using 4-thiazolamine. Reaction heated for 60 minutes then added to 6 M HCl. Resultant precipitate was extracted from 2 M HCl into ethyl acetate then washed with a solution of sodium hydrogen carbonate before purification by preparative HPLC. |
| 14 | 4-[(1,3-Thiazol-5-yl amino)sulfonyl]-N-[4-(trifluoromethyl)benzyl] benzamide | 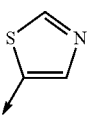 | LCMS Rt = 3.17-3.24 min MS m/z 442 [MH]+ | Method F, using 5-thiazolamine. Reaction heated for 60 minutes. Reaction added to 6 N HCl then extracted into ethyl acetate and washed with a saturated sodium hydrogen carbonate solution. |
| 15 | 4-{[(2-Methyl-1,3-thiazol-4-yl)amino]sulfonyl}-N-[4-(trifluoromethyl)benzyl] benzamide | 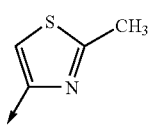 | LCMS Rt = 3.38-3.45 min MS m/z 456 [MH]+ | Method F, using 2-methyl-4-thiazolamine. Reaction heated for 60 minutes. Reaction added to 6 N HCl then extracted into ethyl acetate and washed with a saturated sodium hydrogen carbonate solution |
| 16 | 4-{[(2-Methyl-1,3-thiazol-5-yl)amino]sulfonyl}-N-[4-(trifluoromethyl)benzyl] benzamide | 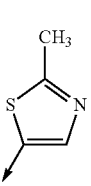 | LCMS Rt = 3.25-3.29 min MS m/z 456 [MH]+ | Method F, using 2-methyl-5-thiazolamine. Reaction heated for 60 minutes. Reaction added to 6 N HCl then extracted into ethyl acetate and washed with a saturated sodium hydrogen carbonate solution |

TABLE 1-continued

| Example | Name | Z | Data | Preparation Information |
|---|---|---|---|---|
| 17 | Methyl 2-({[4-({[4-(trifluoromethyl)benzyl]amino}carbonyl)phenyl]sulfonyl}amino)-1,3-thiazole-4-carboxylate | | LCMS Rt = 3.37-3.41 min MS m/z 500 [MH]+ | Method F, using methyl 2-amino-1,3-thiazole-4-carboxylate. Reaction heated for 60 minutes. Reaction added to 6 N HCl then extracted into ethyl acetate and washed with a saturated sodium hydrogen carbonate solution |
| 18 | 4-{[(5-Methylisoxazol-3-yl)amino]sulfonyl}-N-[4-(trifluoromethyl)benzyl]benzamide | | LCMS Rt = 2.11 min MS m/z 440 [MH]+ | Method D, using 3-amino-5-methylisoxazole. Reaction stirred for 18 hours. Reaction added to 6 N HCl, precipitate forms which was collected by filtration. |
| 19 | 4-{[(3-Ethyl-1,2,4-thiadiazol-5-yl)amino]sulfonyl}-N-[4-(trifluoromethyl)benzyl]benzamide | | LCMS Rt = 1.58 min MS m/z 470 [MH]+ $^1$HNMR (d$_4$-MeOD): 1.3 (t, 3 H), 2.65 (q, 2 H), 4.6 (s, 2 H), 7.55 (m, 2 H), 7.6 (m, 2 H), 7.95 (m, 4 H), 9.2 (m, 1 H). | Method F, using 5-amino-3-ethyl-1,2,4-thiadiazole. Reaction heated for 4 hours then dropped into 6 N HCl. Crude material was purified by trituration with DCM. |
| 20 | 4-[(1,2,4-Thiadiazol-5-ylamino)sulfonyl]-N-[4-(trifluoromethyl)benzyl]benzamide | | LCMS Rt = 4.17 min MS m/z 441 [M − H]− $^1$HNMR (d$_6$-DMSO): 4.5 (s, 2 H), 7.5 (m, 2 H), 7.65 (m, 2 H), 7.9 (m, 2 H), 8.0 (m, 2 H), 8.4 (s, 1 H), 9.35 (m, 1 H). | Method H using 5-amino-1,2,4-thiadiazole. |

TABLE 1-continued

| Example | Name | Z | Data | Preparation Information |
|---|---|---|---|---|
| 21 | 4-[1,3,4-Thiadiazol-2-ylamino)sulfonyl]-N-[4-(trifluoromethyl)benzyl]benzamide | 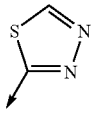 | LCMS Rt = 1.40 min MS m/z [MH]+ $^1$HNMR (d$_6$-DMSO): 4.5 (s, 2 H), 7.5 (m, 2 H), 7.7 (m, 2 H), 7.9 (m, 2 H), 8.0 (m, 2 H), 8.8 (s, 1 H), 9.3 (m, 1 H). | Method D using 2-amino-1,3,4-thiadiazole. Reaction mixture stirred at room temperature for 1 hour. Crude material purified by column chromatography eluting with 90:10 DCM:MeOH. |

The following examples of the general formula

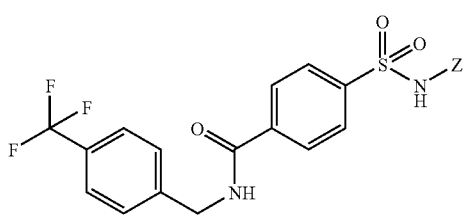

were prepared by the following method using the indicated amines:

25

To a 0.15M solution of 4-({[4-(trifluoromethyl)benzyl]amino}carbonyl)benzenesulfonyl chloride (Preparation 1, 0.75 mmol, 1 eq) in dimethylformamide (0.5 ml) was added an amine (0.1 mmol, 1.3 eq) and diisopropylethylamine (0.75 mmol, 1 eq). The reaction mixture was sealed and shaken at 30° C. for 16 hours. The solvent was evaporated in vacuo and the residue purified by preparative HPLC to yield the title compound.

TABLE 2

| Example | Name | Z | Data | Preparation Information |
|---|---|---|---|---|
| 22 | 4-{[(5-Methyl-1,3-thiazol-2-yl)amino]sulfonyl}-N-[4-(trifluoromethyl)benzyl]benzamide | 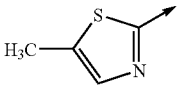 | LCMS Rt = 2.929 min MS m/z 456 [MH]+ | using 5-methyl-1,3-thiazol-2-amine |
| 23 | 4-[(Isoxazol-4-ylamino)sulfonyl]-N-[4-(trifluoromethyl)benzyl]benzamide | 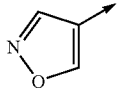 | LCMS Rt = 3.188 min MS m/z 426 [MH]+ | using 4-Isoxazolamine |
| 24 | 4-[(1H-Pyrazol-5-ylamino)sulfonyl]-N-[4-(trifluoromethyl)benzyl]benzamide | 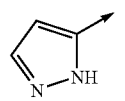 | LCMS Rt = 3.121 min MS m/z 425 [MH]+ | using 1H-pyrazol-4-amine |
| 25 | 4-{[(2-Ethyl-2H-1,2,3-triazol-4-yl)amino]sulfonyl}-N-[4-(trifluoromethyl)benzyl]benzamide | 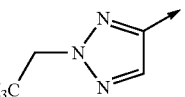 | LCMS Rt = 3.237 min MS m/z 454 [MH]+ | using 2-ethyl-2H-1,2,3-triazol-4-amine |

TABLE 2-continued

| Example | Name | Z | Data | Preparation Information |
|---|---|---|---|---|
| 26 | 4-{[(3,5-Dimethylisoxazol-4-yl)amino]sulfonyl}-N-[4-(trifluoromethyl)benzyl]benzamide | 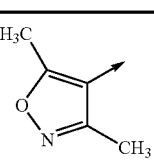 | LCMS Rt = 3.26 min MS m/z 454 [MH]+ | using 3,5-Dimethyl-isoxazol-4-ylamine |
| 27 | N-[4-(Trifluoromethyl)benzyl]-4-{[(1,3,5-trimethyl-1H-pyrazol-4-yl)amino]sulfonyl}benzamide | 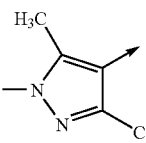 | LCMS Rt = 3.079 min MS m/z 467 [MH]+ | using 1,3,5-trimethyl-1H-pyrazol-4-amine |

The following examples of the general formula

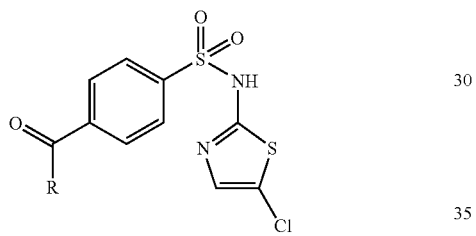

were prepared by Method C as described for Example 1 above. Unless otherwise noted, preparation details are as described for the method referred to.

TABLE 3

| Example | Name | R | Data | Preparation Information |
|---|---|---|---|---|
| 28 | 4-{[(5-Chloro-1,3-thiazol-2-yl)amino]sulfonyl}-N-[3-(trifluoromethyl)benzyl]benzamide | 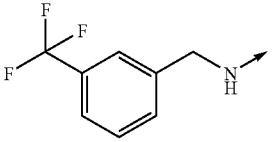 | LCMS Rt = 3.39 min MS m/z 476 [MH[+ | Method C, using 3-(trifluoromethyl)benzylamine. |
| 29 | 4-{[(5-Chloro-1,3-thiazol-2-yl)amino]sulfonyl}-N-[3-(trifluoromethoxy)benzyl]benzamide | 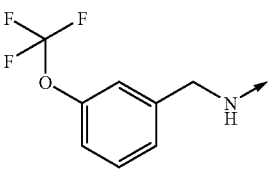 | LCMS Rt = 3.46 min MS m/z 492 [MH[+ | Method C, using 3-(trifluoromethoxy)benzylamine |

TABLE 3-continued

| Example | Name | R | Data | Preparation Information |
|---|---|---|---|---|
| 30 | 4-{[(5-Chloro-1,3-thiazol-2-yl)amino]sulfonyl}-N-[3-chloro-4-(trifluoromethyl)benzyl]benzamide | | $^1$HNMR (d$_6$-DMSO): 4.6 (s, 2 H), 7.45 (m, 1 H), 7.55 (s, 1 H), 7.65 (s, 1 H), 7.8 (m, 1 H), 7.9 (m, 2 H), 8.0 (m, 2 H), 9.35 (m, 1 H). LCMS Rt = 3.23 min MS m/z 509 [MH]+ | Method C, using 3-chloro-4-(trifluoromethyl)benzylamine. Compound was purified by trituration with water. |
| 31 | 4-{[(5-Chloro-1,3-thiazol-2-yl)amino]sulfonyl}-N-[3-fluoro-4-(trifluoromethyl)benzyl]benzamide | | LCMS Rt = 3.55 min MS m/z 494 [MH]+ $^1$HNMR (d$_6$-DMSO (4.55 (d, 2 H), 7.34 (d, 1 H), 7.42 (d, 1 H), 7.52 (s, 1 H), 7.73 (t, 1 H), 7.89 (d, 2 H), 8.01 (d, 2 H), 9.31 (t, NH) | Method C, using 3-fluoro-4-(trifluoromethyl)benzylamine. |
| 32 | 4-{[(5-Chloro-1,3-thiazol-2-yl)amino]sulfonyl}-N-[4-fluoro-3-(trifluoromethyl)benzyl]benzamide | | LCMS Rt = 3.49 min MS m/z 510 [MH]+ $^1$HNMR (d$_6$-DMSO 4.48 (d, 2 H), 7.40 (m, 1 H), 7.44 (d, 1 H), 7.48 (m, 1 H), 7.54 (s, 1 H), 7.88 (d, 2 H), 7.99 (d, 2 H), 9.25 (t, NH) | Method C, using 4-fluoro-3-(trifluoromethoxy)benzylammine. |

TABLE 3-continued

| Example | Name | R | Data | Preparation Information |
|---|---|---|---|---|
| 33 | 4-{[(5-Chloro-1,3-thiazol-2-yl)amino]sulfonyl}-N-(3,4-difluorobenzyl)benzamide | 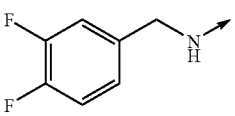 | LCMS Rt = 3.33 min MS m/z 444 [MH]+ $^1$HNMR (d$_6$-DMSO): 4.44 (d, 2 H), 7.15 (m, 1 H), 7.35 (m, 2 H), 7.54 (s, 1 H), 7.89 (d, 2 H), 8.00 (d, 2 H), 9.23 (t, NH) | Method C, using 3,4-difluoro benzylamine |
| 34 | 4-{[(5-Chloro-1,3-thiazol-2-yl)amino]sulfonyl}-N-[4-fluoro-3-(trifluoromethyl)benzyl]benzamide | 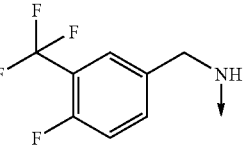 | LCMS Rt = 3.11 min MS m/z 494 [MH]+ | Method C, using 4-fluoro-3-trifluoromethyl)benzylamine. |
| 35 | 4-{[(5-Chloro-1,3-thiazol-2-yl)amino]sulfonyl}-N-(3,4-dichlorobenzyl)benzamide | 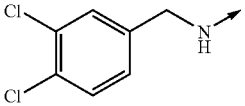 | LCMS Rt = 3.16 min MS m/z 478 [MH]+ | Method C, using 3,4-dichloro benzylamine. |
| 36 | N-(3-Chloro-4-fluorobenzyl)-4-{[(5-chloro-1,3-thiazol-2-yl)amino]sulfonyl}benzamide | 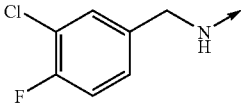 | LCMS Rt = 3.37 min MS m/z 460 [MH]+ $^1$HNMR (d$_6$-DMSO): 4.44 (d, 2 H), 7.33 (m, 2 H), 7.52 (m, 2 H), 7.87 (d, 2 H), 8.00 (d, 2 H), 9.23 (t, NH) | Method C, using 3-chloro-4-fluoro benzylamine. |
| 37 | N-(4-Chloro-3-fluorobenzyl)-4-{[(5-chloro-1,3-thiazol-2-yl)amino]sulfonyl}benzamide | 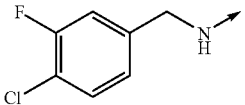 | LCMS Rt = 3.4 min MS m/z 460 [MH]+ $^1$HNMR (d$_6$-DMSO): 4.46 (d, 2 H), 7.18 (d, 1 H), 7.33 (d, 1 H), 7.51 (d, 1 H), 7.55 (s, 1 H), 7.88 (d, 2 H), 8.00 (d, 2 H), 9.25 (t, NH) | Method C, using 4-chloro-3-fluoro benzylamine. |

TABLE 3-continued

| Example | Name | R | Data | Preparation Information |
|---|---|---|---|---|
| 38 | 4-{[(5-Chloro-1,3-thiazol-2-yl)amino]sulfonyl}-N-[3-fluoro-4-(trifluoromethoxy benzyl]benzamide | | LCMS Rt = 2.41 min MS m/z 510 [MH]+ $^1$HNMR (d$_6$-DMSO): 4.49 (d, 2 H), 7.24 (d, 1 H), 7.43 (d, 1 H), 7.50 (m, 1 H), 7.55 (s, 1 H), 7.88 (d, 2 H), 8.01 (d, 2 H), 9.26 (t, NH) | Method C, using 3-fluoro-4-(trifluoromethoxy) benzylamine. 2 M HCl added and the reaction mixture extracted into ethyl acetate then dried over sodium sulphate. |
| 39 | 4-{[(5-Chloro-1,3-thiazol-2-yl)amino]sulfonyl}-N-[2-fluoro-4-(trifluoromethyl) benzyl]benzamide | | LCMS Rt = 1.58 min MS m/z 493 [MH]+ (d$_6$-DMSO): 4.55 (s, 2 H), 7.6 (m, 3 H), 7.65 (m, 1 H), 7.9 (d, 2 H), 8.0 (d, 2 H), 9.3 (m, 1 H). | Method C, using 2-fluoro-4-(trifluoromethyl) benzylamine. Reaction stirred at room temperature overnight. Reaction mixture was extracted from water into ethyl acetate, washed with saturated sodium hydrogen carbonate and dried over sodium sulphate. Crude material was purified by column chromatography eluting with DCM: MeOH (95:5). |
| 40 | 4-{[(5-Chloro-1,3-thiazol-2-yl)amino]sulfonyl}-N-[2-fluoro-3-(trifluoromethyl) benzyl]benzamide | | LCMS Rt = 1.55 min MS m/z 493 [MH]+ $^1$HNMR (d$_6$-DMSO): 4.6 (s, 2 H), 7.4 (m, 1 H), 7.6 (s, 1 H), 7.7 (m, 2 H), 7.9 (m, 2 H), 8.0 (m, 2 H), 9.3 (m, 1 H). | Method C, using 2-fluoro-3-(trifluoromethyl) benzylamine. Reaction stirred at room temperature overnight. Reaction mixture was extracted from water into ethyl acetate, washed with saturated sodium hydrogen carbonate and dried over sodium sulphate. Crude material was purified by column chromatography eluting with DCM: MeOH (95:5). |

TABLE 3-continued

| Example | Name | R | Data | Preparation Information |
|---|---|---|---|---|
| 41 | 4-{[(5-Chloro-1,3-thiazol-2-yl)amino]sulfonyl}-N-methyl-N-[4-(trifluoromethyl)benzyl]benzamide | 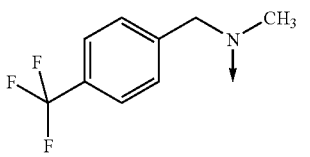 | LCMS Rt = 3.43 min MS m/z 490 [MH]+ | Method C, using N-methyl-1-[4-(trifluoromethyl)phenyl]methanamine |
| 42 | 4-{[(5-Chloro-1,3-thiazol-2-yl)amino]sulfonyl}-N-[(1S,2R)-2-phenylcyclopropyl]benzamide | 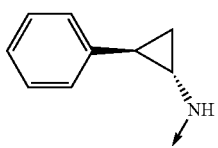 | LCMS Rt = 3.21 min MS m/z 434 [MH]+ | Method C, using (1S,2R)-2-phenylcyclopropyl-anamine hydrochloride |
| 43 | 4-{[(5-Chloro-1,3-thiazol-2-yl)amino]sulfonyl}-N-(4-fluorobenzyl)-N-methylbenzamide | 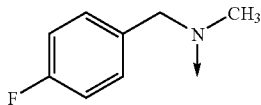 | LCMS Rt = 3.20 min MS m/z 440 [MH]+ | Method C, using 1-(4-fluorophenyl)-N-methylmethanamine |
| 44 | 4-{[(5-Chloro-1,3-thiazol-2-yl)amino]sulfonyl}-N-{1-[4-(trifluoromethyl)phenyl]ethyl}benzamide | 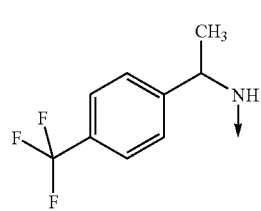 | LCMS Rt = 3.45 min MS m/z 490 [MH]+ | Method C, using 1-[4-(trifluoromethyl)phenyl]ethanamine |
| 45 | 4-{[(5-Chloro-1,3-thiazol-2-yl)amino]sulfonyl}-N-[4-(trifluoromethoxy)benzyl]benzamide | 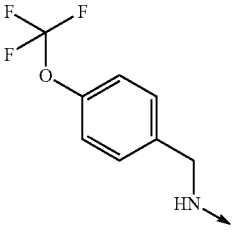 | LCMS Rt = 3.43 min MS m/z 492 [MH]+ $^1$HNMR (d$_6$-DMSO): 4.49 (d, 2 H), 7.31 (m, 2 H), 7.43 (d, 1 H), 7.53 (s, 1 H), 7.87 (d, 2 H), 8.00 (d, 2 H), 9.24 (t, 1 H) | Method C, using 4-(trifluoromethoxy)benzylamine |

The following examples of the general formula

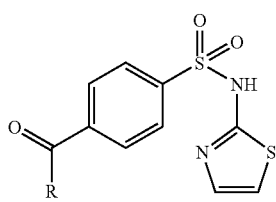

were prepared by the following method using the indicated amines.

4-{[(2,4-Dimethoxybenzyl)(1,3-thiazol-2-yl)amino]sulfonyl}benzoic acid (Preparation 99, 50 mg, 0.12 mmol, 1 eq), amine (0.13 mmol, 1.1 eq), Et$_3$N (40 mg, 0.288 mmol, 2.5 eq), and 2-(1H-benzotriazol-1-yl)-1,1,1,3,3-tetramethyluronium tetrafluoroborate (TBTU, 44 mg, 0.138 mmol, 1.2 eq) were combined in dimethylformamide (0.5 ml) and the reaction mixture stirred at room temperature for 1 to 18 hours. 4M HCl (4 ml) was added and the reaction stirred at room temperature for 2 hours, DCM (0.5 ml) was added and the reaction stirred for a further 30 minutes. The mixture was passed through a phase separation cartridge and the organic phase evaporated in vacuo. TFA (0.8 mL) was added to the residue and the mixture stirred for 2 hours. The reaction mixture was concentrated in vacuo and the residue purified by preparative HPLC.

Amines used for the amide bond formation are commercially available, synthesized via known literature methods (referenced in table) or synthesized by analogous methods known to those skilled in the art.

TABLE 4

| Example | Name | R | Data | Preparation Information |
|---|---|---|---|---|
| 46 | 4-{[3-(2-Chlorophenyl)thiomorpholin-4-yl]carbonyl}-N-1,3-thiazol-2-yl benzenesulfonamide | | LCMS Rt = 3.22 min MS m/z 480 [MH]+ | using 2-(2-chlorophenyl) thiomorpholine |
| 47 | 4-{[3-(3-Fluorobenzyl) piperidin-1-yl]carbonyl}-N-1,3-thiazol-2-yl benzenesulfonamide | | LCMS Rt = 3.21 min MS m/z 460 [MH]+ | using 3-(3-fluorobenzyl) piperidine |
| 48 | 4-{[(3R)-3-phenyl morpholin-4-yl]carbonyl}-N-1,3-thiazol-2-yl benzenesulfonamide | | LCMS Rt = 2.91 min MS m/z 430 [MH]+ | using (3R)-3-phenyl morpholine |
| 49 | 4-{[(3R,4R)-3-methyl-4-(phenoxymethyl)pyrrolidin-1-yl]carbonyl}-N-1,3-thiazol-2-yl benzenesulfonamide | | LCMS Rt = 3.12 min MS m/z 458 [MH]+ | using (3R,4R)-3-methyl-4-(phenoxymethyl) pyrrolidine |
| 50 | 4-{[6-(2-Fluorobenzyl)-6-hydroxy-1,4-oxazepan-4-yl]carbonyl}-N-1,3-thiazol-2-yl-benzenesulfonamide | Preparation 46 | LCMS Rt = 2.74 min MS m/z 492 [MH]+ | using 6-(2-fluorobenzyl)-1,4-oxazepan-6-ol hydrochloride |
| 51 | 4-{[3-(3-Methylphenoxy)piperidin-1-yl]carbonyl}-N-1,3-thiazol-2-yl-benzenesulfonamide | | LCMS Rt = 3.15 min MS m/z 458 [MH]+ | using 3-(3-methylphenoxy) piperidine |
| 52 | 4-[(4aR,9aS)-2,3,9,9a-tetrahyroindeno[2,1-b][1,4]oxazin-4(4aH)-ylcarbonyl}-N-1,3-thiazol-2-ylbenzenesulfonamide | 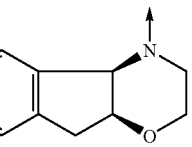 WO2007125398 | LCMS Rt = 2.83 min MS m/z 442 [MH]+ | using (4aR,9aS)-2,3,4,4a,9,9a-hexahydroindeno [2,1-b]1,4]oxazine |

TABLE 4-continued

| Example | Name | R | Data | Preparation Information |
|---|---|---|---|---|
| 53 | 4-[(4aS,9aR)-2,3,9,9a-tetrahyroindneo[2,1-b][1,4]oxazin-4(4aH)-ylcarbonyl]-N-1,3-thiazol-2-ylbenzenesulfonamide | WO2006114606 | LCMS Rt = 2.84 min MS m/z 442 [MH]+ | using (4aS,9aR)-2,3,4,4a,9,9a-hexahyroindeno [2,1-b][1,4]oxazine |
| 54 | N-(3-cyclopropyl-4-fluorobenzyl)-4-[(1,3-thiazol-2-ylamino)sulfonyl]benzamide | Preparation 58 | LCMS Rt = 2.21 min MS m/z 432 [MH]+ | using 1-(3-cyclopropyl-4-fluorophenyl) methanamine |
| 55 | N-(3-cyano-4-fluorobenzyl)-4-[(1,3-thiazol-2-ylamino)sulfonyl]benzamide | | LCMS Rt = 1.98 min MS m/z 417 [MH]+ | using 5-(Aminomethyl)-2-fluoro benzonitrile |
| 56 | N-[1-(2-chlorophenyl)-2-hydroxyethyl]-4-[(1,3-thiazol-2-ylamino)sulfonyl]benzamide | | LCMS Rt = 1.94 min MS m/z 438 [MH]+ | using 2-Amino-2-(2-chlorophenyl) ethanol |
| 57 | N-(2-hydroxy-1-phenylethyl)-4-[(1,3-thiazol-2-ylamino)sulfonyl]benzamide | | LCMS Rt = 1.69 min MS m/z 404 [MH]+ | using 2-amino-2-phenylethanol |
| 58 | N-(5-fluoro-2-methylbenzyl)-4-[(1,3-thiazol-2-ylamino)sulfonyl]benzamide | | LCMS Rt = 2.08 min MS m/z 406 [MH]+ | using 5-fluoro-2-methylbenzylamine |
| 59 | N-[3-(1H-pyrazol-1-yl)benzyl]-4-[(1,3-thiazol-2-ylamino)sulfonyl]benzamide | | LCMS Rt = 2.01 min MS m/z 440 [MH]+ | using 3-(1H-pyrazol-1-yl)benzylamine |
| 60 | N-[4-(1H-pyrazol-1-yl)benzyl]-4-[(1,3-thiazol-2-ylamino)sulfonyl]benzamide | | LCMS Rt = 1.91 min MS m/z 440 [MH]+ | using 4-(1H-pyrazol-1-yl)benzylamine |
| 61 | N-(3-chloro-2-methylbenzyl)-4-[(1,3-thiazol-2-ylamino)sulfonyl]benzamide | | LCMS Rt = 2.23 min MS m/z 422 [MH]+ | using 3-chloro-2-methylbenzylamine |

TABLE 4-continued

| Example | Name | R | Data | Preparation Information |
|---|---|---|---|---|
| 62 | N-(3-fluoro-4-methylbenzyl)-4-[(1,3-thiazol-2-ylamino)sulfonyl]benzamide | | LCMS Rt = 2.07 min MS m/z 406 [MH]+ | using 2-fluoro-4-methylbenzylamine |
| 63 | N-[3-(difluoromethoxy)benzyl]-4-[(1,3-thiazol-2-ylamino)sulfonyl]benzamide | | LCMS Rt = 2.06 min MS m/z 440 [MH]+ | using 3-(difluoromethoxy)benzylamine |
| 64 | N-(5-chloro-2-methylbenzyl)-4-[(1,3-thiazol-2-yl amino)sulfonyl]benzamide | | LCMS Rt = 2.16 min MS m/z 422 [MH]+ | using 3-chloro-2-methylbenzamine |
| 65 | 4-[(1,3-Thiazol-2-ylamino)sulfonyl]-N-(2,3,5-trifluorobenzyl)benzamide | | LCMS Rt = 1.99 min MS m/z 428 [MH]+ | using 2,3,5-trifluoro benzylamine |
| 66 | N-[2-(difluoromethoxy)benzyl]-4-[(1,3-thiazol-2-yl amino)sulfonyl]benzamide | | LCMS Rt = 2.08 min MS m/z 440 [MH]+ | using 2-(difluoromethoxy)benzylamine |
| 67 | 4-[(1,3-Thiazol-2-ylamino)suflonyl]-N-(3,4,5-trifluorobenzyl)benzamide | | LCMS Rt = 428 min MS m/z 2.97 [MH]+ | using 3,4,5-trifluoro benzylamine |
| 68 | 4-[(1,3-Thiazol-2-ylamino)sulfonyl]-N-(2,3,6-trifluorobenzyl)benzamide | | LCMS Rt = 2.87 min MS m/z 426 [M − H] | using 2,3,6-trifluoro benzylamine |
| 69 | 4-[(1,3-Thiazol-2-ylamino)sulfonyl]-N-(4-isopropyloxybenzyl)benzamide | | LCMS Rt = 2.07 min MS m/z 440 [MH]+ | using 3-isopropoxy-benzylamine |

TABLE 4-continued

| Example | Name | R | Data | Preparation Information |
|---|---|---|---|---|
| 70 | N-[2-(3-chlorophenyl)ethyl]-4-[(1,3-thiazol-2-ylamino)sulfonyl]benzamide | | LCMS Rt = 2.13 min MS m/z 422 [MH]+ | using 2-(3-chlorophenyl) ethylamine |
| 71 | N-(3-methylbenzyl)-4-[(1,3-thiazol-2-yl amino)sulfonyl]benzamide | | LCMS Rt = 2.09 min MS m/z 388 [MH]+ | using 3-methyl benzylamine |
| 72 | N-[2-(4-chlorophenyl)ethyl]-4-[(1,3-thiazol-2-yl amino)sulfonyl]benzamide | | LCMS Rt = 2.13 min MS m/z 422 [MH]+ | using 2-(4-chlorophenyl) ethylamine |
| 73 | 4-[(1,3-Thiazol-2-ylamino)sufonyl]-N-[3-(trifluoromethoxy)benzyl] benzamide | | LCMS Rt = 2.22 min MS m/z 458 [MH]+ | using 3-(trifluoromethoxy) benzylamine |
| 74 | 4-[(1,3-Thiazol-2-ylamino)sulfonyl]-N-{2-[3-(trifluoromethyl)phenyl] ethyl}benzamide | | LCMS Rt = 2.23 min MS m/z 456 [MH]+ | using 2-[3-(trifluoromethyl) phenyl] ethylamine |
| 75 | N-[2-(3-fluorophenyl)ethyl]-4-[(1,3-thiazol-2-yl amino)sulfonyl]benzamide | | LCMS Rt = 2.09 min MS m/z 406 [MH]+ | using 2-(3-fluorophenyl) ethylamine |
| 76 | N-[2-fluoro-5-(trifluoromethyl)benzyl]-4-[(1,3-thiazol-2-yl amino)sulfonyl]benzamide | | LCMS Rt = 2.23 min MS m/z 460 [MH]+ | using 2-fluoro-5-(trifluoromethyl) benzylamine |
| 77 | N-[2-(2-fluorophenyl)ethyl]-4-[(1,3-thiazol-2-yl amino)sulfonyl]benzamide | | LCMS Rt = 1.99 min MS m/z 406 [MH]+ | using 2-(2-fluorophenyl) ethylamine |
| 78 | 4-[(1,3-Thiazol-2-ylamino)sulfonyl]-N-[2-(trifluoromethoxy) benzyl]benzamide | | LCMS Rt = 2.24 min MS m/z 458 [MH]+ | using 2-(trifluoromethoxy) benzylamine |

TABLE 4-continued

| Example | Name | R | Data | Preparation Information |
|---|---|---|---|---|
| 79 | N-[(1S)-1-(4-methylphenyl)ethyl]-4-[(1,3-thiazol-2-yl amino)sulfonyl]benzamide | (1S)-CH(CH₃)-NH- attached to 4-methylphenyl | LCMS Rt = 2.13 min MS m/z 402 [MH]+ | using (1S)-1-(4-methylphenyl) ethylamine |
| 80 | N-[4-fluoro-2-(trifluoromethyl)benzyl]-4-[(1,3-thiazol-2-yl amino)sulfonyl]benzamide | 4-fluoro-2-(trifluoromethyl)benzyl-NH- | LCMS Rt = 2.23 min MS m/z 460 [MH]+ | using 4-fluoro-2-(trifluoromethyl) benzylamine |
| 81 | N-[5-fluoro-2-(trifluoromethyl)benzyl]-4-[(1,3-thiazol-2-yl amino)sulfonyl]benzamide | 5-fluoro-2-(trifluoromethyl)benzyl-NH- | LCMS Rt = 2.24 min MS m/z 460 [MH]+ | using 5-fluoro2-(trifluoromethyl) benzylamine |
| 82 | N-(2,3-dimethylbenzyl)-4-[(1,3-thiazol-2-yl amino)sulfonyl]benzamide | 2,3-dimethylbenzyl-NH- | LCMS Rt = 2.07 min MS m/z 402 [MH]+ | using 2,3-dimethylbenzyl amine |
| 83 | N-(3,5-difluorobenzyl)-4-[(1,3-thiazol-2-yl amino)sulfonyl]benzamide | 3,5-difluorobenzyl-NH- | LCMS Rt = 1.98 min MS m/z 410 [MH]+ | using 3,5-difluorobenzyl amine |
| 84 | N-[2-fluoro-6-(trifluoromethyl)benzyl]-4-[(1,3-thiazol-2-yl amino)sulfonyl]benzamide | 2-fluoro-6-(trifluoromethyl)benzyl-NH- | LCMS Rt = 2.15 min MS m/z 460 [MH]+ | using 2-fluoro-6-(trifluoromethyl) benzylamine |
| 85 | N-(2,6-difluorobenzyl)-[(1,3-thiazol-2-yl amino)sulfonyl]benzamide | 2,6-difluorobenzyl-NH- | LCMS Rt = 2.91 min MS m/z 410 [MH]+ | using 2,6-difluorobenzyl amine |
| 86 | N-(2-chloro-6-fluorobenzyl)-4-[(1,3-thiazol-2-yl amino)sulfonyl]benzamide | 2-chloro-6-fluorobenzyl-NH- | LCMS Rt = 2.09 min MS m/z 426 [MH]+ | using 2-chloro-6-fluorobenzyl amine |
| 87 | N-(2,5-difluorobenzyl)-4-[(1,3-thiazol-2-yl amino)sulfonyl]benzamide | 2,5-difluorobenzyl-NH- | LCMS Rt = 1.91 min MS m/z 410 [MH]+ | using 2,5-difluorobenzyl amine |

TABLE 4-continued

| Example | Name | R | Data | Preparation Information |
|---|---|---|---|---|
| 88 | 4-[(1,3-Thiazol-2-ylamino)sulfonyl]-N-[2-(trifluoromethyl)benzyl]benzamide | 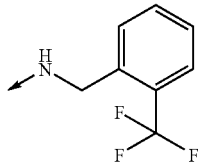 | LCMS Rt = 2.16 min MS m/z 442 [MH]+ | using 2-(trifluoromethyl)benzylamine |
| 89 | N-(2-ethoxybenzyl)-4-[(1,3-thiazol-2-yl amino)sulfonyl]benzamide | 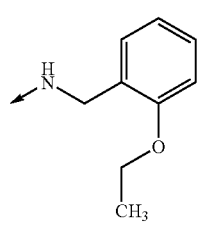 | LCMS Rt = 2.15 min MS m/z 418 [MH]+ | using 2-ethoxy benzylamine |
| 90 | N-(3-fluorobenzyl)-4-[(1,3-thiazol-2-ylamino)sulfonyl]benzamide | 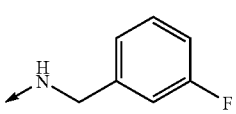 | LCMS Rt = 1.91 min MS m/z 392 [MH]+ | using 3-fluorobenzyl amine |
| 91 | N-(2-methylbenzyl)-4-[(1,3-thiazol-2-ylamino)sulfonyl]benzamide | 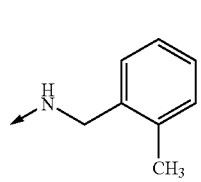 | LCMS Rt = 1.99 min MS m/z 388 [MH]+ | using 2-methylbenzyl amine |
| 92 | N-(4-fluorobenzyl)-4-[(1,3-thiazol-2-ylamino)sulfonyl]benzamide | 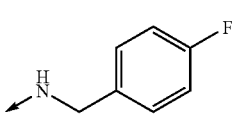 | LCMS Rt = 1.93 min MS m/z 392 [MH]+ | using 4-fluorobenzyl amine |
| 93 | N-(4-chloro-2-fluorobenzyl)-4-[(1,3-thiazol-2-ylamino)sulfonyl]benzamide | 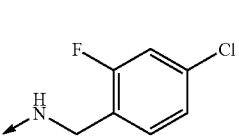 | LCMS Rt = 2.16 min MS m/z 426 [MH]+ | using 4-chloro-2-fluorobenzyl amine |
| 94 | N-(2,4-difluorobenzyl)-4-[(1,3-thiazol-2-yl amino)sulfonyl]benzamide | 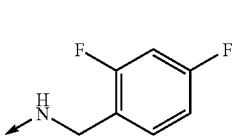 | LCMS Rt = 1.99 min MS m/z 410 [MH]+ | using 2,4-difluorobenzyl amine |
| 95 | N-(2-chloro-4-fluorobenzyl)-4-[(1,3-thiazol-2-yl amino)sulfonyl]benzamide | 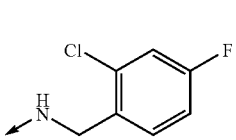 | LCMS Rt = 2.06 min MS m/z 426 [MH]+ | using 2-chloro-4-fluorobenzyl amine |
| 96 | N-[2-(2-chlorophenyl)ethyl]-4-[(1,3-thiazol-2-yl amino)-sulfonyl]benzamide | 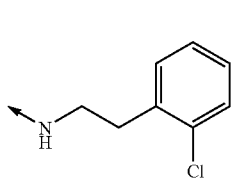 | LCMS Rt = 2.16 min MS m/z 422 [MH]+ | using 2-(2-chlorophenyl)ethylamine |
| 97 | N-(2,3-dichlorobenzyl)-4-[(1,3-thiazol-2-yl amino)sulfonyl]benzamide | 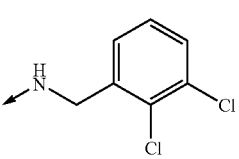 | LCMS Rt = 2.23 min MS m/z 441 [MH]+ | using 2,3-dichlorobenzyl amine |

TABLE 4-continued

| Example | Name | R | Data | Preparation Information |
|---|---|---|---|---|
| 98 | N-(4-methylbenzyl)-4-[(1,3-thiazol-2-yl amino)sulfonyl]benzamide | 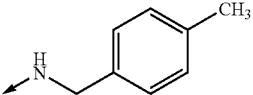 | LCMS Rt = 1.99 min MS m/z 388 [MH]+ | using 4-methylbenzyl amine |
| 99 | N-(2-chlorobenzyl)-4-[(1,3-thiazol-2-yl amino)sulfonyl]benzamide | 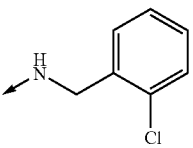 | LCMS Rt = 3.0 min MS m/z 408 [MH]+ | using 2-chlorobenzyl amine |
| 100 | N-(4-chlorobenzyl)-4-[(1,3-thiazol-2-yl amino)sulfonyl]benzamide | 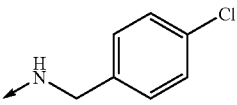 | LCMS Rt = 2.06 min MS m/z 408 [MH]+ | using 4-chlorobenzyl amine |
| 101 | 4-[(1,3-Thiazol-2-ylamino)sulfonyl]-N-{2-[4-(trifluoromethyl)phenyl]ethyl}benzamide | 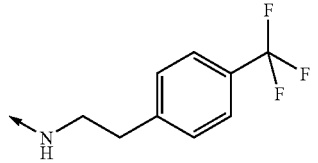 | LCMS Rt = 2.23 min MS m/z 456 [MH]+ | using 2-[4-(trifluoromethyl) phenylamine |
| 102 | N-[2-(4-fluorophenyl)ethyl]-4-[(1,3-thiazol-2-ylamino)sulfonyl]benzamide | 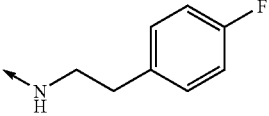 | LCMS Rt = 1.99 min MS m/z 406 [MH]+ | using 2-(4-fluorophenyl) ethylamine |
| 103 | N-[1-(4-fluorophenyl)ethyl]-4-[(1,3-thiazol-2-ylamino)sulfonyl]benzamide | 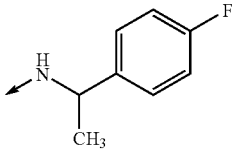 | LCMS Rt = 2.99 min MS m/z 406 [MH]+ | using 1-(4-fluorophenyl) ethylamine |
| 104 | N-methyl-4-[(1,3-thiazol-2-ylamino)sulfonyl]-N-[3-(trifluoromethyl)benzyl]benzamide | 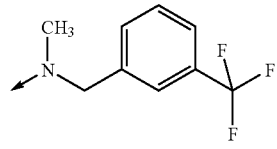 | LCMS Rt = 3.12 min MS m/z 456 [MH]+ | using N-methyl-3-(trifluoromethyl) benzylamine |
| 105 | 4-[(5-Chloro-3,4-dihydroisoquinolin-2(1H)-yl)carbonyl]-N-1,3-thiazol-2-ylbenzensulfonamide | 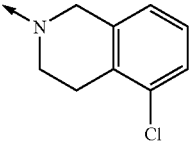 | LCMS Rt = 3.14 min MS m/z 434 [MH]+ | using 5-chloro-1,2,3,4-tetrahydroisoquinoline |
| 106 | 4-(3,5-Dihydroisoquinolin-2(1H)-ylcarbonyl)-N-1,3-thiazol-2-ylbenzenesulfonamide | 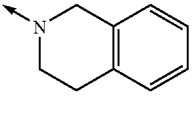 | LCMS Rt = 2.90 min MS m/z 400 [MH]+ | using 1,2,3,4-tetrahydroisoquinoline |
| 107 | 4-[(5-Chloro-1,3-dihydro-2H-isoindole-2-yl)carbonyl]-N-1,3-thiazol-2-yl benzenesulfonamide | 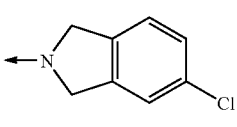 | LCMS Rt = 3.07 min MS m/z 420 [MH]+ | using 5-Chloro-2,3-dihydro-1H-isoindole |

EP343560

TABLE 4-continued

| Example | Name | R | Data | Preparation Information |
|---|---|---|---|---|
| 108 | N-[(1R)-1-phenylethyl]-4-[(1,3-thiazol-2-yl amino)sulfonyl]benzamide | | LCMS Rt = 2.90 min MS m/z 388 [MH]+ | using (1R)-1-phenylethyl amine |
| 109 | 4-[(4-Chloro-1,3-dihydro-2H-isoindole-2-yl)carbonyl]-N-1,3-thiazol-2-yl benzenesulfonamide | | LCMS Rt = 3.05 min MS m/z 420 [MH]+ | using 4-chloro-2,3-dihydro-1H-isoindole |
| 110 | N-methyl-4-[(1,3-thiazol-2-ylamino)sulfonyl]-N-[4-(trifluoromethyl)benzyl]benzamide | | LCMS Rt = 3.13 min MS m/z 456 [MH]+ | using N-methyl-4-(trifluoromethyl)benzylamine |
| 111 | N-(1-methyl-1-phenylethyl)-4-[(1,3-thiazol-2-ylamino)sulfonyl]benzamide | | LCMS Rt = 3.07 min MS m/z 402 [MH]+ | using 1-methyl-1-phenylethyl amine |
| 112 | N-[(1S,2R)-2-phenylcyclopropyl]-4-[(1,3-thiazol-2-yl amino)sulfonyl]benzamdie | | LCMS Rt = 2.97 min MS m/z 400 [MH]+ | using (1S,2R)-2-cyclopropyl amine |
| 113 | N-[(1S)-1-phenylethyl]-4-[(1,3-thiazol-2-yl amino)sulfonyl]benzamide | | LCMS Rt = 2.99 min MS m/z 388 [MH]+ | using (1S)-1-phenylethyl amine |
| 114 | N-[(1R)-1-(4-fluorophenyl)ethyl]-4-[(1,3-thiazol-2-yl amino)sulfonyl]benzamide | | LCMS Rt = 3.00 min MS m/z 406 [MH]+ | using (1R)-1-(4-fluorophenyl) ethylamine |
| 115 | N-(1-phenylcyclopropyl)-4-[(1,3-thiazol-2-yl amino)sulfonyl]benzamide | | LCMS Rt = 2.89 min MS m/z 400 [MH]+ | using 1-phenyl cyclopropyl amine |
| 116 | N-1,7-naphthyridin-8-yl-4-[(1,3-thiazol-2-yl amino)sulfonyl]benzamide | | LCMS Rt = 2.31 min MS m/z 412 [MH]+ | using 1,7-naphthyridin-8-amine |

TABLE 4-continued

| Example | Name | R | Data | Preparation Information |
|---|---|---|---|---|
| 117 | N-isoquinolin-1-yl-4-[(1,3-thiazol-2-yl amino)sulfonyl]benzamide | (isoquinolin-1-yl-amino structure) | LCMS Rt = 2.77 min MS m/z 411 [MH]+ | using 1-isoquinolinamine |
| 118 | 4-[(1,3-Thiazol-2-ylamino)sulfonyl]-N-{1-[4-(trifluoromethyl)phenyl]ethyl}benzamide | (1-[4-(trifluoromethyl)phenyl]ethylamino structure) | LCMS Rt = 3.20 min MS m/z 456 [MH]+ | using 1-[4-(trifluoromethyl)phenyl] ethylamine |

The following examples of the general formula

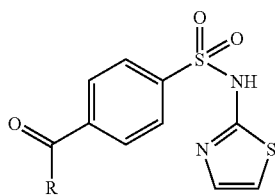

were prepared by the following method using the indicated amines:

To a 0.2M solution of an amine (0.120 mmol, 1.2 eq) in dimethylformamide:Et$_3$N (95:5) (0.6 ml) was added a solution of 4-{[(2,4-dimethoxybenzyl)(1,3-thiazol-2-yl)amino] sulfonyl}benzoic acid (Preparation 99, 0.1 mmol, 1 eq) in dimethylformamide:Et$_3$N (95:5) (0.5 ml) and HBTU (0.120 mmol, 1.2 eq) in dimethylformamide (0.6 ml). The reaction mixture was sealed and shaken at room temperature for 5 hours. The solvent was evaporated in vacuo and the residue dissolved in 4M HCl in dioxane (1.5 ml), the reaction mixture sealed and shaken at room temperature for 65 hours. The solvent was evaporated in vacuo. The residue was dissolved in DCM, 2M HCl was added (0.8 ml) and the mixture sonicated for 10 minutes before the aqueous layer was removed. This procedure was repeated twice before the remaining organic layer was evaporated in vacuo. The residue was purified by preparative HPLC to yield the title compound.

Amines used for the amide bond formation are commercially available, synthesized via known literature methods (referenced in table) or synthesized by analogous methods known to those skilled in the art.

TABLE 5

| Example | Name | R | Data | Preparation Information |
|---|---|---|---|---|
| 119 | N-{cyclopropyl[2-fluoro-3-(trifluoromethyl)phenyl]methyl}-4-[(1,3-thiazol-2-yl amino)sulfonyl]benzamide | (cyclopropyl[2-fluoro-3-(trifluoromethyl)phenyl]methylamino structure) | LCMS Rt = 2.44 min MS m/z 500 [MH]+ | using cyclopropyl[2-fluoro-3-(trifluoromethyl)phenyl]methylamine |
| 120 | N-[2-chloro-5-(trifluoromethyl)benzyl]-4-[(1,3-thiazol-2-ylamino)sulfonyl]benzamide | (2-chloro-5-(trifluoromethyl)benzylamino structure) | LCMS Rt = 2.29 min MS m/z 476 [MH]+ | using 2-chloro-5-(trifluoromethyl)benzylamine |

TABLE 5-continued

| Example | Name | R | Data | Preparation Information |
|---|---|---|---|---|
| 121 | N-[(1-phenylcyclopentyl)methyl]-4-[(1,3-thiazol-2-ylamino)sulfonyl]benzamide | | LCMS Rt = 2.31 min MS m/z 442 [MH]+ | using 1-phenyl cyclopentyl) methylamine |
| 122 | 4-[(1,3-Thiazol-2-ylamino)sulfonyl]-N-{2-[(trifluoromethyl)thio]benzyl]benzamide | | LCMS Rt = 2.3 min MS m/z 474 [MH]+ | using 2-[(trifluoro methyl)thio] benzylamine |
| 123 | N-{1-methyl-1-[4-(trifluoromethyl)phenyl]ethyl}-4-[(1,3-thiazol-2-ylamino)sulfonyl]benzamide | | LCMS Rt = 2.44 min MS m/z 470 [MH]+ | using 2-[4-(trifluoromethyl)phenyl]propan-2-amine |
| 124 | N-[1-(4-chlorophenyl)-1-methylethyl]-4-[(1,3-thiazol-2-yl amino)sulfonyl]benzaamide | 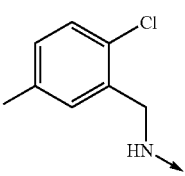 | LCMS Rt = 3.28 min MS m/z 436 [MH]+ | using 2-(4-chlorophenyl) propan-2-amine |
| 125 | N-{1-methyl-1-[3-(trifluoromethyl)phenyl]ethyl}-4-[(1,3-thiazol-2-ylamino)sulfonyl]benzamide | | LCMS Rt = 3.37 min MS m/z 470 [MH]+ | using 2-[3-(trifluoromethyl) phenyl]propan-2-amine |
| | | WO2007134862 | | |
| 126 | N-(2,5-dichlorobenzyl)-4-[(1,3-thiazol-2-yl amino)sulfonyl]benzamide | | LCMS Rt = 3.21 min MS m/z 441 [MH]+ | using 2,5-dichloro benzylamine |
| 127 | N-[1-(3-chlorophenyl)-1-methylethyl]-4-[(1,3-thiazol-2-yl amino)sulfonyl]benzamide | 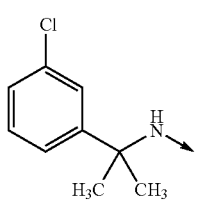 | LCMS Rt = 3.35 min MS m/z 436 [MH]+ | using 2-(3-chlorophenyl) propan-2-amine |
| | | Mendeleev Communications 2000, 1, 31-32 | | |

TABLE 5-continued

| Example | Name | R | Data | Preparation Information |
|---|---|---|---|---|
| 128 | N-[(1R,2R)-2-(3,5-difluorophenyl)cyclopentyl]-4-[(1,3-thiazol-2-yl amino)sulfonyl] benzamide | | LCMS Rt = 3.3 min MS m/z 464 [MH]+ | using -[(1R,2R)-2-(3,5-difluorophenyl) cyclopentyl amine |
| 129 | N-[1-(2-chlorobenzyl)cyclopropyl]-4-[(1,3-thiazol-2-yl amino)sulfonyl] benzamide | | LCMS Rt = 3.16 min MS m/z 448 [MH]+ | using 1-(2-chlorobenzyl) cyclopropyl amine |
| 130 | N-{1-methyl-2-[4-(trifluoromethyl)phenyl] ethyl}-4-[(1,3-thiazol-2-yl amino)sulfonyl]benzamide | | LCMS Rt = 3.29 min MS m/z 470 [MH]+ | using 1-methyl-2-[4-(trifluoromethyl) phenyl] ethylamine |
| 131 | N-[(1S,2R)-2-phenylcyclopentyl]-4-[(1,3-thiazol-2-yl amino)sulfonyl] benzamide | *Synlett* 2006, 5, 697-700 | LCMS Rt = 3.22 min MS m/z 428 [MH]+ | using -[(1S,2R)-2-phenyl cyclopentyl amine |
| 132 | N-[(1R,2R)-2-(4-fluorophenyl)cyclopentyl]-4-[(1,3-thiazol-2-yl amino)sulfonyl]benzamide | *Journal of Medicinal Chemistry* 2002, 45(10), 2101-2111 | LCMS Rt = 3.27 min MS m/z 446 [MH]+ | using -[(1R,2R)-2-(4-fluoro phenyl)cyclopentyl amine |
| 133 | N-[2-(4-chlorophenyl)propyl]-4-[(1,3-thiazol-2-yl amino)sulfonyl] benzamide | | LCMS Rt = 3.2 min MS m/z 436 [MH]+ | using 2-(4-chlorophenyl) propylamine |
| 134 | N-[1-(4-chlorobenzyl)cyclopropyl]-4-[(1,3-thiazol-2-yl amino)sulfonyl] benzamide | EP 1595873 | LCMS Rt = 3.21 min MS m/z 448 [MH]+ | using 1-(4-chlorobenzyl) cyclopropyl amine |

TABLE 5-continued

| Example | Name | R | Data | Preparation Information |
|---|---|---|---|---|
| 135 | N-[1-(3-chlorophenyl)cyclopropyl]-4-[(1,3-thiazol-2-yl amino)sulfonyl]benzamide | | LCMS Rt = 3.13 min MS m/z 434 [MH]+ | using 1-(3-chlorophenyl) cyclopropyl amine |
| 136 | N-[1-(3-chlorophenyl)-2-(3-methylisoxazol-5-yl)ethyl]-4-[(1,3-thiazol-2-ylamino)sulfonyl]benzamide | Preparation 49 | LCMS Rt = 3.27 min MS m/z 503 [MH]+ | using 1-(3-Chloro-phenyl)-2-(3-methyl-isoxazol-5-yl)-ethylamine |
| 137 | N-[1-(3-chlorobenzyl)cyclopropyl]-4-[(1,3-thiazol-2-yl amino)sulfonyl]benzamide | *Journal of Medicinal Chemistry* 1970, 13(5), 820-826 | LCMS Rt = 3.2 min MS m/z 448 [MH]+ | using 1-(3-chlorobenzyl) cyclopropyl amine |
| 138 | N-[(1R,2R)-2-phenylcyclopentyl]-4-[(1,3-thiazol-2-ylamino)sulfonyl]benzamide | | LCMS Rt = 3.14 min MS m/z 428 [MH]+ | using -[(1R,2R)-2-phenyl cyclopentyl amine |
| 139 | N-[1-(4-chlorophenyl)cyclopropyl]-4-[(1,3-thiazol-2-ylamino)sulfonyl]benzamide | | LCMS Rt = 3.2 min MS m/z 434 [MH]+ | using 1-(4-chlorophenyl) cyclopropyl amine |
| 140 | N-[cyclopropyl(2,6-difluorophenyl)methyl]-4-[(1,3-thiazol-2-yl amino)sulfonyl]benzamide | | LCMS Rt = 3.22 min MS m/z 450 [MH]+ | using cyclopropyl(2,6-difluorophenyl) methylamine |

TABLE 5-continued

| Example | Name | R | Data | Preparation Information |
|---|---|---|---|---|
| 141 | N-[1-(3,5-difluorophenyl)-1-methylethyl]-4-[(1,3-thiazol-2-ylamino)sulfonyl]benzamide | 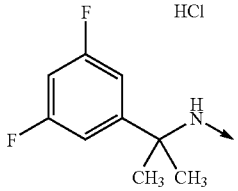<br>Preparation 52 | LCMS Rt = 3.2 min MS m/z 438 [MH]+ | using 2-(3,5-difluorophenyl)propan-2-amine hydrochloride |
| 142 | N-[1-(4-fluorophenyl)propyl]-4-[(1,3-thiazol-2-ylamino)sulfonyl]benzamide | 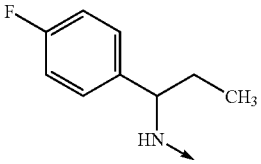 | LCMS Rt = 3.2 min MS m/z 420 [MH]+ | using 1-(4-fluorophenyl)propylamine |
| 143 | N-[1-(2-chlorophenyl)ethyl]-4-[(1,3-thiazol-2-ylamino)sulfonyl]benzamide | 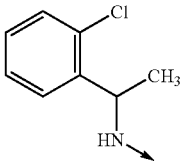 | LCMS Rt = 3.14 min MS m/z 422 [MH]+ | using 1-(2-chlorophenyl)ethylamine |
| 144 | N-[2-(3-chlorophenoxy)ethyl]-4-[(1,3-thiazol-2-ylamino)sulfonyl]benzamide | 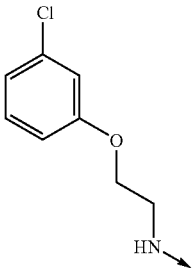 | LCMS Rt = 3.13 min MS m/z 438 [MH]+ | using 2-(3-chlorophenoxy)ethylamine |
| 145 | N-[(1S)-1-phenylpropyl]-4-[(1,3-thiazol-2-ylamino)sulfonyl]benzamide | 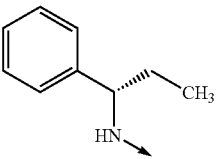 | LCMS Rt = 3.1 min MS m/z 400 [MH]+ | using (1S)-1-phenylpropyl amine |
| 146 | N-[1-(3,4-difluorophenyl)-1-methylethyl]-4-[(1,3-thiazol-2-ylamino)sulfonyl]benzamide | 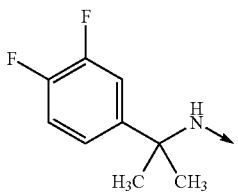<br>WO2007006546 | LCMS Rt = 3.14 min MS m/z 438 [MH]+ | using 2-(3,4-difluorophenyl)propan-2-amine |
| 147 | N-[2-(2-chlorophenoxy)propyl]-4-[(1,3-thiazol-2-ylamino)sulfonyl]benzamide | 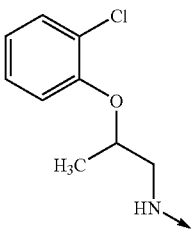 | LCMS Rt = 3.22 min MS m/z 452 [MH]+ | using 2-(2-chlorophenoxy)propylamine |

TABLE 5-continued

| Example | Name | R | Data | Preparation Information |
|---|---|---|---|---|
| 148 | N-[2-(2-chlorophenoxy)ethyl]-4-[(1,3-thiazol-2-ylamino)sulfonyl]benzamide | 2-chlorophenoxyethyl-NH- structure | LCMS Rt = 3.06 min MS m/z 438 [MH]+ | using 2-(2-chlorophenoxy)ethylamine |
| 149 | N-[2-(4-fluorophenyl)-1-methylethyl]-4-[(1,3-thiazol-2-ylamino)sulfonyl]benzamide | 4-fluorobenzyl-CH(CH₃)-NH- structure | LCMS Rt = 3.2 min MS m/z 420 [MH]+ | using 2-(4-fluorophenyl)-1-methylethyl amine |
| 150 | N-[(1R)-1-phenylpropyl]-4-[(1,3-thiazol-2-yl amino)sulfonyl]benzamide | phenyl-CH(CH₂CH₃)-NH- structure | LCMS Rt = 3.05 min MS m/z 402 [MH]+ | using -[(1R)-1-phenylpropyl-amine |
| 151 | N-[(2-(3,4-difluorophenyl)-1-methylethyl]-4-[(1,3-thiazol-2-ylamino)sulfonyl]benzamide | 3,4-difluorobenzyl-CH(CH₃)-NH- structure | LCMS Rt = 3.15 min MS m/z 438 [MH]+ | using 2-(3,4-difluorophenyl)-1-methylethyl amine |
| 152 | N-(3-chlorobenzyl)-4-[(1,3-thiazol-2-yl amino)sulfonyl]benzamide | 3-chlorobenzyl-NH- structure | LCMS Rt = 3.12 min MS m/z 408 [MH]+ | using 3-chloro benzylamine |
| 153 | N-[(1-phenylcyclopropyl)methyl]-4-[(1,3-thiazol-2-ylamino)sulfonyl]benzamide | (1-phenylcyclopropyl)methyl-NH- structure | LCMS Rt = 3.15 min MS m/z 414 [MH]+ | using (1-phenyl cyclopropyl) methylamine |
| 103 | N-[1-(4-fluorophenyl)ethyl]-4-[(1,3-thiazol-2-ylamino)sulfonyl]benzamide | 4-fluorophenyl-CH(CH₃)-NH- structure | LCMS Rt = 3.07 min MS m/z 406 [MH]+ | using 1-(4-fluorophenyl) ethylamine |

TABLE 5-continued

| Example | Name | R | Data | Preparation Information |
|---|---|---|---|---|
| 154 | N-[2-(4-methylphenoxy)ethyl]-4-[(1,3-thiazol-2-ylamino)sulfonyl]benzamide | | LCMS Rt = 3.05 min MS m/z 418 [MH]+ | using 2-(4-methylphenoxy)ethylamine |
| 155 | N-(2-phenylpropyl)-4-[(1,3-thiazol-2-ylamino)sulfonyl]benzamide | | LCMS Rt = 3.06 min MS m/z 402 [MH]+ | using 2-phenyl propylamine |
| 156 | N-[1-(4-fluorophenyl)-2-(3-methylisoxazol-5-yl)ethyl]-4-[(1,3-thiazol-2-ylamino)sulfonyl]benzamide | | LCMS Rt = 3.12 min MS m/z 487 [MH]+ | using 1-(4-fluoro-phenyl)-2-(3-methyl-isoxazol-5-yl)-ethylamine |
| 157 | N-[1-(2-methoxybenzyl)cyclopropyl]-4-[(1,3-thiazol-2-ylamino)sulfonyl]benzamide | | LCMS Rt = 3.05 min MS m/z 444 [MH]+ *Journal of Medicinal Chemistry*, 1970, 13(5), 820-826 | using 1-(2-methoxybenzyl) cyclopropyl amine |
| 158 | N-(2,3-dihydro-1H-inden-1-yl)-4-[(1,3-thiazol-2-yl amino)sulfonyl]benzamide | | LCMS Rt = 3.06 min MS m/z 400 [MH]+ | using 2,3-dihydro-1H-inden-1-amine |
| 159 | N-[1-(3-methoxybenzyl)cyclopropyl]-4-[(1,3-thiazol-2-yl amino)sulfonyl]benzamide | | LCMS Rt = 2.99 min MS m/z 444 [MH]+ | using 1-(3-methoxybenzyl) cyclopropyl amine |

TABLE 5-continued

| Example | Name | R | Data | Preparation Information |
|---|---|---|---|---|
| 160 | N-[1-(4-methoxyphenyl)cyclopropyl]-4-[(1,3-thiazol-2-ylamino)sulfonyl]benzamide | | LCMS Rt = 2.91 min MS m/z 430 [MH]+ | using 1-(4-methoxyphenyl) cyclopropyl amine |
| 161 | N-(2-phenoxypropyl)-4-[(1,3-thiazol-2-ylamino)sulfonyl]benzamide | | LCMS Rt = 3.07 min MS m/z 418 [MH]+ | using 2-phenoxy propylamine |
| 162 | N-[1-(4-methoxybenzyl)cyclopropyl]-4-[(1,3-thiazol-2-ylamino)sulfonyl]benzamide | | LCMS Rt = 3.12 min MS m/z 444 [MH]+ | using 1-(4-methoxybenzyl) cyclopropyl amine |
| 163 | N-(2-phenylethyl)-4-[(1,3-thiazol-2-ylamino)sulfonyl]benzamide | | LCMS Rt = 3.04 min MS m/z 388 [MH]+ | using 2-phenylethyl amine |
| 164 | N-[1-(3-methoxyphenyl)cyclopropyl]-4-[(1,3-thiazol-2-ylamino)sulfonyl]benzamide | | LCMS Rt = 2.98 min MS m/z 430 [MH]+ | using 1-(3-methoxyphenyl) cyclopropyl amine |
| 165 | N-[2-(2-methoxyphenyl)ethyl]-4-[(1,3-thiazol-2-ylamino)sulfonyl]benzamide | | LCMS Rt = 2.99 min MS m/z 418 [MH]+ | using 2-(2-methoxyphenyl) ethylamine |

TABLE 5-continued

| Example | Name | R | Data | Preparation Information |
|---|---|---|---|---|
| 166 | N-[2-(3-methoxyphenyl)ethyl]-4-[(1,3-thiazol-2-ylamino)sulfonyl]benzamide | | LCMS Rt = 2.9 min MS m/z 418 [MH]+ | using 2-(3-methoxyphenyl) ethylamine |
| 167 | N-[2-(2-fluorophenoxy)ethyl]-4-[(1,3-thiazol-2-yl amino)sulfonyl]benzamide | | LCMS Rt = 2.92 min MS m/z 422 [MH]+ | using 2-(2-fluorophenoxy) ethylamine |
| 168 | N-(2-phenoxyethyl)-4-[(1,3-thiazol-2-yl amino)sulfonyl]benzamide | | LCMS Rt = 2.92 min MS m/z 404 [MH]+ | using 2-phenoxy ethylamine |
| 169 | N-[2-(4-methoxyphenyl)ethyl]-4-[(1,3-thiazol-2-yl amino)sulfonyl]benzamide | | LCMS Rt = 2.97 min MS m/z 418 [MH]+ | using 2-(4-methoxyphenyl) ethylamine |
| 170 | N-(3-methoxybenzyl)-4-[(1,3-thiazol-2-yl amino)sulfonyl]benzamide | | LCMS Rt = 2.83 min MS m/z 404 [MH]+ | using 3-methoxy benzylamine |
| 171 | N-benzyl-4-[(1,3-thiazol-2-yl amino)sulfonyl]benzamide | | LCMS Rt = 2.97 min MS m/z 374 [MH]+ | using benzylamine |
| 172 | N-(6,7-dihydro-5H-cyclopenta[b]pyridin-2-yl)-4-[(1,3-thiazol-2-ylamino)sulfonyl]benzamide | | LCMS Rt = 2.83 min MS m/z 401 [MH]+ | using 6,7-dihydro-5H-cyclopenta[b]pyridin-2-amine |

TABLE 5-continued

| Example | Name | R | Data | Preparation Information |
|---|---|---|---|---|
| 173 | N-(2,3-dihydro-1H-inden-2-yl)-4-[(1,3-thiazol-2-ylamino)sulfonyl]benzamide | 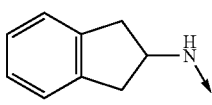 | LCMS Rt = 2.99 min MS m/z 400 [MH]+ | using 2,3-dihydro-1H-inden-2-amine |
| 174 | N-(2-methoxybenzyl)-4-[(1,3-thiazol-2-yl amino)sulfonyl]benzamide | 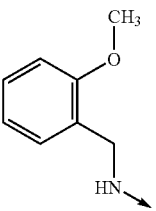 | LCMS Rt = 2.97 min MS m/z 404 [MH]+ | using 2-methoxy benzylamine |
| 175 | N-(5,6-dimethylpyridin-3-yl)-4-[(1,3-thiazol-2-ylamino)sulfonyl]benzamide | 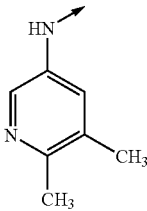 | LCMS Rt = 2.0 min MS m/z 389 [MH]+ | using 5,6-dimethylpyridin-3-amine |
| 176 | N-(4-methoxybenzyl)-4-[(1,3-thiazol-2-ylamino)sulfonyl]benzamide | 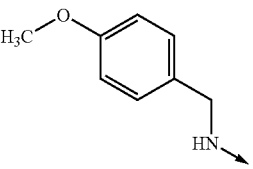 | LCMS Rt = 2.84 min MS m/z 404 [MH]+ | using 4-methoxy benzylamine |
| 177 | N-(6-methoxypyridin-3-yl)-4-[(1,3-thiazol-2-ylamino)sulfonyl]benzamide | 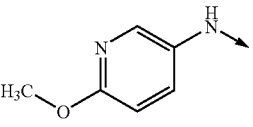 | LCMS Rt = 2.82 min MS m/z 391 [MH]+ | using 6-methoxypyridin-3-amine |
| 178 | N-(3-ethyl-6-methylpyridin-2-yl)-4-[(1,3-thiazol-2-ylamino)sulfonyl]benzamide | 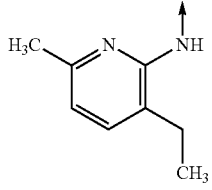 | LCMS Rt = 2.46 min MS m/z 403 [MH]+ | using 3-ethyl-6-methylpyridin-2-amine |
| 179 | N-[(3S,4R)-4-(4-fluorophenyl)tetrahydrofuran-3-yl]-4-[(1,3-thiazol-2-yl amino)sulfonyl]benzamide | 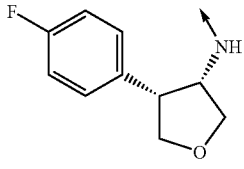 Preparation 62 | LCMS Rt = 2.84 min MS m/z 448 [MH]+ | using (3S*,4R*)-4-(4-Fluorophenyl)tetrahydrofuran-3-amine |
| 180 | N-(3-cyanobenzyl)-4-[(1,3-thiazol-2-yl amino)sulfonyl]benzamide | 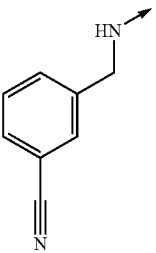 | LCMS Rt = 2.77 min MS m/z 399 [MH]+ | using 3-cyano benzylamine |

TABLE 5-continued

| Example | Name | R | Data | Preparation Information |
|---|---|---|---|---|
| 181 | N-(4-methylpyridin-2-yl)-4-[(1,3-thiazol-2-ylamino)sulfonyl]benzamide | 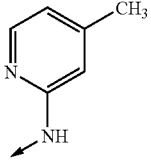 | LCMS Rt = 2.44 min MS m/z 375 [MH]+ | using 4-methyl pyridin-2-amine |
| 182 | N-[(1S)-1-benzyl-2-hydroxyethyl]-4-[(1,3-thiazol-2-ylamino)sulfonyl]benzamide | 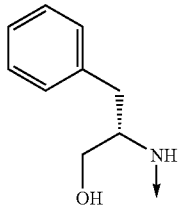 | LCMS Rt = 2.22 min MS m/z 418 [MH]+ | using (1S)-1-benzyl-2-hydroxyethyl amine |
| 183 | N-[(3-methyl-1,2,4-oxadiazol-5-yl)(phenyl)methyl]-4-[(1,3-thiazol-2-ylamino)sulfonyl]benzamide | 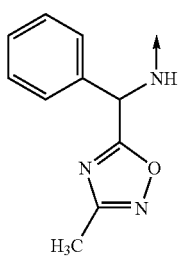 | LCMS Rt = 2.98 min MS m/z 456 [MH]+ | using (3-methyl-1,2,4-oxadiazol-5-yl)(phenyl)methylamine |
| 184 | N-(3,5-dimethylpyridin-2-yl)-4-[(1,3-thiazol-2-ylamino)sulfonyl]benzamide | 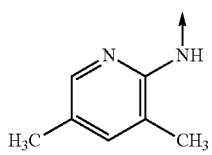<br>*Journal of Heterocyclic Chemistry* 1981, 18(8), 1613-1618 | LCMS Rt = 2.39 min MS m/z 389 [MH]+ | using 3,5-dimethyl pyridin-2-amine |
| 185 | N-[(1R)-1-benzyl-2-hydroxyethyl]-4-[(1,3-thiazol-2-yl amino)sulfonyl]benzamide | 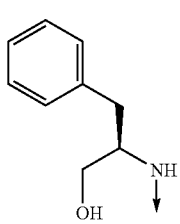 | LCMS Rt = 2.36 min MS m/z 418 [MH]+ | using (1R)-1-benzyl-2-hydroxyethylamine |

TABLE 5-continued

| Example | Name | R | Data | Preparation Information |
|---|---|---|---|---|
| 186 | N-[2-(4-chlorophenoxy)ethyl]-4-[(1,3-thiazol-2-yl amino)sulfonyl] benzamide | ![Cl-phenyl-O-CH2CH2-NH-] | LCMS Rt = 2.79 min MS m/z 438 [MH]+ $^1$HNMR ($d_6$-DMSO: 3.6 (m, 2 H), 4.1 (s, 2 H), 6.4 (s, 1 H), 6.9 (s, 1 H), 7.0 (m, 2 H), 7.3 (m, 3 H), 7.8 (m, 3 H), 8.7 (m, 1 H). | using 2-(4-chlorophenoxy ethylamine |

The following examples of the general formula

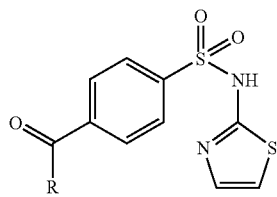

were prepared by the following method using the indicated amines.

To a 1M solution of 4-{[(2,4-Dimethoxybenzyl)(1,3-thiazol-2-yl)amino]sulfonyl}benzoic acid (Preparation 99, 1 ml, 0.1 mmol, 1 eq) in dimethylformamide was added an amine (0.1 mmol, 1 eq), $Et_3N$ (0.03 ml, 0.2 mmol, 2 eq) and HATU (38 mg, 0.1 mmol, 1 eq), the reaction mixture was sealed and shaken at 30° C. for 16 hours. The reaction mixture was concentrated in vacuo and the residue redissolved in DCM: TFA (1:3) (1 ml). The reaction mixture was sealed and shaken at 30° C. for 2 hours. The solvent was evaporated in vacuo and the residue purified by preparative HPLC to yield the title compound.

Amines used for the amide bond formation are commercially available, synthesized via known literature methods (referenced in table) or synthesized by analogous methods known to those skilled in the art.

TABLE 6

| Example | Name | R | Data | Preparation Information |
|---|---|---|---|---|
| 187 | N-benzyl-N-isopropyl-4-[(1,3-thiazol-2-ylamino)sulfonyl] benzamide | ![benzyl-N-isopropyl] | LCMS Rt = 2.903 min MS m/z 416 [MH]+ | using N-benzyl-N-isopropyl amine |
| 188 | N-[(1S,2R)-2-hydroxy-1-methyl-2-phenylethyl]-N-methyl-4-[(1,3-thiazol-2-ylamino)sulfonyl] benzamide | ![phenyl-CH(OH)-CH(CH3)-N(CH3)-] | LCMS Rt = 2.401 min MS m/z 432 [MH]+ | using (1S,2R)-2-hydroxy-1-methyl-2-phenyl ethylamine |

TABLE 6-continued

| Example | Name | R | Data | Preparation Information |
|---|---|---|---|---|
| 189 | 4-{[2-Methyl-2-(3-methylphenyl)morpholin-4-yl]carbonyl}-N-1,3-thiazol-2-yl benzenesulfonamide | | LCMS Rt = 2.899 min MS m/z 458 [MH]+ | using 2-methyl-2-(3-methylphenyl)-morpholine |
| 190 | 4-({2-[2-(1H-pyrazol-1-yl)ethyl]piperidin-1-yl}carbonyl)-N-1,3-thiazol-2-yl benzenesulfonamide | | LCMS Rt = 2.52 min MS m/z 446 [MH]+ | using 2-[2-(1H-pyrazol-1-yl) ethyl]piperidine |
| 191 | 4-[(3-Phenylpyrrolidin-1-yl)carbonyl]-N-1,3-thiazol-2-yl benzenesulfonamide | | LCMS Rt = 2.808 min MS m/z 414 [MH]+ | using 3-phenyl pyrrolidine |
| 192 | 4-{[(3S,3aR,6R,7aS)-8-oxo-2-phenyloctahydro-1H-3,6-methanoindol-1-yl]carbonyl}-N-1,3-thiazol-2-yl benzenesulfonamide | TFA Preparation 77 | LCMS Rt = 2.301 min MS m/z 494 [MH]+ | using 5-Phenyl-4-aqza-tricyclo[4.3.1.0$^{3,7}$]-decan-10-one trifluoro acetic acid salt |
| 193 | 4-{[3-(4-Cyano-3-fluorophenoxy)piperidin-1-yl]carbonyl}-N-1,3-thiazol-2-yl benzenesulfonamide | | LCMS Rt = 2.826 min MS m/z 487 [MH]+ | using 3-(4-cyano-3-fluorophenoxy) piperidine |
| 194 | 4-{[4-(2-Fluoro-5-methylphenyl)-4-hydroxypiperidin-1-yl]carbonyl}-N-1,3-thiazol-2-yl benzenesulfonamide | WO2005077912 | LCMS Rt = min MS m/z 476 [MH]+ | using 4-(2-fluoro-5-methylphenyl)-4-hydroxy-piperidine |

TABLE 6-continued

| Example | Name | R | Data | Preparation Information |
|---|---|---|---|---|
| 195 | 4-{[4-(4-Chlorophenyl)-4-methylpiperidin-1-yl]carbonyl}-N-1,3-thiazol-2-yl benzenesulfonamide | *Tetrahedron Letters* 2000, 41(46), 8853-8856 | LCMS Rt = min MS m/z 476 [MH]$^+$ | using 4-(4-chlorophenyl)-4-methyl piperidine |
| 196 | 4-{[3-(2-Methoxybenzyl)piperidin-1-yl]carbonyl}-N-1,3-thiazol-2-yl benzenesulfonamide | | LCMS Rt = 3.069 min MS m/z 472 [MH]$^+$ | using 3-(2-methoxybenzyl) piperidine |
| 197 | 4-[(2-Benzylpyrrolidin-1-yl)carbonyl]-N-1,3-thiazol-2-yl benzenesulfonamide | | LCMS Rt = 2.887 min MS m/z 428 [MH]$^+$ | using 2-benzyl pyrrolidine |
| 198 | 4-{[(3S)-3-(2-methylphenoxy)pyrrolidin-1-yl]carbonyl}-N-1,3-thiazol-2-yl benzenesulfonamide | | LCMS Rt = 2.904 min MS m/z 444 [MH]$^+$ | using (3S)-3-(2-methyl phenoxy) pyrrolidine |
| 199 | 4-{[6-(3-Fluoro-4-methoxybenzyl)-1,4-oxazepan-4-yl]carbonyl}-N-1,3-thiazol-2-yl benzenesulfonamide | | LCMS Rt = 2.785 min MS m/z 506 [MH]$^+$ | using 6-(3-fluoro-4-methoxybenzyl)-1,4-oxazepane |
| 200 | 4-{[(3S)-3-(2-chlorophenoxy)pyrrolidn-1-yl]carbonyl}-N-1,3-thiazol-2-yl benzenesulfonamide | US2006160786 | LCMS Rt = 2.867 min MS m/z 464 [MH]$^+$ | using (3S)-3-(2-chlorophenoxy) pyrrolidine |

TABLE 6-continued

| Example | Name | R | Data | Preparation Information |
|---|---|---|---|---|
| 201 | 4-{[2-(3-Methoxyphenyl)piperidin-1-yl]carbonyl}-N-1,3-thiazol-2-yl benzenesulfonamide | | LCMS Rt = 2.76 min MS m/z 458 [MH]+ | using 2-(3-methoxyphenyl) piperidine |
| 202 | 4-{[2-(2,5-Dimethylphenyl)pyrrolidin-1-yl]carbonyl}-N-1,3-thiazol-2-yl benzenesulfonamide | | LCMS Rt = 2.733 min MS m/z 442 [MH]+ | using 2-(2,5-dimethylphenyl) pyrrolidine |
| 203 | 4-{[3-(4-Methoxyphenoxy)piperidin-1-yl]carbonyl}-N-1,3-thiazol-2-yl benzenesulfonamide | | LCMS Rt = 2.827 min MS m/z 474 [MH]+ | using 3-(4-methoxyphenoxy)-piperidine |
| 204 | 4-{[(3R)-3-(2-methylphenoxy)pyrrolidin-1-yl]carbonyl}-N-1,3-thiazol-2-yl benzenesulfonamide | | LCMS Rt = 2.904 min MS m/z 444 [MH]+ | using (3R)-3-(2-methyl phenoxy) pyrrolidine |
| 205 | 4-[(2-Phenylpyrrolidin-1-yl)carbonyl]-N-1,3-thiazol-2-yl benzenesulfonamide | | LCMS Rt = 2.725 min MS m/z 414 [MH]+ | using 2-phenyl pyrrolidine |
| 206 | 4-{[2-(4-Methoxybenzyl)pyrrolidin-1-yl]carbonyl}-N-1,3-thiazol-2-yl benzenesulfonamide | | LCMS Rt = 2.868 min MS m/z 458 [MH]+ | using 2-(4-methoxy benzyl) pyrrolidine |
| 207 | 4-{[2-(4-Methylphenyl)piperidin-1-yl]carbonyl}-N-1,3-thiazol-2-yl benzenesulfonamide | | LCMS Rt = 2.916 min MS m/z 442 [MH]+ | using 2-(4-methylphenyl)-piperidine |

TABLE 6-continued

| Example | Name | R | Data | Preparation Information |
|---|---|---|---|---|
| 208 | N-benzyl-N-[(1R)-2-hydroxy-1-phenylethyl]-4-[(1,3-thiazol-2-yl amino)sulfonyl] benzamide | | LCMS Rt = 2.374 min MS m/z 494 [MH]+ | using (2R)-2-(benzylamino)-2-phenyl ethanol |
| 209 | N-ethyl-N-(1-methyl-2-oxo-2-phenylethyl)-4-[(1,3-thiazol-2-yl amino)sulfonyl] benzamide | | LCMS Rt = 2.795 min MS m/z 444 [MH]+ | using 2-(ethylamino)-1-phenyl propan-1-one |
| 210 | 4-({2-[(1-Oxo-1,3-dihydro-2H-isoindol-2-yl)methyl]morpholin-4-yl}carbonyl)-N-1,3-thiazol-2-ylbenzenesulfonamide | | LCMS Rt = 2.528 min MS m/z 499 [MH]+ | using 2-[(1-oxo-1,3-dihydro-2H-isoindol-2-yl)methyl] morpholine |
| 211 | 4-{[3-(benzyloxy)piperidin-1-yl]carbonyl}-N-1,3-thiazol-2-yl benzenesulfonamide | | LCMS Rt = 2.872 min MS m/z 458 [MH]+ | using 3-(benzyloxy) piperidine |
| 212 | 4-{[2-(2-Methylpyrimidin-4-yl)pyrrolidin-1-yl]carbonyl}-N-1,3-thiazol-2-yl benzenesulfonamide | | LCMS Rt = 2.217 min MS m/z 430 [MH]+ | using 2-(2-methylpyrimidin-4-yl)pyrrolidine |
| 213 | N-benzyl-N-[(1R,2R)-2-hydroxycyclohexyl]-4-[(1,3-thiazol-2-yl amino)sulfonyl] benzamide | | LCMS Rt = 2.834 min MS m/z 472 [MH]+ | using (1R,2R)-2-(benzylamino) cyclohexanol |
| 214 | 4-{[(2S)-2-benzyl-1,3-oxazinan-3-yl]carbonyl}-N-1,3-thiazol-2-yl benzenesulfonamide | | LCMS Rt = 2.66 min MS m/z 444 [MH]+ | using (2S)-2-benzyl-1,3-oxazinane |

TABLE 6-continued

| Example | Name | R | Data | Preparation Information |
|---|---|---|---|---|
| 215 | 4-{[2-(2-Chlorophenyl)pyrrolidin-1-yl]carbonyl}-N-1,3-thiazol-2-yl benzenesulfonamide | [2-chlorophenyl pyrrolidine structure] | LCMS Rt = 2.659 min MS m/z 448 [MH]⁺ | using 2-(2-chlorophenyl) pyrrolidine |
| 216 | 4-({6-[(5-Fluoropyridin-2-yl)methyl]-1,4-oxazepan-4-yl}carbonyl)-N-1,3-thiazol-2-yl benzenesulfonamide | [5-fluoropyridin-2-yl methyl oxazepane structure] | LCMS Rt = 2.312 min MS m/z 477 [MH]⁺ | using 6-[(5-fluoropyridin-2-yl)methyl]-1,4-oxazepane |
| 217 | 4-{[3-(3-Methoxyphenyl)piperidin-1-yl]carbonyl}-N-1,3-thiazol-2-yl benzenesulfonamide | [3-methoxyphenyl piperidine structure] | LCMS Rt = 2.934 min MS m/z 458 [MH]⁺ | using 3-(3-methoxyphenyl) piperidine |
| 218 | N-benzyl-N-(2-cyanoethyl)-4-[(1,3-thiazol-2-yl amino)sulfonyl] benzamide | [benzyl cyanoethyl amine structure] | LCMS Rt = 2.642 min MS m/z 427 [MH]⁺ | using 3-(benzylamino) propanenitrile |
| 219 | N-ethyl-N-[(1S)-2-hydroxy-1-phenylethyl]-4-[(1,3-thiazol-2-yl amino)sulfonyl] benzamide | [(2S)-2-(ethylamino)-2-phenylethanol structure] | LCMS Rt = 2.348 min MS m/z 432 [MH]⁺ | using (2S)-2-(ethylamino)-2-phenylethanol |
| 220 | 4-{[4-(3-Fluorophenyl)-4-hydroxypiperidin-1-yl]carbonyl}-N-1,3-thiazol-2-yl benzenesulfonamide | [4-(3-fluorophenyl)-4-hydroxypiperidine structure] WO2005118587 | LCMS Rt = 2.618 min MS m/z 462 [MH]⁺ | using 4-(3-fluorophenyl)-4-hydroxy piperidine |
| 221 | 4-{[2-(3-Fluorophenyl)piperidin-1-yl]carbonyl}-N-1,3-thiazol-2-yl benzenesulfonamide | [2-(3-fluorophenyl)piperidine structure] | LCMS Rt = 2.798 min MS m/z 446 [MH]⁺ | using 2-(3-fluorophenyl) piperidine |

TABLE 6-continued

| Example | Name | R | Data | Preparation Information |
|---|---|---|---|---|
| 222 | 4-{[3-(4-Fluorobenzyl)piperidin-1-yl]carbonyl}-N-1,3-thiazol-2-yl benzenesulfonamide | | LCMS Rt = 2.863 min MS m/z 460 [MH]+ | using 3-(4-fluorobenzyl) piperidine |
| 223 | 4-{[3-(4-Fluorophenyl)thiomorpholin-4-yl]carbonyl}-N-1,3-thiazol-2-yl benzenesulfonamide | | LCMS Rt = 2.912 min MS m/z 464 [MH]+ | using 3-(4-fluorophenyl) thiomorpholine |
| 224 | 4-{[2-(Phenoxymethyl)piperidine-1-yl]carbonyl}-N-1,3-thiazol-2-yl benzenesulfonamide | | LCMS Rt = 2.775 min MS m/z 458 [MH]+ | using 2-(phenoxymethyl) piperidine |
| 225 | 4-({6-[(6-Methylpyridin-2-yl)methyl]-1,4-oxazepan-4-yl}carbonyl)-N-1,3-thiazol-2-yl benzenesulfonamide | Preparation 84 | LCMS Rt = 1.951 min MS m/z 473 [MH]+ | using 6-[(6-Methylpyridin-2-yl)methyl]1,4-oxazepane dihydrochloride |
| 226 | N-benzyl-N-[(1R,2S)-2-(hydroxymethyl)cyclohexyl]-4-[(1,3-thiazol-2-ylamino)sulfonyl] benzamide | | LCMS Rt = 2.25 min MS m/z 486 [MH]+ | using ((1S,2R)-2-(benzylamino) cyclohexyl) methanol |
| 227 | 4-{[3-(2-Phenylethyl)pyrrolidin-1-yl]carbonyl}-N-1,3-thiazol-2-yl benzenesulfonamide | | LCMS Rt = 3.046 min MS m/z 442 [MH]+ | using 3-(2-phenylethyl) pyrrolidine |
| 228 | 4-{[2-(3-Methylphenyl)pyrrolidin-1-yl]carbonyl}-N-1,3-thiazol-2-yl benzenesulfonamide | | LCMS Rt = 2.558 min MS m/z 428 [MH]+ | using 2-(3-methylphenyl) pyrrolidine |

TABLE 6-continued

| Example | Name | R | Data | Preparation Information |
|---|---|---|---|---|
| 229 | N-(2-hydroxyethyl)-N-(1-phenylethyl)-4-[(1,3-thiazol-2-yl amino)sulfonyl] benzamide | 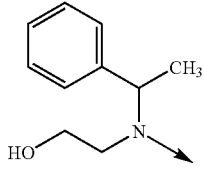 | LCMS Rt = 2.325 min MS m/z 432 [MH]+ | using 2-(1-phenylethyl amino)ethanol |
| 230 | N-cyclopropyl-N-(4-fluorobenzyl)-4-[(1,3-thiazol-2-yl amino)sulfonyl] benzamide | 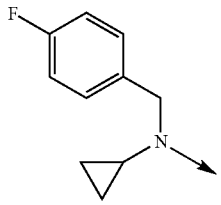 | LCMS Rt = 2.908 min MS m/z 432 [MH]+ | using Cyclopropyl-(4-fluoro-benzyl)-amine |
| 231 | 4-[(2-Cyclopropylmorpholin-4-yl)carbonyl]-N-1,3-thiazol-2-yl benzenesulfonamide | 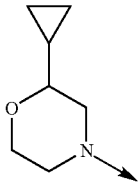 | LCMS Rt = 2.4 min MS m/z 394 [MH]+ | using 2-cyclopropyl morpholine |
| 232 | 4-{[2-(2-Methoxyphenyl)morpholin-4-yl]carbonyl}-N-1,3-thiazol-2-yl benzenesulfonamide | 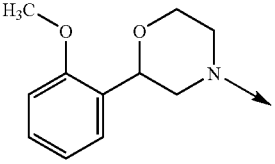 WO2008006372 | LCMS Rt = 2.815 min MS m/z 460 [MH]+ | using 2-(2-methoxyphenyl) morpholine |
| 233 | 4-{[2-(2-Fluorobenzyl)pyrrolidin-1-yl]carbonyl}-N-1,3-thiazol-2-yl benzenesulfonamide | 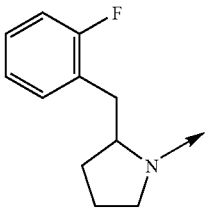 | LCMS Rt = 2.895 min MS m/z 446 [MH]+ | using 2-(2-fluorobenzyl) pyrrolidine |
| 234 | 4-({2-[(3-Chlorophenoxy)methyl]morpholin-4-yl}carbonyl)-N-1,3-thiazol-2-yl benzenesulfonamide | 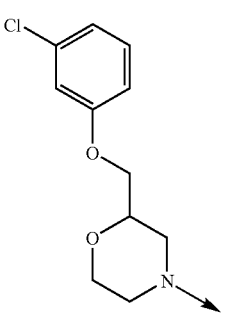 WO2006117669 | LCMS Rt = 2.985 min MS m/z 494 [MH]+ | using 2-[(3-chlorophenoxy) methyl] morpholine |

TABLE 6-continued

| Example | Name | R | Data | Preparation Information |
|---|---|---|---|---|
| 235 | N-(3-hydroxy-3-phenylpropyl)-N-methyl-4-[(1,3-thiazol-2-yl amino)sulfonyl]benzamide | 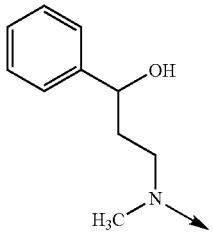 | LCMS Rt = 2.392 min MS m/z 432 [MH]+ | using N-(3-hydroxy-3-phenylpropyl)-N-methyl amine |
| 236 | 4-{[4-(4-Chlorophenyl)-4-hydroxypiperidin-1-yl]carbonyl}-N-1,3-thiazol-2-ylbenzene sulfonamide | 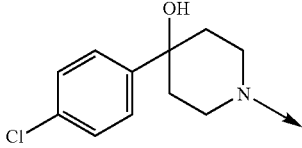 | LCMS Rt = 2.767 min MS m/z 478 [MH]+ | using 4-(4-chlorophenyl)-4-hydroxy piperidine |
| 237 | 4-{[3-(Pyrimidin-2-ylmethyl)piperidin-1-yl]carbonyl}-N-1,3-thiazol-2-yl benzenesulfonamide | 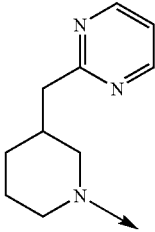  Preparation 71 | LCMS Rt = 2.332 min MS m/z 444 [MH]+ | using 2-(piperidin-3-ylmethyl) pyrimidine |
| 238 | 4-[(2-Pyridin-2-ylpiperidin-1-yl)carbonyl]-N-1,3-thiazol-2-yl benzenesulfonamide | 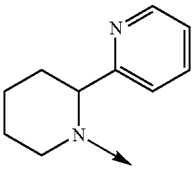 | LCMS Rt = 2.257 min MS m/z 429 [MH]+ | using 2-pyridin-2-ylpiperidine |
| 239 | 4-[(2-Phenylpiperidin-1-yl)carbonyl]-N-1,3-thiazol-2-yl benzenesulfonamide | 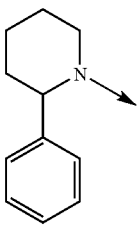 | LCMS Rt = 2.752 min MS m/z 428 [MH]+ | using 2-phenylpiperidine |
| 240 | 4-{[2-(3-Methoxybenzyl)pyrrolidin-1-yl]carbonyl}-N-1,3-thiazol-2-yl benzenesulfonamide | 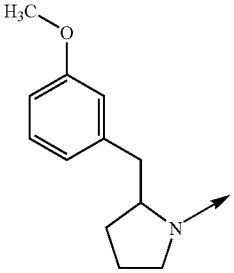 | LCMS Rt = 2.882 min MS m/z 458 [MH]+ | using 2-(3-methoxybenzyl) pyrrolidine |

TABLE 6-continued

| Example | Name | R | Data | Preparation Information |
|---|---|---|---|---|
| 241 | N-[(1R,2S)-2-hydroxy-1-methyl-2-phenylethyl]-N-methyl-4-[(1,3-thiazol-2-ylamino)sulfonyl]benzamide | | LCMS Rt = 2.4 min MS m/z 432 [MH]+ | using N-[(1R,2S)-2-hydroxy-1-methyl-2-phenylethyl]-N-methylamine |
| 242 | 4-({2-[(6-Methylpyridin-2-yl)methyl]piperidin-1-yl}carbonyl)-N-1,3-thiazol-2-yl benzenesulfonamide | | LCMS Rt = 2.105 min MS m/z 457 [MH]+ | using 2-[(6-methylpyridin-2-yl)methyl]piperidine |
| 243 | 4-[(2-{[(2-Methylpyridin-3-yl)oxy]methyl}morpholin-4-yl)carbonyl]-N-1,3-thiazol-2-yl benzenesulfonamide | | LCMS Rt = 2.024 min MS m/z 475 [MH]+ | using 2-{[(2-methylpyridin-3-yl)oxy]methyl}-morpholine |
| 244 | 4-{[2-(Pyridin-2-ylmethyl)piperidin-1-yl]carbonyl}-N-1,3-thiazol-2-yl benzenesulfonamide | | LCMS Rt = 2.09 min MS m/z 443 [MH]+ | using 2-(pyridin-2-ylmethyl) piperidine |
| 245 | N-benzyl-N-[(1S,2R)-2-(hydroxymethyl)cyclohexyl]-4-[(1,3-thiazol-2-ylamino)sulfonyl]benzamide | | LCMS Rt = 2.25 min MS m/z 486 [MH]+ | using ((1R,2S)-2-(benzylamino) cyclohexyl) methanol |
| 246 | 4-({2-[(4,6-Dimethylpyridin-2-yl)methyl]azepan-1-yl}carbonyl)-N-1,3-thiazol-2-yl benzenesulfonamide | | LCMS Rt = 1.95 min MS m/z 485 [MH]+ | using 2-[(4,6-dimethylpyridin-2-yl)methyl] azepane |

WO2007125398

TABLE 6-continued

| Example | Name | R | Data | Preparation Information |
|---|---|---|---|---|
| 247 | 4-{[(3R)-3-(2-chlorophenoxy)pyrrolidin-1-yl]carbonyl}-N-1,3-thiazol-2-yl benzenesulfonamide | (2-chlorophenoxy on (3R)-pyrrolidine) *Journal of Medicinal Chemistry* 2007, 50(2), 182-185 | LCMS Rt = 2.867 min MS m/z 464 [MH]$^+$ | using -{[(3R)-3-(2-chlorophenoxy) pyrrolidine |
| 248 | 4-({2-[(4-Methylpyridin-2-yl)methyl]pyrrolidin-1-yl}carbonyl)-N-1,3-thiazol-2-yl benzenesulfonamide | (4-methylpyridin-2-yl)methyl pyrrolidine | LCMS Rt = 2.07 min MS m/z 443 [MH]$^+$ | using 2-[(4-methylpyridin-2-yl)methyl]-pyrrolidine |
| 249 | 4-{[3-(4-mMethylphenoxy)-piperidin-1-yl]-carbonyl}-N-1,3-thiazol-2-yl benzenesulfonamide | 3-(4-methylphenoxy)piperidine | LCMS Rt = 2.786 min MS m/z 458 [MH]$^+$ | using 3-(4-methylphenoxy) piperidine |
| 250 | N-(2-hydroxy-2-phenylethyl)-N-methyl-4-[(1,3-thiazol-2-yl amino)sulfonyl] benzamide | N-(2-hydroxy-2-phenylethyl)-N-methylamine | LCMS Rt = 2.339 min MS m/z 418 [MH]$^+$ | using N-(2-hydroxy-2-phenylethyl)-N-methylamine |
| 251 | N-(1,2-diphenylethyl)-N-methyl-4-[(1,3-thiazol-2-ylamino)sulfonyl] benzamide | N-(1,2-diphenylethyl)-N-methylamine | LCMS Rt = 2.933 min MS m/z 478 [MH]$^+$ | using N-(1,2-diphenylethyl)-N-methylamine |
| 252 | 4-{[4-Hydroxy-4-(4-methylphenyl)piperidin-1-yl]carbonyl}-N-1,3-thiazol-2-yl benzenesulfonamide | 4-hydroxy-4-(4-methylphenyl)piperidine | LCMS Rt = 2.691 min MS m/z 458 [MH]$^+$ | using 4-hydroxy-4-(4-methylphenyl)-piperidine |

TABLE 6-continued

| Example | Name | R | Data | Preparation Information |
|---|---|---|---|---|
| 253 | 4-[(3-Benzoylpiperidin-1-yl)carbonyl]-N-1,3-thiazol-2-yl benzenesulfonamide | | LCMS Rt = 2.786 min MS m/z 456 [MH]+ | using 3-benzoyl piperidine |
| 254 | 4-{[2-(2-Methoxyphenyl)pyrrolidin-1-yl]carbonyl}-N-1,3-thiazol-2-yl benzenesulfonamide | | LCMS Rt = 2.78 min MS m/z 444 [MH]+ | using 2-(2-methoxyphenyl) pyrrolidine |
| 255 | 4-[(2-Pyridin-2-ylazepan-1-yl)carbonyl]-N-1,3-thiazol-2-yl benzenesulfonamide | | LCMS Rt = 2.283 min MS m/z 443 [MH]+ | using 2-pyridin-2-ylazepane |
| 256 | N-methyl-N-[(1S)-1-phenylethyl]-4-[(1,3-thiazol-2-yl amino)sulfonyl] benzamide | | LCMS Rt = 2.786 min MS m/z 402 [MH]+ | using N-methyl-N-[(1S)-1-phenylethyl amine |
| 257 | N-cyclohexyl-N-(2-hydroxy-2-phenylpropyl)-4-[(1,3-thiazol-2-yl amino)sulfonyl] benzamide | *Journal of Organic Chemistry* 1986, 51(9), 1383-1389 | LCMS Rt = 2.431 min MS m/z 500 [MH]+ | using N-cyclohexyl-N-(2-hydroxy-2-phenylpropyl amine |
| 258 | 4-[(6-Benzyl-6-hydroxy-1,4-oxazepan-4-yl)carbonyl]-N-1,3-thiazol-2-yl benzenesulfonamide | Preparation 82 | LCMS Rt = 2.555 min MS m/z 474 [MH]+ | using 6-benzyl-1,4-oxazepan-6-ol hydrochloride |
| 259 | 4-[(6-Benzyl-1,4-oxazepan-4-yl)carbonyl]-N-1,3-thiazol-2-yl benzenesulfonamide | 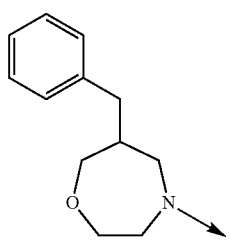 | LCMS Rt = 2.739 min MS m/z 458 [MH]+ | using 6-benzyl-1,4-oxazepane |

TABLE 6-continued

| Example | Name | R | Data | Preparation Information |
|---|---|---|---|---|
| 260 | 4-{[3-(3-Methoxypropoxy)piperidin-1-yl]carbonyl}-N-1,3-thiazol-2-yl benzenesulfonamide | | LCMS Rt = 2.503 min MS m/z 440 [MH]+ | using 3-(3-methoxypropoxy)-piperidine |
| 261 | 4-{[(2R)-2-pyridin-2-yl piperidin-1-yl]carbonyl}-N-1,3-thiazol-2-yl benzenesulfonamide | | LCMS Rt = 2.256 min MS m/z 429 [MH]+ | using (2R)-2-pyridin-2-yl piperidine |
| 262 | 4-({2-[(3,5-Difluorophenoxy)methyl]morpholin-4-yl}carbonyl)-N-1,3-thiazol-2-yl benzenesulfonamide | WO2006117669 | LCMS Rt = 2.941 min MS m/z 496 [MH]+ | using 2-[(3,5-difluorophenoxy)methyl] morpholine |
| 263 | 4-{[3-(3-Methoxybenzyl)piperidin-1-yl]carbonyl}-N-1,3-thiazol-2-yl benzenesulfonamide | | LCMS Rt = 3.016 min MS m/z 472 [MH]+ | using 2-(3-methoxybenzyl) piperidine |
| 264 | 4-({3-[(4-Fluorophenoxy)methyl]piperidin-1-yl}carbonyl)-N-1,3-thiazol-2-yl benzenesulfonamide | | LCMS Rt = 3.028 min MS m/z 476 [MH]+ | using 3-[(4-fluorophenoxy)methyl] piperidine |

TABLE 6-continued

| Example | Name | R | Data | Preparation Information |
|---|---|---|---|---|
| 265 | 4-{[3-(3-Cyanophenoxy)piperidin-1-yl]carbonyl}-N-1,3-thiazol-2-yl benzenesulfonamide | 3-cyanophenoxy group attached via O to piperidine N-linked | LCMS Rt = 2.768 min MS m/z 469 [MH]+ | using 3-(3-cyanophenoxy)piperidine |
| 266 | 4-({2-[(2-Chloro-4-fluorophenoxy)methyl]morpholin-4-yl}carbonyl)-N-1,3-thiazol-2-ylbenzenesulfonamide | 2-chloro-4-fluorophenoxymethyl morpholine; WO2006117669 | LCMS Rt = 2.952 min MS m/z 512 [MH]+ | using 2-[(2-chloro-4-fluorophenoxy)methyl]morpholine |
| 267 | 4-{[3-(Phenoxymethyl)piperidin-1-yl]carbonyl}-N-1,3-thiazol-2-yl benzenesulfonamide | phenoxymethyl piperidine | LCMS Rt = 2.99 min MS m/z 458 [MH]+ | using 3-(phenoxymethyl)piperidine |
| 268 | 4-[(2-Phenylazepan-1-yl)carbonyl]-N-1,3-thiazol-2-yl benzenesulfonamide | 2-phenylazepane | LCMS Rt = 2.835 min MS m/z 442 [MH]+ | using 2-phenylazepane |
| 269 | 4-({3-[(Cyclopropylmethoxy)methyl]pyrrolidin-1-yl}carbonyl)-N-1,3-thiazol-2-yl benzenesulfonamide | cyclopropylmethoxymethyl pyrrolidine; Preparation 67 | LCMS Rt = 2.644 min MS m/z 422 [MH]+ | using 3-cyclopropyl methoxymethyl-pyrrolidine |

TABLE 6-continued

| Example | Name | R | Data | Preparation Information |
|---|---|---|---|---|
| 270 | 4-{[3-(4-Methoxybenzyl)piperidin-1-yl]carbonyl}-N-1,3-thiazol-2-yl benzenesulfonamide | 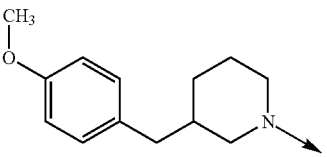 | LCMS Rt = 3.037 min MS m/z 472 [MH]+ | using 3-(4-methoxybenzyl)piperidine |
| 271 | 4-({3-[(3,5-Difluorophenoxy)methyl]-piperidin-1-yl}carbonyl)-N-1,3-thiazol-2-yl benzenesulfonamide | 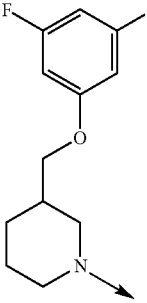 | LCMS Rt = 3.134 min MS m/z 494 [MH]+ | using 3-[(3,5-difluorophenoxy)methyl] piperidine |
| 272 | 4-{[3-(Pyrimidin-5-ylmethyl)piperidin-1-yl]carbonyl}-N-1,3-thiazol-2-yl benzenesulfonamide | 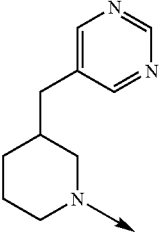<br>Preparation 72 | LCMS Rt = 2.345 min MS m/z 444 [MH]+ | using 5-(piperidin-3-ylmethyl) pyrimidine |
| 273 | 4-{[2-(3-Methoxyphenyl)pyrrolidin-1-yl]carbonyl}-N-1,3-thiazol-2-yl benzenesulfonamide | 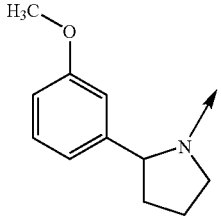 | LCMS Rt = 2.748 min MS m/z 444 [MH]+ | using2-(3-methoxyphenyl) pyrrolidine |
| 274 | N-(2,3-dihydro-1-benzofuran-2-ylmethyl)-N-methyl-4-[(1,3-thiazol-2-ylamino)sulfonyl] benzamide | 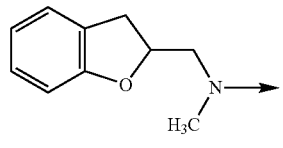 | LCMS Rt = 2.708 min MS m/z 430 [MH]+ | using N-(2,3-dihydro-1-benzofuran-2-ylmethyl))-N-methylamine |
| 275 | 4-{[2-(3-Methoxyphenyl)azepan-1-yl]carbonyl}-N-1,3-thiazol-2-yl benzenesulfonamide | 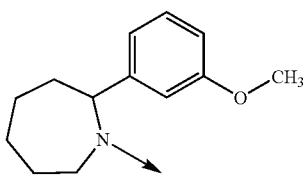 | LCMS Rt = 2.848 min MS m/z 472 [MH]+ | using 2-(3-methoxyphenyl) azepane |
| 276 | 4-{[4-(3-Methylbenzyl)-3-oxopiperazin-1-yl]carbonyl}-N-1,3-thiazol-2-yl benzenesulfonamide | 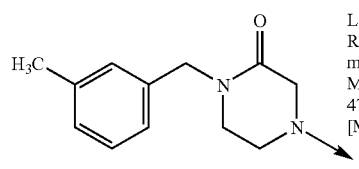 | LCMS Rt = 2.689 min MS m/z 471 [MH]+ | using 4-(3-methylbenzyl)-3-oxopiperazine |

TABLE 6-continued

| Example | Name | R | Data | Preparation Information |
|---|---|---|---|---|
| 277 | 4-[(3-Phenoxypiperidin-1-yl)carbonyl]-N-1,3-thiazol-2-yl benzenesulfonamide | | LCMS Rt = 2.829 min MS m/z 444 [MH]+ | using 3-phenoxy piperidine |
| 278 | 4-({3-[(3-Cyanophenoxy)methyl]-piperidin-1-yl}carbonyl)-N-1,3-thiazol-2-yl benzenesulfonamide | | LCMS Rt = 2.934 min MS m/z 483 [MH]+ | using 3-[(3-cyanophenoxy)methyl] piperidine |
| 279 | 4-{[2-(3-Chlorobenzyl)pyrrolidin-1-yl]carbonyl}-N-1,3-thiazol-2-yl benzenesulfonamide | | LCMS Rt = 2.853 min MS m/z 462 [MH]+ | using 2-(3-chlorobenzyl) pyrrolidine |
| 280 | 4-{[4-(Hydroxymethyl)-2-(4-methoxyphenyl)pyrrolidin-1-yl]carbonyl}-N-1,3-thiazol-2-yl benzenesulfonamide | | LCMS Rt = 2.4 min MS m/z 474 [MH]+ | using 4-(hydroxymethyl)-2-(4-methoxyphenyl) pyrrolidine |
| 281 | 4-{[2-(2-Fluorophenyl)pyrrolidin-1-yl]carbonyl}-N-1,3-thiazol-2-yl benzenesulfonamide | | LCMS Rt = 2.772 min MS m/z 432 [MH]+ | using 2-(2-fluorophenyl) pyrrolidine |
| 282 | 4-[(3-Benzylpyrrolidin-1-yl)carbonyl]-N-1,3-thiazol-2-yl benzenesulfonamide | | LCMS Rt = 2.903 min MS m/z 428 [MH]+ | using 3-benzyl pyrrolidine |

TABLE 6-continued

| Example | Name | R | Data | Preparation Information |
|---------|------|---|------|------------------------|
| 283 | 4-[(2-Pyridin-2-yl pyrrolidin-1-yl) carbonyl]-N-1,3-thiazol-2-yl benzenesulfonamide | 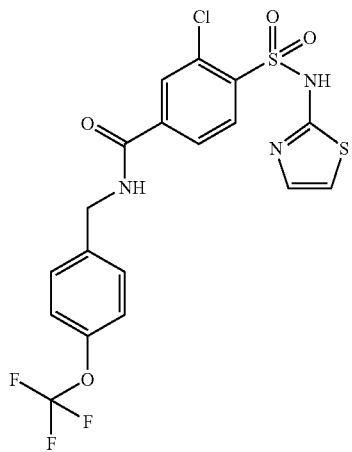 | LCMS Rt = 1.99 min MS m/z 415 [MH]$^+$ | using 2-pyridin-2-ylpyrrolidine |

Example 284

3-Chloro-4-[(1,3-thiazol-2-ylamino)sulfonyl]-N-[4-(trifluoromethoxy)benzyl]benzamide

Method I

To a cooled solution of methyl 3-chloro-4-{[(2,4-dimethoxybenzyl)(1,3-thiazol-2-yl)amino]sulfonyl}benzoate (Preparation 7, 100 mg, 0.21 mmol, 1 eq) and Et$_3$N (44 μL, 0.32 mmol, 1.5 eq) in THF (6 ml) was added 1-(3-dimethylaminopropyl)-3-ethylcarbodiimide hydrochloride (106 mg, 0.55 mmol, 1.3 eq) and 1-hydroxybenzotriazole (58 mg, 0.43 mmol, 1 eq). The reaction mixture was stirred at 0° C. for 20 minutes before the addition of 4-(trifluoromethoxy)benzylamine (36 μL, 0.23 mmol, 1.1 eq) and then stirred for a further 18 hours. The solvent was evaporated in vacuo and the residue partitioned between DCM (15 ml) and water (15 ml) then passed through a phase separation cartridge. The organic phase was concentrated and the residue redissolved in 4.5M HCl in 1,4-dioxane (5 ml) and the solution stirred at room temperature for 18 hours. The solvent was evaporated in vacuo and the residue purified by preparative HPLC to yield the title compound.

LCMS Rt=3.27 min. MS m/z 491.99 [MH]+.

The following examples of the general formula

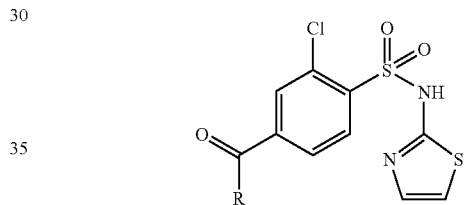

were prepared by Method I as described for Example 284 above. Unless otherwise noted, preparation details are as described for the method referred to.

TABLE 7

| Example | Name | R | Data | Preparation Information |
|---------|------|---|------|------------------------|
| 285 | 3-Chloro-4-[(1,3-thiazol-2-ylamino)sulfonyl]-N-[3-(trifluoromethoxy)benzyl]benzamide | | LCMS Rt = 3.37 min MS m/z 491 [MH]$^+$ | Method I, using 3-(trifluoromethoxy)benzylamine |
| 286 | 3-Chloro-N-[3-fluoro-4-(trifluoromethoxy)benzyl]-4-[(1,3-thiazol-2-yl amino)sulfonyl]benzamide | | LCMS Rt = 2.39 min MS m/z 509 [MH]$^+$ | Method I, using 3-fluoro-4-(trifluoromethoxy)benzylamine |

TABLE 7-continued

| Example | Name | R | Data | Preparation Information |
|---|---|---|---|---|
| 287 | 3-Chloro-4-[(1,3-thiazol-2-ylamino)sulfonyl]-N-[4-(trifluoromethyl)benzyl]benzamide | | LCMS Rt = 3.20 min MS m/z 476 [MH]+ | Method I, using 4-(trifluoromethyl)benzylamine, Crude product partitioned between DCM and sodium hydrogen carbonate. A solid precipitated from the DCM which was collected and purified by HPLC. |
| 288 | 3-Chloro-4-[(1,3-thiazol-2-ylamino)sulfonyl]-N-[3-(trifluoromethyl)benzyl]benzamide | | LCMS Rt = 3.21 min MS m/z 476 [MH]+ | Method I, using 3-(trifluoromethyl)benzylamine |
| 289 | 3-Chloro-N-[3-fluoro-4-(trifluoromethyl)benzyl]-4-[(1,3-thiazol-2-ylamino)sulfonyl]benzamide | | LCMS Rt = 3.27 min MS m/z 493 [MH]+ | Method I, using 3-fluoro-4-(trifluoromethyl)benzylamine |
| 290 | 3-Chloro-N-[4-fluoro-3-(trifluoromethyl)benzyl]-4-[(1,3-thiazol-2-yl amino)sulfonyl] | | LCMS Rt = 3.27 min MS m/z 493 [MH]+ | Method I, using 4-fluoro-3-trifluoromethyl benzylamine |
| 291 | 3-Chloro-N-(3,4-dichlorobenzyl)-4-[(1,3-thiazol-2-ylamino)sulfonyl]benzamide | | LCMS Rt = 3.37 min MS m/z 475 [MH]+ | Method I, using 3,4-dichloro benzylamine |
| 292 | 3-Chloro-N-(4-chloro-3-fluorobenzyl)-4-[(1,3-thiazol-2-yl amino)sulfonyl]benzamide | | LCMS Rt = 3.20 min MS m/z 459 [MH]+ | method I, using 4-chloro-3-fluorobenzylamine |
| 293 | 3-Chloro-N-[4-fluoro-3-(trifluoromethoxy)benzyl]-4-[(1,3-thiazol-2-yl amino)sulfonyl]benzamide | | LCMS Rt = 3.28 min MS m/z 509 [MH]+ | Method I, using 4-fluoro-3-(trifluoromethoxy)benzylamine |

TABLE 7-continued

| Example | Name | R | Data | Preparation Information |
|---|---|---|---|---|
| 294 | 3-Chloro-N-(3-chloro-4-fluorobenzyl)-4-[(1,3-thiazol-2-yl amino)sulfonyl]benzamide | 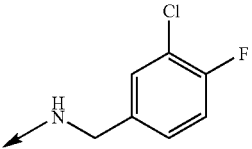 | LCMS Rt = 3.13 min MS m/z 459 [MH]+ | Method I, using 3-chloro-4-fluorobenzyl-amine |

Example 295

N-(4-chloro-3-fluorobenzyl)-3-fluoro-4-[(1,3-thiazol-2-ylamino)sulfonyl]benzamide

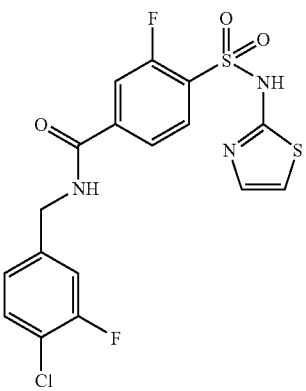 [SMILES: O=C(NCc1ccc(Cl)c(F)c1)c1ccc(S(=O)(=O)Nc2nccs2)c(F)c1]

Method J

4-{[(2,4-Dimethoxybenzyl)(1,3-thiazol-2-yl)amino]sulfonyl}-3-fluorobenzoic acid (Preparation 10, 75 mg, 0.166 mmol, 1 eq), Et$_3$N (36 mg, 0.36 mmol, 2.2 eq), 2-(1H-benzotriazol-1-yl)-1,1,1,3,3-tetramethyluronium tetrafluoroborate (TBTU, 66 mg, 0.206 mmol, 1.24 eq) and 4-chloro-3-fluorobenzylamine (48 mg, 0.301 mmol, 1.81 eq) were combined in THF (3 ml) and the reaction mixture stirred at room temperature for 18 hours. The solvent was evaporated and the residue dissolved in DCM:TFA (2 ml: 2 ml), the reaction mixture was stirred at room temperature for 2 hours. Water (4 ml) was added and the mixture was passed through a phase separation cartridge. The DCM was collected, washed with saturated sodium hydrogen carbonate, dried over sodium sulphate, filtered and evaporated in vacuo. The crude material was triturated with DCM then purified further by preparative HPLC to yield the title compound.

LCMS Rt=3.14-3.18 min. MS m/z 443 [MH]+.

The following examples of the general formula

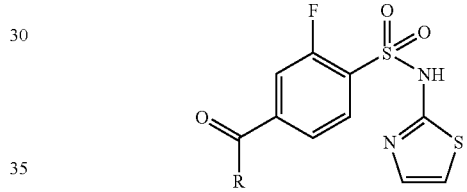

were prepared by Method J as described for Example 295 above. Unless otherwise noted, preparation details are as described for the method referred to.

TABLE 8

| Example | Name | R | Data | Preparation Information |
|---|---|---|---|---|
| 296 | 3-Fluoro-4-[(1,3-thiazol-2-ylamino)sulfonyl]-N-[3-(trifluoromethoxy)benzyl]benzamide | 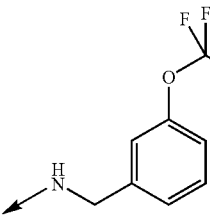 | LCMS Rt = 3.13-3.20 min MS m/z 476 [MH]+ | Method J using 3-(trifluoromethoxy) benzylamine |
| 297 | N-(3,4-dichlorobenzyl)-3-fluoro-4-[(1,3-thiazol-2-ylamino)sulfonyl]benzyamide | 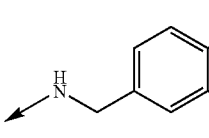 | LCMS Rt = 3.25-3.30 min MS m/z 459 [MH]+ | Method J using, 3,4-dichloro benzylamine |

TABLE 8-continued

| Example | Name | R | Data | Preparation Information |
|---|---|---|---|---|
| 298 | N-(3,4-difluorobenzyl)-3-fluoro-4-[(1,3-thiazol-2-ylamino)sulfonyl]benzamide | (3,4-difluorobenzyl-NH-) | LCMS Rt = 1.36 min MS m/z 428 [MH]$^+$ $^1$HNMR (d$_6$-DMSO): 4.4 (s, 2H), 6.9 (s, 1H), 7.15 (m, 1H), 7.3 (m, 3H), 7.8 (m, 2H), 7.9 (m, 1H), 9.25 (m, 1H), 13.0 (m, 1H). | Method J using, 3,4-difluoro benzylamine No HPLC purification was required. |
| 299 | N-(3-chloro-4-fluorobenzyl)-3-fluoro-4-[(1,3-thiazol-2-yl amino)sulfonyl]benzamide | (3-chloro-4-fluorobenzyl-NH-) | LCMS Rt = 3.11-3.17 min MS m/z 443 [MH]$^+$ | Method J using, 3-chloro-4-fluorobenzyl-amine |
| 300 | 3-Fluoro-N-[4-fluoro-3-(trifluoromethoxy)benzyl]-4-[(1,3-thiazol-2-ylamino)sulfonyl]benzamide | (4-fluoro-3-(trifluoromethoxy)benzyl-NH-) | LCMS Rt = 3.21-3.25 min MS m/z 494 [MH]$^+$ | Method J using, 4-fluoro-3-(trifluoromethoxy) benzylamine |
| 301 | 3-Fluoro-4-[(1,3-thiazol-2-ylamino)sulfonyl]-N-[4-(trifluoromethoxy)benzyl]benzamide | (4-(trifluoromethoxy)benzyl-NH-) | LCMS Rt = 1.47 min MS m/z 475 [MH]$^+$ $^1$HNMR (d$_6$-DMSO): 4.5 (s, 2H), 6.8 (s, 1H), 7.25 (s, 1H), 7.3 (d, 2H), 7.4 (d, 2H), 7.8 (m, 2H), 7.9 (m, 1H), 9.3 (m, 1H). | Method J using, 4-(trifluoromethoxy) benzylamine. After amide formation an aqueous work up was performed using ethyl acetate and sodium bicarbonate. No HPLC purification was required. |
| 302 | 3-Fluoro-4-[(1,3-thiazol-2-ylamino)sulfonyl]-N-[3-(trifluoromethyl)benzyl]benzamide | (3-(trifluoromethyl)benzyl-NH-) | LCMS Rt = 1.45 min MS m/z 459 [MH]$^+$ $^1$HNMR (d$_6$-DMSO): 4.5 (s, 2H), 6.4 (s, 1H), 6.9 (s, 1H), 7.6 (m, 6H), 7.8 (m, 1H), 9.2 (m, 1H). | Method J using, 3-(trifluoromethyl) benzylamine, After amide formation an aqueous work up was performed using ethyl acetate and sodium bicarbonate. No HPLC purification was required. |

TABLE 8-continued

| Example | Name | R | Data | Preparation Information |
|---|---|---|---|---|
| 303 | 3-Fluoro-4-[(1,3-thiazol-2-ylamino)sulfonyl]-N-[4-(trifluoromethyl)benzyl]benzamide | | LCMS Rt = 2.98 min MS m/z 459 [MH]$^+$ $^1$HNMR (d$_6$-DMSO): 4.5 (s, 2H), 6.8 (s, 1H), 7.25 (s, 1H), 7.55 (d, 2H), 7.65 (d, 2H), 7.8 (m, 2H), 7.95 (m, 1H), 9.3 (m, 1H). | Method J using, 4-(trifluoromethyl)benzylamine. Ethyl acetate was used in the Aqueous work up and the organic phase dried over sodium sulphate. No HPLC purification was required. |
| 304 | 3-Fluoro-N-[3-fluoro-4-(trifluoromethyl)benzyl]-4-[(1,3-thiazol-2-yl amino)sulfonyl]benzamide | | LCMS Rt = 1.45 min MS m/z 477 [MH]$^+$ $^1$HNMR (d$_6$-DMSO): 4.5 (s, 2H), 6.9 (s, 1H), 7.3 (s, 1H), 7.35 (m, 1H), 7.4 (m, 1H), 7.7 (m, 1H), 7.8 (m, 2H), 7.95 (m, 1H), 9.35 (m, 1H), 13.0 (m, 1H). | Method J using, 3-fluoro-4-(trifluoromethyl)benzylamine. After amide formation an aqueous work up was performed using ethyl acetate and sodium bicarbonate. No HPLC purification was required. |
| 305 | 3-Fluoro-N-[3-fluoro-4-(trifluoromethoxy)benzyl]-4-[(1,3-thiazol-2-ylamino)sulfonyl]benzylamide | | LCMS Rt = 1.47 min MS m/z 493 [MH]$^+$ $^1$HNMR (d$_6$-DMSO): 4.5 (s, 2H), 6.9 (s, 1H), 7.3 (m, 2H), 7.4 (m, 1H), 7.5 (m, 1H), 7.8 (m, 2H), 7.9 (m, 1H), 9.3 (m, 1H), 13.0 (m, 1H). | Method J using, 3-fluoro-4-(trifluoromethoxy)benzylamine. After amide formation an aqueous work up was performed using ethyl acetate and sodium bicarbonate followed by 2N HCl. Ethyl acetate was used in the final aqueous work up and the organic phase dried over sodium sulphate. No HPLC purification was required. |
| 306 | N-[3-chloro-4-(trifluoromethyl)benzyl]-3-fluoro-4-[(1,3-thiazol-2-ylamino)sulfonyl]benzamide | | LCMS Rt = 1.48 min MS m/z 493 [MH]$^+$ $^1$HNMR (d$_6$-DMSO): 4.5 (s, 2H), 6.9 (s, 1H), 7.3 (s, 1H), 7.5 (m, 1H), 7.65 (s, 1H), 7.8 (m, 3H), 8.0 (m, 1H), 9.4 (m, 1H). | Method J using, 3-chloro-4-(trifluoromethyl)benzylamine. No HPLC purification was required. |

Example 307

N-(3-methyl-1-phenyl-1H-pyrazol-5-yl)-4-[(1,3-thiazol-2-ylamino)sulfonyl]benzamide

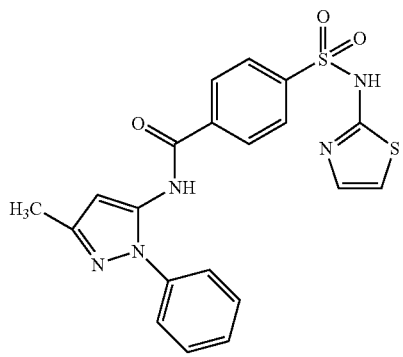 [SMILES: Cc1cc(NC(=O)c2ccc(S(=O)(=O)Nc3nccs3)cc2)n(-c2ccccc2)n1]

The title compound was prepared from Preparation 99 and 1-phenyl-3-methyl-5-amino pyrazole following Method J, described for Example 295. N,N diisopropylethylamine was used as the base and DMF was used as the solvent. The reaction mixture was evaporated in vacuo. The residue was dissolved in acetone and the remaining solid removed by filtration. The filtrated was evaporated in vacuo and the residue purified by preparative HPLC to yield the title compound.

LCMS Rt=1.83 min. MS m/z 440 [MH]+.

Example 308

N-[1-(4-chlorobenzyl)-1H-pyrazol-3-yl]-4-[(1,3-thiazol-2-ylamino)sulfonyl]benzamide

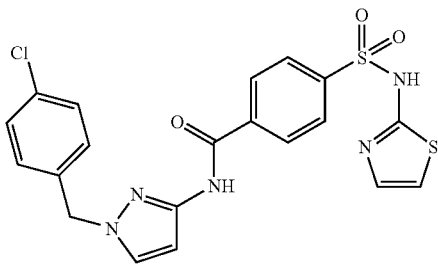 [SMILES: O=C(Nc1ccn(Cc2ccc(Cl)cc2)n1)c1ccc(S(=O)(=O)Nc2nccs2)cc1]

The title compound was prepared from Preparation 99 and 1-(4-chlorobenzyl)-1H-pyrazol-3-amine following Method J, described for Example 295. N,N diisopropylethylamine was used as the base and DMF was used as the solvent. The reaction mixture was evaporated in vacuo. The residue was dissolved in acetone and the remaining solid removed by filtration. The filtrated was evaporated in vacuo and the residue purified by preparative HPLC to yield the title compound.

LCMS Rt=3.05 min.

Example 309

4-{[(5-Chloro-1,3-thiazol-2-yl)amino]sulfonyl}-3-fluoro-N-[3-fluoro-4-(trifluoromethoxy)benzyl]benzamide

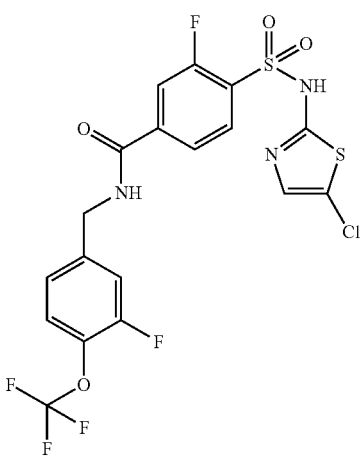 [SMILES: O=C(NCc1ccc(OC(F)(F)F)c(F)c1)c1ccc(S(=O)(=O)Nc2ncc(Cl)s2)c(F)c1]

Method K

4-{[(5-Chloro-1,3-thiazol-2-yl)amino]sulfonyl}-3-fluorobenzoic acid (Preparation 25, 200 mg, 0.627 mmol, 1 eq), 3-fluoro-4-(trifluoromethoxy)benzylamine (157 mg, 0.752 mmol, 1.2 eq), Et$_3$N (190 mg, 1.88 mmol, 3 eq) and 2-(1H-benzotriazol-1-yl)-1,1,1,3,tetramethyluronium tetrafluoroborate (TBTU, 262 mg, 0.815 mmol, 1.3 eq) were combined in dimethylformamide and the reaction mixture stirred at room temperature for 18 hours. The reaction mixture was extracted from 2M HCl into DCM, dried over sodium sulphate, filtered and evaporated. The crude material was purified by column chromatography eluting with DCM:MeOH (95:5) to yield the title compound (72 mg, 0.136 mmol, 22%).

$^1$HNMR (d$_6$-DMSO): 4.5 (s, 2H), 7.2 (m, 1H), 7.4 (m, 1H), 7.5 (m, 1H), 7.6 (s, 1H), 7.8 (m, 2H), 7.9 (m, 1H), 9.3 (m, 1H). LCMS Rt=3.22 min. MS m/z 527 [MH]+.

The following examples of the general formula

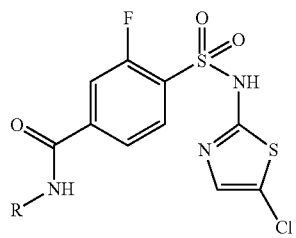

were prepared by Method K described for Example 309 above. Unless otherwise noted, preparation details are as described for the method referred to.

TABLE 9

| Example | Name | R | Data | Preparation Information |
|---|---|---|---|---|
| 310 | 4-{[(5-Chloro-1,3-thiazol-2-yl)amino]sulfonyl}-3-fluoro-N-[3-fluoro-4-(trifluoromethyl)benzyl]benzamide | | LCMS Rt = 3.17 min MS m/z 511 [MH]+ ¹HNMR (d₆-DMSO): 4.5 (s, 2H), 7.4 (d, 1H), 7.45 (m, 1H), 7.6 (s, 1H), 7.7 (m, 1H), 7.8 (m, 2H), 8.0 (m, 1H), 9.4 (m, 1H). | Method K, using 3-Fluoro-(trifluoromethyl)benzylamine. |
| 311 | 4-{[(5-Chloro-1,3-thiazol-2-yl)amino]sulfonyl}-N-(3,4-dichlorobenzyl)-3-fluorobenzamide | | LCMS Rt = 3.50 min MS m/z 493 [MH]+ | Method K, using 3,4-dichlorobenzylamine. Compound was purified by preparative HPLC. |
| 312 | 4-{[(5-Chloro-1,3-thiazol-2-yl)amino]sulfonyl}-N-(3,4-difluorobenzyl)-3-fluorobenzamide | | LCMS Rt = 3.30 min MS m/z 461 [MH]+ | Method K, using 3,4-difluorobenzylamine. Compound was purified by preparative HPLC. |
| 313 | 4-{[(5-Chloro-1,3-thiazol-2-yl)amino]sulfonyl}-3-fluoro-N-[4-fluoro-3-(trifluoromethoxy)benzyl]benzamide | | LCMS Rt = 3.60 min MS m/z 527 [MH]+ | Method K, using 4-fluoro-3-(trifluoromethoxy)benzylamine. Compound was purified by preparative HPLC. |
| 314 | 4-{[(5-Chloro-1,3-thiazol-2-yl)amino]sulfonyl}-3-fluoro-N-[4-(trifluoromethoxy)benzyl]benzamide | | LCMS Rt = 3.50 min MS m/z 509 [MH]+ | Method K, using 4-(trifluoromethoxy)benzylamine. Compound was purified by preparative HPLC. |
| 315 | 4-{[(5-Chloro-1,3-thiazol-2-yl)amino]sulfonyl}-3-fluoro-N-[4-(trifluoromethyl)benzyl]benzamide | | LCMS Rt = 3.45 min MS m/z 493 [MH]+ | Method K, using 4-(trifluoromethyl)benzylamine. Compound was purified by preparative HPLC. |

TABLE 9-continued

| Example | Name | R | Data | Preparation Information |
|---------|------|---|------|------------------------|
| 316 | 4-{[(5-Chloro-1,3-thiazol-2-yl)amino]sulfonyl}-3-fluoro-N-[4-fluoro-3-(trifluoromethyl)benzyl]benzamide | (structure) | LCMS Rt = 3.44 min MS m/z 511 [MH]+ | Method K, using 4-fluoro-3-(trifluoromethyl)benzylamine. Compound was purified by preparative HPLC. |

The following examples of the general formula

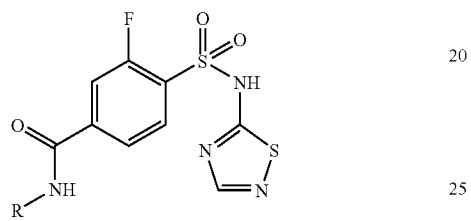

were prepared from 3-fluoro-4-[(1,2,4-thiadiazol-5-ylamino)sulfonyl]benzoic acid (Preparation 27) by Method K described for Example 309 above. Unless otherwise noted, preparation details are as described for the method referred to.

TABLE 10

| Example | Name | R | Data | Preparation Information |
|---------|------|---|------|------------------------|
| 317 | N-[3-chloro-4-(trifluoromethyl)benzyl]-3-fluoro-4-[(1,2,4-thiadiazol-5-yl amino)sulfonyl]benzamide | (structure) | LCMS Rt = 3.14-3.19 min MS m/z 495 [MH]+ $^1$HNMR (d$_6$-DMSO): 4.5 (s, 2H), 7.45 (m, 1H), 7.6 (s, 1H), 7.8 (m, 3H), 8.0 (m, 1H), 8.5 (s, 1H), 9.4 (m, 1H). | Method K, using 3-chloro-(trifluoromethyl)benzylamine. The reaction mixture was stirred at room temperature for 1 hour and the compound purified by trituration with DCM. |
| 318 | 3-Fluoro-N-[3-fluoro-4-(trifluoromethoxy)benzyl]-4-[(1,2,4-thiadiazol-5-yl amino)sulfonyl]benzamide | (structure) | LCMS Rt = 2.38 min MS m/z 495 [MH]+ | Method K, using 3-fluoro-4-(trifluoromethoxy)benzylamine. Compound was purified by preparative HPLC. |

TABLE 10-continued

| Example | Name | R | Data | Preparation Information |
|---|---|---|---|---|
| 319 | 3-Fluoro-N-[3-fluoro-4-(trifluoromethyl)benzyl]-4-[(1,2,4-thiadiazol-5-yl amino)sulfonyl]benzamide | 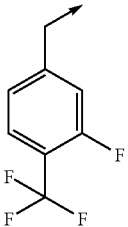 | LCMS Rt = 2.22 min MS m/z 479 [MH]+ | Method K, using 3-fluoro-4-(trifluoromethyl)benzylamine. Compound was purified by preparative HPLC. |
| 320 | 3-Fluoro-4-[(1,2,4-thiadiazol-5-yl amino)sulfonyl]-N-{1-[4-(trifluoromethyl)phenyl]ethyl}benzamide | 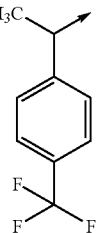 | LCMS Rt = 2.29 min MS m/z 475 [MH]+ | Method K, using 4-(trifluoromethyl)benzylamine. Compound was purified by preparative HPLC. |

Example 321

N-[3-fluoro-4-(trifluoromethoxy)benzyl]-4-[(1,2,4-thiadiazol-5-ylamino)sulfonyl]benzamide

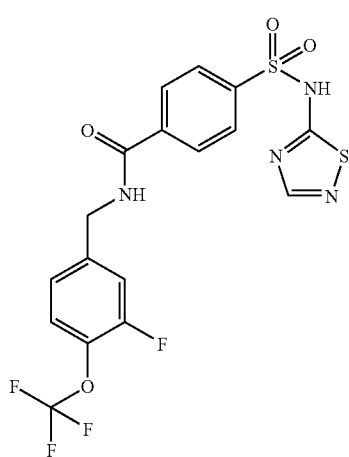 [SMILES: O=C(NCc1ccc(OC(F)(F)F)c(F)c1)c1ccc(S(=O)(=O)Nc2ncns2)cc1]

The title compound was prepared from 4-[(1,2,4-thiadiazol-5-ylamino)sulfonyl]benzoic acid (Preparation 29) and 3-fluoro-4-(trifluoromethoxy)benzylamine following the procedure described in Example 309. The reaction mixture was extracted from saturated sodium hydrogen carbonate into DCM and the crude product purified by preparative HPLC.
LCMS Rt=2.31 min. MS m/z 477 [MH]+.

Example 322

4-[(1,2,4-Thiadiazol-5-ylamino)sulfonyl]-N-[1-[4-(trifluoromethyl)phenyl]ethyl]benzamide

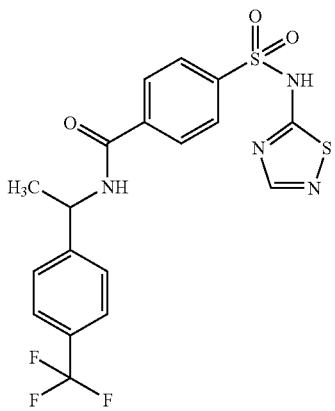 [SMILES: CC(NC(=O)c1ccc(S(=O)(=O)Nc2ncns2)cc1)c1ccc(C(F)(F)F)cc1]

The title compound was prepared from 4-[(1,2,4-thiadiazol-5-ylamino)sulfonyl]benzoic acid (Preparation 29) and 1-[4-(trifluoromethyl)phenyl]ethanamine following the procedure described in Example 309. The reaction mixture was extracted from saturated sodium hydrogen carbonate into DCM and the crude product purified by preparative HPLC.
LCMS Rt=2.36 min. MS m/z 457 [MH]+.

Example 323

N-[3-fluoro-4-(trifluoromethyl)benzyl]-4-[(1,2,4-thiadiazol-5-ylamino)sulfonyl]benzamide

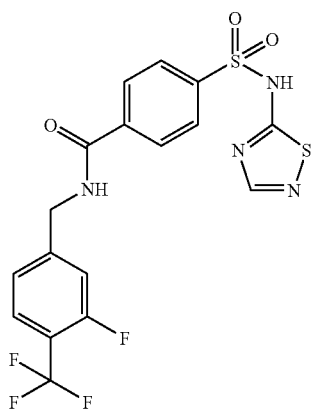 [SMILES: O=C(NCc1ccc(C(F)(F)F)c(F)c1)c1ccc(S(=O)(=O)Nc2ncns2)cc1]

The title compound was prepared from 4-[(1,2,4-thiadiazol-5-ylamino)sulfonyl]benzoic acid (Preparation 29) and 3-fluoro-4-(trifluoromethyl)benzylamine following the procedure described in Example 309. The reaction mixture was extracted from saturated sodium hydrogen carbonate into DCM and the crude product purified by preparative HPLC.

LCMS Rt=3.44 min. MS m/z 461 [MH]+.

Example 324

N-[3-chloro-4-(trifluoromethyl)benzyl]-4-[(1,2,4-thiadiazol-5-ylamino)sulfonyl]benzamide

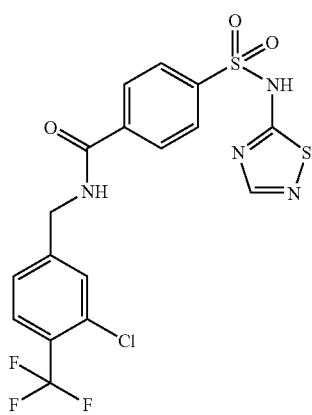 [SMILES: O=C(NCc1ccc(C(F)(F)F)c(Cl)c1)c1ccc(S(=O)(=O)Nc2ncns2)cc1]

The title compound was prepared from 4-({[3-chloro-4-(trifluoromethyl)benzyl]amino}carbonyl)benzenesulfonyl chloride (Preparation 30) and 5-amino-1,2,4-thiadiazole in 16% yield following the Method H described for Example 6.

$^1$HNMR (d$_6$-DMSO): 4.55 (d, 2H), 7.45 (d, 1H), 7.65 (s, 1H), 7.80 (d, 1H), 7.90 (d, 2H), 8.00 (d, 2H), 8.45 (s, 1H), 9.30 (t, 1H). LCMS Rt=1.75 min. MS m/z 476-478 [M-H]-.

Example 325

2-Fluoro-4-[(1,3-thiazol-2-ylamino)sulfonyl]-N-[4-(trifluoromethyl)benzyl]benzamide

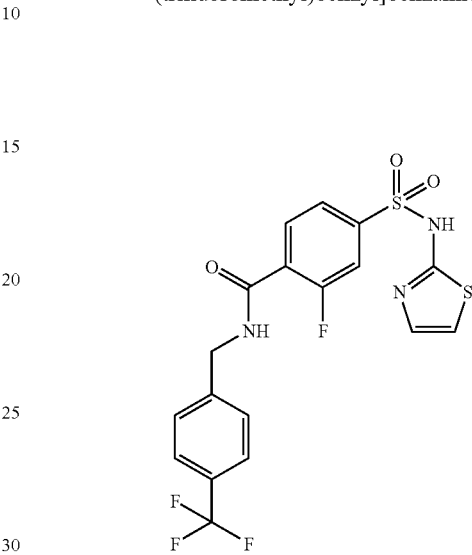

Method L

To a solution of 2-fluoro-4-[(1,3-thiazol-2-ylamino)sulfonyl]benzoic acid (Preparation 15, 50 mg, 0.165 mmol, 1 eq) and Et$_3$N (0.035 ml, 0.248 mmol, 1.5 eq) in THF (0.5 ml) at 0° C. was added 1-(3-dimethylaminopropyl)-3-ethylcarbodiimide hydrochloride (EDCI HCl, 41 mg, 0.215 mmol, 1.3 eq) and the reaction mixture stirred at 0° C. for 10 minutes then at room temperature for a further 1 hour. The reaction mixture was cooled to 0° C., 4-trifluoromethylbenzylamine (0.031 ml, 0.215 mmol, 1.3 eq) and 1-hydroxybenzotriazole hydrate (HOBt, 33.5 mg, 0.248 mmol, 1.5 eq) were added and the reaction mixture stirred at room temperature overnight. The reaction mixture was extracted from 1M HCl into DCM, washed with brine, dried over magnesium sulphate, filtered and evaporated in vacuo The residue was purified by preparative HPLC to yield the title compound.

LCMS Rt=2.39 min. MS m/z 460 [MH]+.

The following examples of the general formula

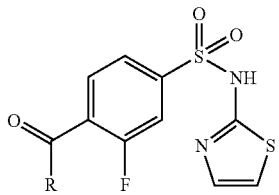

were prepared by Method L as described for Example 325 above. Unless otherwise noted, preparation details are as described for the method referred to.

TABLE 11

| Example | Name | R | Data | Preparation Information |
|---|---|---|---|---|
| 326 | N-(3,4-dichlorobenzyl)-2-fluoro-4-[(1,3-thiazol-2-ylamino)sulfonyl]benzamide | 3,4-dichlorobenzyl-NH- | LCMS Rt = 1.47 min MS m/z 460 [MH]+ | Method L using 3,4-dichlorobenzylamine. |
| 327 | 2-Fluoro-4-[(1,3-thiazol-2-ylamino)sulfonyl]-N-[3-(trifluoromethyl)benzyl]benzamide | 3-(trifluoromethyl)benzyl-NH- | LCMS Rt = 1.45 min MS m/z 460 [MH]+ | Method L using 3-(trifluoromethyl)benzylamine. |
| 328 | 2-Fluoro-N-[3-fluoro-4-(trifluoromethoxy)benzyl]-4-[(1,3-thiazol-2-ylamino)sulfonyl]benzamide | 3-fluoro-4-(trifluoromethoxy)benzyl-NH- | LCMS Rt = 1.50 min MS m/z 494 [MH]+ | Method L using 3-fluoro-4-(trifluoromethoxy)benzylamine. |
| 329 | N-(3,4-difluorobenzyl)-2-fluoro-4-[(1,3-thiazol-2-ylamino)sulfonyl]benzamide | 3,4-difluorobenzyl-NH- | LCMS Rt = 1.37 min MS m/z 428 [MH]+ | Method L using 3,4-difluorobenzylamine. |
| 330 | 2-Fluoro-4-[(1,3-thiazol-2-ylamino)sulfonyl]-N-[4-(trifluoromethoxy)benzyl]benzamide | 4-(trifluoromethoxy)benzyl-NH- | LCMS Rt = 1.47 min MS m/z 476 [MH]+ | Method L using 4-(trifluoromethoxy)benzylamine. |
| 331 | 2-Fluoro-N-[4-fluoro-3-(trifluoromethoxy)benzyl]-4-[(1,3-thiazol-2-ylamino)sulfonyl]benzamide | 4-fluoro-3-(trifluoromethoxy)benzyl-NH- | LCMS Rt = 1.48 min MS m/z 494 [MH]+ | Method L using 3-(trifluoromethoxy)-4-fluorobenzylamine. |
| 332 | N-(3-chloro-4-fluorobenzyl)-2-fluoro-4-[(1,3-thiazol-2-ylamino)sulfonyl]benzamide | 3-chloro-4-fluorobenzyl-NH- | LCMS Rt = 1.41 min MS m/z 444 [MH]+ | Method L using 3-chloro-4-fluorobenzylamine. |
| 333 | 2-Fluoro-N-[3-fluoro-4-(trifluoromethyl)benzyl]-4-[(1,3-thiazol-2-ylamino)sulfonyl]benzamide | 3-fluoro-4-(trifluoromethyl)benzyl-NH- | LCMS Rt = 1.46 min MS m/z 478 [MH]+ | Method L using 3-fluoro-4-(trifluoromethyl)benzylamine. |
| 334 | N-(4-chloro-3-fluorobenzyl)-2-fluoro-4-[(1,3-thiazol-2-ylamino)sulfonyl]benzamide | 4-chloro-3-fluorobenzyl-NH- | LCMS Rt = 1.42 min MS m/z 444 [MH]+ | Method L using 3-fluoro-4-chlorobenzylamine |
| 335 | 2-Fluoro-4-[(1,3-thiazol-2-ylamino)sulfonyl]-N-[3-(trifluoromethoxy)benzyl]benzamide | 3-(trifluoromethoxy)benzyl-NH- | LCMS Rt = 1.46 min MS m/z 476 [MH]+ | Method L using 3-(trifluoromethoxy)benzylamine. |

TABLE 11-continued

| Example | Name | R | Data | Preparation Information |
|---|---|---|---|---|
| 336 | 2-Fluoro-N-[4-fluoro-3-(trifluoromethyl)benzyl]-4-[(1,3-thiazol-2-yl amino)sulfonyl]benzamide | 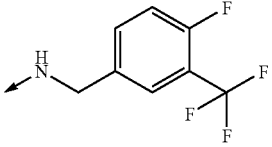 | LCMS Rt = 1.45 min MS m/z 478 [MH]+ | Method L using 3-(trifluoromethyl)-4-fluorobenzylamine |

Example 337

2-Chloro-4-{[(5-chloro-1,3-thiazol-2-yl)amino]sulfonyl}-N-[3-fluoro-4-(trifluoromethoxy)benzyl]benzamide

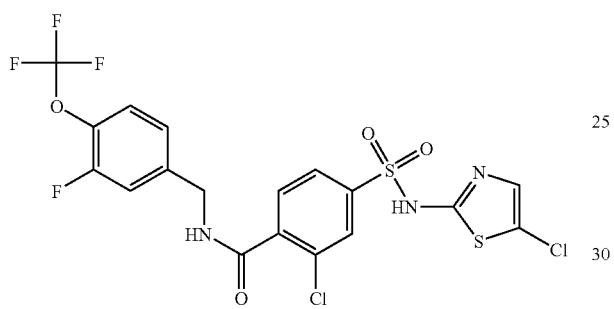

Method M

2-Chloro-4-{[(5-chloro-1,3-thiazol-2-yl)amino]sulfonyl}benzoic acid (Preparation 37, 78 mg, 0.221 mmol, 1 eq), Et$_3$N (58 mg, 0.57 mmol, 2.6 eq) 3-fluoro-4-(trifluoromethoxy)benzylamine (55 mg, 0.263 mmol, 1.119 eq) were combined in dimethylformamide (3 ml), 2-(1H-benzotriazol-1-yl)-1,1,1,3,tetramethyluronium tetrafluoroborate (TBTU, 93 mg, 0.29 mmol, 1.31 eq) was added and the reaction mixture stirred at room temperature for 1 hour. The reaction mixture was diluted with ethyl acetate (10 ml), washed with water (10 ml), sat sodium hydrogen carbonate (10 ml), dried over sodium sulphate, filtered and evaporated in vacuo. The crude material was purified by column chromatography eluting with 0-100% DCM:MeOH:AcOH (95:5:0.5). The obtained compound was further triturated in DCM and filtered to yield the title compound (50.1 mg, 0.092 mmol, 42%).

$^1$HNMR (d$_6$-DMSO): 4.50 (d, 2H), 7.30 (d, 1H), 7.45 (d, 1H), 7.55 (m, 2H), 7.65 (d, 1H), 7.80 (d, 1H), 9.20 (t, 1H). LCMS Rt=3.28 min. MS m/z 544-545 [MH]+.

The following examples of the general formula:

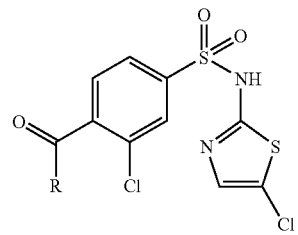

were prepared by Method M as described for Example 337 above. Unless otherwise noted, preparation details are as described for the method referred to.

TABLE 12

| Example | Name | R | Data | Preparation Information |
|---|---|---|---|---|
| 338 | 2-Chloro-4-{[(5-chloro-1,3-thiazol-2-yl)amino]sulfonyl}-N-[4-(trifluoromethyl)benzyl]benzamide | 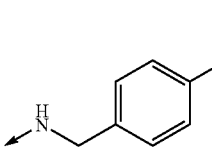 | LCMS Rt = 3.19 min MS m/z 510-512 [MH]+ $^1$HNMR (d$_6$-DMSO): 4.55 (d, 2H), 7.55 (m, 3H), 7.65 (d, 1H), 7.70 (2s, 2H), 7.80 (d, 2H), 9.20 (t, 1H) | Method M using 4-(trifluoromethyl)benzylamine. |
| 339 | 2-Chloro-4-{[(5-chloro-1,3-thiazol-2-yl)amino]sulfonyl}-N-[3-fluoro-4-(trifluoromethyl)benzyl]benzamide | 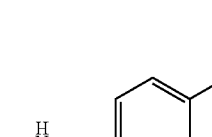 | LCMS Rt = 1.62 min (2 min) $^1$HNMR (d$_6$-DMSO): 4.55 (d, 2H), 7.40 (d, 1H), 7.45 (d, 1H), 7.55 (s, 1H), 7.70 (d, 1H), 7.75-7.85 (m, 3H), 9.20 (t, 1H) | Method M using 3-fluoro-4-(trifluoromethyl)benzylamine. |

Example 340

N-[3-fluoro-4-(trifluoromethyl)benzyl]-5-[(1,3-thiazol-2-ylamino)sulfonyl]pyridine-2-carboxamide

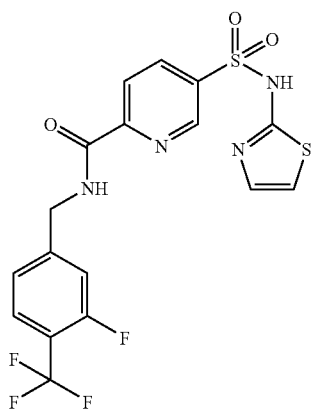 [SMILES: O=C(NCc1ccc(C(F)(F)F)c(F)c1)c1ccc(S(=O)(=O)Nc2nccs2)cn1]

Method N

5-{[(2,4-Dimethoxybenzyl)(1,3-thiazol-2-yl)amino]sulfonyl}pyridine-2-carboxylic acid (Preparation 17, 75 mg, 0.173 mmol, 1 eq), 3-fluoro-4-(trifluoromethyl)benzylamine (44 mg, 0.228 mmol, 1.32 eq) and Et₃N (36 mg, 0.36 mmol, 2.1 eq) were combined in dimethylformamide (3 ml), 2-(1H-benzotriazol-1-yl)-1,1,1,3,tetramethyluronium tetrafluoroborate (TBTU, 68 mg, 0.212 mmol) was added and the reaction mixture stirred at room temperature for 2 hours. The reaction mixture was diluted with ethyl acetate (10 ml), washed with water (10 ml), saturated sodium hydrogen carbonate (10 ml), dried over sodium sulphate, filtered and evaporated in vacuo. The residue was dissolved in TFA (2 ml) and DCM (2 ml) and the reaction mixture stirred at room temperature for 2 hours. The solvent was evaporated and the material redissolved in ethyl acetate (10 ml), washed with water (10 ml), saturated sodium hydrogen carbonate, dried over sodium sulphate, filtered and evaporated in vacuo. The crude material was purified by preparative HPLC to yield the title compound.

LCMS Rt=3.25-3.29 min. MS m/z 461 [MH]+.

The following examples of the general formula

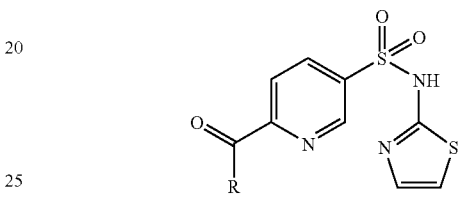

were prepared by Method N as described for Example 340 above. Unless otherwise noted, preparation details are as described for the method referred to.

TABLE 13

| Example | Name | R | Data | Preparation Information |
|---|---|---|---|---|
| 341 | N-[3-chloro-4-(trifluoromethyl)benzyl]-5-[(1,3-thiazol-2-ylamino)sulfonyl]pyridine-2-carboxamide | ![R group with 3-chloro-4-(trifluoromethyl)benzyl] | LCMS Rt = 3.24-3.32 min MS m/z 476 [MH]+ | Method N using 3-chloro-4-(trifluoromethyl)benzylamine. |
| 342 | 5-[(1,3-Thiazol-2-ylamino)sulfonyl]-N-[4-(trifluoromethyl)benzyl]pyridine-2-carboxamide | ![R group with 4-(trifluoromethyl)benzyl] | LCMS Rt = 3.15-3.22 min MS m/z 443 [MH]+ | Method N using 4-(trifluoromethyl)benzylamine. |
| 343 | N-[3-fluoro-4-(trifluoromethoxy)benzyl]-5-[(1,3-thiazol-2-ylamino)sulfonyl]pyridine-2-carboxamide | ![R group with 3-fluoro-4-(trifluoromethoxy)benzyl] | LCMS Rt = 3.23-3.32 min MS m/z 477 [MH]+ | Method N using 3-fluoro-4-(trifluoromethoxy)benzylamine. THF used as the reaction solvent and the reaction mixture was heated at 50° C. for 18 hours. |

Example 344

5-{[(5-Chloro-1,3-thiazol-2-yl)amino]sulfonyl}-N-[4-(trifluoromethyl)benzyl]pyridin-2-carboxamide

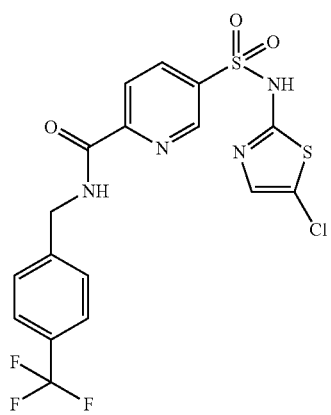 [SMILES: O=C(NCc1ccc(C(F)(F)F)cc1)c1ccc(S(=O)(=O)Nc2ncc(Cl)s2)cn1]

Method O

5-{[(5-Chloro-1,3-thiazol-2-yl)amino]sulfonyl}pyridine-2-carboxylic acid (Preparation 18, 29 mg, 0.092 mmol, 1 eq), Et₃N (47 mg, 0.47 mmol, 5.1 eq) 4-(trifluoromethyl)benzylamine (35 mg, 0.2 mmol, 2.17 eq) were combined in dimethylformamide (3 ml)), 2-(1H-benzotriazol-1-yl)-1,1,1,3,tetramethyluronium tetrafluoroborate (TBTU, 40 mg, 0.125 mmol, 1.36 eq) was added and the reaction mixture stirred at room temperature for 1 hour. The reaction mixture was diluted with ethyl acetate (10 ml), washed with water (10 ml), sat sodium hydrogen carbonate (10 ml), dried over sodium sulphate, filtered and evaporated in vacuo. The crude material was purified by preparative HPLC to yield the title compound.

LCMS Rt=3.43-3.49 min. MS m/z 476 [MH]+.

The following examples of the general formula

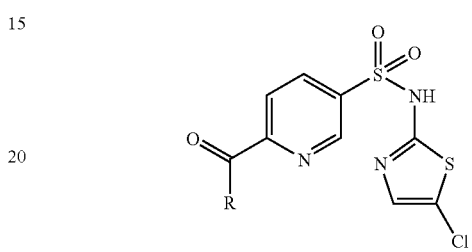

were prepared by Method O as described for Example 344 above. Unless otherwise noted, preparation details are as described for the method referred to.

TABLE 14

| Example | Name | R | Data | Preparation Information |
|---|---|---|---|---|
| 345 | 5-{[(5-Chloro-1,3-thiazol-2-yl)amino]sulfonyl}-N-[3-fluoro-4-(trifluoromethyl)benzyl]pyridine-2-carboxamide | ![3-fluoro-4-(trifluoromethyl)benzyl] | LCMS Rt = 3.52-3.57 min MS m/z 494 [MH]+ | Method O using 3-fluoro-4-(trifluoromethyl)benzylamine. |
| 346 | 5-{[(5-Chloro-1,3-thiazol-2-yl)amino]sulfonyl}-N-[3-chloro-4-(trifluoromethyl)benzyl]pyridine-2-carboxamide | ![3-chloro-4-(trifluoromethyl)benzyl] | LCMS Rt = 3.68-3.76 min MS m/z 510 [MH]+ | Method O using 3-chloro-4-(trifluoromethyl)benzylamine |

Example 347

4-{[(5-Chloro-1,3-thiazol-2-yl)amino]sulfonyl}-2-cyano-N-[4-(trifluoromethyl)benzyl]benzamide

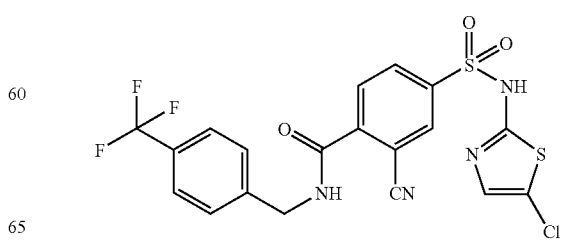

The title compound was prepared from 4-(trifluoromethyl)benzylamine and 4-{[(5-chloro-1,3-thiazol-2-yl)amino]sulfonyl}-2-cyanobenzoic acid of Preparation 22, following Method O described for Example 344. The reaction mixture was stirred at room temperature for 18 hours.

LCMS Rt=2.47-2.52 min. MS m/z 498 [MH]+.

Example 348

4-{[(5-Chloro-1,3-thiazol-2-yl)amino]sulfonyl}-2-cyano-N-[3-fluoro-4-(trifluoromethyl)benzyl]benzamide

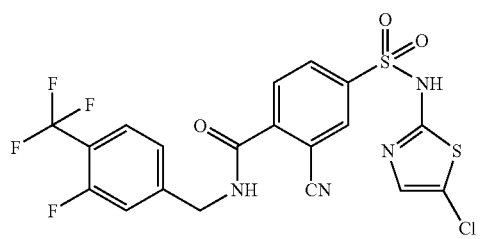 [SMILES: N#Cc1cc(S(=O)(=O)Nc2ncc(Cl)s2)ccc1C(=O)NCc1ccc(C(F)(F)F)c(F)c1]

The title compound was prepared from 3-fluoro-4-(trifluoromethyl)benzylamine and 4-{[(5-chloro-1,3-thiazol-2-yl)amino]sulfonyl}-2-cyanobenzoic acid of Preparation 22, following Method O described for Example 344. The reaction mixture was stirred at room temperature for 18 hours.

LCMS Rt=2.46-2.51 min. MS m/z 518 [MH]+.

Example 349

3-[(1,3-Thiazol-2-ylamino)sulfonyl]-N-[4-(trifluoromethyl)benzyl]benzamide

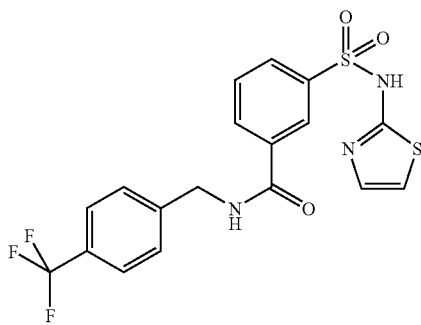 [SMILES: O=C(NCc1ccc(C(F)(F)F)cc1)c1cccc(S(=O)(=O)Nc2nccs2)c1]

To a solution of 3-{[(2,4-Dimethoxybenzyl)(1,3-thiazol-2-yl)amino]sulfonyl}benzoic acid (Preparation 23, 90 mg, 0.207 mmol, 1 eq) THF (2 ml) was added Et₃N (0.04 ml, 0.311 mmol, 1.5 eq), 1-(3-dimethylaminopropyl)-3-ethylcarbodiimide hydrochloride (EDCI.HCl, 52 mg, 0.27 mmol, 1.3 eq) and 1-hydroxybenzotriazole hydrate (HOBt, 28 mg, 0.207 mmol, 1 eq) at 0° C. and the reaction mixture stirred for 10 minutes before the addition of 4-(trifluoromethyl)benzylamine (0.032 ml, 0.228 mmol, 1.1 eq). The reaction mixture was stirred at room temperature for 18 hours. The mixture was extracted from water into DCM, dried over magnesium sulphate, filtered and evaporated in vacuo. The residue was dissolved in 4M HCl in dioxane (2 ml) and the reaction mixture stirred at room temperature for 18 hours. The resulting precipitate was collected by filtration and washed with dioxane. The material was purified further by preparative HPLC to yield the title compound.

LCMS Rt=2.15 min. MS m/z 442 [MH]+.

Example 350

3-[(1,3,4-Thiadiazol-2-ylamino)sulfonyl]-N-[4-(trifluoromethyl)benzyl]benzamide

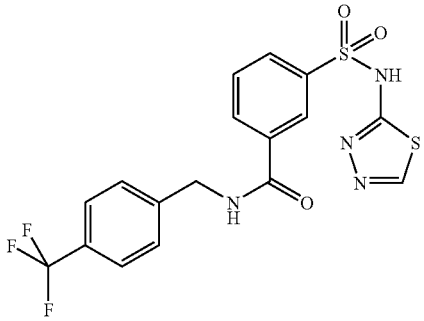 [SMILES: O=C(NCc1ccc(C(F)(F)F)cc1)c1cccc(S(=O)(=O)Nc2nncs2)c1]

To a solution of 3-[(1,3,4-thiadiazol-2-ylamino)sulfonyl]benzoic acid (100 mg, 0.350, mmol, 1 eq) in THF (1 ml) was added Et₃N (0.19 ml, 1.4 mmol, 4 eq), 1-(3-dimethylaminopropyl)-3-ethylcarbodiimide hydrochloride (EDCI HCl, 87 mg, 0.455 mmol, 1.3 eq), 1-hydroxybenzotriazole hydrate (HOBt, 61 mg, 0.455 mmol, 1.3 eq) and 4-(trifluoromethyl)benzylamine (0.075 ml, 0.525 mmol, 1.5 eq) at 0° C. The reaction mixture was stirred at 30-40° C. for 18 hours. The reaction mixture was extracted from 2M HCl into ethyl acetate, washed with sat sodium hydrogen carbonate, brine, dried over magnesium sulphate, filtered and evaporated in vacuo. The crude material was purified by preparative HPLC to yield the title compound.

LCMS Rt=2.24 min. MS m/z 443 [MH]+.

The following examples of the general formula

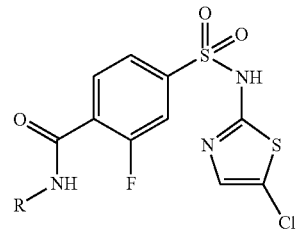

were prepared by the following method using the indicated amines:

To a solution of 4-{[(5-chloro-1,3-thiazol-2-yl)amino]sulfonyl}-2-fluorobenzoic acid (Preparation 33, 75 mg, 0.213 mmol, 1 eq) in THF (0.75 ml) was added Et₃N (0.09 ml, 0.64 mmol, 3 eq), 1-(3-dimethylaminopropyl)-3-ethylcarbodiimide hydrochloride (EDCI HCl, 53 mg, 0.278 mmol, 1.3 eq), 1-hydroxybenzotriazole hydrate (HOBt, 43 mg, 0.320 mmol, 1.5 eq) and an amine (0.278 mmol, 1.3 eq) at 0° C. The reaction mixture was stirred at 25° C. for 16 hours. The reaction mixture was extracted from 2M HCl into DCM and the solvent evaporated in vacuo. The crude material was purified by preparative HPLC to yield the title compound.

TABLE 15

| Example | Name | R | Data | Preparation Information |
|---|---|---|---|---|
| 351 | 4-{[(5-Chloro-1,3-thiazol-2-yl)amino]sulfonyl}-N-(3,4-dichlorobenzyl)-2-fluorobenzamide | 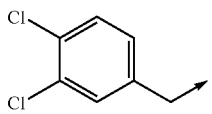 | LCMS Rt = 2.47 min MS m/z 493 [MH]+ | using 3,4-dichlorobenzyl amine |
| 352 | 4-{[(5-Chloro-1,3-thiazol-2-yl)amino]sulfonyl}-2-fluoro-N-[4-(trifluoromethyl)benzyl]benzamide | 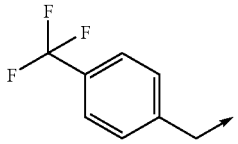 | LCMS Rt = 2.37 min MS m/z 493 [MH]+ | using 4-(trifluoromethyl)benzylamine |
| 353 | 4-{[(5-Chloro-1,3-thiazol-2-yl)amino]sulfonyl}-2-fluoro-N-[4-fluoro-3-(trifluoromethyl)benzyl]benzamide | 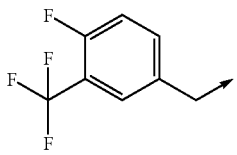 | LCMS Rt = 2.47 min MS m/z 511 [MH]+ | using 4-fluoro-3-(trifluoromethyl)benylamine |
| 354 | 4-{[(5-Chloro-1,3-thiazol-2-yl)amino]sulfonyl}-2-fluoro-N-[3-(trifluoromethyl)benzyl]benzamide |  | LCMS Rt = 2.46 min MS m/z 493 [MH]+ | using 3-(trifluoromethyl)benzylamine |
| 355 | N-(4-chloro-3-fluorobenzyl)-4-{[(5-chloro-1,3-thiazol-2-yl)amino]sulfonyl}-2-fluorobenzamide | 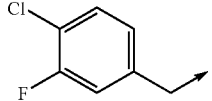 | LCMS Rt = 3.45 min MS m/z 477 [MH]+ | using 4-chloro-3-fluoro benzylamine |
| 356 | 4-{[(5-Chloro-1,3-thiazol-2-yl)amino]sulfonyl}-2-fluoro-N-[3-fluoro-4-(trifluoromethyl)benzyl]benzamide | 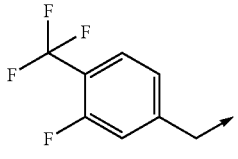 | LCMS Rt = 3.18 min MS m/z 512 [MH]+ | using 3-fluoro-4-(trifluoromethyl)benzylamine |
| 357 | 4-{[(5-Chloro-1,3-thiazol-2-yl)amino]sulfonyl}-2-fluoro-N-[3-(trifluoromethoxy)benzyl]benzamide | 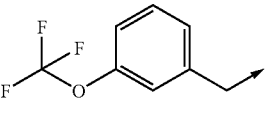 | LCMS Rt = 2.44 min MS m/z 509 [MH]+ | using 3-(trifluoromethoxy)benzylamine |
| 358 | 4-{[(5-Chloro-1,3-thiazol-2-yl)amino]sulfonyl}-2-fluoro-N-[4-fluoro-3-(trifluoromethoxy)benzyl]benzamide | 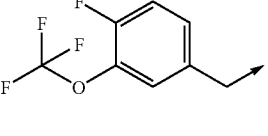 | LCMS Rt = 2.44 min MS m/z 527 [MH]+ | using 4-fluoro-3-(trifluoromethoxy)benzylamine |
| 359 | 4-{[(5-Chloro-1,3-thiazol-2-yl)amino]sulfonyl}-2-fluoro-N-[3-fluoro-4-(trifluoromethoxy)benzyl]benzamide | 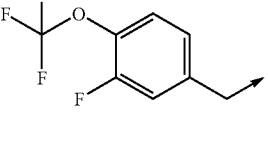 | LCMS Rt = 3.24 min MS m/z 526 [M − H]− | using 3-fluoro-4-(trifluoromethoxy)benzylamine |
| 360 | 4-{[(5-Chloro-1,3-thiazol-2-yl)amino]sulfonyl}-2-fluoro-N-[4-(trifluoromethoxy)benzyl]benzamide | 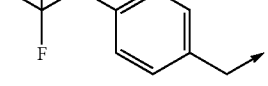 | LCMS Rt = 2.53 min MS m/z 509 [MH]+ | using 4-(trifluoromethoxy)benzylamine |

TABLE 15-continued

| Example | Name | R | Data | Preparation Information |
|---|---|---|---|---|
| 361 | 4-{[(5-Chloro-1,3-thiazol-2-yl)amino]sulfonyl}-N-(3,4-difluorobenzyl)-2-fluorobenzamide | 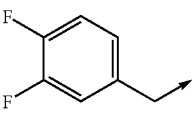 | LCMS Rt = 2.39 min MS m/z 461 [MH]+ | using 3,4-difluoro benzylamine |

The following examples of the general formula

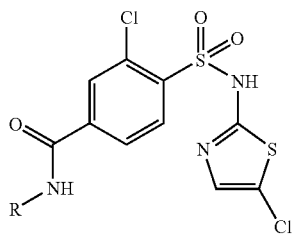

were prepared by the following method using the indicated amines:

To a solution of 3-chloro-4-{[(5-chloro-1,3-thiazol-2-yl)amino]sulfonyl}benzoic acid (Preparation 35, 200 mg, 0.57, mmol, 1 eq) in THF (5 ml) was added Et₃N (0.116 ml, 0.85 mmol, 1.5 eq), 1-(3-dimethylaminopropyl)-3-ethylcarbodiimide hydrochloride (EDCI HCl, 141 mg, 0.62 mmol, 1.1 eq), 1-hydroxybenzotriazole hydrate (HOBt, 77 mg, 0.57 mmol, 1.0 eq) and an amine (0.62 mmol, 1.1 eq) at 0° C. The reaction mixture was stirred at 25° C. for 16 hours. The reaction mixture was extracted from 2M HCl into DCM and the solvent evaporated in vacuo. The crude material was purified by preparative HPLC to yield the title compound.

TABLE 16

| Example | Name | R | Data | Preparation Information |
|---|---|---|---|---|
| 362 | 3-Chloro-4-{[(5-chloro-1,3-thiazol-2-yl)amino]sulfonyl}-N-[4-(trifluoromethoxy)benzyl]benzamide | 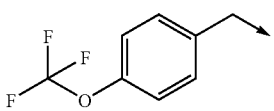 | LCMS Rt = 3.58 min MS m/z 525 [MH]+ | using 4-(trifluoromethoxy)benzylamine |
| 363 | 3-Chloro-N-(3-chloro-4-fluorobenzyl)-4-{[(5-chloro-1,3-thiazol-2-yl)amino]sulfonyl}benzamide | 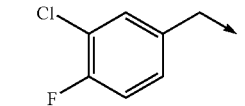 | LCMS Rt = 2.36 min MS m/z 493 [MH]+ | using 3-chloro-4-fluoro benzylamine |
| 364 | 3-Chloro-4-{[(5-chloro-1,3-thiazol-2-yl)amino]sulfonyl}-N-[3-(trifluoromethoxy)benzyl]benzamide | 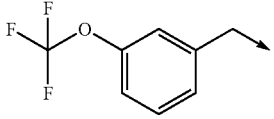 | LCMS Rt = 3.67 min MS m/z 525 [MH]+ | using 3-(trifluoromethoxy)benzylamine |
| 365 | 3-Chloro-4-{[(5-chloro-1,3-thiazol-2-yl)amino]sulfonyl}-N-[3-fluoro-4-(trifluoromethoxy)benzyl]benzamide | 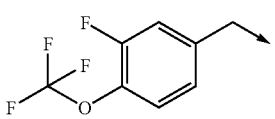 | LCMS Rt = 2.44 min MS m/z 543 [MH]+ | using 3-fluoro-4-(trifluoromethoxy)benzylamine |
| 366 | 3-Chloro-4-{[(5-chloro-1,3-thiazol-2-yl)amino]sulfonyl}-N-[3-fluoro-4-(trifluoromethyl)benzyl]benzamide | 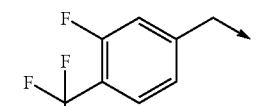 | LCMS Rt = 3.61 min MS m/z 527 [MH]+ | using 3-fluoro-4-(trifluoromethyl)benzylamine |
| 367 | 3-Chloro-4-{[(5-chloro-1,3-thiazol-2-yl)amino]sulfonyl}-N-[4-fluoro-3-(trifluoromethoxy)benzyl]benzamide | 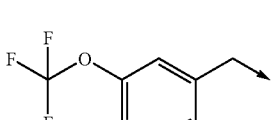 | LCMS Rt = 2.45 min MS m/z 543 [MH]+ | using 4-fluoro-3-(trifluoromethoxy)benzylamine |

TABLE 16-continued

| Example | Name | R | Data | Preparation Information |
|---|---|---|---|---|
| 368 | 3-Chloro-4-{[(5-chloro-1,3-thiazol-2-yl)amino]sulfonyl}-N-(3,4-dichlorobenzyl)benzamide | | LCMS Rt = 2.47 min MS m/z 509 [MH]+ | using 3,4-dichloro benzylamine |
| 369 | 3-Chloro-N-(4-chloro-3-fluorobenzyl)-4-{[(5-chloro-1,3-thiazol-2-yl)amino]sulfonyl}benzamide | | LCMS Rt = 3.44 min MS m/z 493 [MH]+ | using 4-chloro-3-fluoro benzylamine |
| 370 | 3-Chloro-4-{[(5-chloro-1,3-thiazol-2-yl)amino]sulfonyl}-N-[4-fluoro-3-(trifluoromethyl)benzyl]benzamide | | LCMS Rt = 3.50 min MS m/z 527 [MH]+ | using 4-fluoro-3-(trifluoromethyl) benzylamine |
| 371 | 3-Chloro-4-{[(5-chloro-1,3-thiazol-2-yl)amino]sulfonyl}-N-(3,4-difluorobenzyl)benzamide | | LCMS Rt = 2.31 min MS m/z 477 [MH]+ | using 3,4-difluoro benzylamine |
| 372 | 3-Chloro-4-{[(5-chloro-1,3-thiazol-2-yl)amino]sulfonyl}-N-[3-(trifluoromethyl)benzyl]benzamide | | LCMS Rt = 3.44 min MS m/z 509 [MH]+ | using 3-(trifluoromethyl) benzylamine |
| 373 | 3-Chloro-4-{[(5-chloro-1,3-thiazol-2-yl)amino]sulfonyl}-N-[4-(trifluoromethyl)benzyl]benzamide | | LCMS Rt = 2.27 min MS m/z 509.95 [MH]+ | using 4-(trifluoromethyl) benzylamine |

Example 374

2-Chloro-N-[3-chloro-4-(trifluoromethyl)benzyl]-4-[(1,2,4-thiadiazol-5-ylamino)sulfonyl]benzamide

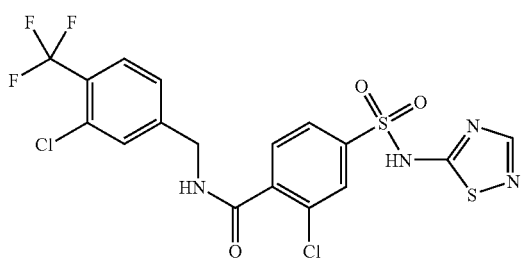 [SMILES: O=C(NCc1ccc(C(F)(F)F)c(Cl)c1)c1ccc(S(=O)(=O)Nc2ncns2)cc1Cl]

The title compound was prepared from 3-chloro-4-({[3-chloro-4-(trifluoromethyl)benzyl]amino}carbonyl)benzenesulfonyl chloride (Preparation 38) and 5-amino-1,2,4-thiadiazole in following Method H described for Example 6. The reaction mixture was added to 2M HCl, extracted into ethyl acetate, dried over sodium sulphate, filtered and evaporated. The crude material was purified by column chromatography eluting with DCM:MeOH:AcOH (95:5:0.5) to yield the title compound.

$^1$HNMR (d$_6$-DMSO): 4.55 (d, 2H), 7.55 (d, 1H), 7.65 (m, 2H), 7.80-7.85 (m, 3H), 8.45 (s, 1H), 9.25 (t, 1H). LCMS Rt=3.14 min. MS m/z 510-512 [MH]+.

Example 375

2-Chloro-N-[3-fluoro-4-(trifluoromethyl)benzyl]-4-[(1,2,4-thiadiazol-5-ylamino)sulfonyl]benzamide

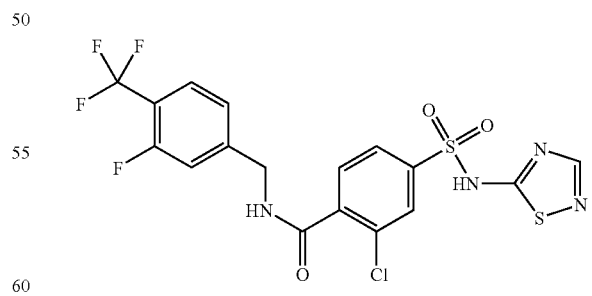

Method P

2-Chloro-4-[(1,2,4-thiadiazol-5-ylamino)sulfonyl]benzoic acid (Preparation 42, 63.4 mg, 0.198 mmol, 1 eq), Et$_3$N (50 mg, 0.5 mmol, 3 eq) 3-fluoro-4-(trifluoromethyl)benzylamine (55 mg, 0.285 mmol, 1.33 eq) were combined in dimethylformamide (3 ml), 2-(1H-benzotriazol-1-yl)-1,1,1, 3,tetramethyluronium tetrafluoroborate (TBTU, 83 mg, 0.258 mmol, 1.30 eq) was added and the reaction mixture stirred at room temperature for 1 hour. The reaction mixture was diluted with ethyl acetate (10 ml), washed with water (10 ml), sat sodium hydrogen carbonate (10 ml), dried over sodium sulphate, filtered and evaporated in vacuo. The crude material was purified by column chromatography eluting with 0-100% DCM:MeOH:AcOH (95:5:0.5). The obtained compound was further triturated in DCM and filtered to yield a white solid (30 mg, 0.061 mmol, 31%).

$^1$HNMR (d$_6$-DMSO): 4.55 (d, 2H), 7.40 (d, 1H), 7.45 (d, 1H), 7.70 (s, 1H), 7.75-7.85 (m, 3H), 8.50 (s, 1H) 9.25 (t, 1H). LCMS Rt=1.92 min. MS m/z 495-497 [MH]+.

The following examples of the general formula:

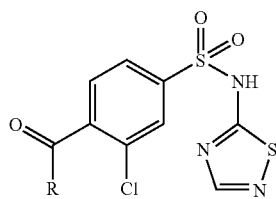

were prepared by Method P as described for Example 375 above. Unless otherwise noted, preparation details are as described for the method referred to.

Example 379

N-[3-(4-chlorobenzyl)-1-methyl-1H-pyrazol-5-yl]-4-{[(5-chloro-1,3-thiazol-2-yl)amino]sulfonyl}-3-fluorobenzamide

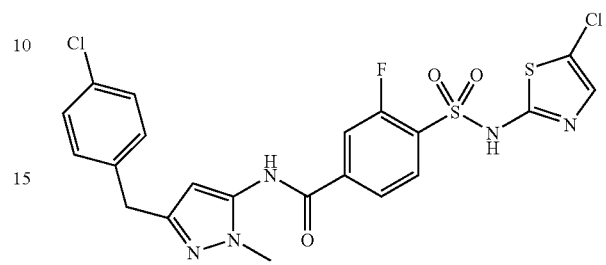

Method O

4-[(5-Chloro-1,3-thiazol-2-yl)(2,4-dimethoxy-benzyl) sulfonyl]-3-fluorobenzoic acid (Preparation 25, 0.0500 g, 0.000103 mol), 5-(4-chloro-benzyl)-2-methyl-2H-pyrazol-3-ylamine (0.0239 g, 0.000108 mol) and Et$_3$N (43 uL, 0.00031 mol) were dissolved in methylene chloride (2 mL, 0.03 mol). HBTU (0.0477 g, 0.000108 mol) was added and the reaction was shaken overnight. The reaction was chro-

TABLE 17

| Example | Name | R | Data | Preparation Information |
|---|---|---|---|---|
| 376 | 2-Chloro-N-[3-fluoro-4-(trifluoromethoxy)benzyl]-4-[(1,2,4-thiadiazol-5-ylamino)sulfonyl]benzamide | | LCMS Rt = 2.00 min MS m/z 511-513 [MH]+ $^1$HNMR (d$_6$-DMSO): 4.45 (d, 2H) 7.30 (d, 1H), 7.45 (d, 1H), 7.55 (t, 1H), 7.65 (d, 1H), 7.85 (m, 2H), 8.45 (s, 1H), 9.20 (t, 1H) | Method P using, 3-fluoro-4-(trifluoromethoxy) benzylamine |
| 377 | 2-Chloro-4-[(1,2,4-thiadiazol-5-ylamino)sulfonyl]-N-[4-(trifluoromethyl)benzyl]benzamide | | LCMS Rt = 3.01 min MS m/z 477-479 [MH]+ $^1$HNMR (d$_6$-DMSO): 4.55 (d, 2H), 7.55 (d, 2H), 7.65 (d, 1H), 7.70 (d, 2H), 7.85 (m, 2H), 8.45 (s, 1H), 9.20 (t, 1H) | Method P using, 4-(trifluoromethyl) benzylamine. |
| 378 | 2-Chloro-N-[3-chloro-4-(trifluoromethoxy)benzyl]-4-[(1,2,4-thiadiazol-5-ylamino)sulfonyl]benzamide | | LCMS Rt = 1.76 min MS m/z 527-531 [MH]+ $^1$HNMR (d$_6$-DMSO): 4.45 (d, 2H), 7.45 (d, 1H), 7.55 (d, 1H), 7.65 (m, 1H), 7.70 (s, 2H), 7.80 (m, 2H), 8.45 (s, 1H) 9.25 (t, 1H) | Method P using, 3-chloro-4-(trifluoromethoxy) benzylamine | matographed (12 g silica gel column, hexanes to ethyl acetate gradient elution) and product fractions were combined and evaporated to a residue. The residue was dissolved in methylene chloride and TFA (0.25 mL) was added. The reaction was allowed to stir for 3 hours. The reaction was concentrated onto Celite and purified by column chromatography (4 g silica gel column, hexanes to 10% MeOH in ethyl acetate gradient elution). Product fractions were combined and evaporate to give product as a white solid (19 mg, 33%)

LCMS Rt=1.67. MS m/z 540 [M+H]+.

The following examples of general formula:

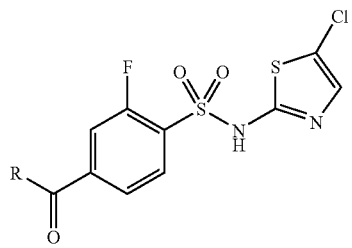

were prepared by Method Q as described for Example 379 above. Unless otherwise noted, preparation details are as described for the method referred to.

(Preparation 93, 205 mg, 0.510 mmol) in acetonitrile (1.0 mL, 19 mmol) was added dropwise to a solution of 1,2,4-thiadiazol-5-amine (155 mg, 1.53 mmol) and sodium hydroxide (61.1 mg, 1.53 mmol) in 1,4-dioxane (1.6 mL, 2.01 mmol) and water (0.32 mL, 18 mmol). After stirring 30 min at ambient temperature, the reaction mixture was quenched with 2 N HCl. The mixture was partitioned with methylene chloride. The aqueous layer was washed with methylene chloride, and the combined organic layers were dried over sodium sulfate, filtered and concentrated onto Celite. The residue was purified via automated flash chromatography (12 g SiO$_2$, chloroform to 20% MeOH in chloroform). The product containing fractions were concentrated in vacuo, and the residue was dissolved in 1 mL of DMSO, filtered, and purified via reverse-phase HPLC (Prep: Phenomenex 250×30.0 mm 15 micron C18 column. 40 mL/min. Gradient 15% B to 100% B over 25 min. Solvent A: 7800 water/200 acetonitrile/8 TFA. Solvent B: 7200 acetonitrile/800 water/8 TFA). The product containing fractions were lyophilized to afford the product as a white powder (37 mg, 15%).

LCMS Rt=1.64. MS m/z 467 [M+H]+.

TABLE 18

| Example | Name | R | Data | Preparation Information |
|---|---|---|---|---|
| 380 | N-[1-(4-chlorobenzyl)-1H-pyrazol-3-yl]-4-{[(5-chloro-1,3-thiazol-2-yl)amino]sulfonyl}-3-fluorobenzamide | | LCMS Rt = 1.63 MS m/z 526 [M + H]+ | Method Q using 1-(4-chlorobenzyl)-1H-pyrazol-3-ylamine |
| 381 | N-[1-(4-chlorobenzyl)-1H-pyrazol-4-yl]-4-{[(5-chloro-1,3-thiazol-2-yl)amino]sulfonyl}-3-fluorobenzamide | | LCMS Rt = 1.61 MS m/z 526 [M + H]+ | Method Q using 1-(4-chlorobenzyl)-1H-pyrazol-4-ylamine |

Example 382

N-{[1-(4-chlorophenyl)cyclopropyl]methyl}-3-fluoro-4-[(1,2,4-thiadiazol-5-ylamino)sulfonyl]benzamide

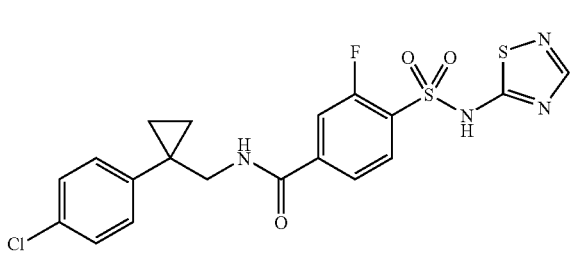 [SMILES: O=C(NCC1(c2ccc(Cl)cc2)CC1)c1ccc(S(=O)(=O)Nc2ncns2)c(F)c1]

A solution of 4-[({[1-(4-chlorophenyl)cyclopropyl]methyl}amino)carbonyl]-2-fluorobenzenesulfonyl chloride Example 383

3-Fluoro-N-[2-(4-fluorophenoxy)-2-methylpropyl]-4-[(1,2,4-thiadiazol-5-ylamino)sulfonyl]benzamide

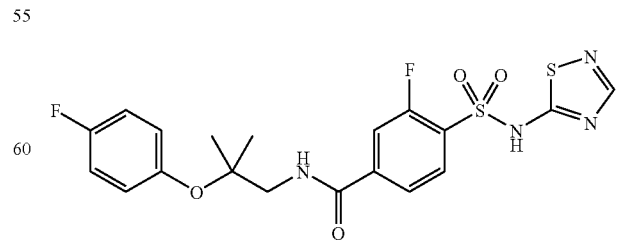

2-Fluoro-4-({[2-(4-fluorophenoxy)-2-methylpropyl]amino}carbonyl)benzenesulfonyl chloride (Preparation 95, 242 mg, 0.599 mmol) was added portion-wise to a solution of 1,2,4-thiadiazol-5-amine (182 mg, 1.80 mmol) and sodium hydroxide (71.9 mg, 1.80 mmol) in 1,4-dioxane (1.9 mL, 24 mmol) and water (0.37 mL, 21 mmol). After stirring 30 min at ambient temperature, the reaction was quenched with 2 N HCl. The mixture was partitioned with methylene chloride. The aqueous layer was washed with methylene chloride, and the combined organic layers were dried over sodium sulfate, filtered and concentrated onto Celite. The residue was purified via automated flash chromatography (12 g SiO$_2$, chloroform to 20% MeOH in chloroform). The product containing fractions were concentrated in vacuo, and the residue was dissolved in 1 mL of DMSO, filtered, and purified via reverse-phase HPLC (Prep: Phenomenex 250×30.0 mm 15 micron C18 column. 40 mL/min. Gradient 15% B to 100% B over 25 min. Solvent A: 7800 water/200 acetonitrile/8 TFA. Solvent B: 7200 acetonitrile/800 water/8 TFA). The product containing fractions were lyophilized to afford the product as a white powder (48 mg, 16%).

LCMS Rt=1.54. MS m/z 469 [M+H]+.

Example 384

4-({(2S)-2-[(3-chlorophenoxy)methyl]pyrrolidin-1-yl}carbonyl)-N-1,3-thiazol-2-ylbenzenesulfonamide

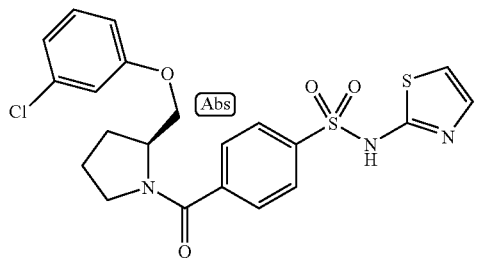 [SMILES: O=C(c1ccc(S(=O)(=O)Nc2nccs2)cc1)N1CCC[C@H]1COc1cccc(Cl)c1]

A mixture of 4-iodo-N-1,3-thiazol-2-ylbenzenesulfonamide (Preparation 98, 150 mg, 0.41 mmol), (2S)-2-(3-chlorophenoxymethyl)-pyrrolidine hydrochloride (Preparation 90, 430 mg, 2.0 mmol), hexacarbonylmolybdenum (50 mg, 0.2 mmol), palladium(II) acetate (4 mg, 0.02 mmol), and sodium carbonate (130 mg, 1.2 mmol) in water (0.82 mL, 45 mmol) was heated 20 min at 110° C. in the microwave. The reaction mixture was diluted with 1 N HCl and extracted with ethyl acetate. The combined organic layers were washed with brine, dried over sodium sulfate, filtered and concentrated in vacuo. The residue was taken up in 1.2 mL of DMSO, filtered, and purified via HPLC (Prep: Phenomenex 250×30.0 mm 15 micron C18 column. 40 mL/min. Gradient 15% B to 100% B over 25 min. Solvent A: 7800 water/200 acetonitrile/8 TFA. Solvent B: 7200 acetonitrile/800 water/8 TFA)

LCMS Rt=1.58 min. MS m/z 478 [M+H]+. .

Example 385

N-{2-[(4-chlorophenyl)amino]ethyl}-4-[(1,3-thiazol-2-ylamino)sulfonyl]benzamide

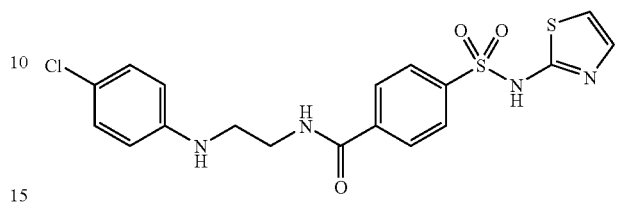

A mixture of 4-iodo-N-1,3-thiazol-2-ylbenzenesulfonamide (Preparation 98, 0.2 g, 0.5 mmol), N-(2)-(4-tert-butylphenyl)-2-methyl-propane-1,2-diamine (0.55 g, 2.5 mmol), hexacarbonylmolybdenum (70 mg, 0.2 mmol), palladium(ii) acetate (6 mg, 0.02 mmol), and sodium carbonate (200 mg, 2 mmol) in water (1.5 mL, 83 mmol) was heated 30 min at 110° C. in the microwave. The reaction mixture was diluted with 1 N HCl and extracted with ethyl acetate. The combined organic layers were washed with brine, dried over sodium sulfate, filtered and concentrated in vacuo. The residue was dissolved in methylene chloride/MeOH and MP-Carbonate (2.73 mmol/g loading; 0.9 g, 2.50 mmol) was added. After stirring 1 h, LC/MS analysis indicated complete capture of the target compound. The resin was washed with methylene chloride then stirred in 8:1 methylene chloride/AcOH. LC/MS analysis indicated the target compound was released from the resin (not quantified). The mixture was filtered. The filtrate was concentrated in vacuo, and the residue was lyophilized from water/acetonitrile. The resulting solid was triturated with methylene chloride and ether. The resulting solid was purified via HPLC (Prep: Phenomenex 250×30.0 mm 15 micron C18 column. 40 mL/min. Gradient 15% B to 100% B over 25 min. Solvent A: 7800 water/200 acetonitrile/8 TFA. Solvent B: 7200 acetonitrile/800 water/8 TFA).

LCMS Rt=1.41 min. MS m/z 437 [M+H]$^+$

Example 386

4-[(1,3-Thiazol-2-ylamino)sulfonyl]-N-(2-thienylmethyl)benzamide

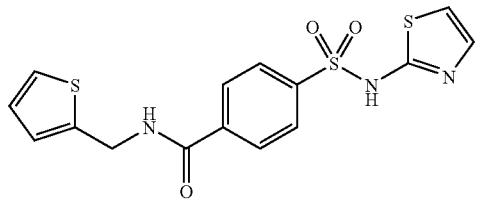 [SMILES: O=C(NCc1cccs1)c1ccc(S(=O)(=O)Nc2nccs2)cc1]

4-Iodo-N-1,3-thiazol-2-ylbenzenesulfonamide Preparation 98, 200 mg, 0.5 mmol), thiophene-2-methanamine (280 uL, 2.7 mmol), hexacarbonylmolybdenum (70 mg, 0.3 mmol), palladium(II) acetate (6 mg, 0.03 mmol), and sodium carbonate (170 mg, 1.6 mmol) in water (1.1 mL, 61 mmol) was heated 30 min at 110° C. in the microwave. The reaction mixture was diluted with 1 N HCl and extracted with ethyl acetate. The combined organic layers were washed with brine, dried over sodium sulfate, filtered and concentrated in vacuo. The residue was dissolved in methylene chloride/MeOH and MP-Carbonate (2.73 mmol/g loading; 1.0 g, 2.73 mmol) was added. After stirring 1 h, LC/MS analysis indicated complete capture of the target compound. The resin was washed with methylene chloride then stirred in 8:1 methylene chloride/AcOH. LC/MS analysis indicated the target compound was released from the resin (not quantified). The material was further purified on the Isco (12 g SiO$_2$, ethyl acetate to 4:1 ethyl acetate-MeOH).

LCMS Rt=1.26 min. MS m/z 380 [M+H]+.

Example 387

N-(4-tert-butylbenzyl)-4-[(1,3-thiazol-2-ylamino) sulfonyl]benzamide

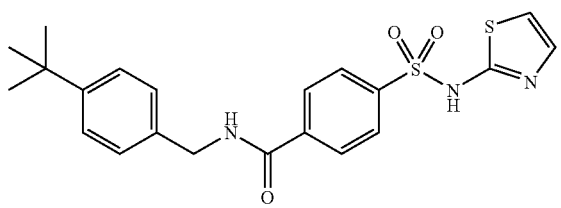 [SMILES: CC(C)(C)c1ccc(CNC(=O)c2ccc(S(=O)(=O)Nc3nccs3)cc2)cc1]

4-{[(2,4-Dimethoxybenzyl)(1,3-thiazol-2-yl)amino] sulfonyl}benzoic acid (Preparation 99, 1.30E3 mg, 0.00300 mol), HBTU (1400.8 mg, 0.0031671 mol) and Et$_3$N (1.07 mL, 0.00766 mol) were mixed in methylene chloride (10 mL, 0.2 mol). 4-tert-butylbenzylamine (424.1 mg, 0.002598 mol) was added and the reaction stirred overnight. The reaction was washed with saturated sodium bicarbonate (aq) followed by 0.5N HCl. The organic phase was separated and dried over magnesium sulfate, then treated with activated carbon and filtered through a Celite pad. The solvent was removed in vacuo to give an oily residue. The residue was triturated with DCM and the solid collected by filtration. LCMS analysis of the solid revealed cleavage of the dimethoxybenzyl protection group had occurred. The gray solid was saved. The filtrate was purified by column chromatography, chloroform to 10% MeOH in chloroform gradient eluent. Product fractions were combined and evaporated to an oily residue. The residue was triturated with methylene chloride and beige solid collected. The solid products from steps 4 and 5 were combined and dissolved in 1N NaOH (aq). The solution was washed 3× with diethyl ether. The basic aqueous phase was treated with activated carbon and filtered through a Celite pad. The pale yellow filtrate was slowly acidified to pH 2-3 with 6N HCl (aq). The resultant precipitate was collected by filtration. Vacuum drying yielded 511 mg of product as a white powder.

LCMS Rt=1.58 min. MS m/z 430 [M+H]+.

Example 388

N-(3,4-dichlorobenzyl)-4-[(1,3-thiazol-2-ylamino) sulfonyl]benzamide

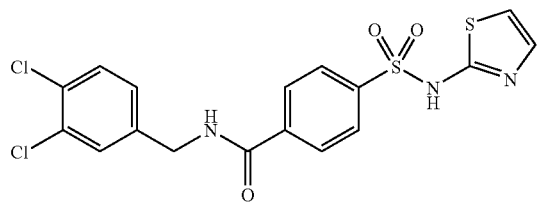 [SMILES: O=C(NCc1ccc(Cl)c(Cl)c1)c1ccc(S(=O)(=O)Nc2nccs2)cc1]

4-{[(2,4-Dimethoxybenzyl)(1,3-thiazol-2-yl)amino] sulfonyl}benzoic acid (Preparation 99, 1.30E3 mg, 0.00300 mol), HBTU (1400.8 mg, 0.0031671 mol) and Et$_3$N (1.07 mL, 0.00766 mol) were mixed in methylene chloride (10 mL, 0.2 mol). 3,4-dichlorobenzylamine (457.3 mg, 0.002598 mol) was added and the reaction stirred overnight. The reaction was washed with saturated sodium bicarbonate (aq). The organic phase was separated and dried over magnesium sulfate, the solvent was removed in vacuo to give an oily residue. The residue was purified by column chromatography (40 g silica gel column, hexanes to 50% ethyl acetate-hexanes gradient elution). Product fractions were combined and evaporated to give 1.13 g of the protected benzamide intermediate. The residue was dissolved in DCM and TFA was added dropwise until wet pH paper turned acidic when held above the reaction. After 30 minutes of stirring at room temperature, the solid precipitate was collected by filtration. The solid was rinsed with DCM, then ethyl ether. The solid was dissolved in 0.5N NaOH (5 mL) and filtered. The filtrate was washed 2× with ethyl ether, then treated with activated carbon and filtered through Celite. The pale yellow filtrate was acidified to pH 2 with 6N HCl. The white precipitate was collected by filtration and rinsed with water then ethyl ether. Vacuum drying yielded 446 mg of product as a white powder.

LCMS Rt=1.49 min. MS m/z 442 [M+H]+.

Example 389

4-{[(5-Chloro-1,3-thiazol-2-yl)amino]sulfonyl}-N-(3,3-dimethylbutyl)-3-fluorobenzamide

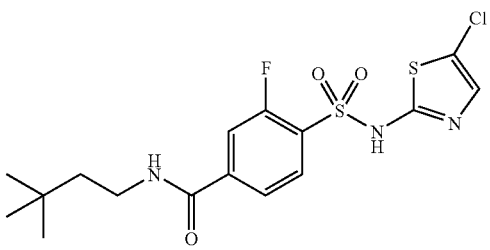 [SMILES: CC(C)(C)CCNC(=O)c1ccc(S(=O)(=O)Nc2ncc(Cl)s2)c(F)c1]

4-{[(5-Chloro-1,3-thiazol-2-yl)amino]sulfonyl}-3-fluorobenzoic acid (Preparation 25, 55.0 mg, 0.113 mmol) and Et$_3$N (40.2 µL, 0.288 mmol) were mixed in N,N-dimethylformamide (0.6 mL, 8 mmol). 3,3-dimethylbutylamine (16.7 µL, 0.124 mmol) was added and the reaction stirred overnight. After 18 h, the reaction mixture was diluted with saturated aqueous sodium bicarbonate and extracted with ethyl acetate. The combined organic layers were washed with brine, dried over sodium sulfate, filtered and concentrated in vacuo. The residue was purified via automated flash chromatography (12 g SiO$_2$, hexanes to ethyl acetate) to afford the product as a yellow oil. The intermediate was taken up in methylene chloride (5.0 mL, 78 mmol) and TFA (500 µL, 6 mmol) was added. After stirring 30 min, the reaction mixture was diluted with ether and concentrated onto Celite. The residue was purified via automated flash chromatography (12 g SiO$_2$, chloroform to 20% MeOH in chloroform). The product containing fractions were concentrated onto Celite and re-purified via automated flash chromatography (12 g SiO$_2$, hexanes to 10% MeOH in ethyl acetate) to afford the product as a white solid.

LCMS Rt=1.59 min. MS m/z 420 [M+H]+.

MeOH in chloroform) to afford the title compound (150 mg, 60%).

LCMS Rt=1.46 min. MS m/z 426 [M+H]+.

The following examples of general formula:

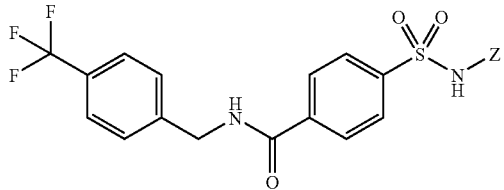

were prepared by Method R as described for Example 390 above. Unless otherwise noted, preparation details are as described for the method referred to.

TABLE 19

| Example | Name | Z | Data | Preparation Information |
|---------|------|---|------|------------------------|
| 22 | 4-{[(5-methyl-1,3-thiazol-2-yl)amino]sulfonyl}-N-[4-(trifluoromethyl)benzyl]benzamide | | Rt = 1.49 min MS m/z 456 [M + H]+ | Method R using 2-amino-5-methylthiazole |
| 391 | 4-{[(4-methyl-1,3-thiazol-2-yl)amino]sulfonyl}-N-[4-(trifluoromethyl)benzyl]benzamide | | Rt = 1.47 min MS m/z 456 [M + H]+ | Method R using 2-amino-4-methylthiazole |

Example 390

4-[(1H-1,2,4-triazol-3-ylamino)sulfonyl]-N-[4-(trifluoromethyl)benzyl]benzamide

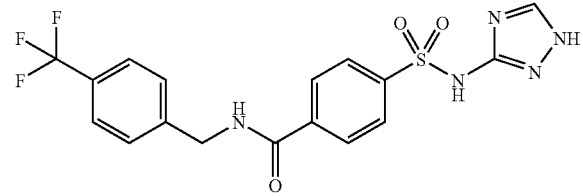 [SMILES: O=C(NCc1ccc(C(F)(F)F)cc1)c1ccc(S(=O)(=O)Nc2nc[nH]n2)cc1]

Method R 4-(1H-1,2,4-Triazol-3-ylsulfamoyl)-N-(4-trifluoromethyl-benzyl)-benzamide. A solution/suspension of 4-(4-trifluoromethyl-benzylcarbamoyl)-benzenesulfonyl chloride (200 mg, 0.5 mmol) in methylene chloride (1.0 mL, 16 mmol) was added portion-wise to a 0° C. solution of 3-amino-1,2,4-triazole (48.9 mg, 0.581 mmol) in pyridine (1.0 mL, 12 mmol). After addition was complete, the ice-bath was removed, and the reaction mixture was warmed to rt. After 16 h, the reaction mixture was diluted with methylene chloride and partitioned with 1 N HCl. The layers were separated and the aqueous layer was extracted with methylene chloride. The combined organic layers were washed with water, diluted with ethyl acetate, dried over sodium sulfate, filtered and concentrated in vacuo. The residue was loaded onto Celite and purified on the Isco (12 g cartridge, chloroform to 12%

Example 392

N-[2-fluoro-3-(trifluoromethyl)benzyl]-4-[(1,3-thiazol-2-ylamino)sulfonyl]benzamide

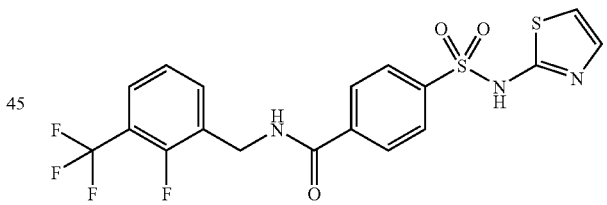

Method S

4-[(2,4-Dimethoxy-benzyl)-thiazol-2-yl-sulfamoyl]-benzoic acid (Preparation 99, 3.00 g, 6.90 mmol) was mixed with N,N-dimethylformamide (9 mL, 100 mmol) and stirred in an icebath. HATU (2.783 g, 7.319 mmol) was added to the reaction. While cooling in an icebath, N,N-diisopropylethylamine (3.61 mL, 20.7 mmol) was added to the reaction portion-wise, keeping the temperature below 10° C. during the addition. The solution cleared after the addition of the DIEA. 2-Fluoro-3-(trifluoromethyl)benzylamine (1.60 g, 8.28 mmol) was added dropwise, keeping the temperature below 10° C. during the addition. The addition was exothermic. The reaction was quenched with water (30 mL, 2000 mmol). The reaction was extracted with 3× with ether (30 mL, 300 mmol). The combined organic phase was washed with saturated sodium bicarbonate (100 mL) and brine (100 mL) then dried over magnesium sulfate and evaporated to a residue. The residue was chromatographed through a silica gel column (80 g Isco column). The column was eluted with a gradient from hexanes to 1-1 ethyl acetate-hexanes. Product fractions were combined and evaporated to give a yellow oil. The product was used as-is in the next step.

4-[(2,4-Dimethoxy-benzyl)-thiazol-2-yl-sulfamoyl]-N-(2-fluoro-3-trifluoromethyl-benzyl)-benzamide (4.21 g, 0.00677 mol) was dissolved in methylene chloride (40 mL, 0.6 mol) and TFA (1.06 mL, 0.0138 mol) was added. After stirring for 2 hours the reaction was diluted with ethyl ether (80 mL) and the solid collected by filtration. The solids from step 2 was slurried in water (10 mL, 0.6 mol) and 1.0 M of sodium hydroxide in water (1.0E1 mL) was added. EtOH (20 mL) was added to help solubilize the sample. The combined filtrate was treated with activated carbon and filtered through a Celite pad. 50 mL of 0.5N NaOH was used to rinse the Celite pad. The yellow solution was acidified to pH 2-3 with 6N HCl (aq). The precipitate was allowed to stir for 1 hour, then collected by filtration. The solid was rinsed with water, then ether (2×). Vacuum drying yielded 1.30 g of white powder (41%).

Rt=1.47 min. MS m/z 460 [M+H]+.

The following examples of the general formula

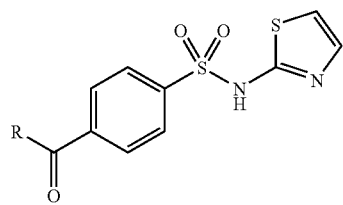

were prepared by Method S as described for Example 392 above. Unless otherwise noted, preparation details are as described for the method referred to.

The following examples of general formula:

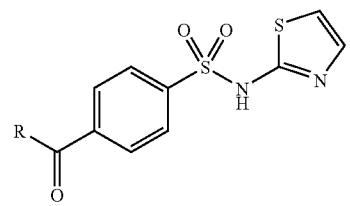

were prepared by the following method using the indicated amines.

A solution of 4-{[(2,4-Dimethoxybenzyl)(1,3-thiazol-2-yl)amino]sulfonyl}benzoic acid (Preparation 99), (1 eq) in DMF (10 ml) was cooled by ice-water bath, HATU (1.2 g, 1.06 eq) was added. DIEA (1.6 ml, 3 eq) was added to the reaction dropwise, keeping the temperature below 10° C. during the addition. The solution cleared after the addition of the DIEA, then stirred for 20 min at 10° C. The amine (1.2 eq) was added dropwise, keeping the temperature below 10° C. during the addition. The reaction was stirred at room temperature overnight. The reaction mixture was poured into water (50 ml), extracted with EtOAc (3×10 ml). The combined organic phase was washed with saturated sodium bicarbonate (20 mL×3) and brine (20 mL), then dried over $Na_2SO_4$ and concentrated. The residue was chromatographed through on silica gel column to afford the benzyl amide. The benzyl amide thus formed (1 eq) was dissolved in DCM (13 ml) and TFA (0.29 ml, 2 eq) and stirred at room temperature for 2 hours to remove the dimethoxybenzyl protecting group. The solid was collected by filtration. The filtrate was evaporated, the residual material was triturated with DCM (5 ml), and the solid was collected by filtration and then purified by preparative TLC. The solid from preparative TLC was extracted with THF (2×100 ml). The THF was concentrated to provide a white solid, washed with DCM, petroleum ether and dried to secure the final product.

TABLE 20

| Example | Name | R | Data | Preparation Information |
|---|---|---|---|---|
| 393 | N-[3-fluoro-4-(trifluoromethyl)benzyl]-4-[(1,3-thiazol-2-yl amino)sulfonyl]benzamide | | Rt = 1.46 min MS m/z 460 [M + H]+ | Method S using 3-fluoro-4-(trifluoromethyl) benzylamine |
| 394 | N-[3-fluoro-4-(trifluoromethoxy)benzyl]-4-[(1,3-thiazol-2-yl amino)sulfonyl]benzamide | | Rt = 1.50 min MS m/z 476 [M + H]+ | Method S using 3-fluoro-4-(trifluromethoxy) benzylamine |
| 395 | N-[4-chloro-3-(trifluoromethyl)benzyl]-4-[(1,3-thiazol-2-yl amino)sulfonyl]benzamide | | Rt = 1.51 min MS m/z 476 [M + H]+ | Method S using 4-chloro-3-(trifluoromethyl) benzylamine |

TABLE 21

| Example | Name | R | Data | Preparation Information |
|---|---|---|---|---|
| 396 | N-[3-chloro-4-(trifluoromethyl)benzyl]-4-[(1,3-thiazol-2-yl amino)sulfonyl] benzamide | 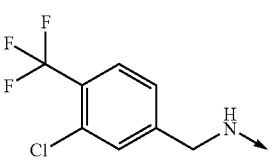 | Rt = 1.51 min MS m/z 476 [M + H]$^+$ | using 3-chloro-4-(trifluoromethyl) benzylamine |
| 397 | N-[2-fluoro-4-(trifluoromethyl)benzyl]-4-[(1,3-thiazol-2-yl amino)sulfonyl] benzamide | 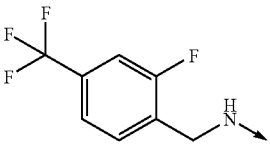 | Rt = 1.44 min MS m/z 460 [M + H]$^+$ | using 2-fluoro-4-(trifluoromethyl) benzylamine |
| 398 | 4-[(1,3-Thiazol-2-yl amino)sulfonyl]-N-[3-(trifluoromethyl)benzyl] benzamide | 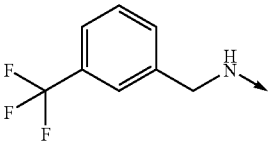 | Rt = 1.43 min MS m/z 442 [M + H]$^+$ | using 3-(trifluoromethyl) benzylamine |
| 399 | N-(biphenyl-4-ylmethyl)-4-[(1,3-thiazol-2-ylamino)sulfonyl] benzamide | 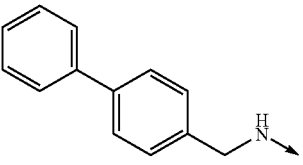 | Rt = 1.54 min MS m/z 450 [M + H]$^+$ | using 4-phenyl benzylamine |
| 400 | N-(3-chloro-4-methylbenzyl)-4-[(1,3-thiazol-2-yl amino)sulfonyl] benzamide | 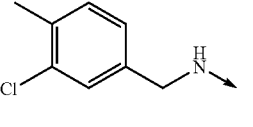 | Rt = 1.47 min MS m/z 422 [M + H]$^+$ | using 3-chloro-4-methyl benzylamine |
| 401 | N-(3-chloro-4-fluorobenzyl)-4-[(1,3-thiazol-2-yl amino)sulfonyl] benzamide | 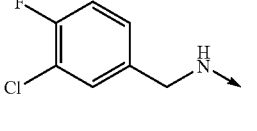 | Rt = 1.40 min MS m/z 426 [M + H]$^+$ | using 3-chloro-4-fluoro benzylamine |
| 402 | 4-[(1,3-Thiazol-2-yl amino)sulfonyl]-N-[4-(trifluoromethoxy) benzyl]benzamide | 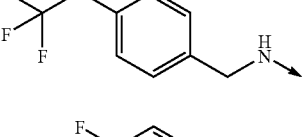 | Rt = 1.48 min MS m/z 458 [M + H]$^+$ | using 4-(trifluoromethoxy) benzylamine |
| 403 | N-[4-fluoro-3-(trifluoromethoxy)benzyl]-4-[(1,3-thiazol-2-ylamino)sulfonyl] benzamide | 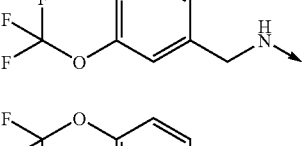 | Rt = 1.49 min MS m/z 476 [M + H]$^+$ | using 4-fluoro-3-(trifluoromethoxy) benzylamine |
| 404 | N-[2-methoxy-4-(trifluoromethoxy)benzyl]-4-[(1,3-thiazol-2-ylamino)sulfonyl] benzamide | 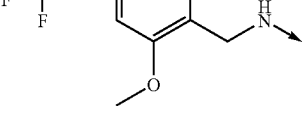 | Rt = 1.50 min MS m/z 488 [M + H]$^+$ | using 2-methoxy-4-(trifluoromethoxy) benzylamine |
| 405 | N-(3-chloro-4-methoxybenzyl)-4-[(1,3-thiazol-2-yl amino)sulfonyl] benzamide | 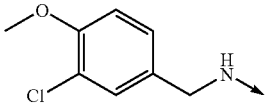 | Rt = 1.35 min MS m/z 438 [M + H]$^+$ | using 3-chloro-4-methoxy-benzylamine |

TABLE 21-continued

| Example | Name | R | Data | Preparation Information |
|---|---|---|---|---|
| 406 | N-[4-chloro-2-(trifluoromethyl)benzyl]-4-[(1,3-thiazol-2-yl amino)sulfonyl]benzamide | | Rt = 1.52 min MS m/z 476 [M + H]$^+$ | using 4-chloro-2-(trifluoromethyl)benzylamine |
| 407 | N-[(6-chloropyridin-3-yl)methyl]-4-[(1,3-thiazol-2-yl amino)sulfonyl]benzamide | | Rt = 1.20 min MS m/z 409 [M + H]$^+$ | using 2-chloro-5-amino methylpyridine |
| 408 | 4-[(1,3-Thiazol-2-ylamino)sulfonyl]-N-{[6-(trifluoromethyl)pyridin-3-yl]methyl}benzamide | | Rt = 1.25 min MS m/z 443 [M + H]$^+$ | using 3-aminomethyl-6-(trifluoromethyl)pyridine |
| 409 | N-(4-phenoxybenzyl)-4-[(1,3-thiazol-2-yl amino)sulfonyl]benzamide | | Rt = 1.51 min MS m/z 466 [M + H]$^+$ | using 4-phenoxy benzylamine |
| 410 | N-(3-phenoxybenzyl)-4-[(1,3 thiazol-2-yl amino)sulfonyl]benzamide | | Rt = 1.52 min MS m/z 466 [M + H]$^+$ | using 3-phenoxy benzylamine |
| 411 | N-(biphenyl-3-ylmethyl)-4-[(1,3-thiazol-2-yl amino)sulfonyl]benzamide | | Rt = 1.53 min MS m/z 450 [M + H]$^+$ | using 3-phenylbenzylamine |
| 412 | N-[4-methoxy-3-(trifluoromethyl)benzyl]-4-[(1,3-thiazol-2-yl amino)sulfonyl]benzamide | | Rt = 1.42 min MS m/z 472 [M + H]$^+$ | using 4-methoxy-3-(trifluoromethyl)benzylamine |
| 413 | N-(24-dichlorobenzyl)-4-[(1,3-thiazol-2-yl amino)sulfonyl]benzamide | | Rt = 1.48 min MS m/z 442 [M + H]$^+$ | using 2,4-dichloro benzylamine |
| 414 | N-(4-chloro-2-methyl benzyl)-4-[(1,3-thiazol-2-ylamino)sulfonyl]benzamide | | Rt = 1.46 min MS m/z 422 [M + H]$^+$ | using 4-chloro-2-methylbenzylamine |

TABLE 21-continued

| Example | Name | R | Data | Preparation Information |
|---|---|---|---|---|
| 415 | N-(biphenyl-2-ylmethyl)-4-[(1,3-thiazol-2-yl amino)sulfonyl] benzamide | | Rt = 1.50 min MS m/z 450 [M + H]+ | using 2-phenyl benzylamine |
| 416 | N-(4-cyanobenzyl)-4-[(1,3-thiazol-2-ylamino)sulfonyl] benzamide | | Rt = 1.20 min MS m/z 399 [M + H]+ | using 4-aminomethyl-benzonitrile |

Example 417

6-[(1,3-Thiazol-2-ylamino)sulfonyl]-N-[4-(trifluoromethyl)benzyl]nicotinamide

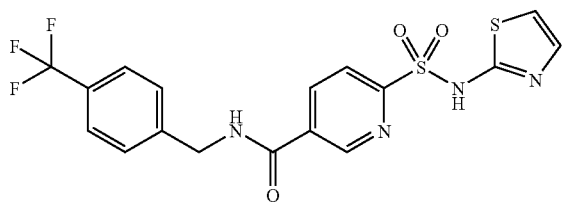 [SMILES: O=C(NCc1ccc(C(F)(F)F)cc1)c1ccc(S(=O)(=O)Nc2nccs2)nc1]

TFA (750 L, 9.7 mmol) was added to a solution of 6-{[(2,4-dimethoxybenzyl)(1,3-thiazol-2-yl)amino]sulfonyl}-N-[4-(trifluoromethyl)benzyl]nicotinamide (Preparation 88, 1.15 g, 1.94 mmol) in methylene chloride (12 mL, 180 mmol). After 30 min, the reaction mixture was diluted with ether. Triethylamine was added until basic to neutralize the residual TFA. Celite was added, and the mixture was concentrated in vacuo. The residue was purified on the Isco (120 g $SiO_2$ cartridge, chloroform to 12% MeOH in chloroform). The appropriate fractions were concentrated in vacuo. The residue was treated with acetonitrile, generating a white precipitate. The volume was reduced in vacuo, and the solids were collected via filtration, washing with acetonitrile. The off-white product was dried under vacuum (428 mg, 47%).

LCMS Rt=1.51 min. MS m/z 443 [M+H]+.

Example 418

N-(3,3-dimethylbutyl)-4-[(1,3-thiazol-2-ylamino) sulfonyl]benzamide

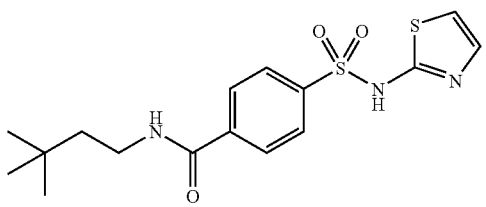 [SMILES: CC(C)(C)CCNC(=O)c1ccc(S(=O)(=O)Nc2nccs2)cc1]

A mixture of 4-iodo-N-1,3-thiazol-2-yl-benzenesulfonamide (Preparation 98, 0.2 g, 0.5 mmol), 3,3-dimethylbutylamine (0.25 g, 2.5 mmol), hexacarbonylmolybdenum (70 mg, 0.2 mmol), palladium (II) acetate (6 mg, 0.02 mmol), and sodium carbonate (200 mg, 2 mmol) in water (1.5 mL, 83 mmol) was heated 30 min at 110° C. in the microwave. The reaction mixture was diluted with 1 N HCl and extracted with ethyl acetate. The combined organic layers were washed with brine, dried over sodium sulfate, filtered and concentrated in vacuo. The residue was dissolved in methylene chloride/methanol and MP-Carbonate (2.73 mmol/g loading; 0.9 g, 2.500 mmol) was added. After stirring 1 h, LC/MS analysis indicated complete capture of the target compound. The resin was washed with methylene chloride then stirred in 8:1 methylene chloride/acetic acid. LC/MS analysis indicated the target compound was released from the resin (not quantified). The mixture was filtered. The filtrate was concentrated in vacuo, and the residue was lyophilized from water/acetonitrile. The resulting solid was triturated with methylene chloride and ether. The resulting solid was purified on the Gilson (Semi-prep: Phenomenex 100×21.2 mm 10 micron C18 column. 20 mL/min. Gradient 15% B to 100% B over 25 min. Solvent A: 7800 water/200 acetonitrile/8 TFA. Solvent B: 7200 acetonitrile/800 water/8 TFA) to afford the title compound (39 mg, 20%).

LCMS Rt=1.41 min. MS m/z 368 [M+H]+.

Example 419

Example 418 provides methods for testing the efficacy of the compounds of the invention.

419.a. Cell Line Construction and Maintenance

Human Embryonic Kidney (HEK) cells were transfected with an hSCN3A construct using lipofectamine reagent (Invitrogen), using standard techniques. Cells stably expressing the hSCN3A constructs were identified by their resistance to G-418 (400 µg/ml). Clones were screened for expression using the whole-cell voltage-clamp technique.

419.b. Cell Culture

HEK cells stably transfected with hSCN3A were maintained in DMEM medium supplemented with 10% heat-inactivated fetal bovine serum and 400 µg/ml G418 sulfate in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and replated at low density onto glass cover slips. Cells were typically used for electrophysiological experiments within 24 to 72 h after plating.

419.c. Electrophysiological Recording

Cover slips containing HEK cells expressing hSCN3A were placed in a bath on the stage of an inverted microscope and perfused (approximately 1 ml/min) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 to 7.4, and had a resistance of 1 to 2 mega ohms. The osmolarity of the extracellular and intracellular solutions was 300 mmol/kg and 295 mmol/kg, respectively. All recordings were made at room temperature (22-24° C.) using AXOPATCH 200B amplifiers and PCLAMP software (Axon Instruments, Burlingame, Calif.) or PatchXpress 7000 hardware and associated software (Axon Instruments, Burlingame, Calif.).

hSCN3A currents in HEK cells were measured using the whole-cell configuration of the patch-clamp technique (Hamill et al., 1981). Uncompensated series resistance was typically 2 to 5 mega ohms and >85% series resistance compensation (50% for PatchXpress) was routinely achieved. As a result, voltage errors were negligible and no correction was applied. Current records were acquired at 20 to 50 KHz and filtered at 5 to 10 KHz.

HEK cells stably transfected with hSCN3A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN3A sodium currents.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage midpoint of inactivation ($V_{1/2}$). Cells were then voltage clamped at the empirically determined $V_{1/2}$.

Compounds were tested for their ability to inhibit hSCN3A sodium channels by activating the channel with a 20 msec voltage step to 0 mV following an 8 second conditioning prepulse to the empirically determined $V_{1/2}$ (Table B). Compound effect (% inhibition) was determined by difference in current amplitude before and after application of test compounds. For ease of comparison, "estimated IC-50" (EIC-50) values were calculated from single point electrophysiology data by the following equation, (tested concentration, uM)×(100-% inhibition/% inhibition). Inhibition values <20% and >80% were excluded from the calculation.

In some cases electrophysiological assays were conducted with PatchXpress 7000 hardware and associated software (Molecular Devices Corp) (Table B). All assay buffers and solutions were identical to those used in conventional whole-cell voltage clamp experiments described above. hSCN3A cells were grown as above to 50%-80% confluency and harvested by trypsinization. Trypsinized cells were washed and resuspended in extracellular buffer at a concentration of $1\times10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined $V_{1/2}$ and current was activated by a 20 msec voltage step to 0 mV.

Electrophysiological assays were also conducted using the Ionworks Quattro automated electrophysiological platform (Molecular Devices Corp) (Table C). Intracellular and extracellular solutions were as described above with the following changes, 100 µg/ml amphotericin was added to the intracellular solution to perforate the membrane and allow electrical access to the cells. hSCN3A cells were grown and harvested as for PatchXpress and cells were resuspended in extracellular solution at a concentration of $3\text{-}4\times10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

419.d. High-Throughput Screening Assays

Confluent cells in multi-well plates were incubated with a permeant radioactive ion ($^{22}Na$, $^{14}C$-guanidinium, etc) for 4-16 hours to allow uptake of the radiotracer. Excess radioactive ions were removed by washing with prewarmed buffer of the following composition: 138 mM NaCl, 2 mM $CaCl_2$, 5.4 mM KCl, 1 mM $MgCl_2$, 10 mM glucose, and 10 mM HEPES, pH 7.4, with NaOH. Efflux was initiated by addition of buffer containing any necessary chemical activators (e.g., 100 µM veratridine, 10-20 µg/ml Lqh scorpion venom, etc.). Various concentrations of test compounds or reference sodium channel blockers were added concurrently with the initiation of efflux. Efflux was allowed to progress for a defined period of time, typically 30-90 minutes, at 37° C. in a humidified 10% $CO_2$ atmosphere. Stimulated efflux was determined by collecting the extracellular solution and transferring to a multiwell plate for scintillation counting. Residual intracellular radioactivity was also determined by scintillation counting following lysis of the cells in the assay plate. Inhibition of efflux was determined by comparing efflux in the presence of test compounds to efflux in untreated control cells.

Example 420

Biological data is provided below. Methods of obtaining this data are described herein (see Example 419).

TABLE B

| Example # | SCN3A EIC-50 (µM) |
|---|---|
| 1 | 0.07 |
| 2 | >1 |
| 4 | 2.53 |
| 5 | 15.08 |
| 6 | 1.11 |
| 7 | 5.87 |
| 9 | >10 |

TABLE B-continued

| Example # | SCN3A EIC-50 (μM) |
|---|---|
| 10 | 1.51 |
| 11 | 2.56 |
| 12 | 29.57 |
| 13 | 0.68 |
| 14 | 28.14 |
| 15 | 31.00 |
| 16 | >10 |
| 17 | 2.94 |
| 18 | 2.26 |
| 19 | 13.84 |
| 20 | 0.26 |
| 21 | 1.97 |
| 22 | 0.95 |
| 22 | 0.95 |
| 23 | 23.26 |
| 24 | >10 |
| 26 | >10 |
| 27 | 23.29 |
| 28 | 0.24 |
| 29 | 0.17 |
| 30 | 0.03 |
| 31 | 0.07 |
| 32 | 0.07 |
| 33 | 0.15 |
| 34 | 0.09 |
| 35 | 0.04 |
| 36 | 0.07 |
| 37 | 0.07 |
| 38 | 0.06 |
| 39 | 0.12 |
| 40 | 0.21 |
| 41 | 2.35 |
| 42 | 0.51 |
| 43 | 4.83 |
| 44 | 0.27 |
| 45 | 0.07 |
| 46 | 1.55 |
| 47 | 0.92 |
| 48 | >1 |
| 49 | 1.15 |
| 50 | 2.85 |
| 51 | 6.58 |
| 52 | 2.91 |
| 53 | 2.86 |
| 54 | 0.12 |
| 55 | 1.41 |
| 59 | 1.69 |
| 60 | 1.50 |
| 61 | 0.16 |
| 62 | 1.02 |
| 63 | 1.09 |
| 64 | 0.45 |
| 65 | 3.84 |
| 69 | 0.77 |
| 70 | >0.3 |
| 72 | 0.66 |
| 73 | 0.18 |
| 74 | 0.54 |
| 75 | >0.3 |
| 78 | 1.63 |
| 80 | >.1 |
| 83 | 0.62 |
| 88 | >.1 |
| 90 | 1.66 |
| 91 | 1.22 |
| 92 | 0.58 |
| 93 | 0.46 |
| 94 | >.1 |
| 95 | >.1 |
| 96 | 0.91 |
| 97 | 0.64 |
| 100 | 0.43 |
| 101 | 0.57 |
| 116 | >0.1 |
| 117 | 12.67 |
| 118 | 0.76 |

TABLE B-continued

| Example # | SCN3A EIC-50 (μM) |
|---|---|
| 119 | 1.29 |
| 120 | 0.50 |
| 122 | 1.30 |
| 123 | 1.44 |
| 124 | 1.81 |
| 125 | 6.45 |
| 126 | 0.29 |
| 133 | 1.15 |
| 134 | 2.28 |
| 136 | 4.26 |
| 139 | 1.66 |
| 144 | 1.18 |
| 147 | 2.52 |
| 148 | 2.50 |
| 158 | 2.39 |
| 163 | 5.05 |
| 165 | 4.18 |
| 170 | 3.92 |
| 172 | 6.52 |
| 173 | 2.67 |
| 174 | 3.97 |
| 175 | 4.05 |
| 176 | 4.50 |
| 177 | 5.67 |
| 180 | >1 |
| 186 | 0.42 |
| 191 | 2.25 |
| 193 | 3.27 |
| 195 | 0.28 |
| 196 | >1 |
| 198 | 3.03 |
| 200 | 3.60 |
| 217 | 2.91 |
| 218 | 21.17 |
| 220 | >1 |
| 222 | 0.98 |
| 232 | 3.42 |
| 236 | 3.11 |
| 239 | 2.97 |
| 245 | 2.22 |
| 247 | >1 |
| 249 | 1.66 |
| 252 | 2.11 |
| 254 | >1 |
| 257 | >1 |
| 262 | 6.85 |
| 263 | 1.13 |
| 266 | 1.67 |
| 277 | 2.19 |
| 279 | 2.20 |
| 284 | 1.22 |
| 286 | 0.14 |
| 287 | 0.22 |
| 289 | 0.34 |
| 290 | 1.39 |
| 291 | 0.71 |
| 292 | 0.90 |
| 293 | 2.32 |
| 294 | 1.84 |
| 295 | 0.22 |
| 296 | 0.19 |
| 297 | 0.06 |
| 298 | 0.16 |
| 299 | 0.11 |
| 300 | 0.13 |
| 301 | 0.18 |
| 302 | 0.35 |
| 303 | 0.14 |
| 304 | 0.07 |
| 305 | 0.06 |
| 306 | 0.04 |
| 307 | 23.70 |
| 308 | 0.32 |
| 309 | 0.10 |
| 310 | 0.05 |
| 311 | 0.06 |

TABLE B-continued

| Example # | SCN3A EIC-50 (μM) |
|---|---|
| 312 | 0.14 |
| 313 | 0.16 |
| 314 | 0.07 |
| 315 | 0.11 |
| 316 | 0.14 |
| 317 | 0.04 |
| 318 | 0.14 |
| 319 | 0.07 |
| 320 | 2.66 |
| 321 | 0.04 |
| 322 | 0.34 |
| 323 | 0.19 |
| 324 | 0.03 |
| 325 | 0.46 |
| 326 | 0.10 |
| 327 | 0.26 |
| 328 | 0.12 |
| 329 | 0.36 |
| 330 | 0.13 |
| 331 | 0.90 |
| 332 | 0.38 |
| 333 | 0.21 |
| 334 | 0.34 |
| 335 | 0.20 |
| 336 | 0.24 |
| 337 | 0.39 |
| 338 | 1.07 |
| 339 | 0.59 |
| 340 | 0.28 |
| 341 | 0.19 |
| 342 | 0.51 |
| 343 | 0.31 |
| 344 | 0.52 |
| 345 | 0.27 |
| 346 | 0.07 |
| 347 | 1.62 |
| 348 | 1.58 |
| 349 | 9.87 |
| 350 | >10 |
| 351 | 0.10 |
| 352 | 0.20 |
| 353 | 0.22 |
| 354 | 0.21 |
| 355 | 0.15 |
| 356 | 0.21 |
| 357 | 0.19 |
| 358 | 0.37 |
| 359 | 0.17 |
| 360 | 0.16 |
| 361 | 0.31 |
| 362 | 1.09 |
| 363 | 1.20 |
| 364 | 2.18 |
| 365 | 0.60 |
| 366 | 0.73 |
| 367 | 1.51 |
| 368 | 0.40 |
| 369 | 6.17 |
| 370 | 1.22 |
| 371 | 1.30 |
| 372 | 2.26 |
| 373 | 0.49 |
| 374 | 0.23 |
| 375 | 0.45 |
| 376 | 0.59 |
| 377 | 0.85 |
| 378 | 0.18 |
| 379 | 0.02 |
| 380 | 0.17 |
| 381 | 0.12 |
| 382 | 0.14 |
| 383 | 0.30 |
| 384 | 0.35 |
| 385 | 0.78 |
| 386 | 3.41 |
| 387 | 0.17 |
| 388 | 0.11 |
| 389 | 0.61 |
| 390 | 9.95 |
| 391 | 1.35 |
| 392 | 0.23 |
| 393 | 0.10 |
| 394 | 0.09 |
| 395 | 0.03 |
| 396 | 0.03 |
| 397 | 0.22 |
| 398 | 0.26 |
| 399 | 0.03 |
| 400 | 0.07 |
| 401 | 0.17 |
| 402 | 0.19 |
| 403 | 0.10 |
| 404 | 0.14 |
| 405 | 0.06 |
| 406 | 0.26 |
| 407 | 1.78 |
| 408 | 1.09 |
| 409 | 0.04 |
| 410 | 0.10 |
| 411 | 0.12 |
| 412 | 0.27 |
| 413 | 0.18 |
| 414 | 0.24 |
| 415 | 0.38 |
| 416 | 0.86 |
| 417 | 0.21 |
| 418 | 2.74 |

TABLE C

| Example # | SCN3A % INHIB HTS IWQ 3 μM | SCN3A % INHIB HTS IWQ 10 μM | SCN3A IWQ IC-50 (μM) | SCN3A INHIB INACT DRC EP IWQ EMAX |
|---|---|---|---|---|
| 56 | 3.23 | 2.53 | | |
| 57 | 25.17 | 47.78 | | |
| 58 | 37.42 | 49.73 | | |
| 66 | 16.42 | 34.37 | | |
| 71 | 38.75 | 37.14 | | |
| 76 | 35.84 | 52.15 | | |
| 77 | 16.56 | 27.87 | | |
| 79 | 17.66 | −1.9 | | |
| 81 | 34.72 | 65.74 | | |
| 82 | 29.66 | 62.97 | | |
| 84 | 17.67 | 22.25 | | |
| 86 | 22.34 | 26.3 | | |
| 87 | 36.92 | 46.17 | | |
| 89 | 14.01 | 48.24 | | |
| 98 | 28.09 | 36.59 | | |
| 102 | 22.44 | 37.18 | | |
| 103 | 21.16 | 46.77 | | |
| 121 | 31.06 | 30.22 | | |
| 127 | 28.94 | 28.72 | | |
| 128 | 11.66 | −1.66 | | |
| 129 | 13.58 | 24.24 | | |
| 130 | 23.07 | 16.52 | | |
| 131 | 27.24 | 13.06 | | |
| 132 | 19.73 | 15.26 | | |
| 135 | 27.43 | 30.11 | | |
| 137 | 21.75 | 36.18 | | |
| 138 | 16.19 | 11.2 | | |
| 140 | 2.34 | 18.85 | | |
| 141 | 6.82 | 25.02 | | |
| 142 | 30.39 | 31.53 | | |
| 143 | 16.04 | 31.96 | | |
| 145 | 2.05 | 19.45 | | |

TABLE C-continued

| Example # | SCN3A % INHIB HTS IWQ 3 μM | SCN3A % INHIB HTS IWQ 10 μM | SCN3A IWQ IC-50 (μM) | SCN3A INHIB INACT DRC EP IWQ EMAX |
|---|---|---|---|---|
| 146 | 24.29 | 27.85 | | |
| 149 | 12.51 | 14.6 | | |
| 150 | −7.12 | 22.57 | | |
| 151 | 17.37 | 12.69 | | |
| 152 | 42.18 | 56.34 | | |
| 153 | 15.95 | 32.94 | | |
| 154 | 28 | 30.77 | | |
| 155 | 30.14 | 40.79 | | |
| 156 | 13.33 | 30.29 | | |
| 157 | 11.27 | 15.27 | | |
| 159 | 28.7 | 35.85 | | |
| 160 | 15.59 | 14.77 | | |
| 161 | 30.32 | 32.4 | | |
| 162 | 28.03 | 13.73 | | |
| 164 | 16.63 | 24.11 | | |
| 166 | 30.57 | 36.32 | | |
| 167 | 30.82 | 43 | | |
| 168 | 31.44 | 39.27 | | |
| 169 | 35.29 | 27.27 | | |
| 171 | 39.48 | 52.77 | | |
| 178 | 2.71 | 1.55 | | |
| 179 | 9.95 | 15.94 | | |
| 181 | −12.23 | 11.2 | | |
| 182 | 4.7 | 4.83 | | |
| 183 | 8.9 | 1.34 | | |
| 184 | 28.97 | 20.83 | | |
| 185 | 20.88 | 20.78 | | |
| 187 | 5.69 | 4.2 | | |
| 188 | 14.54 | 1.03 | | |
| 189 | 25.3 | 20.96 | | |
| 190 | 2.77 | −8.21 | | |
| 192 | 6.18 | 25.96 | | |
| 197 | 17.65 | 17.38 | | |
| 199 | 10.2 | 7.42 | | |
| 201 | 13.71 | −0.98 | | |
| 202 | 15.8 | 13.66 | | |
| 203 | 13.06 | 17.7 | | |
| 204 | 18.14 | 16.25 | | |
| 205 | 11.29 | 27.3 | | |
| 206 | 4.17 | 16.67 | | |
| 207 | 27.25 | −16.86 | | |
| 208 | 3.57 | −14.16 | | |
| 209 | 5.72 | −5.23 | | |
| 210 | 4.03 | 11.89 | | |
| 211 | 2.5 | 10.05 | | |
| 212 | 14.66 | −8.45 | | |
| 213 | −0.67 | 1.51 | | |
| 214 | 9.25 | 4.51 | | |
| 215 | 30.54 | 51.86 | 8.408183 | 64.7 |
| 216 | 10.77 | 6.67 | | |
| 219 | 13.07 | 1.08 | | |
| 221 | 19.94 | 21.79 | | |
| 223 | 36.88 | 47.53 | 33.04956 | 46.3 |
| 224 | 3.47 | 9.34 | | |
| 225 | 6.08 | −8.14 | | |
| 226 | −1.52 | 13.91 | | |
| 227 | 29.33 | 45.75 | 20.33274 | 53 |
| 228 | 19.31 | 3.53 | | |
| 229 | 12.5 | 3.91 | | |
| 230 | 16.68 | −0.51 | | |
| 231 | 3.22 | −7.02 | | |
| 233 | 18.54 | 15.95 | | |
| 234 | 32.02 | 45.88 | | 43.1 |
| 235 | 21.45 | −2.43 | | |
| 237 | 24.72 | 17.57 | | |
| 238 | 3.68 | 9.77 | | |
| 240 | 14.4 | 20.24 | | |
| 241 | 21.73 | 11.61 | | |
| 242 | 13.78 | 8.48 | | |
| 243 | 15.29 | 14.69 | | |
| 244 | 14.16 | 21.95 | | |
| 246 | −0.31 | −1.47 | | |
| 248 | 20.14 | 14.71 | | |
| 250 | −4.32 | 0.12 | | |
| 251 | 19.94 | 0.8 | | |
| 253 | 5.99 | 31.33 | | |
| 255 | 4.16 | 6.56 | | |
| 256 | 1.49 | 6.44 | | |
| 258 | 0.17 | 12.01 | | |
| 259 | 5.51 | 19.64 | | |
| 260 | −3.05 | 10.52 | | |
| 261 | 6.02 | 10.39 | | |
| 264 | 16.9 | 14.81 | | |
| 265 | 22.64 | 44.32 | | 32.2 |
| 267 | 30.12 | 23.14 | | |
| 268 | 11.01 | 10.58 | | |
| 269 | 0.37 | 16.48 | | |
| 270 | 19.16 | 45.72 | 27.70677 | 53.7 |
| 271 | 35.83 | 41.35 | 26.35945 | 52.4 |
| 272 | 1.88 | 8.31 | | |
| 273 | 4.82 | 2.72 | | |
| 274 | 14.56 | 19.55 | | |
| 275 | 9.93 | −0.2 | | |
| 276 | 18.1 | 20.57 | | |
| 278 | 25.44 | 29.99 | | |
| 280 | 13.2 | 16.96 | | |
| 281 | 10.25 | 28.9 | | |
| 282 | 29.13 | 11.41 | | |
| 283 | −1.98 | 0.98 | | |
| 285 | 15.13 | 39.15 | | |
| 288 | 4.38 | 13.42 | | |

Example 421

WO2005/013914 discusses compounds which are stated to be inhibitors of voltage gated sodium channels. Compounds exemplified in WO2005/013914 possess the following aniline type moiety:

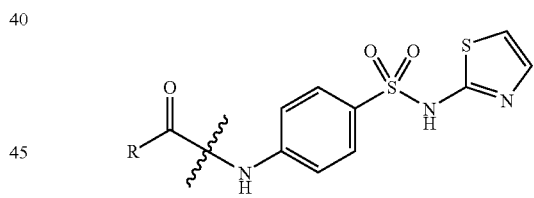

Such compounds are metabolized in vivo by cleavage of the amide bond, thus producing an aniline containing analogue of sulfathiazole. Sulfathiazole is an agent previously prescribed to treat infections been withdrawn from market except in topical form. Furthermore, analogues of sulfathiazole have been reported to cause allergic or toxic reactions (Cribb et al. Drug Metabolism and Disposition, 19, 900-906).

In vivo cleavage of the amides in compounds I, II and III depicted below (compounds 186, 441 and a related compound from WO2005/013914) were tested in rats and were found to be rapidly cleaved in vivo to form the sulfathiazole metabolite within 15 minutes of dosing. Bioanalysis of plasma from rats dosed orally at 10 mg/kg of body weight with compounds I, II and III demonstrated that formation of sulfathiazole could be detected within 15 minutes of dosing and reached levels of 1-69% (0.032-0.84 μM) of parent in that time.

In contrast, the corresponding Example 100, Example 186, and Example 418 of the present invention do not metabolize to form the aniline containing sulfathiazole.

Bioanalysis:

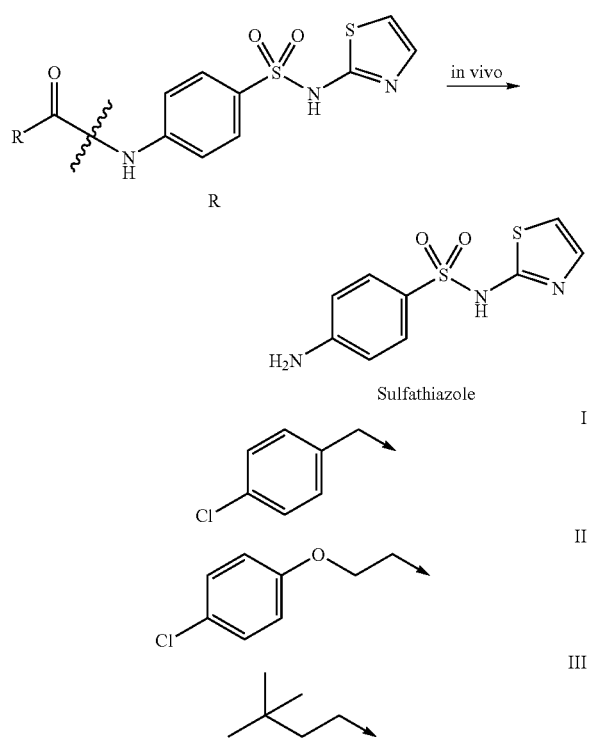

The bioanalysis of plasma samples from rats dosed with LC/MS/MS detection of sulfathiazole as measured against an internal standard. Extraction was performed on-line with a turbulent flow chromatography system (HTLC). The transfer from the HTLC to the analytical HPLC is automatic. The mass spectrometer was operated in API ionization mode with an electrospray interface between the analytical HPLC and the mass spectrometer. Multiple reaction monitoring (mrm) detection was used for each analyte on a triple quadrupole mass spectrometer.

A. Bioanalytical Instrumentation and Materials
  1. Equipment

| | |
|---|---|
| Micromass Quattro Micromass Quattro Ultima mass spectrometer | Serial # VB151 |
| CTC Analytics Leap Technologies HTS-PAL autosampler | Serial # 110566 |
| Cohesive Technologies TurboFlow 2300 HTLC System | Serial # FO286 23144 |
| Agilent 1100 Binary pump | Serial # DE91604604 |
| Agilent 1100 Quaternary pump | Serial # DE91607755 |
| IEC Centra - CL3R Centrifuge | Serial # 37550836 |
| Mettler AT261 Analytical Balance | Serial # 1119231691 |

2. Materials
    HPLC grade reagents were used such as:
      Water (Hydro Services Picosystem water filtration)
      Methanol (Fisher Ultima)
      Ammonium formate (Sigma), and
      Formic acid (Sigma)
    Rat plasma
    sulfathiazole
    internal standard B. Instrument Conditions
  Mass spectrometer:
    Positive ion, mrm detection at
      m/z 256 to m/z 108 for ICA-000024
      m/z 342 to m/z 218 for ICA-18756 (internal standard)
      100 ms Dwell time
    Cone voltage, capillary voltage and collision energy were optimized for each compound
    Source Temperature: 125 C, Desolvation temperature: 325 C
    Cone gas at 73 L/hr, and Desolvation gas at 740 L/hr C. Chromatography Conditions
  1. Mobile Phases:
    A: 98% water:2% methanol with
      4 mM ammonium formate, 0.1% formic acid
    B: 98% methanol:2% water with
      4 mM ammonium formate, 0.1% formic acid
  2. HTLC Turbulent Flow Quaternary Pump
    Column: Cohesive Cyclone Turbo-Flow
    Timetable:

| | Turbulent Flow Step Changes | | | |
|---|---|---|---|---|
| Step | Time (min) | % A | Flow (mL/min) | Valve Status |
| 1 | 0 | 99 | 4 | All open |
| 2 | 0.5 | 99 | 0.60** | A & B closed |
| 3 | 1.5 | 1 | 4 | B open |
| 4 | 2.9 | 1 | 4 | A open |
| 5 | 3.0 | 98 | 4 | |
| 6 | 3.3 | 98 | 4 | |

**transfer period

3. Analytical Binary Pump
    Column: Phenomenex Synergi Hydro-RP 4u 50 mm×2.1 mm
    Timetable:

| | ANALYTICAL PUMP GRADIENT | | | |
|---|---|---|---|---|
| Step | Time (min) | % A | Flow (mL/min) | Type of Change |
| 1 | 0 | 98 | 0.7 | |
| 2 | 0.5 | 98 | 0.7 | Begin gradient % A |
| 3 | 1.75 | 50 | 0.7 | Modulate gradient |
| 4 | 2.3 | 2 | 0.7 | End gradient % A |
| 5 | 3.25 | 2 | 0.7 | |
| 6 | 3.30 | 98 | 0.7 | |

4. Injection Volume

20 μL

D. Preparation of Standards and Samples

Plasma standards and samples were prepared for injection according to the standard operating procedure, HTLC Plasma Analysis by LC/MS/MS.

Preparations

Preparation 1a 4-([[4-(Trifluoromethyl)benzyl]amino]carbonyl) benzenesulfonyl chloride

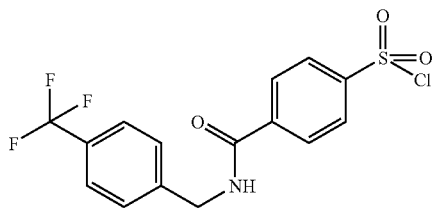 [SMILES: O=C(NCc1ccc(C(F)(F)F)cc1)c1ccc(S(=O)(=O)Cl)cc1]

4-Sulphobenzoic acid monopotassium salt (25 g, 104 mmol, 1 eq) was added to thionyl chloride (72 ml, 1000 mmol, 9.6 eq), dimethylformamide (1.8 ml, 23.2 mmol, 0.2 eq) was added dropwise and the resulting reaction mixture heated at reflux (77° C.) for 18 hours. The solvent was evaporated in vacuo, azeotroping with toluene (2×125 ml) to yield a yellow solid. The material was slurried in DCM (100 ml) and cooled in an ice bath. A solution of 4-(trifluoromethyl-benzylamine (13.5 ml, 94.7 mmol, 0.9 eq) and Et$_3$N (17 ml, 122 mmol, 1.17 eq) in DCM (40 ml) was added dropwise over 1.5 hours and the resulting reaction mixture stirred at 100° C. for 1 hour. After this time the reaction mixture was washed with water (2×100 ml), dried over sodium sulphate, filtered and the solvent evaporated in vacuo. The resulting beige solid was suspended with warm t-butylmethyl ether, cooled in the fridge, filtered and evaporated to yield the title compound as an off white solid (24.4 g, 64.7 mmol 62%).

$^1$HNMR (d$_6$-DMSO): 4.5 (s, 2H), 7.5 (m, 2H), 7.6 (m, 4H), 7.8 (m, 2H), 9.15 (t, 1H). LCMS Rt=1.63 min. MS m/z 378 [MH]+.

Preparation 1b

4-Amino-N-(4-trifluoromethyl-benzyl)-benzamide (1.0 g, 3.4 mmol) was dissolved in acetonitrile (30 mL, 500 mmol) at ambient temperature. The solution was cooled to −5° C. in an acetone bath. Concentrated HCl (3 mL, 90 mmol) was added slowly. A solution of sodium nitrite (0.26 g, 3.7 mmol) in water (1 mL, 70 mmol) was added slowly. The reaction mixture turned orange over the course of the addition. After addition was complete, the reaction mixture was stirred at ~0° C. for 35 min. A 0° C. solution of sulfur dioxide in AcOH (8:25, sulfur dioxide:AcOH, 30 mL) was added followed by copper(II) chloride dihydrate (0.58 g, 3.4 mmol). No gas evolution was evident. The mixture warmed to ambient temperature and stirred for 2 hours. The reaction mixture was poured onto ice, and the resulting solid was collected by filtration. The solid was washed with hexanes to afford the product as an off-white solid (1.00 g, 70%).

Preparation 2

Methyl 4-(chlorosulfonyl)benzoate

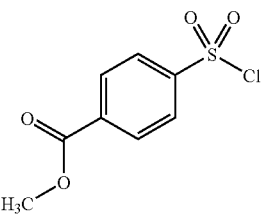

4-Chlorosulphonylbenzoic acid (15 g, 68 mmol, 1 eq) was suspended in thionyl chloride (60 ml) and DCM (60 ml) and the reaction mixture heated at reflux for 2 hours. The solvent was evaporated in vacuo and ice cold MeOH (120 ml) was added to the residue. The reaction was stirred for 10 minutes in an ice bath before the addition of ice cold water (100 ml). The resulting precipitate was collected by filtration to yield the title compound as a white solid (15.3 g, 0.065 mmol, 96%).

$^1$HNMR (CDCl$_3$): 4.0 (s, 3H), 8.1 (d, 2H), 8.3 (d, 2H).

Preparation 3

Methyl 4-{[(5-chloro-1,3-thiazol-2-yl)amino] sulfonyl}benzoate

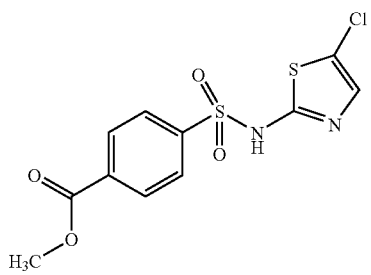 [SMILES: COC(=O)c1ccc(S(=O)(=O)Nc2ncc(Cl)s2)cc1]

Methyl 4-(chlorosulfonyl)benzoate (Preparation 2, 8.0 g, 34 mmol, 1 eq) was added portionwise to a solution of 2-amino-5-chlorothiazole hydrochloride (23.3 g, 136 mmol, 4 eq) in pyridine (80 ml) and the reaction mixture stirred at room temperature for 1 hour. The solution was added to a stirred solution of 6M HCl (300 ml) and the resulting precipitate collected by filtration and washed with water. The title compound was obtained as a dark brown solid (3.35 g, 0.01 mmol, 30%).

$^1$HNMR (d$_6$-DMSO): 3.9 (s, 3H), 7.6 (s, 1H), 7.9 (d, 2H), 8.1 (d, 2H). LCMS Rt=1.36 min (ELSD). MS m/z 334 [MH]+.

Preparation 4

4-{[(5-Chloro-1,3-thiazol-2-yl)amino]sulfonyl}benzoic acid

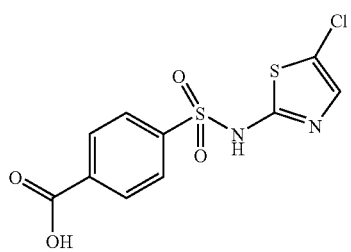 [SMILES: O=C(O)c1ccc(S(=O)(=O)Nc2ncc(Cl)s2)cc1]

To a solution of methyl 4-{[(5-chloro-1,3-thiazol-2-yl)amino]sulfonyl}benzoate (Preparation 3, 3.2 g, 9.6 mmol, 1 eq) in dioxane (20 ml) was added a 2M solution of lithium hydroxide (20 ml) and the reaction mixture stirred at room temperature for 2 hours. The reaction mixture was diluted with water, washed with ethyl acetate and then acidified with concentrated HCl. The resulting precipitate was collected by filtration to yield the title compound as a light brown solid (3.0 g, 9.0 mmol, 98%).

$^1$HNMR (d$_6$-DMSO): 7.6 (s, 1H), 7.9 (d, 2H), 8.1 (d, 2H).

Preparation 5

Methyl 3-chloro-4-(chlorosulfonyl)benzoate

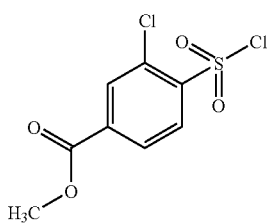

To a suspension of methyl 4-amino-3-chlorobenzoate (33 g, 146 mmol, 1 eq) in a 1:1 mixture of concentrated HCl and water (140 ml) cooling in an ice/MeOH bath was added a solution of sodium nitrite (11.1 g, 160 mmol, 1.1 eq) in warm water (20 ml) dropwise, ensuring that the reaction temperature was maintained below 5° C. The mixture was filtered through a pad of Celite and the solids washed with water. The resulting filtrate was added portionwise to a mixture of sulphur dioxide (47 g, 729 mmol, 5 eq) and copper (I) chloride (catalytic) in AcOH, maintaining the reaction temperature below 10° C. The reaction mixture was extracted into DCM (600 ml), washed with water (600 ml), dried over sodium sulphate, filtered and the solvent evaporated in vacuo. The residue was redissolved in DCM, washed with saturated sodium hydrogen carbonate, dried over sodium sulphate, filtered and evaporated in vacuo. The crude material was purified by column chromatography eluting with 0-15% ethyl acetate:hexane then triturated with hexane to yield the title compound (19.6 g, 73.6 mmol, 50%).

$^1$HNMR (CDCl$_3$): 4.0 (s, 3H), 8.1 (d, 1H), 8.2 (d, 1H), 8.25 (s, 1H).

Preparation 6a

N-(2,4-dimethoxybenzyl)-1,3-thiazol-2-amine

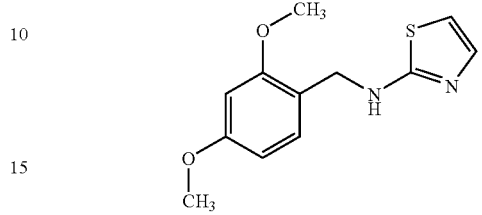

2,4 Dimethoxybenzaldehyde (25 g, 150 mmol, 1 eq), 2 aminothiazole (15.1 g, 150 mmol, 1 eq) and piperidine (150 mg, 1.76 mmol, 0.012 eq) were combined in dichloroethane (500 ml) and the reaction mixture heated to reflux over sieves for 18 hours. The sieves were removed by filtration and the reaction mixture diluted with MeOH (300 ml). Sodium borohydride (25 g, 662 mmol, 4.4 eq) was added portionwise and the reaction mixture heated to reflux for 2 hours. The mixture was cooled, quenched with water and the organic solvent evaporated in vacuo. The reaction mixture was extracted into ethyl acetate and the combined organic solutions extracted with 2M HCl. The acidic solution was basified with potassium carbonate, re-extracted into ethyl acetate, dried over sodium sulphate, filtered and evaporated in vacuo. The crude material was purified by column chromatography eluting with 9:1 DCM:MeOH to yield the title compound (24 g, 96 mmol, 64%).

$^1$HNMR (d$_6$-DMSO): 3.7 (s, 3H), 3.8 (s, 3H), 4.3 (d, 2H), 6.45 (m, 1H), 6.55 (m, 2H), 7.0 (s, 1H), 7.2 (d, 2H), 7.7 (t, 1H).

Preparation 6b

N-(2,4-dimethoxybenzyl)-1,3-thiazol-2-amine

Also prepared according to Gutierrez et al. Tetrahedron Letters, 46(20), 3595-3597 (2005).

Preparation 7

Methyl 3-chloro-4-{[(2,4-dimethoxybenzyl)(1,3-thiazol-2-yl)amino]sulfonyl}benzoate and 3-Chloro-4-{[(2,4-dimethoxybenzyl)(1,3-thiazol-2-yl)amino]sulfonyl}benzoic acid

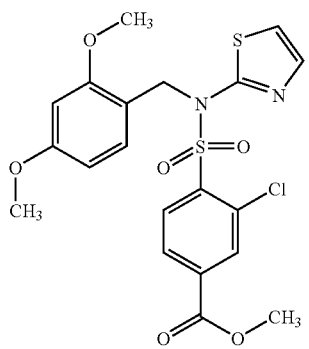

251

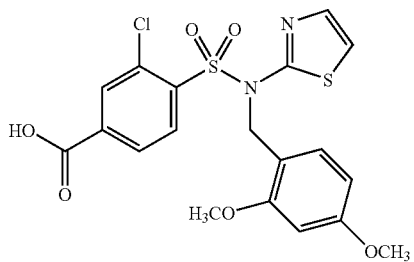

To an ice cooled solution of N-(2,4-dimethoxybenzyl)-1,3-thiazol-2-amine (Preparation 6, 8.4 g, 33.4 mmol, 1 eq) in THF (80 ml) was added 60% sodium hydride (2.0 g, 50.2 mmol, 1.5 eq) portionwise. The mixture was stirred for 15 minutes before the addition of methyl 3-chloro-4-(chlorosulfonyl)benzoate (Preparation 5, 9 g, 33.4 mmol, 1 eq) then stirred for a further 30 minutes. The reaction mixture was added to water (20 ml) and the THF evaporated in vacuo. The residue was diluted with water (200 ml), extracted with ethyl acetate (2×200 ml) and DCM (100 ml). The combined organics were dried over sodium sulphate, filtered and evaporated in vacuo to yield the title compound.

$^1$HNMR (CDCl$_3$): 3.7 (s, 9H), 5.3 (s, 2H), 6.3 (s, 2H), 6.9 (s, 1H), 7.3 (d, 2H), 7.9 (s, 1H), 8.1 (s, 1H), 8.2 (s, 1H). LCMS Rt=2.70 min. MS m/z 482 [MH]+.

A precipitate formed in the aqueous phase during work up. This was collected by filtration and found to be 3-Chloro-4-{[(2,4-dimethoxybenzyl)(1,3-thiazol-2-yl)amino]sulfonyl}benzoic acid.

$^1$HNMR (d$_4$-MeOD): 3.7 (s, H), 5.2 (s, 2H), 6.3 (m, 2H), 7.1 (d, 1H), 7.15 (s, 1H), 7.35 (s, 1H), 7.9 (d, 1H), 8.0 (s, 1H), 8.05 (d, 1H).

Preparation 8

4-(Benzylthio)-3-fluorobenzoic acid

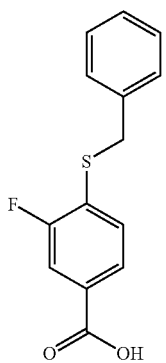 [SMILES: O=C(O)c1ccc(SCc2ccccc2)c(F)c1]

3,4-Difluorobenzoic acid (964 mg, 6.1 mmol, 1 eq), cesium carbonate (3.97 g, 12.1 mmol, 2 eq) and benzyl mercaptan (763 mg, 6.14 mmol, 1 eq) were combined in dimethyl sulphoxide (5 ml) and the reaction mixture heated at 75° C. for 4 hours. The reaction mixture was poured into ethyl acetate (10 ml) then extracted into water (10 ml). The aqueous phase was acidified with 2M HCl, extracted into ethyl acetate (10 ml), dried over sodium sulphate, filtered and evaporated to yield the title compound as a white solid (1.53 g, 5.83 mmol, 95%).

252

$^1$HNMR (CDCl$_3$): 4.2 (s, 2H), 7.3 (m, 6H), 7.75 (m, 2H). LCMS Rt=1.55 min. MS m/z 261 [M−H].

Preparation 9

4-(Chlorosulfonyl)-3-fluorobenzoic acid

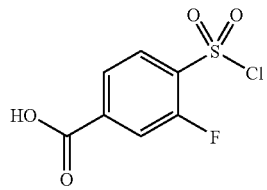 [SMILES: O=C(O)c1ccc(S(=O)(=O)Cl)c(F)c1]

To a solution of 4-(benzylthio)-3-fluorobenzoic acid (Preparation 8, 1.53 g, 5.8 mmol, 1 eq) in DCM (50 ml) and 4N HCl (50 ml) at 0° C. was added sodium hypochlorite (24 ml, 47 mmol, 8 eq) dropwise and the reaction mixture stirred at room temperature for 30 minutes. The layers were separated, extracted with DCM (20 ml), dried over sodium sulphate, filtered and evaporated in vacuo. The residue was triturated with DCM to yield the title compound as a white solid (725 mg, 3.05 mmol, 52%).

$^1$HNMR (CDCl$_3$): 8.1 (m, 3H). LCMS Rt=1.47 min. MS m/z 237 [M−H].

Preparation 10a

4-{[(2,4-Dimethoxybenzyl)(1,3-thiazol-2-yl)amino]sulfonyl}-3-fluorobenzoic acid

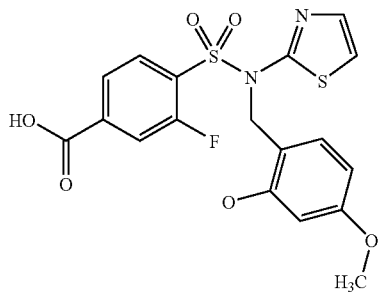 [SMILES: COc1ccc(CN(c2nccs2)S(=O)(=O)c2ccc(C(=O)O)cc2F)c(O)c1]

N-(2,4-dimethoxybenzyl)-1,3-thiazol-2-amine (Preparation 6, 2.34 g, 9.35 mmol, 0.95 eq) was suspended in THF (20 ml) and stirred at 0° C. for 10 minutes. 1,1,1,3,3,3-Hexanemethyldisilazane lithium salt (LiHMDS, 1M in THF, 19.5 ml, 20 mmol, 2.0 eq) was added dropwise maintaining the temperature below 30° C. and the reaction mixture stirred for a further 30 minutes. A solution of 4-(chlorosulfonyl)-3-fluorobenzoic acid (Preparation 9, 2.35 g, 9.85 mmol, 1 eq) in THF (15 ml) was added dropwise maintaining the reaction temperature below 30° C. and the reaction mixture stirred at room temperature for 2 hours. The reaction mixture was diluted with brine (10 ml), extracted into ethyl acetate (10 ml), dried over sodium sulphate, filtered and evaporated in vacuo. The crude material was slurried in t-butylmethyl ether and stirred at room temperature for 72 hours. The resulting solid was collected by filtration to yield the title compound as a beige solid (744 mg, 1.64 mmol, 17%)

LCMS Rt=1.58 min. MS m/z 452 [MH]+. .

Preparation 10b

4-[(2,4-Dimethoxy-benzyl)-thiazol-2-yl-sulfamoyl]-3-fluoro-benzoic acid ethyl ester (496 mg, 1.03 mmol) was taken up in THF (2.3 mL, 29 mmol) and water (1.2 mL, 64 mmol). Lithium hydroxide (25 mg, 1.0 mmol) was added, and the reaction mixture as stirred at rt. After 18 h, the reaction mixture was acidified with citric acid and extracted with ethyl acetate (4×). The combined organic layers were washed with brine, dried over sodium sulfate, filtered and concentrated in vacuo to afford the crude product which was used without further purification (308 mg, 63%).

MS m/z 451 [M–H]⁻

Preparation 11

4-Amino-2-fluorobenzoic acid

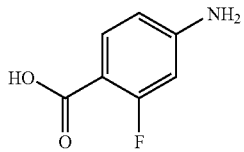 [SMILES: Nc1ccc(C(=O)O)c(F)c1]

A mixture of 4-amino-2-fluorobenzonitrile (25 g, 0.183 mmol) and potassium hydroxide (125 g, 2.23 mol) in water (350 ml) and industrial methylated spirit (50 ml) was heated at reflux for 48 hours. The solvent was evaporated in vacuo and the residue diluted with water and washed with DCM. The aqueous phase was acidified to pH 5.5 with concentrated HCl and the resultant precipitate collected by filtration to yield the title compound as a beige solid (23.94 g, 0.154 mol 84%).

¹HNMR (d₆-DMSO): 5.2 (bs, 2H), 6.05 (d, 1H), 6.1 (m, 1H), 7.4 (m, 1H). MS m/z 156.02 [MH]+.

Preparation 12

Methyl 4-amino-2-fluorobenzoate hydrochloride

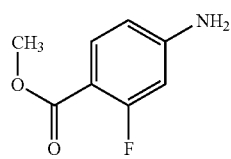

4-Amino-2-fluorobenzoic acid (Preparation 11, 23.9 g, 0.154 mol) was dissolved in MeOH (500 ml), HCl gas was bubbled through the solution until the boiling point of the solution was reached. The reaction mixture was heated at reflux for 72 hours. The solvent was evaporated to yield the title compound as a beige solid (33.2 g, 0162 mol, 105%).

¹HNMR (d₆-DMSO): 3.7 (s, 3H), 6.2 (d, 1H), 6.3 (d, 1H), 7.5 (t, 1H). LCMS Rt=1.63 min. MS m/z 169.99 [MH]+.

Preparation 13

Methyl 4-(chlorosulfonyl)-2-fluorobenzoate

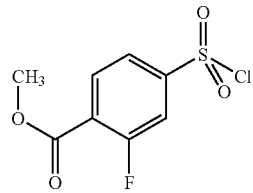

To a suspension of methyl 4-amino-2-fluorobenzoate hydrochloride (Preparation 12, 33.2 g, 0.154 mmol, 1 eq) in a 1:1 mixture of concentrated HCl and water (70 ml:70 ml) cooling in an ice bath was added a solution of sodium nitrite (11.71 g, 0.169 mol, 1.1 eq) in warm water (20 ml) dropwise maintaining the temperature below 50° C. The reaction mixture was allowed to stir for 10 minutes then filtered through a pad of Celite and the solid washed with water. The filtrate was added portionwise to a solution of sulphur dioxide (49.4 g, 0.771 mol, 5 eq) and copper (1) chloride (100 mg) in AcOH (120 ml) at 0° C. and the reaction mixture stirred for 30 minutes. The mixture was extracted with DCM (3×150 ml), washed with saturated sodium hydrogen carbonate, water and brine, dried over magnesium sulphate, filtered and evaporated in vacuo. The crude material was purified by column chromatography eluting with 10% ethyl acetate:hexane to yield the title compound as a red oil (19.68 g, 0.078 mol, 50%).

¹HNMR (CDCl₃): 4.0 (s, 3H), 7.8 (m, 2H), 8.19 (m, 1H). MS m/z 251 [M–H]–.

Preparation 14

Methyl 4-{[(2,4-dimethoxybenzyl)(1,3-thiazol-2-yl)amino]sulfonyl}-2-fluorobenzoate

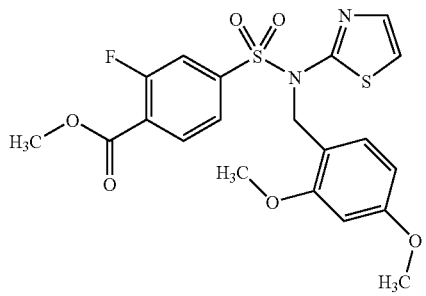 [SMILES: COC(=O)c1ccc(S(=O)(=O)N(Cc2ccc(OC)cc2OC)c2nccs2)cc1F]

To an ice cooled solution of N-(2,4-dimethoxybenzyl)-1,3-thiazol-2-amine (Preparation 6, 9.0 g, 35.9 mmol, 1 eq) in THF (80 ml) was added 60% sodium hydride (2.15 g, 53.9 mmol, 1.5 eq) portionwise. The mixture was stirred for 30 minutes before the addition of methyl 4-(chlorosulfonyl)-2-fluorobenzoate (Preparation 13, 9.06 g, 35.9 mmol, 1 eq) then stirred for a further hour at room temperature. The reaction mixture was added to water (20 ml) and the THF evaporated in vacuo. The residue was diluted with water (200 ml), extracted into DCM (3×200 ml), dried over sodium sulphate, Preparation 15

2-Fluoro-4-[(1,3-thiazol-2-ylamino)sulfonyl]benzoic acid

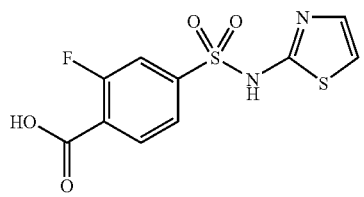 [SMILES: O=C(O)c1ccc(S(=O)(=O)Nc2nccs2)cc1F]

A mixture of methyl 4-{[(2,4-dimethoxybenzyl)(1,3-thiazol-2-yl)amino]sulfonyl}-2-fluorobenzoate (Preparation 14, 10 g, 21 mmol, 1 eq) and sodium hydroxide 4.3 g, 0.107 mol, 5 eq) in THF: MeOH: water (25 ml:2 ml:75 ml) was heated at 50° C. for 4 hours. The reaction mixture was acidified to pH 2.0 with 2M HCl and the resulting precipitate collected by filtration. The crude material was purified by column chromatography eluting with 90:10:1 DCM:MeOH: ammonia to yield the title compound as a yellow solid (706 mg, 2.33 mmol, 11%).
$^1$HNMR (d$_4$-MeOD): 6.7 (s, 1H), 7.1 (s, 1H), 7.6 (m, 1H), 7.7 (m, 1H), 8.0 (m, 1H). MS m/z 303 [MH]+.

Preparation 16

Methyl 5-(chlorosulfonyl)pyridine-2-carboxylate

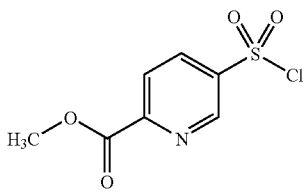

6-Methylpyridine-3-sulfonic acid (2.78 g, 16.1 mmol, 1 eq) and potassium hydroxide (2.3 g, 41 mmol, 2.55 eq) were dissolved in water (10 ml), potassium permanganate (16 g, 101 mmol, 6.31 eq) was added portionwise over 3 hours and the reaction mixture heated at 90° C. for 4 hours. The reaction mixture was allowed to cool to room temperature and the resulting precipitate collected by filtration. The material was dissolved in thionyl chloride (10 ml) and heated to reflux, dimethylformamide (1 ml) was added dropwise over 1 hour and the resulting reaction mixture heated at reflux for a further 2 hours. The thionyl chloride was evaporated in vacuo and the residue azeotroped with DCM (10 ml). The material was redissolved in DCM (30 ml), MeOH (15 ml) was added dropwise and the reaction mixture stirred at room temperature for 30 minutes. The solvent was evaporated and the residue extracted from saturated sodium hydrogen carbonate (10 ml) into ethyl acetate (10 ml), dried over sodium sulphate, filtered and evaporated to yield the title compound as a white solid (1 g, 4.27 mmol, 26%).
$^1$HNMR (CDCl$_3$): 4.05 (s, 3H), 8.4 (d, 1H), 8.45 (d, 1H), 9.35 (s, 1H). LCMS Rt=1.21 min. MS m/z 235 [MH]+.

Preparation 17

5-{[(2,4-Dimethoxybenzyl)(1,3-thiazol-2-yl)amino]sulfonyl}pyridine-2-carboxylic acid

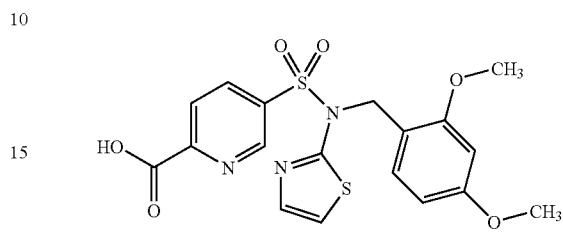

N-(2,4-dimethoxybenzyl)-1,3-thiazol-2-amine (Preparation 6, 961 mg, 3.84 mmol, 1.0 eq) was suspended in THF (10 ml) and stirred at −78° C. for 10 minutes. 1,1,1,3,3,3-Hexanemethyldisilazane lithium salt (LiHMDS, 1M in THF, 4.2 ml, 4.2 mmol, 1.1 eq) was added dropwise maintaining the temperature below −70° C. and the reaction mixture stirred for a further 30 minutes. A solution of methyl 5-(chlorosulfonyl)pyridine-2-carboxylate (Preparation 16, 1 g, 3.8 mmol, 1 eq) in THF (5 ml) was added dropwise maintaining the reaction temperature below −72° C. and the reaction mixture allowed to warm to room temperature for 2 hours. The reaction mixture was diluted with water (10 ml), extracted into ethyl acetate (5 ml), dried over sodium sulphate, filtered and evaporated in vacuo. The crude material was dissolved in dioxane (5 ml), a solution of sodium hydroxide (311 mg, 7.77 mmol, 2 eq) in water (2 ml) was added and the reaction mixture stirred at room temperature for 30 minutes. The MeOH was evaporated and the remaining aqueous solution washed with ethyl acetate (10 ml). Brine (10 ml) was added to the aqueous phase and the solution extracted with ethyl acetate (10 ml). A precipitate formed in the organic phase which was collected by filtration to yield the title compound as a white solid (415 mg, 0.95 mmol, 25%).
$^1$HNMR (d$_6$-DMSO): 3.65 (s, 3H), 3.7 (s, 3H), 4.95 (s, 2H), 6.4 (m, 1H), 6.5 (s, 1H), 7.0 (s, 1H), 7.45 (s, 2H), 8.0 (m, 1H), 8.1 (m, 1H), 8.8 (s, 1H). LCMS Rt=1.40 min. MS m/z 435 [M−H]−.

Preparation 18

5-{[(5-Chloro-1,3-thiazol-2-yl)amino]sulfonyl}pyridine-2-carboxylic acid

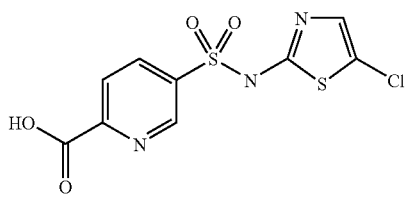 [SMILES: O=C(O)c1ccc(S(=O)(=O)Nc2ncc(Cl)s2)cn1]

2-Amino-5-chlorothiazole hydrochloride (2.63 g, 15.4 mmol, 3.96 eq) was dissolved in pyridine (10 ml) and stirred at room temperature for 10 minutes before the addition of methyl 5-(chlorosulfonyl)pyridine-2-carboxylate (Preparation 16, 915 mg, 3.8 mmol, 1 eq) portionwise and the resulting reaction mixture stirred at room temperature for a further hour. The mixture was dropped slowly into 6M HCl (20 ml), extracted into ethyl acetate (15 ml), washed with saturated sodium hydrogen carbonate (15 ml), dried over sodium sulphate, filtered and evaporated in vacuo. The residue was suspended in dioxane (5 ml), a solution of sodium hydroxide (300 mg, 7.5 mmol, 1.9 eq) in water (2 ml) was added and the reaction mixture stirred at room temperature for 30 minutes. The reaction mixture was washed with ethyl acetate (10 ml). The remaining aqueous phase diluted with brine (10 ml), acidified to pH 1, extracted into ethyl acetate (10 ml), dried over sodium sulphate, filtered and evaporated in vacuo to yield the title compound as an orange solid (90 mg, 0.28 mmol, 7%).

LCMS Rt=1.16 min. MS m/z 319 [MH]+.

Preparation 19

Methyl 2-cyano-4-fluorobenzoate

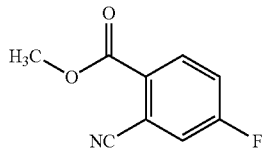

2-Bromo-5-fluorobenzonitrile (5.0 g, 25 mmol, 1 eq), Et$_3$N (5.08 g, 50.2 mmol, 2 eq) and [1,1'-bis(diphenylphosphino)ferrocine]dichloropalladium (11), complex with DCM (1; 1) (2.05 g, 2.5 mmol, 0.1 eq) were combined in MeOH (50 ml) and heated at 60° C. under 100 psi of carbon monoxide for 24 hours. The catalyst was removed by filtration through arbocel and the filtrate evaporated in vacuo. The crude material was purified by column chromatography eluting with heptane:ethyl acetate (70:30) to yield the title compound as a white solid (796 mg, 4.44 mmol, 18%).

$^1$HNMR (CDCl$_3$): 4.0 (s, 3H), 7.4 (m, 1H), 7.5 (m, 1H), 8.2 (m, 1H).

Preparation 20

Methyl 4-(chlorosulfonyl)-2-cyanobenzoate

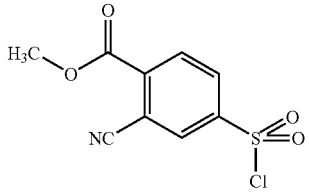

Methyl 2-cyano-4-fluorobenzoate (Preparation 19, 790 mg, 4.4 mmol, 1 eq), potassium carbonate (934 mg, 6.7 mmol, 1.5 eq) and phenylmethanethiol (560 mg, 4.5 mmol, 1 eq) were combined in dimethylsulphoxide (10 ml) and the reaction mixture was stirred at room temperature for 2 hours. The reaction mixture was extracted from water (10 ml) into ethyl acetate (10 ml), washed with water (2×10 ml), dried over sodium sulphate, filtered and evaporated in vacuo. The material was dissolved in DCM (30 ml) and 4M HCl (23 ml), sodium hypochlorite (18 ml, 35.3 mmol, 7.9 eq) was added dropwise at 0° C. and the reaction mixture stirred for a further 45 minutes. The reaction mixture was extracted into DCM (20 ml), dried over sodium sulphate, filtered and evaporated in vacuo. The crude material was triturated with t-butylmethyl ether to yield the title compound as a white solid (580 mg, 2.23 mmol, 50%).

$^1$HNMR (CDCl$_3$): 4.1 (s, 3H), 8.3 (m, 1H), 8.4 (m, 2H).

Preparation 21

Methyl 4-{[(5-chloro-1,3-thiazol-2-yl)amino]sulfonyl}-2-cyanobenzoate

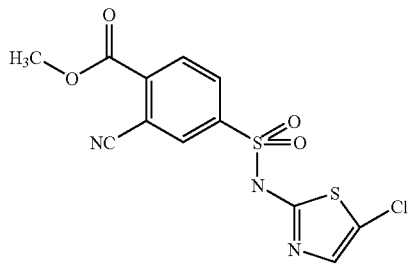

To a solution of 5-chloro-1,3-thiazol-2-amine hydrochloride (1.15 g, 6.7 mmol, 3 eq) in pyridine (7.5 ml) was added methyl 4-(chlorosulfonyl)-2-cyanobenzoate (Preparation 20, 580 mg, 2.2 mmol, 1 eq) portionwise and the reaction mixture was stirred at room temperature for 1 hour. The mixture was slowly added to 6M HCl (40 ml) and the resulting precipitate was collected by filtration and triturated with MeOH to yield the title compound as a brown solid (138 mg, 0.38 mmol, 17%).

$^1$HNMR (d$_6$-DMSO): 3.9 (s, 3H), 7.6 (s, 1H), 8.2 (m, 3H). LCMS Rt=1.39 min. MS m/z 357[M–H]–.

Preparation 22

4-{[(5-Chloro-1,3-thiazol-2-yl)amino]sulfonyl}-2-cyanobenzoic acid

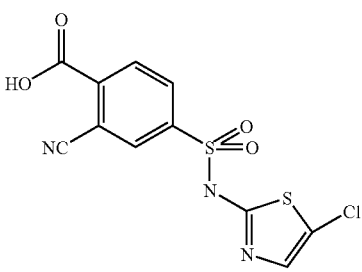

Methyl 4-{[(5-chloro-1,3-thiazol-2-yl)amino]sulfonyl}-2-cyanobenzoate (Preparation 21, 124 mg, 0.348 mmol, 1 eq) was dissolved in dioxane (2.5 ml): water (2.5 ml), lithium hydroxide (200 mg, 5 mmol, 14 eq) was added and the reaction mixture stirred at room temperature for 1 hour. The reaction mixture was diluted with water (5 ml), washed with ethyl acetate (10 ml), acidified with 2M HCl (10 ml), extracted into ethyl acetate (10 ml), dried over sodium sulphate, filtered and evaporated to yield the title compound as a brown solid (95 mg, 0.27 mmol, 79%).

$^1$HNMR (d$_6$-DMSO): 7.6 (s, 1H), 8.2 (m, 1H), 8.25 (m, 2H). LCMS Rt=1.4 min. MS m/z 343-345[M−H]−.

Preparation 23

3-{[(2,4-Dimethoxybenzyl)(1,3-thiazol-2-yl)amino]sulfonyl}benzoic acid

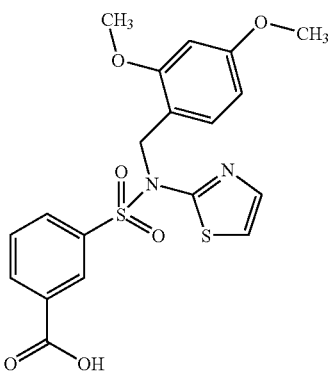 [SMILES: COc1ccc(CN(c2nccs2)S(=O)(=O)c2cccc(C(=O)O)c2)c(OC)c1]

Sodium hydride (60% in mineral oil, 239 mg, 5.99 mmol, 1.5 eq) was added portionwise to a solution of N-(2,4-dimethoxybenzyl)-1,3-thiazol-2-amine (Preparation 6, 1 g, 3.995 mmol, 1 eq) in THF (10 ml) at 0° C. The mixture was stirred for 40 minutes before the addition of methyl 3-(chlorosulfonyl)benzoate (937, 3.995 mmol, 1 eq) and the reaction mixture stirred for a further 1 hour at 0° C. and 5 hours at room temperature. Water (2 ml) was added and the THF evaporated in vacuo. The residue was extracted from water (10 ml) into ethyl acetate (3×5 ml), washed with brine, dried over magnesium sulphate, filtered and evaporated in vacuo to yield methyl 3-{[(2,4-dimethoxybenzyl)(1,3-thiazol-2-yl)amino]sulfonyl}benzoate.

LCMS Rt=2.62 min. MS m/z 449 [MH]+.

A crystalline precipitate formed in the aqueous phase which was collected by filtration to yield the title compound. This material was taken on crude to the next step.

MS m/z 435 [MH]+.

Preparation 24

4-Chloro-N-(2,4-dimethoxybenzyl)-1,3-thiazol-2-amine

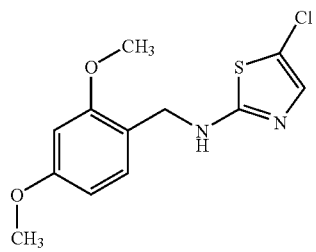 [SMILES: COc1ccc(CNc2ncc(Cl)s2)c(OC)c1]

2,4 Dimethoxybenzaldehyde (5 g, 30 mmol, 1 eq), 2-amino-5-chlorothiazole hydrochloride (5.15 g, 30 mmol, 1 eq), Et$_3$N (3.04 g, 30 mmol, 1 eq) and piperidine (31 mg, 0.361 mmol, 0.012 eq) were combined in DCM (100 ml) and the reaction mixture heated to reflux over sieves for 18 hours. The sieves were removed by filtration and the reaction mixture diluted with MeOH (50 ml). Sodium borohydride (5.01 g, 132 mmol, 4.4 eq) was added portionwise and the reaction mixture heated to reflux for 1 hour. The mixture was cooled, quenched with water and the organic solvent evaporated in vacuo. The residue was extracted from water into ethyl acetate, dried over sodium sulphate, filtered and evaporated in vacuo. The crude material was triturated with isopropanol to yield the title compound as a cream solid.

$^1$HNMR (d$_6$-DMSO): 3.72 (s, 3H), 3.77 (s, 3H), 4.25 (d, 2H), 6.46 (m, 1H), 5.54 (s, 1H), 6.95 (s, 1H), 7.13 (d, 1H), 7.95 (t, 1H). MS m/z 283 [M−H]−.

Preparation 25

4-{[(5-Chloro-1,3-thiazol-2-yl)-(2,4-dimethoxybenzyl)-sulfonyl}-3-fluorobenzoic acid

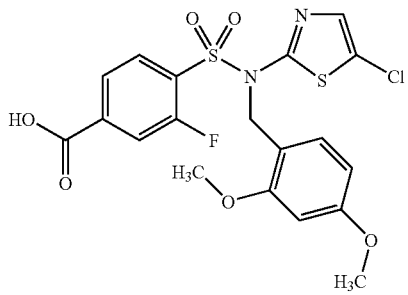 [SMILES: COc1ccc(CN(c2ncc(Cl)s2)S(=O)(=O)c2ccc(C(=O)O)cc2F)c(OC)c1]

The title compound was prepared in 30% yield from 4-chloro-N-(2,4-dimethoxybenzyl)-1,3-thiazol-2-amine (Preparation 24) and 4-(chlorosulfonyl)-3-fluorobenzoic acid (Preparation 9) following the procedure described in Preparation 10.

LCMS Rt=2.52 min. MS m/z 337 [MH]+.

Preparation 26

N-(2,4-dimethoxybenzyl)-1,2,4-thiadiazol-5-amine

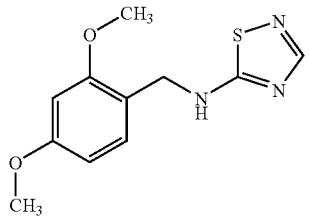 [SMILES: COc1ccc(CNc2ncns2)c(OC)c1]

2,4 Dimethoxybenzaldehyde (4.1 g, 24 mmol, 1 eq), 2 amino-1,2,4-thiadiazole (2.5 g, 24.7 mmol, 1 eq), Et$_3$N (3.04 g, 30 mmol, 1 eq) and piperidine (25 mg, 0.297 mmol, 0.012 eq) were combined in DCM (100 ml) and the reaction mixture heated to reflux over sieves for 72 hours. The reaction mixture was cooled to room temperature and chlorotitaniumisopropoxide (1M solution in hexane, 29.7 ml, 29.7 mmol, 1.2 eq) was added and the reaction mixture stirred at room temperature for 15 minutes. The sieves were removed by filtration and the reaction mixture diluted with MeOH (50 ml). Sodium borohydride (3.7 g, 99 mmol, 4.0 eq) was added portionwise and the reaction mixture stirred for 1 hour. The reaction mixture was diluted with saturated sodium hydrogen carbonate (100 ml) and the resulting titanium precipitate removed by filtration through Celite. The filtrate was dried over sodium sulphate, filtered and evaporated in vacuo. The crude material was purified by column chromatography eluting with 15-60% ethyl acetate: heptane to yield the title compound (111 g, 4.38 mmol, 17%).

$^1$HNMR (d$_6$-DMSO): 3.75 (s, 3H), 3.8 (s, 3H), 4.4 (m, 2H), 6.45 (m, 1H), 6.6 (s, 1H), 7.15 (m, 1H), 7.9 (s, 1H), 8.65 (m, 1H).

Preparation 27

3-Fluoro-4-[(1,2,4-thiadiazol-5-ylamino)sulfonyl]benzoic acid

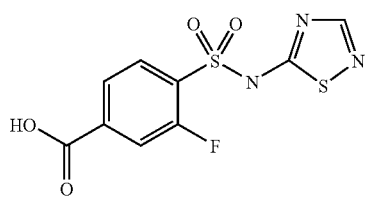 [SMILES: O=C(O)c1ccc(S(=O)(=O)Nc2ncns2)c(F)c1]

N-(2,4-dimethoxybenzyl)-1,2,4-thiadiazol-5-amine (Preparation 26, 500 mg, 2.1 mmol, 1.0 eq) was dissolved in THF (10 ml) and cooled to −78° C. 1,1,1,3,3,3-Hexamethyldisilazane lithium salt (LiHMDS, 1M in THF, 4.2 ml, 4.19 mmol, 2.0 eq) was added dropwise and the reaction mixture stirred for a further 10 minutes. A solution of 4-(chlorosulfonyl)-3-fluorobenzoic acid (Preparation 9, 500 mg, 2.1 mmol, 1 eq) in THF (3 ml) was added dropwise and the reaction mixture stirred at −78° C. for 1 hour then at room temperature for 18 hours. The reaction mixture was diluted with brine, extracted into ethyl acetate, dried over sodium sulphate, filtered and evaporated in vacuo. The crude material was passed through a SCX cartridge to remove remaining amine. The material was redissolved in 4M HCl in dioxane and stirred at room temperature for 2 hours. The resulting precipitate was collected by filtration and washed with diethylether to yield the title compound (100 mg, 0.33 mmol, 16%).

$^1$HNMR (d$_6$-DMSO): 7.8 (m, 1H), 7.9 (m, 1H), 8.0 (m, 1H), 8.55 (s, 1H). LCMS Rt=1.2 min. MS m/z 304 [MH]+.

Preparation 28

Methyl 4-[(pentafluorophenoxy)sulfonyl]benzoate

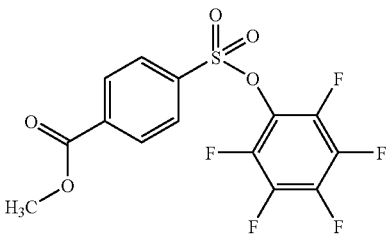 [SMILES: COC(=O)c1ccc(S(=O)(=O)Oc2c(F)c(F)c(F)c(F)c2F)cc1]

To a solution of methyl 4-(chlorosulfonyl)benzoate (Preparation 2, 606 mg, 2.1 mmol, 1 eq) in DCM (35 ml) was added pentafluorophenol (412 mg, 2.2 mmol, 1.1 eq) and Et$_3$N (540 mg, 5.4 mmol, 2.5 eq) and the reaction mixture stirred at room temperature until all of the starting material was consumed. The solvent was evaporated in vacuo and the residue redissolved in ethyl acetate (10 ml), washed with water (10 ml), saturated sodium hydrogen carbonate (10 ml), dried over sodium sulphate, filtered and evaporated to yield the title compound as a white solid (690 mg, 1.8 mmol, 85%).

$^1$HNMR (CDCl$_3$): 4.0 (s, 3H), 8.05 (d, 2H), 8.25 (d, 2H). LCMS Rt=1.71 min. MS m/z 383 [MH]+.

Preparation 29

4-[(1,2,4-Thiadiazol-5-ylamino)sulfonyl]benzoic acid

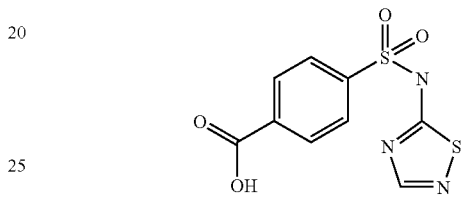

To a solution of 5-amino-1,2,4-thiadiazole (58 mg, 0.574 mmol, 1.1 eq) in THF (5 ml) was added, 1,1,3,3,3-Hexanemethyldisilazane lithium salt (LiHMDS, 1M in THF, 1.15 ml, 1.2 mmol, 2.2 eq) and the reaction mixture stirred at 50° C. for 5 minutes. Methyl 4-[(pentafluorophenoxy)sulfonyl]benzoate (Preparation 28, 196 mg, 0.513 mmol, 1 eq) was added and the reaction monitored. On the disappearance of the starting materials the reaction mixture was quenched with water (5 ml), diluted with ethyl acetate (10 ml), washed with saturated sodium hydrogen carbonate, dried over sodium sulphate, filtered and evaporated in vacuo. The residue was dissolved in dioxane (5 ml) and a solution of sodium hydroxide (100 mg, 2.5 mmol, 4.3 eq) in water (2 ml) was added and the reaction mixture stirred at room temperature for 30 minutes. The reaction mixture was partitioned between ethyl acetate (5 ml) and water (5 ml), the aqueous phase was acidified with concentrated HCl, extracted into ethyl acetate (10 ml), dried over sodium sulphate, filtered and evaporated in vacuo. The crude material was triturated with DCM to yield the title compound as a pale yellow solid (64 mg, 0.22 mmol, 43%).

$^1$HNMR (d$_6$-DMSO): 7.9 (m, 2H), 8.1 (m, 2H), 8.15 (m, 1H). LCMS Rt=1.12 min. MS m/z 285 [MH]+.

Preparation 30

4-([[3-Chloro-4-(trifluoromethyl)benzyl]amino]carbonyl)benzenesulfonyl chloride

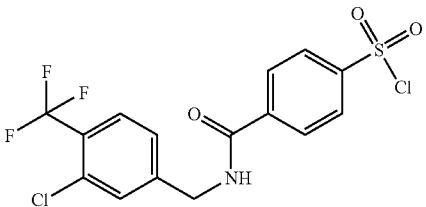 [SMILES: O=C(NCc1ccc(C(F)(F)F)c(Cl)c1)c1ccc(S(=O)(=O)Cl)cc1]

The title compound was prepared from 4-sulphobenzoic acid monopotassium salt and 3-chloro-4-(trifluoromethyl)benzylamine in 45% yield following the procedure described in Preparation 1. The thionyl chloride solution was heated at reflux for 3 hours.

¹HNMR (CDCl₃): 4.70 (d, 2H), 6.70 (m, 1H), 7.15 (d, 1H), 7.50 (s, 1H), 7.65 (d, 1H), 8.05 (d, 2H), 8.15 (d, 2H). LCMS Rt=1.72 min. MS m/z 411-413 [MH]+.

Preparation 31

Methyl 4-{[(5-chloro-1,3-thiazol-2-yl)(2,4-dimethoxybenzyl)amino]sulfonyl}-2-fluorobenzoate

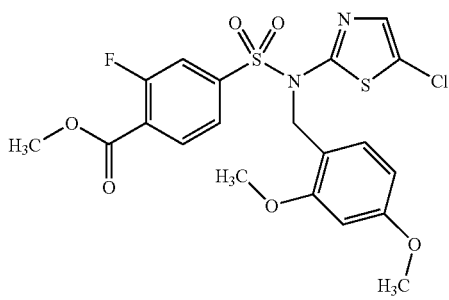 [SMILES: COC(=O)c1ccc(S(=O)(=O)N(Cc2ccc(OC)cc2OC)c2ncc(Cl)s2)cc1F]

The title compound was prepared from methyl 4-(chlorosulfonyl)-2-fluorobenzoate (Preparation 13) and 4-chloro-N-(2,4-dimethoxybenzyl)-1,3-thiazol-2-amine (Preparation 24) in 41% yield, following the procedure described in Preparation 10. 1.2 eq of LiHMDS was used. The crude product was purified by column chromatography eluting with hexane:ethyl acetate (8:2 to 7:3).

¹HNMR (d₆-DMSO): 3.6 (s, 3H), 3.7 (s, 3H), 3.85 (s, 3H), 4.9 (s, 2H), 6.4 (m, 2H), 7.0 (m, 1H), 7.5 (s, 1H), 7.7 (m, 2H), 8.1 (m, 1H). LCMS Rt=2.96 min. MS m/z 500.98 [MH]+.

Preparation 32

Methyl 4-{[(5-chloro-1,3-thiazol-2-yl)amino]sulfonyl}-2-fluorobenzoate

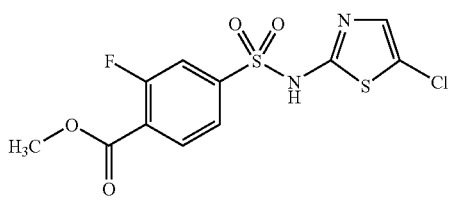 [SMILES: COC(=O)c1ccc(S(=O)(=O)Nc2ncc(Cl)s2)cc1F]

Methyl 4-{[(5-chloro-1,3-thiazol-2-yl)(2,4-dimethoxybenzyl)amino]sulfonyl}-2-fluorobenzoate (Preparation 31, 7.2 g, 14 mmol) was dissolved in dioxane (15 ml), 4M HCl in dioxane was added at 0° C. and the reaction mixture stirred at room temperature for 18 hours. The solvent was evaporated in vacuo and the residue triturated with hot MeOH (100 ml) to yield the title compound as a white solid (3.6 g, 10.2 mmol, 71%).

LCMS Rt=1.82 min. MS m/z 350.97 [MH]+.

Preparation 33

4-{[(5-Chloro-1,3-thiazol-2-yl)amino]sulfonyl}-2-fluorobenzoic acid

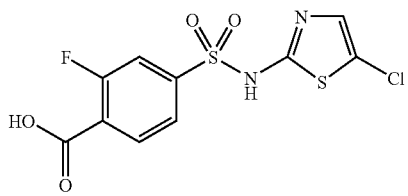 [SMILES: O=C(O)c1ccc(S(=O)(=O)Nc2ncc(Cl)s2)cc1F]

Methyl 4-{[(5-chloro-1,3-thiazol-2-yl)amino]sulfonyl}-2-fluorobenzoate (Preparation 32, 3.6 g, 10.26 mmol, 1 eq) was suspended in 2.5M sodium hydroxide (16.5 ml, 41 mmol, 4 eq) and dioxane (4 ml) and the reaction mixture heated at 50° C. for 2 hours. The organic solvent was removed in vacuo and the residue diluted with ethyl acetate (20 ml). The remaining solid was removed by filtration and the organic layer separated. The aqueous phase was acidified with concentrated HCl, extracted into ethyl acetate, washed with brine, dried over magnesium sulphate, filtered and evaporated in vacuo. The title compound was obtained as a white solid (2.74 g, 8.1 mmol, 79%).

¹HNMR (d₆-DMSO): 7.5 (s, 1H), 7.6 (m, 2H), 8.0 (m, 1H). LCMS Rt=1.81 min. MS m/z 337 [MH]+.

Preparation 34

Methyl 3-chloro-4-{[(2,4-dimethoxybenzyl)(5-chloro-1,3-thiazol-2-yl)amino]sulfonyl}benzoate

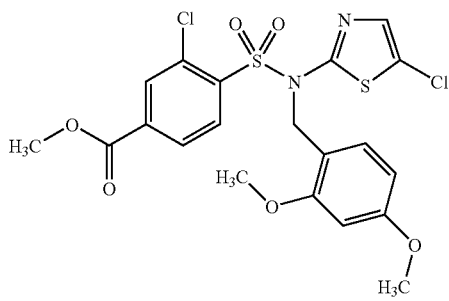 [SMILES: COC(=O)c1ccc(S(=O)(=O)N(Cc2ccc(OC)cc2OC)c2ncc(Cl)s2)c(Cl)c1]

The title compound was prepared from 4-chloro-N-(2,4-dimethoxybenzyl)-1,3-thiazol-2-amine (Preparation 24) and methyl 3-chloro-4-(chlorosulfonyl)benzoate (Preparation 5) in 30% yield, following the procedure described in Preparation 10. 1.2 eq of LiHMDS was used. The aqueous workup was carried out using diethyl ether and the crude product was purified by column chromatography eluting with 0-25% ethyl acetate:hexane.

¹HNMR (d₆-DMSO): 3.6 (s, 6H), 3.8 (s, 3H), 5.1 (s, 2H), 6.4 (m, 2H), 7.0 (m, 1H), 7.5 (s, 1H), 8.0 (m, 2H), 8.1 (m, 1H). LCMS Rt=3.07 min. MS m/z 516.96 [MH]+.

Preparation 35

3-Chloro-4-{[(5-chloro-1,3-thiazol-2-yl)amino]sulfonyl}benzoic acid

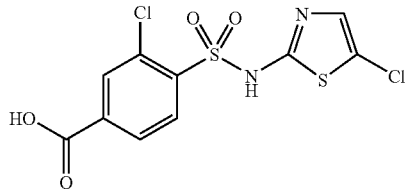 [SMILES: O=C(O)c1ccc(S(=O)(=O)Nc2ncc(Cl)s2)c(Cl)c1]

Methyl 3-chloro-4-{[(2,4-dimethoxybenzyl)(5-chloro-1,3-thiazol-2-yl)amino]sulfonyl}benzoate (Preparation 34, 3.2 g, 6.2 mmol, 1 eq) was suspended in 2.5M sodium hydroxide (7.4 ml, 18.6 mmol, 3 eq) and MeOH (40 ml) and the reaction mixture heated at 50° C. for 2 hours. The reaction mixture was concentrated in vacuo and the residue dissolved in 4M HCl in dioxane at 0° C. and the reaction mixture stirred at room temperature for 18 hours. The resulting precipitate was collected by filtration to yield the title compound as a white solid (3.2 g, 9.1 mmol, >100%).

¹HNMR (d₆-DMSO): 7.5 (s, 1H), 8.0 (m, 2H), 8.1 (m, 1H).

Preparation 36

Methyl 2-chloro-4-{[(5-chloro-1,3-thiazol-2-yl)amino]sulfonyl}benzoate

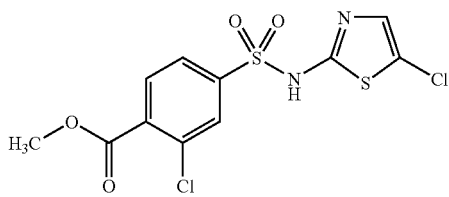 [SMILES: COC(=O)c1ccc(S(=O)(=O)Nc2ncc(Cl)s2)cc1Cl]

To a solution of 2-amino-5-chlorothiazole hydrochloride (2.62 g, 15.3 mmol, 3 eq) in pyridine (10 ml) was added methyl 4-(chlorosulfonyl)-2-chlorobenzoate (2.28 g, 5.1 mmol, 1 eq) portionwise and the reaction mixture stirred at room temperature for 1 hour. The solution was added to 6M HCl (40 ml) and the resultant precipitate collected by filtration. The crude material was triturated with t-butylmethyl ether to yield the title compound (410 mg, 1.1 mmol, 22%).

¹HNMR (d₆-DMSO): 3.85 (s, 3H), 7.20 (s, 1H), 7.8 (m, 2H), 7.90 (d, 1H). LCMS Rt=1.45 min. MS m/z 365-370 [MH]+.

Preparation 37

2-Chloro-4-{[(5-chloro-1,3-thiazol-2-yl)amino]sulfonyl}benzoic acid

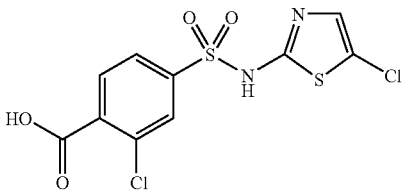 [SMILES: O=C(O)c1ccc(S(=O)(=O)Nc2ncc(Cl)s2)cc1Cl]

To a solution of methyl 2-chloro-4-{[(5-chloro-1,3-thiazol-2-yl)amino]sulfonyl}benzoate (Preparation 36, 410 mg, 1.1 mmol) in dioxane (4 ml) was added a solution of sodium hydroxide (93 mg, 2.32 mmol) in water (1.5 ml) and the reaction mixture stirred at room temperature for 1 hour. The reaction mixture was diluted with water (10 ml), added to concentrated HCl (10 ml) and stirred for 10 minutes at room temperature for 15 minutes. The resultant precipitate was collected by filtration to yield the title compound (239 mg, 0.68 mol, 62%).

¹HNMR (d₆-DMSO): 7.60 (s, 1H), 7.80 (m, 2H), 7.90 (d, 1H). LCMS Rt=1.35 min. MS m/z 352-356 [MH]+.

Preparation 38

3-Chloro-4-({[3-chloro-4-(trifluoromethyl)benzyl]amino}carbonyl)benzenesulfonyl chloride

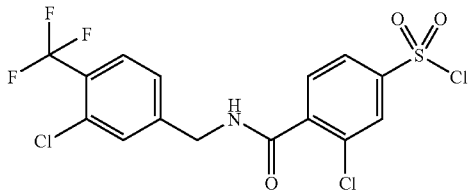 [SMILES: O=C(NCc1ccc(C(F)(F)F)c(Cl)c1)c1ccc(S(=O)(=O)Cl)cc1Cl]

To a solution of 2-chloro-4-(chlorosulfonyl)benzoyl chloride (J. Org. Chem, 56, 16, 1991, 4974) (300 mg, 0.877 mmol, 1 eq) in DCM (3 ml) was added 3-chloro-4-(trifluoromethyl)benzylamine (175 mg, 0.835 mmol, 0.95 eq) and Et₃N (33 mg, 0.32 mmol, 0.37 eq) and the reaction mixture stirred at room temperature for 1 hour. The reaction mixture was diluted with ethyl acetate (10 ml), washed with water (10 ml), dried over sodium sulphate, filtered and evaporated. The crude material was purified by column chromatography eluting with ethyl acetate to yield the title compound (154 mg, 0.34 mmol, 39%).

¹HNMR (CDCl₃): 4.7 (s, 2H), 6.6 (bs, 1H), 7.4 (m, 1H), 7.55 (s, 1H), 7.7 (m, 1H), 7.9 (m, 1H), 8.0 (m, 1H), 8.1 (m, 1H). LCMS Rt=1.70 min. MS m/z 445-449 [MH]+.

Preparation 39

Methyl 4-(benzylthio)-2-chlorobenzoate

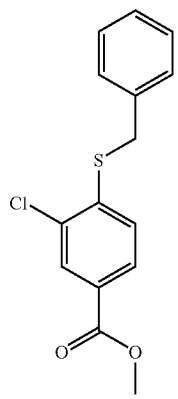 [SMILES: COC(=O)c1ccc(SCc2ccccc2)c(Cl)c1]

Methyl 2-chloro-4-fluorobenzoate (1.92 g, 10.2 mmol, 1 eq), cesium carbonate (3.74 g, 11.5 mmol, 0.13 eq) and benzyl mercaptan (1.3 g, 10.5 mmol, 1.03 eq) were combined in dimethyl sulphoxide (20 ml) and the reaction mixture heated at 50° C. for 4 hours. The reaction mixture was poured into ethyl acetate (10 ml) then washed with water (10 ml). The organic phase was dried over sodium sulphate, evaporated to yield the title compound as pink oil (2.82 g, 9.63 mmol, 95%).

¹HNMR (CDCl₃): 4.95 (s, 3H), 4.20 (s, 2H), 7.15 (d, 1H) 7.25-7.40 (m, 6H), 7.75 (d, 1H). LCMS Rt=1.78 min. MS m/z 261 [M–H].

Preparation 40

4-(Benzylthiol)-2-chlorobenzoic acid

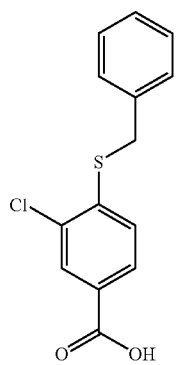 [SMILES: O=C(O)c1ccc(SCc2ccccc2)c(Cl)c1]

Methyl 4-(benzylthio)-2-chlorobenzoate (Preparation 39, 2.82 g, 9.63 mmol, 1 eq) was suspended in dioxane, a solution of sodium hydroxide (550 mg, 13.9 mmol, 1.4 eq) in water (3 ml) was added and the reaction mixture stirred at room temperature for 1 hour. A white solid appeared. MeOH was added and mixture was filtered and washed with MeOH to yield the title compound as a white solid (2.1 g, 7.53 mmol, 78%).

¹HNMR (CDCl₃): 4.20 (s, 2H), 7.10 (d, 1H). 7.15 (s, 1H), 7.20-7.35 (m, 6H). MS m/z 277-279 [M–H].

Preparation 41

4-(Chlorosulfonyl)-3-chlorobenzoic acid

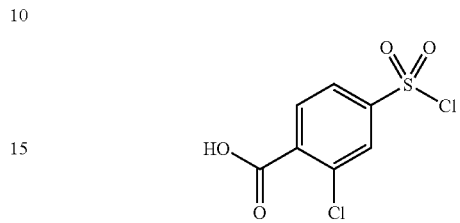

To a solution of 4-(benzylthio)-3-fluorobenzoic acid (Preparation 40, 2.4 g, 8.7 mmol, 1 eq) in DCM (100 ml) and 4N HCl (100 ml) at 0° C. was added sodium hypochlorite (47 ml, 91 mmol, 10.4 eq) dropwise and the reaction mixture stirred at room temperature for 45 minutes. The layers were separated, extracted with DCM (20 ml), dried over sodium sulphate, filtered and evaporated in vacuo. The crude material was purified by column chromatography eluting with 0-100% heptane:ethyl acetate. The obtained compound was a white solid (1.3 g, 5.10 mmol, 59%).

LCMS Rt=1.18 min. MS m/z 253-257 [M–H]–.

Preparation 42

2-Chloro-4-[(1,2,4-thiadiazol-5-ylamino)sulfonyl]benzoic acid

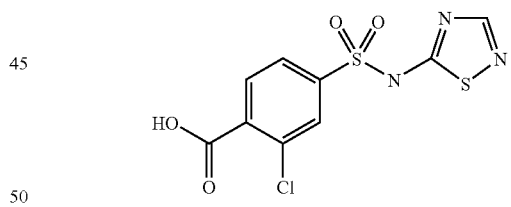

1,2,4-Thiadiazol-5-amine (770 mg, 7.61 mmol, 1.5 eq) was dissolved in dioxane (10 ml), a solution of sodium hydroxide (550 mg, 14 mmol, 2.7 eq) in water (3 ml) was added and the reaction mixture stirred at room temperature for 10 minutes. 4-(chlorosulfonyl)-3-chlorobenzoic acid (Preparation 41, 1.3 g, 5.1 mmol, 1 eq) was added portionwise and the reaction mixture stirred at room temperature for 2 hours. The mixture was dropped into 2M HCl (10 ml) and concentrated in vacuo up to apparition of a solid. The resultant precipitate was discarded and filtrate filtered again to yield the title compound as a white solid (243.3 mg, 0.763 mmol, 15%).

$^1$HNMR (d$_6$-DMSO): 7.80 (m, 2H), 7.90 (d, 1H), 8.50 (s, 1H). LCMS Rt=2.63 min. MS m/z 320-322 [M−H]−.

Preparation 43 tert-Butyl 6-Methylene-1,4-oxazepane-4-carboxylate

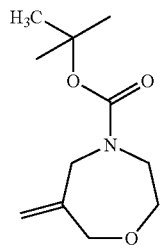

60% Sodium hydride in oil (26 g, 0.65 mol, 2.17 eq) was added in one portion in argon flow at 5° C. to a solution of 3-chloro-2-chloromethyl-1-propene (35 mL, 0.3 mol, 1 eq) in dimethylformamide (500 mL). Then a solution of tert-butyl (2-hydroxyethyl)carbamate (48.3 g, 0.3 mol, 1 eq) in THF (500 mL) was added, and the reaction mixture was heated to 25° C. and stirred at this temperature for 2 h. Then the reaction mixture was neutralized with glacial AcOH (4.5 mL) and evaporated in water aspirator vacuum at 45-55° C. using a 15-cm reflux condenser. The residue was poured with water (300 mL) and extracted with a mixture of ethyl acetate (200 mL), hexane (100 mL) and chloroform (50 mL). The organic layer was separated and washed with water (2×100 mL) and brine. The combined aqueous layer was extracted with a mixture of ethyl acetate (150 mL) and hexane (50 mL). The organic layer was separated and washed with water (2×100 mL) and brine. The extracts were filtered sequentially through silica gel (25 g) and sodium sulfate (50 mL) eluting with chloroform (100 mL). The filtrate was evaporated, and the residue was distilled in vacuum to give title compound as a colorless oil (bp 76-79° C. at 0.7 mmHg) (35.8 g, 0.177 mol, 56%)

Preparation 44 tert-Butyl 6-[(Cyclopropylmethoxy)methyl]-6-hydroxy-1,4-oxazepane-4-carboxylate

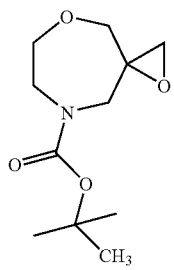 [SMILES: CC(C)(C)OC(=O)N1CCOCC2(CO2)C1]

70-75% m-Chloroperoxobenzoic acid (145 g, 0.59 mol, 1.18 eq) was added in portions to a stirred solution of compound tert-butyl 6-methylene-1,4-oxazepane-4-carboxylate (Preparation 43, 107 g, 0.5 mol, 1 eq) in DCM (1.0 L), which caused heating of the mixture. The reaction mixture was stirred for 24 h at room temperature, diluted with hexane (500 mL), and filtered. The separated precipitate was washed on a filter with the mixture DCM/hexane, and the combined filtrate was washed with aqueous potassium carbonate, dried over sodium sulfate, and evaporated. The residue was vacuum-dried to give title compound (117 g, 0.51 mol, 102%)

Preparation 45 tert-Butyl 6-(2-fluorobenzyl)-6-hydroxy-1,4-oxazepane-4-carboxylate

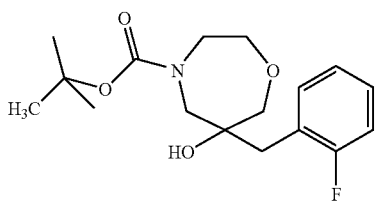 [SMILES: CC(C)(C)OC(=O)N1CCOCC(O)(Cc2ccccc2F)C1]

1.6M Butyllithium/hexane (150 mL, 0.24 mol, 1.09 eq) was added to a solution of 2-fluorobromobenzene (26 mL, 0.24 mol, 1.09 eq) in THF (200 mL) in a stream of argon at −90° C. The reaction mixture was cooled to −80° C., and a solution of compound tert-butyl 6-[(cyclopropylmethoxy)methyl]-6-hydroxy-1,4-oxazepane-4-carboxylate (Preparation 44, 50 mL, 0.22 mol, 1 eq) in THF was added dropwise. Then the mixture was cooled to −100° C., and a solution of borontrifluoride diethyletherate (30.4 g, 0.24 mol, 1.09 eq) in THF (300 mL) was added at this temperature for 30 min. The reaction mixture was heated to 0° C. for 5 h, and a 5M sodium hydrogen sulfate solution (50 mL) was added. The organic layer was separated and evaporated, and the residue was distributed between water and ether. The organic layer was separated, washed with water and brine, dried, and evaporated. The residue was dissolved in MeOH (200 mL). Ethylenediamine (30 mL) was added to the mixture, which was brought to boiling, cooled, evaporated, and coevaporated with dioxane. The residue was subjected to chromatography (silica gel, carbon tetrachloride→chloroform→chloroform/MeOH 19:1), evaporated, and dried to title compound (38 g, 0.12 mol, 55%).

Preparation 46

6-(2-Fluorobenzyl)-1,4-oxazepan-6-ol Hydrochloride

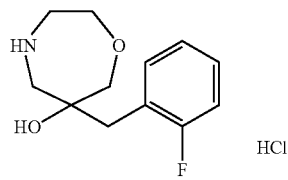 [SMILES: OC1(Cc2ccccc2F)CNCCOC1 ; Cl]

tert-Butyl 6-(2-fluorobenzyl)-6-hydroxy-1,4-oxazepane-4-carboxylate (Preparation 45, 38 g, 0.12 mol, 1 eq) was dissolved in dioxane (200 mL), and 4M hydrogen chloride/dioxane (60.4 mL, 0.24 mol, 2 eq) was added. The mixture was stirred for 24 h, evaporated, and coevaporated with ether. The formed precipitate was washed with ether and dried to give title compound (29.8 g, 0.11 mol, 95%).

$^1$HNMR (d$_6$-DMSO): 2.75 (m, 2H), 2.95 (d, 1H), 3.1 (m, 1H), 3.25 (m, 2H), 3.65 (m, 2H), 3.8 (m, 1H), 3.9 (m, 1H), 5.65 (s, 1H), 7.15 (m, 2H), 7.3 (m, 1H), 7.4 (m, 1H), 8.3 (m, 1H), 9.8 (m, 1H). LCMS Rt=2.34 min. MS m/z 226 [MH]+.

Preparation 47

1-(3-Chlorophenyl)-2-(3-methylisoxazol-5-yl)ethanol

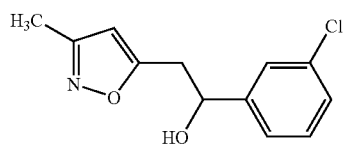 [SMILES: Cc1cc(CC(O)c2cccc(Cl)c2)on1]

To a solution of 3,5-dimethylisoxazole (104 g, 1.07 mol, 1 eq) in THF (1 L) cooled to −78° C. under nitrogen, a solution of lithiumdiisopropylamide (1.8M ethylbenzene in THF) (630 mL, 1.134 mol, 1.06 eq) was added dropwise. After 1 hr, a solution of 3-chlorobenzaldehyde 100 g, 0.711 mole, 0.66 eq) in THF (300 mL) was added drop wise at −78° C. The reaction mixture was allowed to warm to room temperature and stirred overnight. It was cooled to 0° C., and quenched by saturated ammonium chloride solution (130 mL). The organic layer was concentrated to dryness. Water (1 L) was added to the residue was extracted with ethyl acetate (2×1 L). Combined organic extracts were washed with brine (700 mL) dried over anhydrous sodium sulfate. Concentrated and purified by column chromatography (50% ethyl acetate in hexane) over silica gel using a mixture of ethyl acetate and hexanes as eluant. The title compound was obtained as viscous brown oil (120 g, 0.507 mol, 48%).

Preparation 48

[2-Azido-2-(3-chloro-phenyl)-ethyl]-3-methyl-isoxazole

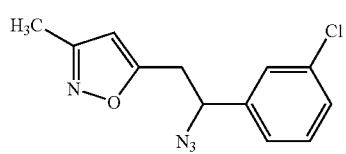

To a solution of 1-(3-chlorophenyl)-2-(3-methylisoxazol-5-yl)ethanol (Preparation 47, 120 g, 0.507 mol, 1 eq) in toluene (400 mL) under nitrogen, diphenylphosphoryl azide (137 mL, 0.633 mol, 1.25 eq) and diaza(1,3)bicyclo[5.4.0]undecane (92 mL, 0.615 mol, 1.21 eq) were added dropwise simultaneously at 0° C. The reaction mixture was stirred at room temperature overnight. It was filtered through a Celite pad and the Celite pad was washed with 5% ethyl acetate in hexane. The collected organic extract was dried, concentrated and purified by column chromatography (20% ethyl acetate in hexane) over silica gel. The title compound was obtained as a viscous liquid (188 g, 0.437 mol, 86%).

Preparation 49

1-(3-Chloro-phenyl)-2-(3-methyl-isoxazol-5-yl)-ethylamine

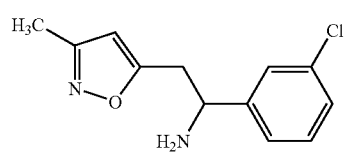 [SMILES: Cc1cc(CC(N)c2cccc(Cl)c2)on1]

Triphenylphosphine (137 g, 0.522 mol, 1.19 eq) was added to a solution of 5-(2-azido-2-(3-chlorophenyl)ethyl)-3-methylisoxazole (Preparation 48, 115 g, 0.437 mol, 1 eq) in THF (1 L) under nitrogen atmosphere. The reaction mixture was stirred for 1 hr after which water (45 mL) was added and it was heated at 50° C. overnight. The reaction mixture was concentrated, the crude oil so obtained was dissolved in 1 L ethyl acetate and cooled to 0° C. It was extracted with 6M HCl (3×500 mL). The aqueous phase was saturated by sodium chloride and basified with 6M sodium hydroxide to pH-10 (2 L) and was extracted with ethyl acetate (2 L). Organics were washed by brine, dried and concentrated to yield a liquid, which solidifies upon refrigeration. The title compound was obtained as white solid (30 g, 0.127 mol, 29%).

Preparation 50

2-(3,5-Difluoro-phenyl)-propan-2-ol

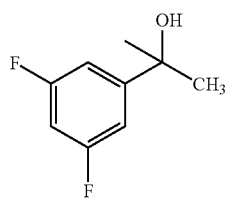

A solution of 1-(3,5-difluoro-phenyl)-ethanone (156 g, 1 mol, 1 eq) in THF (500 mL) was added dropwise under argon to the commercially available solution of methymagnesium bromide (143 g, 1.2 mol, 1.2 eq) in THF at such a rate that gentle refluxing was maintained. After the addition was complete the reaction mixture was stirred at ambient temperature for an hour and poured into ice-cold aqueous saturated ammonium chloride. Phases were separated and aqueous layer extracted two times with ethyl acetate. The combined organic layers were washed with brine and dried over anhydrous magnesium sulfate. After removal of the solvent title compound was purified by distillation under reduced pressure (145 g, 0.84 mol, 84%).

Preparation 51

1-(1-Azido-1-methylethyl)-3,5-difluorobenzene

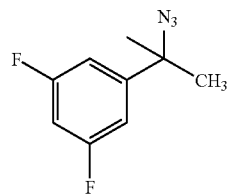

Hydrogen azide (2M in toluene, 1.5 mol) was added to the solution of 2-(3,5-difluoro-phenyl)-propan-2-ol (Preparation 50, 145 g, 0.84 mol, 1 eq) in chloroform (1 L) and the content of the flask was cooled to −5° C. The mixture of TFA (2.5 mol, 2.98 eq) with chloroform (1:1) was added dropwise at such a rate to keep the internal temperature below −5° C. After the addition was complete, the reaction mixture was allowed to warm to room temperature and stirring was continued for 20 h. The reaction was poured into 2M sodium hydroxide and layers were separated. The aqueous phase was extracted two times with chloroform and combined organic extracts were washed with brine and dried over anhydrous magnesium sulfate. After removal of the solvent, the title compound was used in the next step without further purification (171 g, 0.87 mol, 100%).

Preparation 52

2-(3,5-Difluorophenyl)propan-2-amine hydrochloride

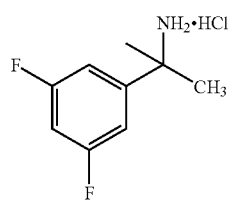

1-(1-Azido-1-methylethyl)-3,5-difluorobenzene (Preparation 51, 171 g, 0.87 mol, 1 eq) diluted with diethyl ether was added dropwise over two hours to the suspension of lithium aluminum hydride (1.05 mol, 1.21 eq) in dry diethyl ether (1.7 L) cooled previously to 0° C. After the addition was complete the reaction mixture was stirred at 0-10° C. for an hour and carefully quenched with dropwise addition of 2M aqueous hydrogen chloride until pH=2 was obtained. The aqueous phase was separated, washed with ethyl acetate, alkalized to pH>12 and filtered through a pad of Celite to remove some insoluble by-products. The Celite was washed several times with hot ethyl acetate. The aqueous layer was separated and extracted three times with ethyl acetate. The combined organic layers were washed with brine and dried over anhydrous magnesium sulfate. The solvent was evaporated and the hydrochloride salt precipitated by addition of stoichiometric amount of hydrogen chloride (as 3M solution in ethyl acetate). It was filtered, washed with ether and dried to give title compound (104 g, 0.5 mol, 57%).

$^1$HNMR (D$_2$O): 1.60 (s, 6H), 6.85 (m, 1H), 7.0 (m, 2H).

Preparation 53

Ethyl 3-bromo-4-fluorobenzoate

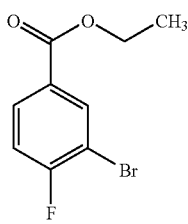

To a solution of compound 3-bromo-4-fluoro-benzoic acid (430 g, 1.97 mol, 1 eq) in EtOH (2.3 L) was added dropwise thionyl chloride (287 mL, 3.94 mol, 2 eq) at 10° C. Then the mixture was heated to reflux overnight. The mixture was concentrated in vacuum to give a residue. The residue was dissolved in ethyl acetate (800 mL), washed with aqueous sodium hydrogen carbonate, brine (300 mL) and water (200 mL), then concentrated in vacuo to give title compound as a white solid (440 g, 1.78 mol, 90.3%).

$^1$HNMR (CDCl$_3$): 1.40 (t, 3H), 4.35 (m, 2H), 7.15 (t, 1H), 7.95 (d, 1H), 8.20 (s, 1H).

Preparation 54

Ethyl 4-fluoro-3-vinylbenzoate

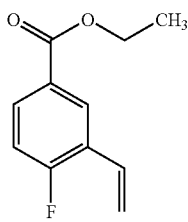

A mixture of compound ethyl 3-bromo-4-fluorobenzoate (Preparation 53, 81 g, 328.8 mmol, 1 eq) and bis(triphenylphosphine)palladium (II) chloride (7 g, 9.9 mmol, 0.03 eq) in dioxane (600 mL) was charged with nitrogen. Tin vinyltributyl (115 g, 361.6 mmol, 1.10 eq) was added and the mixture was heated to reflux overnight. The mixture was filtrated and the filtrate was concentrated in vacuum. The residue was dissolved in ether (2 L) and water (1 L). Then potassium fluoride (10 g, 1.7 mol, 5.17 eq) was added to the mixture and much of solid precipitated. The mixture was filtrated and the filtrate was separated. The aqueous phase was extracted with ether (200 mL×2). The combined organic phases were washed with brine, dried over sodium sulfate and concentrated in vacuo to give a residue. The residue was purified by chromatography (petroleum ether) to title compound as a colorless oil (55.8 g, 286 mmol, 87%).

¹HNMR (CDCl₃): 1.40 (t, 3H), 4.35 (m, 2H), 5.45 (d, 1H), 5.95 (d, 1H), 6.85-6.95 (m, 1H), 7.10 (m, 1H), 7.35 (m, 1H), 7.90 (m, 1H), 8.20 (m, 1H).

Preparation 55

Ethyl 3-cyclopropyl-4-fluorobenzoate

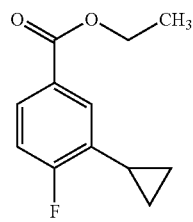

To a mixture of ethyl 4-fluoro-3-vinylbenzoate (Preparation 54, 48 g, 0.25 mol, 1 eq) and palladium (II) acetate (2.5 g, 10 mmol, 0.4 eq) in ether (300 mL) was added diazomethane in ether (1.5 mol, 6.0 eq). Then the mixture was stirred at room temperature overnight. The reaction was quenched with a solution of AcOH (75 mL) in water (100 mL). The mixture was filtrated and the filtrate was added saturated solution of sodium carbonate until pH=10. The organic phase was washed with brine (200 mL) and water (200 mL), dried over sodium sulfate and concentrated in vacuo to give title compound as brown liquid (51 g, 0.248 mol, 99.1%).

¹HNMR (CDCl₃): 0.7 (m, 2H), 0.95 (m, 2H), 1.40 (t, 3H), 2.0 (m, 1H), 4.35 (m, 2H), 6.95 (m, 1H), 7.55 (m, 1H), 7.75 (m, 1H).

Preparation 56

3-Cyclopropyl-4-fluoro-benzoic acid

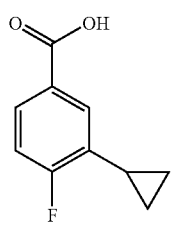 [SMILES: O=C(O)c1ccc(F)c(C2CC2)c1]

To a solution of compound 3 ethyl 4-fluoro-3-vinylbenzoate (Preparation 54, 87 g, 0.42 mol, 1 eq) in THF (470 mL) and water (400 mL) was added lithium hydroxide monohydrate (35.1 g, 0.84 mol, 2.0 eq). The resulting mixture was stirred at 40° C. overnight. THF was removed in vacuum, then 6N hydrogen chloride solution was added dropwise until pH=2. The mixture was extracted with ethyl acetate (3×600 mL). The organic phase was dried over sodium sulfate and concentrated in vacuo to give title compound as a white solid (60.8 g, 0.34 mol, 81%).

¹HNMR (CDCl₃): 0.7 (m, 2H), 0.95 (m, 2H), 2.0 (m, 1H), 7.0 (m, 1H), 7.60 (m, 1H), 7.85 (m, 1H).

Preparation 57

3-Cyclopropyl-4-fluoro-benzamide

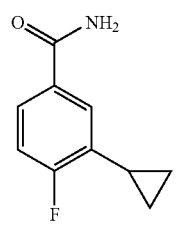 [SMILES: NC(=O)c1ccc(F)c(C2CC2)c1]

To a solution of compound 3-cyclopropyl-4-fluoro-benzoic acid (Preparation 56, 74 g, 0.41 mol, 1 eq) in THF (800 mL) was added N,N'-carbonyldiimidazole (88 g, 0.53 mol, 1.29 eq) at room temperature. The suspension was stirred at room temperature for 3 h, and turned into a brown solution. Ammonia/THF (1 L) was added to the mixture and the resulting mixture was stirred at room temperature overnight. THF was removed in vacuum and the residue was taken up with water (300 mL). The mixture was filtrated and the solid was washed with water (100 mL) and ether (200 mL). The solid was dissolved in DCM (500 mL), dried over sodium sulfate and concentrated in vacuum to title compound as a white solid (66 g, 0.368 mol, 89.7%).

¹HNMR (d₆-DMSO): 0.75 (m, 2H), 1.0 (m, 2H), 2.05 (m, 1H), 7.2 (m, 1H), 7.35 (s, 1H), 7.50 (m, 1H), 7.70 (m, 1H), 7.95 (s, 1H).

Preparation 58

1-(3-Cyclopropyl-4-fluorophenyl)methanamine

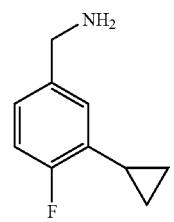 [SMILES: NCc1ccc(F)c(C2CC2)c1]

To a solution of 3-cyclopropyl-4-fluoro-benzamide (Preparation 57, 66 g, 0.37 mol, 1.0 eq) in THF (500 mL) was added portionwise lithium aluminium hydride (42 g, 1.1 mol, 3.0 eq) at 10° C. Then the mixture was stirred at room temperature overnight. Water (100 mL) was added dropwise to the reaction mixture at 10° C. and the mixture was filtrated. The solid was washed with THF (3×700 mL), and filtrate was dried over sodium sulfate and concentrated in vacuum to give crude. The crude product was purified by column chromatography (MeOH/DCM 1:100→1:40) to give title compound as a yellow liquid (42.27 g, 0.257 mol, 69.5%).

¹HNMR (CDCl₃): 0.65 (m, 2H), 0.90 (m, 2H), 1.40 (s, 2H), 1.95 (m, 1H), 6.75 (m, 1H), 6.90 (m, 1H), 6.95 (m, 1H). LCMS Rt=5.73 min. MS m/z 166 [MH]+.

Preparation 59

(3R*,4S*)-4-(4-Fluorophenyl)tetrahydrofuran-3-ol

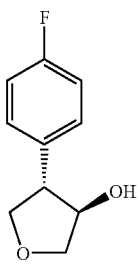 [SMILES: O[C@H]1COC[C@@H]1c1ccc(F)cc1]

1.6M BuLi/hexane (399 mL, 0.64 mol, 1.10 eq) was added to a solution of 1-bromo-4-fluorobenzene (70 mL, 0.64 mol, 1.10 eq) in absolute THF (400 mL) in a stream of argon at −90° C. for 1 h. The mixture was stirred at −90° C. for 30 min, cooled to −100° C., and 3,6-dioxabicyclo[3.1.0]hexane (50 g, 0.58 mol, 1 eq) was added. The mixture was stirred at −100° C. for 15 min, and borontrifluoride diethyletherate (81 mL, 0.64 mol, 1.10 eq) was added at the same temperature for 1 h so that the temperature was no higher than −80° C. The reaction mixture was heated to 0° C. for 3 h and diluted with hexane (300 mL) and water (300 mL). 10N sodium hydroxide (50 mL) was added, and the layers were separated. The aqueous layer was extracted with ether. The organic layer was washed with the saturated sodium chloride solution, dried over sodium sulfate, and evaporated. The mixture was subjected to chromatography on silica (1 L, carbon tetrachloride→25, 50, 75, 100% chloroform) to give title compound as a yellow oil (42 g, 0.23 mol, 39.7%).

Preparation 60

(3R*,4S*)-4-(4-Fluorophenyl)tetrahydrofuran-3-yl methanesulfonate

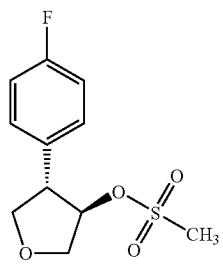 [SMILES: CS(=O)(=O)O[C@H]1COC[C@@H]1c1ccc(F)cc1]

Mesyl chloride (21.4 mL, 0.28 mol, 1.2 eq) was added dropwise to a mixture of compound (3S*,4S*)-4-(4-fluorophenyl)tetrahydrofuran-3-ol (Preparation 59, 42 g, 0.23 mol, 1 eq) and Et₃N (79.6 mL, 0.55 mol, 2.0 eq) in DCM (250 mL) under stirring on an ice bath for 30 min. The mixture was stirred at room temperature for 1 h and diluted with water (500 mL). The layers were separated. The organic layer was subjected to chromatography on silica (1 L, carbon tetrachloride→25, 50, 75, 100% chloroform→MeOH) to give title compound (40 g, 0.15 mol, 67%).

Preparation 61

(3S*,4R*)-3-Azido-4-(4-fluorophenyl)tetrahydrofuran

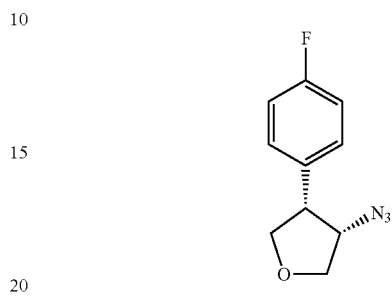

Sodium azide (30 g, 0.46 mol, 3.0 eq) was added under vigorous stirring to a mixture of compound (3S*,4S*)-4-(4-fluorophenyl)tetrahydrofuran-3-yl methanesulfonate (Preparation 60, 40 g, 0.15 mol, 1 eq) in dimethylsulfoxide (200 mL). The mixture was stirred on a water bath at 80 C for 4 h, cooled, diluted with water (700 mL), and extracted with ether (3×300 mL). The combined organic layer was washed with water (300 mL) and the saturated sodium chloride solution, dried over sodium sulfate, and rotary evaporated in the absence of vacuum at a bath temperature of 70° C. The residue was evaporated in water-aspirator vacuum at a bath temperature of 70° C. to give title compound (29.6 g, 0.14 mol, 94%).

Preparation 62

(3S*,4R*)-4-(4-Fluorophenyl)tetrahydrofuran-3-amine

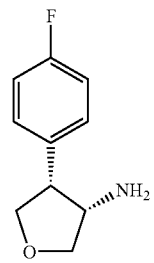 [SMILES: N[C@@H]1COC[C@@H]1c1ccc(F)cc1]

Triphenylphosphine (45 g, 0.17 mol, 1.20 eq) was added in portions to a solution of compound (3S*,4R*)-3-azido-4-(4-fluorophenyl)tetrahydrofuran (Preparation 61, 29.6 g, 0.14 mol, 1 eq) in THF (200 mL) on a water bath under stirring for 1 h. The mixture was stirred at room temperature for 2 h, and ammonia 880 (50 mL) was added. The mixture was refluxed for 2 h and cooled. Then concentrated hydrogen chloride (13 mL) was added, and the mixture was evaporated. The residue was diluted with water (150 mL) and extracted with carbon tetrachloride (3×200 mL). Then the aqueous layer was alkalized with the saturated potassium carbonate solution and extracted with chloroform (3×200 mL). The combined organic layer was dried and evaporated to give title compound as a yellow oil (17.82 g, 0.1 mol, 69%).

¹HNMR (CDCl₃): 1.55 (s, 2H), 3.45 (m, 1H), 3.65 (m, 1H), 3.75 (m, 1H), 4.05-4.25 (m, 3H), 7.05 (m, 2H), 7.20 (m, 2H). LCMS Rt=6.80 min. MS m/z 122 [MH]+.

Preparation 63

Methyl 5-oxopyrrolidine-3-carboxylate

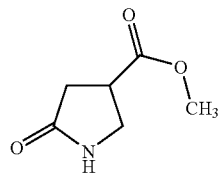

To a solution of 2-methylene-succinic acid dimethyl ester (158 g, 1 mol, 1 eq) in MeOH (150-160 mL) was added dropwise anhydrous liquid ammonia (17 g, 1 mol, 1 eq). The mixture was stirred at room temperature for 1.5-2 h, keeping the outlet of the flask connected with a small mercury trap (1-2 cm Hg), and left to stand overnight. Most part of MeOH was evaporated on a water bath and then residual MeOH was evaporated in vacuo until the mixture transformed into a semisolid mass. This mass was distilled in vacuo. Starting compound was distilled (bp 60-70° C. at 1 mm Hg) followed by distillation of title compound (bp 140-150° C. at 1 mm Hg) as colorless liquid, which crystallized very fast (72 g, 0.5 mol, 50%).

Preparation 64

Pyrrolidin-3-ylmethanol

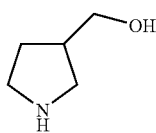

Lithium aluminium hydride (24 g, 0.63 mol, 2 eq) was added slowly in portions under cooling to THF (225 mL). To the suspension obtained was added dropwise under vigorous stirring and slight heating over a period of 1-1.5 h a solution of methyl 5-oxopyrrolidine-3-carboxylate (Preparation 63, 45 g, 0.315 mol, 1 eq) in THF (110 mL) keeping the solvent simmered. After the addition was completed the mixture was refluxed under stirring for 4.5-5 h and left to stand overnight. Then water (23 mL) was added dropwise under stirring and cooling to quench the reaction. The mixture was filtered on a Buchner funnel. The gray layer of aluminates was washed with THF/isopropanol (1:1) mixture (3-4×70-80 mL). The filtrate and extracts were combined and solvents were evaporated in vacuo. Yellowish oily residue was distilled in vacuo (bath temperature was not higher 100° C.) to give title compound as a colorless viscous liquid (bp 80-83° C. at ~1 mm Hg) (16 g, 0.16 mol, 50%).

Preparation 65 tert-Butyl 3-(hydroxymethyl)pyrrolidine-1-carboxylate

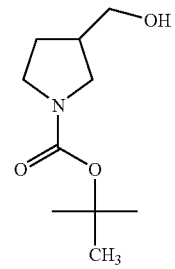

To a boiled solution of pyrrolidin-3-ylmethanol (Preparation 64, 52.4 g, 0.518 mol, 1 eq) in THF (200 mL) was added dropwise under stirring a solution of di-tert-butyl carbonate (114.2 g, 0.523 mol, 1.01 eq) in THF (100-10 mL) during 1.5 h. After carbon dioxide evolution ceased, the mixture was refluxed for 2.5-3 h and cooled to give a yellowish solution. Solvents were removed on a rotary evaporator from this solution. Yellowish viscous oily residue was vacuum-dried to constant weight to give title compound (104 g, 0.518 mol, 100%).

Preparation 66 tert-Butyl 3-[(cyclopropylmethoxy)methyl]pyrrolidine-1-carboxylate

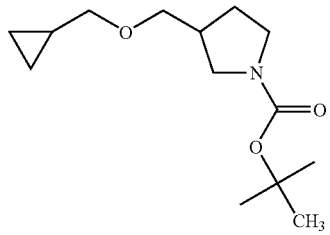 [SMILES: CC(C)(C)OC(=O)N1CCC(COCC2CC2)C1]

To a solution of tert-butyl 3-(hydroxymethyl)pyrrolidine-1-carboxylate (Preparation 65, 46.6 g, 0.232 mol, 1 eq) in anhydrous dimethylformamide (250 mL) was added in portions with stirring and under an atmosphere of argon a dispersion in oil of sodium hydride (11.2 g, 0.28 mol, 1.2 eq) in oil. The mixture was stirred for 45 min and then (chloromethyl)cyclopropane (26 mL, 0.28 mol, 1.2 eq) in anhydrous THF (30 mL) was added. The mixture was stirred for 12 h and then treated with water (100 mL) and extracted with ether (3×200 mL). Ether fractions were washed with water (2×100 mL), dried over sodium sulfate and evaporated. The residue was subjected to chromatography (chloroform/ethylacetate 10:1) on silica to afford title compound (50 g, 0.195 mol, 84%).

Preparation 67

3-Cyclopropylmethoxymethyl-pyrrolidine

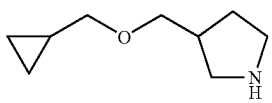 [SMILES: C1CC(COCC2CC2)CN1]

tert-Butyl 3-[(cyclopropylmethoxy)methyl]pyrrolidine-1-carboxylate (Preparation 66, 50 g, 0.2 mol, 1 eq) was dissolved in isopropanol (200 mL) and treated with concentrated hydrogen chloride solution (28 mL, 0.3 mol, 1.5 eq). The mixture was refluxed for 1 h and evaporated. The residue was dissolved in water and washed with ether (2×100 mL). The aqueous fraction was made alkaline with potassium carbonate to pH 12-13 and extracted with chloroform. The extract was dried over sodium sulfate and evaporated to give title compound (20 g, 0.129 mol, 65%).

$^1$HNMR (d$_6$-DMSO): 0.14 (m, 2H), 0.45 (m, 2H), 0.97 (m, 1H), 1.25 (m, 1H), 1.72 (m, 1H), 2.18 (m, 1H), 2.45 (m, 1H), 2.65 (m, 1H), 2.77 (m, 2H), 3.25 (m, 4H), 8.32 (s, NH). MS m/z 156 [MH]+.

Preparation 68 tert-Butyl 3-{[(methylsulfonyl)oxy]methyl}piperidine-1-carboxylate

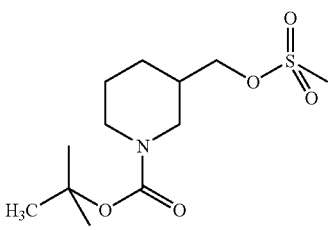 [SMILES: CC(C)(C)OC(=O)N1CCCC(COS(C)(=O)=O)C1]

Di-t-butyl dicarbonate (595.14 g, 2.73 mol, 1.05 eq) was slowly added to a solution of piperidin-3-ylmethanol (300.0 g, 2.60 mol, 1 eq), sodium hydroxide (124.8 g, 3.12 mol, 1.2 eq), DCM (1.5 L) and water (800 mL) while maintaining the internal temperature below 10° C. with an ice-water bath. The reaction was warmed to room temperature and stirred for 24 h. The mixture was filtered and sodium bisulfate was added until the solution was acidic (pH 3). The phases were separated, and the organic phase was washed with water (600 mL) and brine (600 mL). The solution was dried over sodium sulfate, and the solvent removed under vacuum to afford t-butyl 3-(hydroxymethyl)piperidine-1-carboxylate as a colorless oil. Crude t-butyl 3-(hydroxymethyl)piperidine-1-carboxylate was dissolved in DCM (1.5 L), Et$_3$N (315.71 g, 3.12 mol, 1.2 eq) was added, and the reaction vessel was flushed with nitrogen. The reaction mixture was cooled to below 0° C. in a dry ice/isopropyl alcohol bath and methanesulfonyl chloride (357.4 g, 3.12 mol, 1.2 eq) was slowly added. After the addition was complete, the reaction was warmed to ambient temperature and stirred for 24 h. The reaction mixture was filtered, washed with water (500 mL) and saturated sodium bicarbonate (500 mL), and dried over sodium sulfate. The solvent was removed under vacuum, and the yellow oil was added to hexane (2.5 L) and stirred for 3 h. The precipitate was filtered and washed with hexane (700 mL) to afford title compound as a white solid (609.11 g, 2.08 mol, 80%).

Preparation 69 tert-Butyl 3-(iodomethyl)piperidine-1-carboxylate

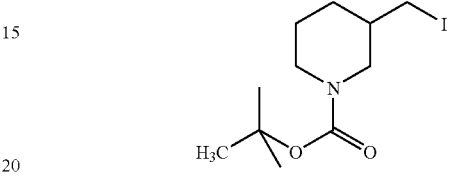

t-Butyl 3-{[(methylsulfonyl)oxy]methyl}piperidine-1-carboxylate (Preparation 68, 609.22 g, 2.08 mol, 1 eq) was dissolved in acetone (3 L), and the reaction mixture was flushed with nitrogen. Sodium iodide (619.84 g, 4.16 mol, 2 eq) was added, and the reaction was stirred at reflux (58° C.) under nitrogen. The reaction mixture was cooled to room temperature, filtered, and the solvent removed under vacuum. The residue was re-dissolved in diethyl ether (1.5 L), and this solution was washed with water (500 mL), saturated sodium bicarbonate (400 mL), 5% sodium thiosulfate (400 mL), and brine (400 mL). The solution was dried over sodium sulfate, and the solvent was removed under vacuum to afford title compound as a yellow oil (616 g, 1.89 mol, 91%).

Preparation 70 tert-Butyl 3-(pyrimidin-2-ylmethyl)piperidine-1-carboxylate

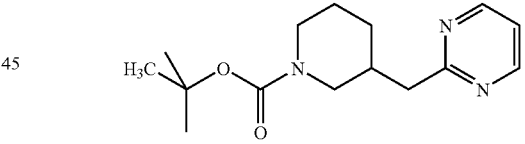

A 1 L, 3-neck round bottom flask, equipped with magnetic stirring bar, thermometer, nitrogen gas inlet, and addition funnel was charged with Zn dust (66 g, 1.01 mol, 3 eq). The flask was evacuated and filled with nitrogen three times. On the third evacuation the flask was thoroughly heated with a heat gun, and then allowed to cool to room temperature. Anhydrous THF (120 mL) and 1,2-dibromoethane (19.7 g, 104.8 mmol, 0.3 eq) were charged and the mixture stirred under nitrogen at 65° C. for 10 min. The reaction was cooled to room temperature, and chlorotrimethylsilane (2.6 g, 23.7 mmol, 0.07 eq) was added and the reaction stirred at room temperature for 45 min. A solution of tert-butyl 3-(iodomethyl)piperidine-1-carboxylate (Preparation 69, 110 g, 338.2 mmol, 1 eq) in THF (60 mL and 20 mL to wash the flask) was added through an addition funnel and the mixture was stirred at room temperature for 45 min (NOTE: fast exothermic reaction which, if necessary, can be controlled by means of an ice/water bath). Then a solution of 2-chloropyrimidine (32.5 g, 284 mmol, 0.84 eq) in THF (80 mL+20 mL to wash the flask) was added followed by bis(dibenzylidene acetone) palladium (0) (9.3 g, 10 mmol, 0.03 eq), and tri-o-tolylphosphine (4.1 g, 13.5 mmol, 0.04 eq) and the reaction mixture was heated at 65° C. for 2 h then allowed to cool to room temperature and stirring was continued at room temperature for 17 h. The reaction mixture was diluted with ethyl acetate (1.2 L) and filtered through Celite. The Celite cake was thoroughly washed with ethyl acetate until the filtrate was no longer ultra-violet absorbent, the organic filtrates were combined and washed with a 10% solution of ammonium chloride (2×250 mL), dried over sodium sulfate, filtered and concentrated under reduced pressure to afford a brown residue that was purified through flash chromatography (Biotage). The fractions eluted with ethyl acetate:hexanes (40:60 v/v) were combined and concentrated in vacuo to title compound as a slightly yellow solid (27.3 g, 98.4 mmol, 34.6%).

Preparation 71

2-(Piperidin-3-ylmethyl)pyrimidine

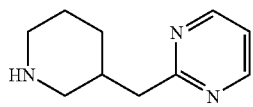 [SMILES: c1cnc(CC2CCCNC2)nc1]

To a solution of tert-butyl 3-(pyrimidin-2-ylmethyl)piperidine-1-carboxylate (Preparation 70, 27.3 g, 98.4 mmol, 1 eq) in diethyl ether (160 mL) and DCM (50 mL) was added dropwise a 2M solution of hydrogen chloride in diethyl ether (246 mL, 492 mmol, 5 eq) while maintaining the internal temperature below 30° C. The reaction mixture was stirred at room temperature for 20 h. The solvent was decanted and fresh diethyl ether (300 mL) added. The solid was collected by filtration and washed with diethyl ether (3×100 mL) then dissolved in water (150 mL). The aqueous layer was washed with DCM (2×150 mL), basified with sodium hydroxide pellets to pH 13-14 and extracted with DCM (5×200 mL). The organic layer was separated, dried over sodium sulphate, filtered and concentrated under reduced pressure to afford title compound (15 g, 84.6 mmol, 86%).

$^1$HNMR (d$_6$-DMSO): 1.07 (m, 1H), 1.31 (m, 1H), 1.52 (m, 1H), 1.64 (m, 1H), 1.97 (m, 1H), 2.21 (m, 1H), 2.39 (m, 1H), 2.70 (m, 2H), 2.81 (m, 2H), 7.32 (t, 1H), 8.71 (d, 2H). MS m/z 178 [MH]+.

Preparation 72

5-(Piperidin-3-ylmethyl)pyrimidine

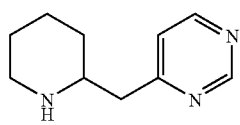 [SMILES: c1cc(CC2CCCCN2)ncn1]

Made in an analogue manner to 2-(piperidin-3-ylmethyl) pyrimidine using 5-bromopyrimidine with tert-butyl 3-(iodomethyl)piperidine-1-carboxylate.

$^1$HNMR (d$_6$-DMSO): 1.21 (m, 1H), 1.50-1.87 (m, 3H), 2.01 (m, 1H), 2.52 (m, 1H), 2.61 (m, 2H), 2.76 (m, 1H), 3.08-3.25 (m, 2H), 8.71 (s, 2H), 9.01 (s, 1H). MS m/z 178 [MH]+.

Preparation 73

5-Oxo-bicyclo[2.2.2]octane-2-carboxylic acid methyl ester

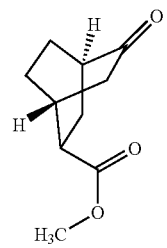

To a cooled (−3° C.) solution of lithiumdiisopropylamide (0.9 M in methylcyclohexane, 607 mL, 546 mmol, 1.05 eq) was added a solution of cyclohex-2-enone (52.6 g, 53 mL, 520 mmol, 1.0 eq) in diethyl ether (650 mL) over 90 min. During addition, the temperature was kept below −3° C. The mixture was stirred for an additional 25 minutes before a solution of methyl acrylate (46.8 mL, 520 mmol, 1.0 eq) in diethyl ether (450 mL) was added dropwise over 60 minutes. The temperature of the mixture was kept below 0° C. overnight. The mixture was poured out in saturated solution of ammonium chloride (1.0M) and stirred for 10 min. The sticky polymer was removed by filtration (P3). The organic layer was separated and the aqueous layer was extracted with tert-butyl methyl ether (2×300 mL). The combined organic layers were dried over sodium sulfate and concentrated. The title compound was isolated by distillation (0.001 mbar at 120-130° C.) and was isolated as a slightly yellow oil (39.8 g, 220 mmol, 42%).

Preparation 74

5-Oxo-bicyclo[2.2.2]octane-2-carboxylic acid

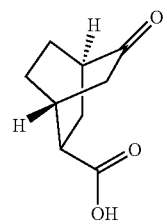

5-Oxo-bicyclo[2.2.2]octane-2-carboxylic acid methyl ester (Preparation 73, 390 g, 2.14 mol, 1.0 eq) was taken up in a mixture of THF:MeOH:water (2:2:1, 2.0 L). A solution of lithiumhydroxide monohydrate (198 g, 4.71 mol, 2.2 eq) in water (1.0 L) was added dropwise while a dark green solution emerged. The temperature was kept below 30° C. by cooling with a waterbath. The reaction mixture was washed with DCM (2×500 mL). The combined organic layers were extracted with water (300 mL). The combined aqueous layers were brought to pH ~1 with concentrated HCl solution and subsequently extracted with DCM (4×300 mL). The combined organic layers were dried over sodium sulfate and the solvent was removed under reduced pressure and stripped with toluene (2×). This furnished title compound as a brownish solid (314 g, 1.87 mol, 87%).

Preparation 75

(5-Oxo-bicyclo[2.2.2]oct-2-yl)-carbamic acid tert-butyl ester

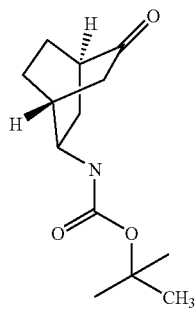 [SMILES: CC(C)(C)OC(=O)NC1C[C@H]2CC[C@@H]1CC2=O]

5-Oxo-bicyclo[2.2.2]octane-2-carboxylic acid (Preparation 74, 314 g, 1.87 mol, 1.0 eq) was taken up in tert-butanol (1.8 L) and cooled to 17° C. Et$_3$N (289 mL, 2.06 mol, 1.1 eq) was added dropwise while the temperature was kept below 21° C. After addition, the reaction mixture was stirred for an additional 90 minutes before diphenylphosphoryl azide (405 mL, 1.87 mol, 1.0 eq) was added in a dropwise fashion over 45 minutes while nitrogen gas evolves. After addition the reaction mixture was heated to 40° C. with a waterbath overnight and more nitrogen gas evolved. The reaction mixture was heated to reflux for 5½ hours after which the mixture was concentrated to ~1.5 L at 55° C. The residue was parted between water (2.0 L) and tert-butyl methyl ether (1.0 L). The aqueous layer was extracted with tert-butyl methyl ether (4×500 mL). The combined organic layers were washed with water (500 mL), 1M sodium hydroxide solution (500 mL) and water (500 mL). The combined aqueous layers were extracted with diethyl ether (500 mL). The combined organic layers were dried over sodium sulfate and concentrated at 40° C. to give a tan solid (279 g, 1.17 mol, 63%).

Preparation 76

5-Amino-bicyclo[2.2.2]octan-2-one trifluoro-acetic acid salt

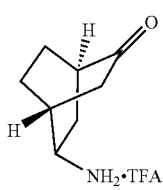

(5-Oxo-bicyclo[2.2.2]oct-2-yl)-carbamic acid tert-butyl ester (Preparation 75, 279 g, 1.17 mol, 10 eq) was taken up in DCM (450 mL). TFA (416 mL, 5.60 mol, 4.8 eq) was added dropwise. On addition, the reaction warms to reflux while much gas evolves. The reaction mixture was kept at reflux temperature for 1 hour after which it was allowed to cool to room temperature overnight. The mixture was concentrated and the residue was taken up in DCM (50 mL) and then tert-butyl methyl ether (1.3 L) was added which resulted in a brown suspension. The solids were collected by filtration (P3) and were washed with tert-butyl methyl ether. The latter was dried in vacuo (40° C.) to furnish title compound as an off-white solid (272 g, 1.07 mol, 92%).

Preparation 77

5-Phenyl-4-aza-tricyclo[4.3.1.0$^{3,7}$]decan-10-one trifluoro-acetic acid salt

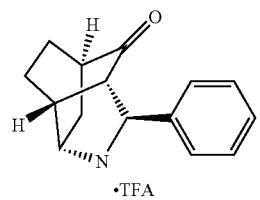 [SMILES: O=C1[C@@H]2CC[C@@H]3[C@H]1[C@@H](c1ccccc1)N[C@H]3C2]

A three neck 3 L flask, fitted with a well isolated soxhlet (300 mL) filled with molecular sieves (3 Å), was charged with 5-amino-bicyclo[2.2.2]octan-2-one trifluoro-acetic acid salt (Preparation 76, 85.0 g, 336 mmol, 1.0 eq), benzaldehyde (37.5 mL, 369 mmol, 1.1 eq) and DCM (1.25 L). The suspension was heated to reflux. The clear reaction mixture was concentrated to a tan solid. The latter was suspended in a mixture of diethyl ether (600 mL) and EtOH (50 mL). The solids were collected by filtration (P3) and thoroughly washed with ethyl acetate and diethyl ether. The filter cake was dried in vacuo to yield title compound as an off-white solid (104 g, 305 mmol, 91%, 97.3% pure (HPLC)).

Preparation 78 tert-Butyl 6-methylene-1,4-oxazepane-4-carboxylate

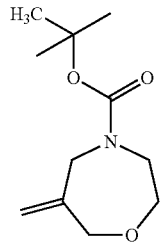

60% Sodium hydride in oil (26 g, 0.65 mol, 2.17 eq) was added in one portion in a stream of argon at 5° C. to a solution of 3-chloro-2-(chloromethyl)prop-1-ene (35 mL, 0.3 mol, 1 eq) in dimethylformamide (500 mL). Then a solution of tert-butyl (2-hydroxyethyl)carbamate (48.3 g, 0.3 mol, 1 eq) in THF (500 mL) was added, and the reaction mixture was heated to 25° C. and stirred at this temperature for 2 h. The reaction mixture was then neutralized with glacial AcOH (4.5 mL) and evaporated in a water aspirator in vacuo at 45-55° C. using a 15-cm reflux condenser. The residue was poured with water (300 mL) and extracted with a mixture of ethylacetate (200 mL), hexane (100 mL) and chloroform (50 mL). The organic layer was separated and washed with water (2×100 mL) and brine. The combined aqueous layer was extracted with a mixture of ethylacetate (150 mL) and hexane (50 mL). The organic layer was separated and washed with water (2×100 mL) and brine. The extracts were filtered sequentially through silica gel (25 g) and sodium sulphate (50 mL), eluting with chloroform (100 mL). The filtrate was evaporated, and the residue was distilled in vacuo to give title compound as a colorless oil (bp 76-79° C. at 0.7 mm Hg) (35.8 g, 0.168 mol, 53%).

Preparation 79 tert-Butyl 6-(hydroxymethyl)-1,4-oxazepane-4-carboxylate

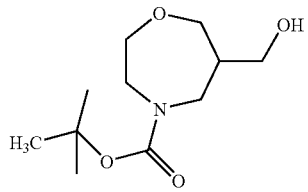 [SMILES: CC(C)(C)OC(=O)N1CCOCC(CO)C1]

1M borane in THF (450 mL, 0.45 mol, 0.9 eq) was added under stirring and cooling on an ice bath to a stirred in a stream of argon solution of tert-butyl 6-methylene-1,4-oxazepane-4-carboxylate (Preparation 79, 107 g, 0.5 mol, 1 eq) in THF (300 mL). The reaction mixture was heated to 25° C. and stirred at this temperature for 3 h. Then the reaction mixture was cooled to 0-10° C. and treated at this temperature sequentially with 3N sodium hydroxide (170 mL) and 30% hydrogen peroxide (66 mL). The obtained homogenous mixture was stirred overnight, then treated with hexane (45 mL), and dried over potassium carbonate. The organic layer was decanted from the precipitate, which was washed with DCM. The organic layers were evaporated in vacuo, and the residue was purified rapidly (due to instability of the product on silica gel) by chromatography (carbon tetrachloride/chloroform/isopropanol 100:0:0→0:100:0→0:90:10) on silica gel (1.2 kg; 63-100 μm) to give title compound as a colorless oil in (85 g, 0.368 mol, 72%).

Preparation 80 tert-Butyl 6-[(cyclopropylmethoxy)methyl]-6-hydroxy-1,4-oxazepane-4-carboxylate

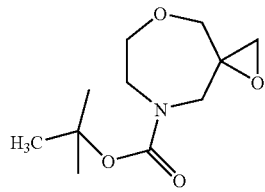 [SMILES: CC(C)(C)OC(=O)N1CCOCC2(CO2)C1]

70-75% m-Chlorobenzenecarboperoxoic acid (145 g, 0.59 mol, 1.2 eq) was added in portions to a stirred solution of tert-butyl 6-(hydroxymethyl)-1,4-oxazepane-4-carboxylate (Preparation 79, 107 g, 0.5 mol, 1 eq) in DCM (1.0 L) that caused heating of the mixture. The reaction mixture was stirred for 24 h at room temperature, then diluted with hexane (500 mL) and filtered. The separated precipitate was washed on a filter with DCM/hexane mixture, and the combined filtrate was washed with aqueous potassium carbonate, dried over sodium sulfate, and evaporated. The residue was vacuum-dried to give title compound (117 g, 0.51 mol, 96%).

Preparation 81 tert-Butyl 6-benzyl-6-hydroxy-1,4-oxazepane-4-carboxylate

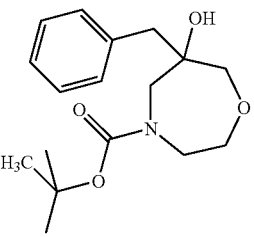 [SMILES: CC(C)(C)OC(=O)N1CCOCC(O)(Cc2ccccc2)C1]

1.6M solution of butyl lithium in hexane (150 mL, 0.24 mol, 1.1 eq) was added to a solution of bromobenzene (25.3 mL, 0.24 mol, 1.1 eq) in THF (200 mL) at −60° C. in a stream of argon. The reaction mixture was cooled to −80° C., and a solution of tert-butyl 6-[(cyclopropylmethoxy)methyl]-6-hydroxy-1,4-oxazepane-4-carboxylate (Preparation 80, 50 g, 0.22 mol, 1 eq) in THF was added. Then the mixture was cooled to −100° C., and a solution of etherate (30.4 g, 0.24 mol, 1.1 eq) was added at this temperature for 30 min. The reaction mixture was heated to 0° C. for 5 h, and 5M sodium hydrogen sulfate solution (50 mL) was added. The organic layer was separated, evaporated, and the residue was distributed between water and ether. The organic layer was separated, washed with water and brine, dried, evaporated, and the residue was dissolved in MeOH (200 mL). Ethylenediamine (30 mL) was added to the mixture, which was heated until boiled, cooled, evaporated, and coevaporated with dioxane. The residue was purified by chromatography on silica (1 L; carbon tetrachloride→chloroform, then MeOH 5%), evaporated and dried to give title compound (37.15 g, 0.12 mol, 55%).

Preparation 82

6-Benzyl-1,4-oxazepan-6-ol hydrochloride

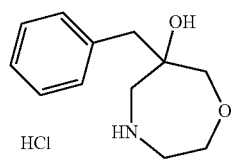

tert-Butyl 6-benzyl-6-hydroxy-1,4-oxazepane-4-carboxylate (Preparation 81, 37.15 g, 0.12 mol, 1 eq) was dissolved in dioxane (200 mL), and 4M hydrogen chloride/dioxane (60.4 mL, 0.24 mol, 2 eq) was added. The mixture was stirred for 24 h, evaporated, and coevaporated with ether. The formed precipitate was washed with ether and dried to title compound (27.3 g, 0.11 mol, 93%)

$^1$HNMR (d$_6$-DMSO): 2.75 (s, 2H), 2.90 (m, 1H), 3.10 (m, 1H), 3.16-3.36 (m, 2H), 3.61 (m, 2H), 3.76 (m, 1H), 3.92, (m, 1H), 5.57 (broad s, 1H), 7.26 (m, 5H). MS m/z 208 [MH]+. .

Preparation 83 tert-Butyl 6-[(6-methylpyridin-2-yl)methyl]-1,4-oxazepane-4-carboxylate

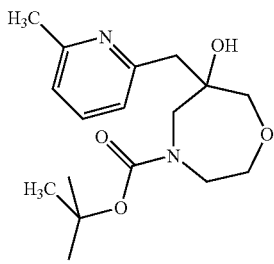 [SMILES: Cc1cccc(CC2(O)COCCN(C(=O)OC(C)(C)C)C2)n1]

0.5M 9-Borobicyclo[3.3.1]nonane in THF (415 mL, 0.21 mol, 1.1 eq) was added under stirring in a stream of argon at room temperature to tert-butyl 6-[(cyclopropylmethoxy)methyl]-6-hydroxy-1,4-oxazepane-4-carboxylate (Preparation 80, 40 g, 0.19 mol, 1 eq). The reaction mixture was stirred at room temperature for 2 h. After this, the catalyst palladium (0) tetrakis(triphenylphosphine) (4 g, 0.003 mol, 0.02 eq) and 2-bromo-6-methylpyridine (36 g, 0.21 mol, 1.1 eq) were added to the mixture, and the latter was stirred for 15 min. Then 3M potassium carbonate solution (125 mL, 0.38 mol, 2 eq) was added, and the reaction mixture was refluxed for 3 h. The mixture was cooled, diluted with hexane (300 mL) and DCM (100 mL). The organic layer was separated, washed with water (2×100 mL), and with the saturated sodium chloride solution. The combined aqueous layer was extracted with ethyl acetate/hexane (3:1) mixture (2×200 mL). The organic layers were sequentially filtered through silica (25 g; 63-100 μm) and sodium sulphate (50 g) and evaporated. The residue was subjected to chromatography (carbon tetrachloride/chloroform/isopropanol 100:0:0→90:10:0→70:30:0→50:50:0→30:70:0→0:100:0→0:99:1→0:98:2→0:97:3→0:95:5→0:93:7→0:92:8→0:90:10) on silica (500 g; 63-100 μm). The fractions, containing the product, were collected and evaporated to give title compound as a light oil in (42.5 g, 0.14 mol, 74%).

Preparation 84

6-[(6-Methylpyridin-2-yl)methyl]-1,4-oxazepane dihydrochloride

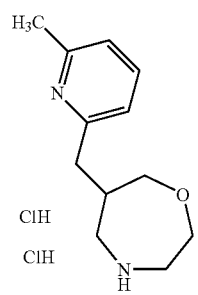

tert-Butyl 6-[(6-methylpyridin-2-yl)methyl]-1,4-oxazepane-4-carboxylate (Preparation 83, 42.5 g, 0.14 mol, 1 eq) was dissolved in isopropanol (250 mL), concentrated hydrogen chloride (38 mL, 0.42 mol, 3 eq) was added under stirring, and the mixture was refluxed for 2 h. The reaction mixture was then evaporated, and the residue was coevaporated twice with isopropanol. The product was crystallized from isopropanol, and the crystals were washed with diethylether/isopropanol (3:1) mixture and ether and finally vacuum-dried to give title compound as white crystals (32.3 g, 0.12 mol, 82%).

$^1$HNMR (d$_6$-DMSO): 2.72-2.85 (m, 4H), 2.98-3.29 (m, 6H), 3.53 (m, 1H), 3.87 (m, 3H), 8.32 (m, 1H), 9.40 (m, 1H), 9.66 (m, 1H). MS m/z 207 [MH]+.

Preparation 85

6-Chloro-N-[4-(trifluoromethyl)benzyl]nicotinamide

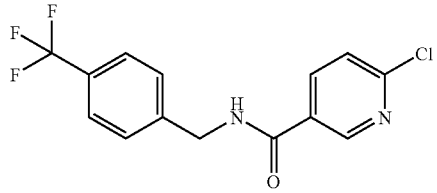 [SMILES: O=C(NCc1ccc(C(F)(F)F)cc1)c1ccc(Cl)nc1]

To a mixture of 6-chloronicotinic acid (2.0 g, 13 mmol) and HBTU (4.8 g, 13 mmol) in DMF (20 mL, 200 mmol) at 0° C. were added N,N-diisopropylethylamine (6.6 mL, 38 mmol) and 4-(trifluoromethyl)benzylamine (2.2 mL, 15 mmol). The reaction mixture was slowly warmed to ambient temperature. The reaction mixture was quenched with an equal volume of saturated aqueous sodium bicarbonate and extracted with ethyl acetate (3×). The combined organic layers were washed successively with water, aqueous lithium chloride, and brine, dried over sodium sulfate, filtered and concentrated in vacuo. The residue was purified on the Isco (120 g cartridge, chloroform to 12% MeOH in chloroform). The product was not thoroughly dried proceeding to the next reaction. Assumed 100% conversion.

MS m/z 315 [M+H]+.

Preparation 86

6-Mercapto-N-[4-(trifluoromethyl)benzyl]nicotinamide

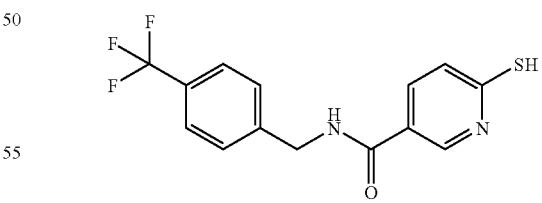

6-Chloro-N-(4-trifluoromethyl-benzyl)-nicotinamide (Preparation 85, 4.0 g, 13 mmol) was added to a warm solution of thiourea (1.01 g, 13.2 mmol) in EtOH (20 mL, 300 mmol). The mixture was heated 1 h at reflux. LC/MS indicated mostly SM. 1 additional equivalent of thiourea was added, and the reaction mixture was heated at reflux. After 16 h, LC/MS shows conversion to the intermediate along with a small amount of product. The reaction mixture was concentrated in vacuo. To the intermediate 6-carbamimidoylsulfanyl-N-(4-trifluoromethyl-benzyl)-nicotinamide; hydrochloride in water (32 mL, 1800 mmol) was added sodium carbonate (1.07 g, 10.1 mmol). After stirring for 15 minutes, sodium hydroxide (1.61 g, 40.3 mmol) in water (2.0E1 mL, 1100 mmol) was added. The reaction mixture was filtered, and the filtrate was slowly acidified with 6 N HCl. The resulting precipitate was collected by filtration, washed with water, and dried under vacuum to afford the product as a bright yellow solid (3.58 g, 86%).
MS m/z 313 [M+H]+.

Preparation 87

5-([[[4-(Trifluoromethyl)benzyl]amino]carbonyl)pyridine-2-sulfonyl chloride

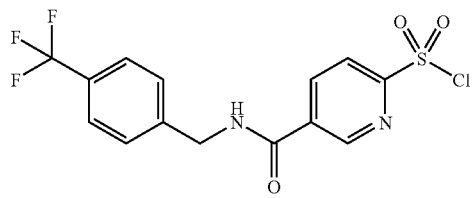 [SMILES: O=C(NCc1ccc(C(F)(F)F)cc1)c1ccc(S(=O)(=O)Cl)nc1]

6-Mercapto-N-(4-trifluoromethyl-benzyl)-nicotinamide (Preparation 86, 2.0 g, 6.4 mmol) was added to cooled to 0° C. 37% HCl (37:63, hydrogen chloride:water, 8.1 mL) and water (2 mL, 100 mmol). Chlorine (400 g, 6000 mmol) gas was bubbled into the solution for 1 h at 0° C. The reaction mixture was slowly poured on ice-water. The sulfonyl chloride was filtered, washing with water to afford a white solid. The product was dried overnight under vacuum to provide a white powder (1.65 g, 68%).

Preparation 88

6-{[(2,4-Dimethoxybenzyl)(1,3-thiazol-2-yl)amino]sulfonyl}-N-[4-(trifluoromethyl)benzyl]nicotinamide

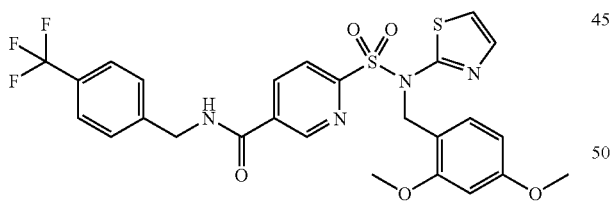

(2,4-Dimethoxy-benzyl)-1,3-thiazol-2-yl-amine (Preparation 6, 1.31 g, 5.25 mmol) was dissolved in THF (20 mL, 200 mmol) and cooled in an ice bath. 1.0 M of lithium hexamethyldisilazide in THF (11 mL) was added dropwise to the reaction. After addition was complete, the reaction mixture was warmed to rt. After 30 min, a solution of 5-(4-chloro-benzylcarbamoyl)-pyridine-2-sulfonyl chloride (1.65 g, 4.78 mmol) in THF (10 mL, 100 mmol) was added dropwise. The reaction mixture was stirred 4 h then quenched with saturated aqueous ammonium chloride. The reaction mixture was concentrated in vacuo. The residue was taken up in ethyl acetate (100 mL) and additional saturated aqueous ammonium chloride was added. The layers were separated, and the aqueous layer was extracted with ethyl acetate (2×100 mL). The combined organic layers were washed with brine. The resulting solution was treated with activated carbon, dried over sodium sulfate, filtered through Celite, and concentrated in vacuo. The residue was purified on the Isco (120 g SiO₂ cartridge, hexanes to ethyl acetate) to afford the product as a viscous oil (1.19 g, 39%).

Preparation 89 tert-Butyl (2S)-2-[(3-chlorophenoxy)methyl]pyrrolidine-1-carboxylate

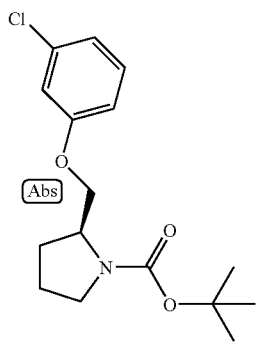 [SMILES: CC(C)(C)OC(=O)N1CCC[C@H]1COc1cccc(Cl)c1]

A solution of diisopropyl azodicarboxylate (1.4 mL, 7.1 mmol) in THF (3.5 mL, 44 mmol) was slowly added to a 0° C. solution of BOC-PRO-OL (1.0 g, 5.0 mmol), 3-chlorophenol (0.68 g, 5.2 mmol) and triphenylphosphine (1.5 g, 5.8 mmol) in THF (17 mL, 210 mmol). The reaction mixture was warmed to ambient temperature. After 3 h the reaction mixture was quenched with 1 N NaOH and extracted with methylene chloride (3×). The combined organic layers were washed with brine, dried over sodium sulfate, filtered and concentrated in vacuo. The residue was purified on the Isco (120 g cartridge, hexanes to ethyl acetate).

Preparation 90

(2S)-2-[(3-Chlorophenoxy)methyl]pyrrolidine hydrochloride

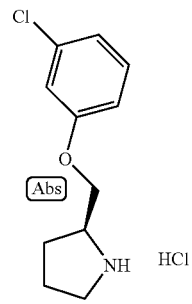 [SMILES: Clc1cccc(OC[C@@H]2CCCN2)c1 ; Cl]

tert-Butyl (2S)-2-[(3-chlorophenoxy)methyl]pyrrolidine-1-carboxylate (Preparation 89, 1.50 g, 4.81 mmol) was stirred with 4 M of hydrogen chloride in 1,4-dioxane (10 mL). After 2 h, the reaction mixture was concentrated in vacuo (TLC analysis showed only baseline material in 3:1 hexanes-ethyl acetate).

Preparation 91

2-(4-Fluorophenoxy)-2-methylpropan-1-amine

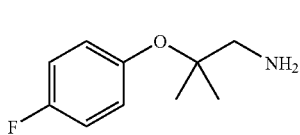

Into a 1 L-single neck round-bottom flask was added 2-(4-fluorophenoxy)-2-methylpropanoic acid (5.10 g, 0.0257 mol), methylene chloride (66.0 mL, 1.03 mol), oxalyl chloride (3.27 mL, 0.0386 mol) and N,N-dimethylformamide (20 µL, 0.0003 mol). The reaction was stirred until bubbling had stopped. Volatiles were removed and crude product then dissolved in DCM and 15 mL of 7N ammonia in MeOH was added. Volatiles were removed and crude product then dissolved in DCM and 15 mL of 7N ammonia in MeOH was added. Borane-dimethyl sulfide complex (5.7 mL, 0.064 mol) was added to the amide in THF (50 mL, 0.6 mol) at room temperature. The reaction was heated at 65° C. overnight. MeOH was added carefully. 1 N HCl was added and was heated at 65° C. for 2 hours. The reaction was concentrated in vacuo. The solid was dissolved in water and was washed with DCM. The aq. layer was basified with 1 N NaOH. The reaction was extracted with DCM. The reaction was dried with MgSO$_4$ and concentrated in vacuo to afford the title compound.

Preparation 92

4-Amino-N-{[1-(4-chlorophenyl)cyclopropyl]methyl}-3-fluorobenzamide

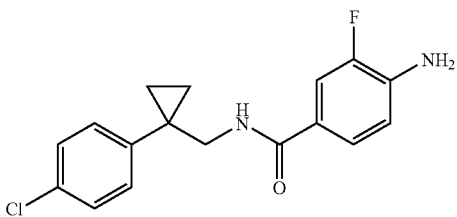 [SMILES: Nc1ccc(C(=O)NCC2(c3ccc(Cl)cc3)CC2)cc1F]

To a mixture of 4-amino-3-fluorobenzoic acid (180.0 mg, 1.160 mmol) and N,N,N',N'-tetramethyl-O-(7-azabenzotriazol-1-yl)uronium hexafluorophosphate (HATU, 0.44 g, 1.2 mmol) in N,N-dimethylformamide (2 mL, 20 mmol) at 0° C. were added N,N-diisopropylethylamine (0.61 mL, 3.5 mmol) and C-[1-(4-chloro-phenyl)-cyclopropyl]-methylamine; hydrochloride (303.7 mg, 1.392 mmol). The reaction mixture was slowly warmed to rt. The reaction mixture was quenched with an equal volume of saturated aqueous sodium bicarbonate and extracted with ethyl acetate (3×). The combined organic layers were washed successively with water, aqueous lithium chloride, and brine, dried over sodium sulfate, filtered and concentrated in vacuo. The residue was purified on the Isco (120 g cartridge, chloroform to 12% methanol in chloroform).

MS m/z 319 [M+H]+.

Preparation 93

4-[({[1-(4-Chlorophenyl)cyclopropyl]methyl}amino)carbonyl]-2-fluorobenzenesulfonyl chloride

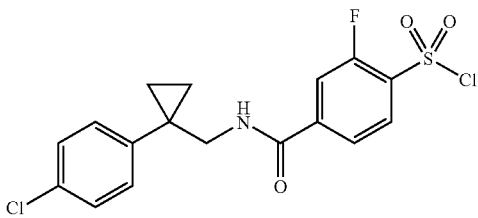 [SMILES: O=C(NCC1(c2ccc(Cl)cc2)CC1)c1ccc(S(=O)(=O)Cl)c(F)c1]

4-Amino-N-{[1-(4-chlorophenyl)cyclopropyl]methyl}-3-fluorobenzamide (Preparation 92, 338 mg, 1.06 mmol) in 6 M of HCl in water (2 mL) was cooled at −5° C. Sodium nitrite (80.5 mg, 1.17 mmol) in water (0.4 mL, 20 mmol) was added slowly. After 20 minutes, sulfur dioxide in AcOH (8:25, sulfur dioxide:AcOH, 3 mL) and copper(II) chloride dihydrate (0.18 g, 1.1 mmol) were added to the reaction mixture. Vigorous gas evolution occurred. After 2 hours, the reaction was poured onto ice and water. The resulting solid was collected by filtration, washed with water, and dried to afford a tan powder.

Preparation 94

4-Amino-3-fluoro-N-[2-(4-fluorophenoxy)-2-methylpropyl]benzamide

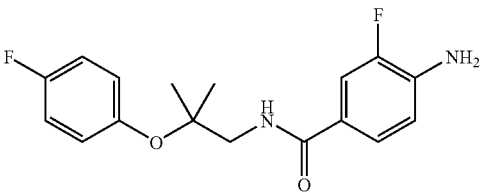 [SMILES: CC(C)(CNC(=O)c1ccc(N)c(F)c1)Oc1ccc(F)cc1]

To a mixture of 4-amino-3-fluorobenzoic acid (200.0 mg, 1.289 mmol) and HBTU (490 mg, 1.3 mmol) in DMF (2 mL, 20 mmol) at 0° C. were added N,N-diisopropylethylamine (0.67 mL, 3.9 mmol) and 2-(4-fluorophenoxy)-2-methylpropan-1-amine (Preparation 91, 280 mg, 1.5 mmol). The reaction mixture was slowly warmed to ambient temperature. The reaction mixture was quenched with an equal volume of saturated aqueous sodium bicarbonate and extracted with ethyl acetate (3×). The combined organic layers were washed successively with water, aqueous lithium chloride, and brine, dried over sodium sulfate, filtered and concentrated in vacuo. The residue was purified on the Isco (120 g cartridge, chloroform to 12% MeOH in chloroform).

MS m/z 321 [M+H]+.

Preparation 95

2-Fluoro-4-({[2-(4-fluorophenoxy)-2-methylpropyl]amino}carbonyl)benzenesulfonyl chloride

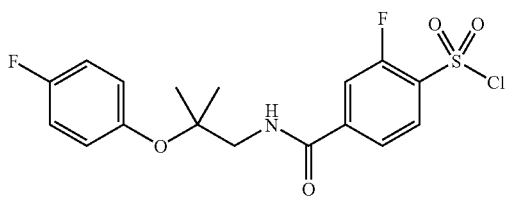 [SMILES: CC(C)(CNC(=O)c1ccc(S(=O)(=O)Cl)c(F)c1)Oc1ccc(F)cc1]

4-Amino-3-fluoro-N-[2-(4-fluorophenoxy)-2-methylpropyl]benzamide (Preparation 94, 441 mg, 1.24 mmol) in 6 M of HCl in water (2 mL) was cooled at −5° C. Sodium nitrite (94.0 mg, 1.36 mmol) in water (0.5 mL, 30 mmol) was added slowly. After 20 minutes, sulfur dioxide in AcOH (8:25, sulfur dioxide:AcOH, 3 mL) and copper(II) chloride dihydrate (0.21 g, 1.2 mmol) were added to the reaction mixture. Vigorous gas evolution occurred. After 2 hours, the reaction was poured onto ice and water. The resulting solid was collected by filtration and washed with water and dried to afford a dark brown solid.

Preparation 96

4-(4-Chlorophenyl)-3-oxobutanenitrile

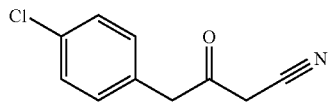 [SMILES: N#CCC(=O)Cc1ccc(Cl)cc1]

2 M of isopropylmagnesium chloride in THF (300 mL) was added to a −78° C. solution of cyanoacetic acid (28.3 g, 333 mmol) in anhydrous THF (600 mL, 7000 mmol). After 1 h, a solution of 4-chlorophenylacetic acid (20 g, 100 mmol) and N,N-carbonyldiimidazole (21.7 g, 134 mmol) in anhydrous THF (200 mL, 2000 mmol) was added. The reaction mixture was warmed to rt. After 16 h, the reaction mixture was poured into water (1 L, 60000 mmol). The mixture was adjusted to pH 4 with glacial AcOH. Gas evolution was evident during addition of the AcOH. The mixture was concentrated in vacuo to remove the THF (in 1 L portions). The product crystallized from the aqueous portions. The solid was collected by filtration, washing with water. Dried under vacuum to afford the product as a fluffy light orange-yellow solid (15.89 g, 60%).

MS m/z 192 [M−H]⁻.

Preparation 97

3-(4-Chlorobenzyl)-1-methyl-1H-pyrazol-5-amine

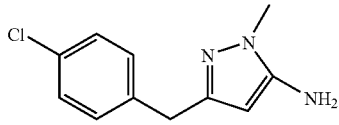

A solution of 4-(4-chlorophenyl)-3-oxo-butyronitrile (Preparation 96, 2.2 g, 11 mmol) and N-methylhydrazine (1.94 mL, 36.5 mmol) in EtOH (40 mL, 800 mmol) was heated at 100° C. in a 40 mL vial (the reaction was split into 2 equal batches). After 20 h, the reaction mixture was cooled to rt and concentrated in vacuo. The residue was purified on the Isco (40 g SiO₂, hexanes to ethyl acetate) to afford the title compound as an off-white solid (1.83 g, 69%).

MS m/z 222 [M+H]⁺.

Preparation 98

4-Iodo-N-1,3-thiazol-2-ylbenzenesulfonamide

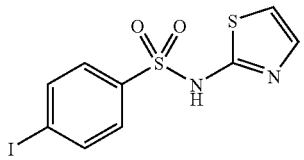 [SMILES: O=S(=O)(Nc1nccs1)c1ccc(I)cc1]

4-Iodobenzenesulfonyl chloride (1.8 g, 6.0 mmol, 1.0 equiv) was added portion-wise to a 0° C. solution of 2-aminothiazole (654 mg, 6.53 mmol, 1.1 equiv) in 4.91 mL of anhydrous pyridine. After addition was complete, the reaction mixture was warmed to ambient temperature. After 3 d, the reaction mixture was concentrated in vacuo. The residue was treated with MeOH and ether to precipitate the product. The solid was collected by filtration, washing with ether, to afford the product as a light brown solid (1.18 g, 49%).

MS m/z 367 [M+H]⁺.

Preparation 99

4-{[(2,4-Dimethoxybenzyl)(1,3-thiazol-2-yl)amino]sulfonyl}benzoic acid

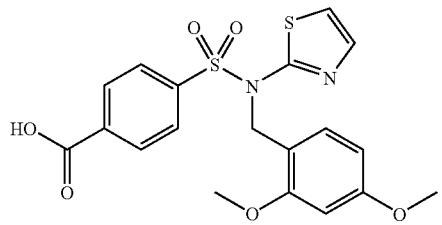 [SMILES: COc1ccc(CN(c2nccs2)S(=O)(=O)c2ccc(C(=O)O)cc2)c(OC)c1]

N-(2,4-dimethoxybenzyl)-1,3-thiazol-2-amine (3.83 g, 0.0153 mol; Icagen) was dissolved in THF (70 mL, 0.8 mol)

and cooled in an ice bath. 1.0 M of Lithium hexamethyldisilazide in THF (33 mL) was added dropwise to the reaction. After 30 minutes, a solution of 4-(chlorosulfonyl)benzoic acid (3.07 g, 0.0139 mol) in THF (30 mL, 0.4 mol) was added dropwise to the reaction. The reaction was stirred overnight then quenched with 0.5 N HCl and diluted with ethyl acetate. The phases were separated and the organic phase was washed with 2× with 0.5N HCl. The organic phase was dried over magnesium sulfate, treated with activated carbon and filtered through Celite. The filtrate was evaporated to a residue and triturated with ethyl acetate. The solid was collected by filtration. Vacuum drying afforded the product as a tan solid (2.55 g, 40%).

Preparation 100

4-Amino-N-(4-(trifluoromethyl)benzyl)benzamide

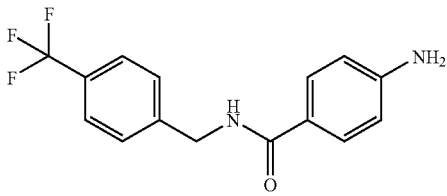 [SMILES: Nc1ccc(C(=O)NCc2ccc(C(F)(F)F)cc2)cc1]

To a mixture of p-aminobenzoic acid (5.0 g, 36 mmol) and HBTU (14 g, 36 mmol) in DMF (50 mL, 600 mmol) at 0° C. were added N,N-diisopropylethylamine (19 mL, 110 mmol) and 4-(trifluoromethyl)benzylamine (6.2 mL, 44 mmol). The reaction mixture was slowly warmed to ambient temperature. The reaction mixture was quenched with an equal volume of saturated aqueous sodium bicarbonate and extracted with ethyl acetate (3×). The combined organic layers were washed successively with water, aqueous lithium chloride, and brine, dried over sodium sulfate, filtered and concentrated in vacuo (8.2 g, 70%).
MS m/z 295 [M+H]$^+$.

Preparation 101

Ethyl 4-(chlorosulfonyl)-3-fluorobenzoate

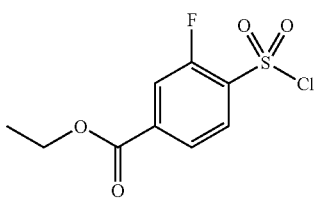 [SMILES: CCOC(=O)c1ccc(S(=O)(=O)Cl)c(F)c1]

4-amino-3-fluoro-benzoic acid ethyl ester (490 mg, 2.7 mmol) was dissolved in acetonitrile (20 mL, 400 mmol) at ambient temperature. The solution was cooled to −5° C. in an acetone bath. 37% HCl (37:63, HCl:water, 2 mL) was added slowly. A solution of sodium nitrite (203 mg, 2.94 mmol) in water (1 mL, 60 mmol) was added slowly. The reaction mixture turned orange over the course of the addition. After addition was complete, the reaction mixture was stirred at 0° C. for 35 min. A 0° C. solution of sulfur dioxide in AcOH (8:25, sulfur dioxide:AcOH, 20 mL) was added followed by copper(II) chloride dihydrate (460 mg, 2.7 mmol). No gas evolution was evident. The mixture warmed to ambient temperature and stirred for 1.5 hours. The reaction mixture was poured into 20 mL of water and extracted with ethyl acetate (3×). The combined organic layers were washed with brine, dried over sodium sulfate, filtered and concentrated in vacuo. The concentrate contained a large excess of AcOH. The residue was diluted with acetonitrile and water, frozen, and lyophilized to afford a mauve powder (559 mg, 74%).

Preparation 102

Ethyl 4-{[(2,4-dimethoxybenzyl)(1,3-thiazol-2-yl)amino]sulfonyl}-3-fluorobenzoate

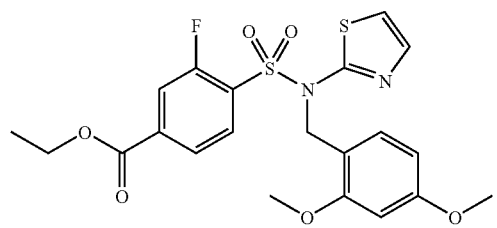 [SMILES: CCOC(=O)c1ccc(S(=O)(=O)N(Cc2ccc(OC)cc2OC)c2nccs2)c(F)c1]

(2,4-Dimethoxy-benzyl)-thiazol-2-yl-amine (576 mg, 2.30 mmol) was dissolved in THF (7 mL, 80 mmol) and cooled in an ice bath. 1.0 M of lithium hexamethyldisilazide in THF (2.5 mL) was added dropwise to the reaction. After 30 minutes, a solution of 4-chlorosulfonyl-3-fluoro-benzoic acid ethyl ester (559 mg, 2.10 mmol) in THF (5 mL, 60 mmol) was added dropwise to the reaction. The reaction was stirred overnight then quenched with 20 mL saturated aqueous ammonium chloride. The aqueous phase was extracted with ethyl acetate (3×). The combined organic layers were washed with brine, dried over sodium sulfate, filtered and concentrated in vacuo. The residue was purified on the Isco (80 g SiO$_2$ cartridge, 60 mL/min, hexanes to ethyl acetate) to afford the product as an orange oil (496 mg, 44%).
MS m/z 295 [M+H]$^+$.

Preparation 103

Methyl 3-[(1,3,4-thiadiazol-2-ylamino)sulfonyl]benzoate

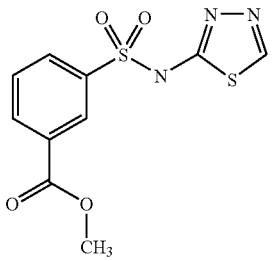 [SMILES: COC(=O)c1cccc(S(=O)(=O)Nc2nncs2)c1]

To a solution of 2-aminothiadiazole (15.08 g, 149.1 mmol, 5 eq) in pyridine (70 ml) heating at 50° C. was added methyl 3-(chlorosulfonyl)benzoate (7.0 g, 29.8 mmol, 1 eq) and the reaction mixture heated for 3 hours. The solvent was evaporated in vacuo and the residue extracted from 2M hydrochloric acid into ethyl acetate, washed with brine, dried over sodium sulphate, filtered and evaporated in vacuo to yield the title compound (4.68 g, 15.7 mmol, 52%).

$^1$HNMR (d$_6$-DMSO): 3.85 (s, 3H), 7.7 (t, 1H), 8.0 (d, 1H), 8.15 (d, 1H), 8.3 (s, 1H), 8.75 (s, 1H). MS m/z 300 [MH]$^+$.

Preparation 104

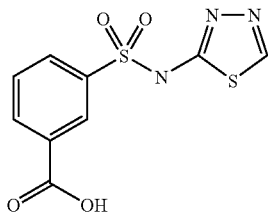 [SMILES: O=C(O)c1cccc(S(=O)(=O)Nc2nncs2)c1]

3-[(1,3,4-Thiadiazol-2-ylamino)sulfonyl]benzoic acid

A solution of methyl 3-[(1,3,4-thiadiazol-2-ylamino)sulfonyl]benzoate (Preparation 103, 1.0 g, 3.35 mmol, 1 eq) in 2.5M sodium hydroxide (5 ml, 13.4 mmol, 4 eq) and dioxane (1 ml) was heated at 50° C. for 4 hours. The organic solvent was evaporated in vacuo and the residue acidified with 2M hydrochloric acid. The resultant precipitate was collected by filtration and washed with water to yield the title compound (0.5 g, 1.75 mmol, 52%).

$^1$HNMR (d$_6$-DMSO): 7.6 (t, 1H), 8.0 (d, 1H), 8.1 (d, 1H), 8.25 (s, 1H), 8.75 (s, 1H).

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in their entirety.

What is claimed is:

1. A compound of the formula (I):

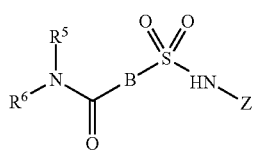

or a pharmaceutically acceptable salt thereof, wherein:
R$^5$ is a member independently selected from H or a group selected from (C$_1$-C$_{10}$)alkyl, heteroalkyl, heterocycloalkyl, (C$_3$-C$_8$)cycloalkyl, heteroaryl, aryl(C$_1$-C$_2$)alkyl, aryloxy(C$_1$-C$_2$)alkyl, heteroaryloxy(C$_1$-C$_2$)alkyl and heteroaryl(C$_1$-C$_2$)alkyl, each optionally substituted at any suitable point with one or more substituents selected from the group consisting of halogen, cyano, hydroxy, (C$_1$-C$_4$)alkyl, halo(C$_1$-C$_4$)alkyl, (C$_1$-C$_4$)alkoxy, halo(C$_1$-C$_4$)alkoxy, amino, (C$_1$-C$_4$)alkylamino, di(C$_1$-C$_4$)alkylamino, trifluoromethylthio, (C$_3$-C$_8$)cycloalkyl or phenyl optionally substituted with halogen, cyano, hydroxy, methyl, methoxy, trifluoromethyl or trifluoromethoxy, R$^6$ is represented by a member selected from the group consisting of heteroaryl, aryl(C$_1$-C$_3$)alkyl, heteroaryl(C$_1$-C$_2$)alkyl, aryloxy(C$_1$-C$_2$)alkyl, heteroaryloxy(C$_1$-C$_2$)alkyl, arylamino(C$_1$-C$_2$)alkyl and heteroarylamino(C$_1$-C$_2$)alkyl,
wherein each is optionally substituted with one or more substituents selected from the group consisting of halogen, cyano, hydroxy, (C$_1$-C$_4$)alkyl, halo(C$_1$-C$_4$)alkyl, (C$_1$-C$_4$)alkoxy, (C$_1$-C$_4$)alkoxy(C$_1$-C$_4$)alkoxy, hydroxy (C$_1$-C$_4$)alkoxy, halo(C$_1$-C$_4$)alkoxy, (C$_3$-C$_8$)cycloalkyl (C$_1$-C$_4$)alkoxy, amino, (C$_1$-C$_4$)alkylamino, di(C$_1$-C$_4$)alkylamino, trifluoromethylthio, (C$_3$-C$_8$)cycloalkyl, pyrazolyl, pyrazolylmethyl, pyrazolylethyl, phenyl, benzyl, phenethyl, pyridyl, pyridylmethyl, phenoxy, phenoxymethyl, pyridyloxy and pyridyloxymethyl,
wherein each pyrazolyl, pyrazolylmethyl, pyrazolylethyl, phenyl, benzyl, phenethyl, pyridyl, pyridylmethyl, phenoxy, phenoxymethyl, pyridyloxy or pyridyloxymethyl is optionally substituted at any suitable point with one or more substituents selected from the group consisting of halogen, cyano, hydroxy, methyl, methoxy, trifluoromethyl or trifluoromethoxy;

Z is a 5-membered heteroaryl selected from the group consisting of 1,3-thiazol-2-yl, 1,3-thiazol-4-yl, and 1,3-thiazol-5-yl in which said heteroaryl may be optionally substituted with one or more substituents selected from the group consisting of halogen, cyano, (C$_1$-C$_4$)alkyl, halo(C$_1$-C$_4$)alkyl, (C$_1$-C$_4$)alkoxy, halo(C$_1$-C$_4$)alkoxy, (C$_3$-C$_8$)cycloalkyl, amino, (C$_1$-C$_4$)alkylamino and di(C$_1$-C$_4$)alkylamino; and B is phenyl as depicted below:

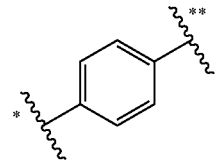 [SMILES: *c1ccc(*)cc1]

in which said phenyl is optionally substituted with one or more substituents selected from the group consisting of halogen, cyano, (C$_1$-C$_4$)alkyl, halo(C$_1$-C$_4$)alkyl, (C$_1$-C$_4$)alkoxy, halo(C$_1$-C$_4$)alkoxy.

2. The compound according to claim 1, or a pharmaceutically acceptable salt thereof, wherein R$^6$ is

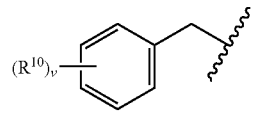

in which R$^{10}$ is a member independently selected from halogen, cyano, hydroxyl and a group which is a member selected from (C$_1$-C$_4$)alkyl halo (C$_1$-C$_4$)alkyl, (C$_3$-C$_8$)cycloalkyl, (C$_1$-C$_4$)alkoxy, halo(C$_1$-C$_4$)alkoxy trifluoromethylthio, phenyl, benzyl, phenethyl, phenoxy, and pyrazolyl, wherein each phenyl, benzyl, phenethyl, phenoxy, and pyrazolyl group is optionally substituted at any suitable point with one or more halogen moieties, and;

v is an integer selected from 0 to 3.

3. The compound according to claim 1, or a pharmaceutically acceptable salt thereof, wherein v is 1.

4. The compound according to claim 2, or a pharmaceutically acceptable salt thereof, wherein $R^{10}$ is a member selected from trifluoromethoxy, trifluoromethyl, chloro and fluoro.

5. The compound according to claim 3, or a pharmaceutically acceptable salt thereof, wherein $R^6$ is a member selected from

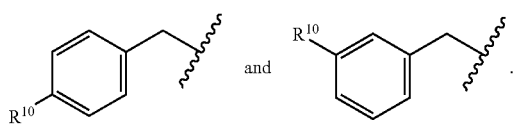

6. The compound according to claim 5, or a pharmaceutically acceptable salt thereof, wherein $R^{10}$ is a member selected from trifluoromethoxy, trifluoromethyl, chloro and fluoro.

7. The compound according to claim 2, or a pharmaceutically acceptable salt thereof, wherein v is 2.

8. The compound according to claim 7, or a pharmaceutically acceptable salt thereof, wherein each $R^{10}$ is a member independently selected from trifluoromethoxy, trifluoromethyl, chloro and fluoro.

9. The compound according to claim 7, or a pharmaceutically acceptable salt thereof, wherein $R^6$ is

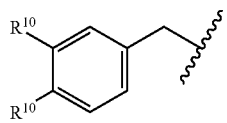

10. The compound according to claim 2, or a pharmaceutically acceptable salt thereof, wherein $R^6$ is a member selected from 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl.

11. The compound according to claim 10, or a pharmaceutically acceptable salt thereof, wherein $R^5$ is H.

12. The compound according to claim 1, or a pharmaceutically acceptable salt thereof, wherein said B is phenyl is substituted with fluoro, chloro, or cyano.

13. The compound according to claim 1, or a pharmaceutically acceptable salt thereof, wherein B is represented by

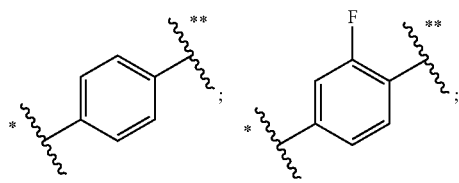

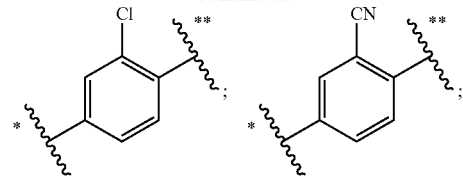

14. The compound according to claim 13, or a pharmaceutically acceptable salt thereof, wherein B is a member selected represented by

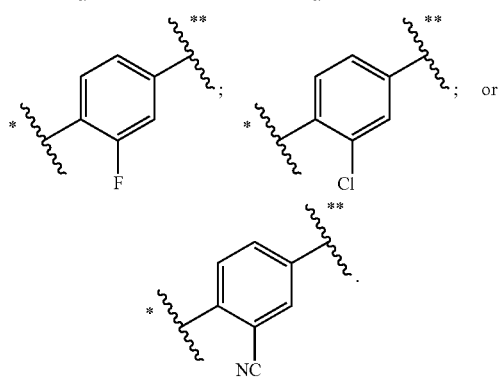

15. The compound according to claim 1, or a pharmaceutically acceptable salt thereof, wherein Z is optionally substituted at any suitable point with one or more substituents selected from the group consisting of halogen, $(C_1$-$C_4)$alkyl, and halo$(C_1$-$C_4)$alkyl.

16. The compound according to claim 1, or a pharmaceutically acceptable salt thereof, wherein Z is optionally substituted at any suitable point with one or more substituents selected from the group consisting of fluorine, chlorine, methyl, and trifluoromethyl.

17. The compound according to claim 1, or a pharmaceutically acceptable salt thereof, wherein Z is a member selected from 1,3-thiazol-2-yl, (5-chloro)-1,3-thiazol-2-yl, (4-methyl)-1,3-thiazol-2-yl, (5-methyl)-1,3-thiazol-2-yl, 4 trifluoromethyl-1,3-thiazol-2-yl, 1,3-thiazol-4-yl, 2-methyl-1,3-thiazol-4-yl, 1,3-thiazol-5-yl, and 2-methyl-1,3-thiazol-5-yl.

18. The compound according to claim 1, or a pharmaceutically acceptable salt thereof, wherein Z is a member selected from 1,3-thiazol-2-yl, 1,3-thiazol-4-yl, 5-halo(1,3-thiazol-2-yl), and 5-$(C_1$-$C_4)$alkyl(1,3-thiazol-2-yl).

19. The compound according to claim 1 or a pharmaceutically acceptable salt thereof, wherein Z is a member selected from 1,3-thiazol-2-yl, 1,3-thiazol-4-yl, 5-chloro(1,3-thiazol-2-yl), and 5-methyl(1,3-thiazol-2-yl).

20. The compound according to claim 1, wherein $R^5$ is H;

$R^6$ is a member selected from 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl;

B is a member selected from

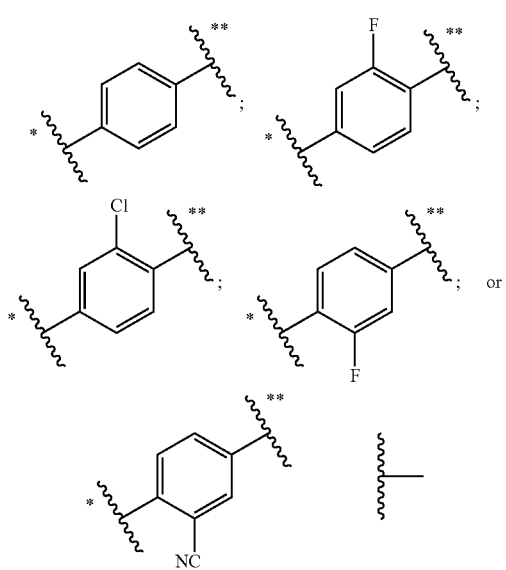

represents a bond covalently attached to said carbon of said carbonyl;

represents a bond covalently attached to said sulfur of said sulfonamide.

21. The compound according to claim 1, wherein $R^5$ is H;

$R^6$ is a member selected from 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl;

Z is a member selected from 1,3-thiazol-2-yl, 1,3-thiazol-4-yl, 5-halo-(1,3-thiazol-2-yl), and 5-($C_1$-$C_4$)alkyl-(1,3-thiazol-2-yl).

22. The compound according to claim 1, wherein B is a member selected from

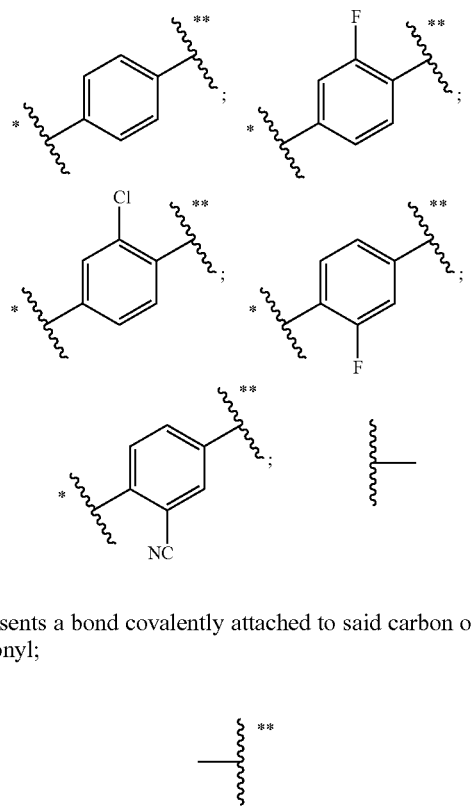

represents a bond covalently attached to said carbon of said carbonyl;

represents a bond covalently attached to said sulfur of said sulfonamide, and;

Z is a member selected from 1,3-thiazol-2-yl, 1,3-thiazol-4-yl, 5-halo-(1,3-thiazol-2-yl), and 5-($C_1$-$C_4$)alkyl-(1,3-thiazol-2-yl).

23. The compound according to claim 1, wherein $R^5$ is H;

$R^6$ is a member selected from 3-chlorobenzyl, 3-fluorobenzyl, 3-trifluoromethylbenzyl, 3-trifluoromethoxybenzyl, 4-chlorobenzyl, 4-fluorobenzyl, 4-trifluoromethylbenzyl, 4-trifluoromethoxybenzyl, 3-chloro-4-trifluoromethoxybenzyl, 3-chloro-4-trifluoromethylbenzyl, 3-fluoro-4-trifluoromethoxybenzyl, 3-fluoro-4-trifluoromethylbenzyl, 3,4 dichlorobenzyl, 2,5 dichlorobenzyl, 3-chloro-4-fluorobenzyl, 3-trifluoromethoxy-4-fluorobenzyl, 3-fluoro-4-chlorobenzyl, 2-fluoro-4-trifluoromethylbenzyl, 3-cyclopropyl-4-fluorobenzyl, 2-methoxy-4-trifluoromethoxybenzyl, 3,4-difluorobenzyl, 3-fluoro-4-chlorobenzyl, 2-methyl-3-chlorobenzyl, 2-fluoro-3-trifluoromethylbenzyl and 3-trifluoromethyl-4-fluorobenzyl;

B is a member selected from

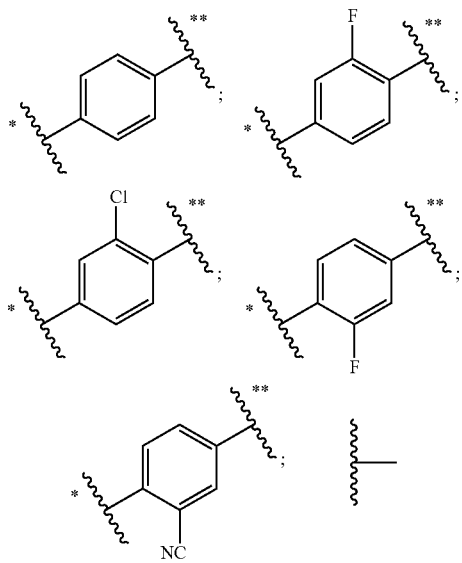

represents a bond covalently attached to said carbon of said carbonyl;

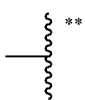

represents a bond covalently attached to said sulfur of said sulfonamide, and;

Z is a member selected from 1,3-thiazol-2-yl, 1,3-thiazol-4-yl, 5-halo-(1,3-thiazol-2-yl), and 5-($C_1$-$C_4$)alkyl-(1,3-thiazol-2-yl).

24. The compound according to claim 23, wherein B is

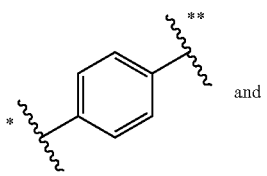 [SMILES: *c1ccc(*)cc1]

Z is a member selected from 1,3-thiazol-2-yl, and 5-chloro-(1,3-thiazol-2-yl).

25. The compound according to claim 24, wherein $R^6$ is a member selected from 3-chloro-4-trifluoromethoxybenzyl, 3-chloro-4-trifluoromethylbenzyl, 3-fluoro-4-trifluoromethoxybenzyl, 3,4 dichlorobenzyl, 3-fluoro-4-trifluoromethylbenzyl, 3-trifluoromethoxy-4-fluorobenzyl, 4-trifluoromethoxybenzyl, 4-trifluoromethylbenzyl, 3-fluoro-4-chlorobenzyl, 3-chloro-4-fluorobenzyl, 3-trifluoromethoxy-4-fluorobenzyl, 3-cyclopropyl-4-fluorobenzyl, 2-methoxy-4-trifluoromethoxybenzyl, 3,4-difluorobenzyl, 2-methyl-3-chlorobenzyl, 3-trifluoromethoxybenzyl, 2-fluoro-4-trifluoromethylbenzyl and 2-fluoro-3-trifluoromethylbenzyl.

26. The compound according to claim 24, wherein when Z is 1,3-thiazol-2-yl, $R^6$ is a member selected from 3-chloro-4-trifluoromethylbenzyl, 3-fluoro-4-trifluoromethoxybenzyl, 3-fluoro-4-trifluoromethylbenzyl, 3-trifluoromethoxy-4-fluorobenzyl, 3-cyclopropyl-4-fluorobenzyl, 3-trifluoromethyl-4-fluorobenzyl, 2-methoxy-4-trifluoromethoxybenzyl, 2-methyl-3-chlorobenzyl, 3-trifluoromethoxybenzyl, 3-fluoro-4-trifluoromethylbenzyl, 2-fluoro-3-trifluoromethylbenzyl and 3-trifluoromethylbenzyl; and when Z is 5-chloro-(1,3-thiazol-2-yl), $R^6$ is a member selected from 3,4 dichlorobenzyl, 3-fluoro-4-trifluoromethoxybenzyl, 3-chloro-4-fluorobenzyl, 3-fluoro-4-trifluoromethylbenzyl, 3-trifluoromethoxy-4-fluorobenzyl, 4-trifluoromethoxybenzyl, 4-trifluoromethylbenzyl, 3-fluoro-4-chlorobenzyl, 3-trifluoromethyl-4-fluorobenzyl, 2-fluoro-3-trifluoromethylbenzyl, 3,4-difluorobenzyl, 3-trifluoromethoxybenzyl and 3-trifluoromethylbenzyl.

27. The compound according to claim 23, wherein B is

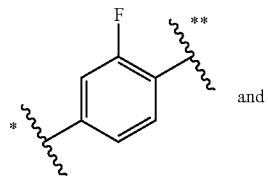 [SMILES: *c1ccc(*)c(F)c1]

and

Z is a member selected from 1,3-thiazol-2-yl, and 5-chloro-(1,3-thiazol-2-yl).

28. The compound according to claim 27, wherein $R^6$ is a member selected from 3-chloro-4-trifluoromethoxybenzyl, 3-chloro-4-trifluoromethylbenzyl, 3-fluoro-4-trifluoromethylbenzyl, 3-fluoro-4-trifluoromethoxybenzyl, 3,4 dichlorobenzyl, 4-trifluoromethoxybenzyl, 4-trifluoromethylbenzyl, 3-chloro-4-fluorobenzyl, 3-fluoro-4-chlorobenzyl, 3-trifluoromethoxy-4-fluorobenzyl, 3,4-difluorobenzyl, 3-trifluoromethyl-4-fluorobenzyl, 3-trifluoromethoxybenzyl and 3-trifluoromethylbenzyl.

29. The compound according to claim 27, wherein when Z is 1,3-thiazol-2-yl, $R^6$ is a member selected from 3-chloro-4-trifluoromethylbenzyl, 3,4 dichlorobenzyl, 3-fluoro-4-trifluoromethoxybenzyl, 3-fluoro-4-trifluoromethylbenzyl, 3-chloro-4-fluorobenzyl, 3-trifluoromethoxy-4-fluorobenzyl, 3,4-difluorobenzyl, 4-trifluoromethoxybenzyl, 3-trifluoromethoxybenzyl, 3-fluoro-4-chlorobenzyl and 3-trifluoromethylbenzyl; and when Z is 5-chloro-(1,3-thiazol-2-yl), $R^6$ is a member selected from 3-fluoro-4-trifluoromethylbenzyl, 3,4 dichlorobenzyl, 4-trifluoromethoxybenzyl, 3-fluoro-4-trifluoromethoxybenzyl, 4-trifluoromethylbenzyl, 3-fluoro-4-chlorobenzyl, 3,4-difluorobenzyl, 3-trifluoromethyl-4-fluorobenzyl and 3-fluoro-4-trifluoromethoxybenzyl.

30. The compound according to claim 23, wherein B is

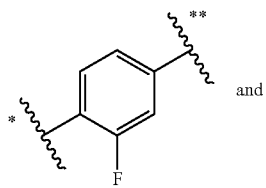 [SMILES: *c1ccc(*)c(F)c1]

Z is a member selected from 1,3-thiazol-2-yl, or 5-chloro-(1,3-thiazol-2-yl).

31. The compound according to claim 30, wherein $R^6$ is a member selected from 3,4 dichlorobenzyl, 3-fluoro-4-trifluoromethoxybenzyl, 3-chloro-4-fluorobenzyl, 4-trifluoromethoxybenzyl, 3-fluoro-4-chlorobenzyl, 4-trifluoromethylbenzyl, 3-trifluoromethoxybenzyl, 3-trifluoromethylbenzyl, 3-fluoro-4-trifluoromethylbenzyl, 3-trifluoromethyl-4-fluorobenzyl, 3,4-difluorobenzyl and 3-trifluoromethoxy-4-fluorobenzyl.

32. The compound according to claim 30, wherein
when Z is 1,3-thiazol-2-yl, $R^6$ is a member selected from 3,4 dichlorobenzyl, 3-fluoro-4-trifluoromethoxybenzyl, 4-trifluoromethoxybenzyl, 3-fluoro-4-trifluoromethylbenzyl, 3-trifluoromethyl-4-fluorobenzyl, 3-trifluoromethylbenzyl, 3-fluoro-4-chlorobenzyl, 3,4-difluorobenzyl, 3-chloro-4-fluorobenzyl and 4-trifluoromethylbenzyl;
when Z is 5-chloro-(1,3-thiazol-2-yl), $R^6$ is a member selected from 3,4 dichlorobenzyl, 3-chloro-4-fluorobenzyl, 3-fluoro-4-chlorobenzyl, 4-trifluoromethoxybenzyl, 3-fluoro-4-trifluoromethoxybenzyl, 4-trifluoromethylbenzyl, 3-trifluoromethoxybenzyl, 3-trifluoromethylbenzyl, 3-fluoro-4-trifluoromethylbenzyl, 3-trifluoromethyl-4-fluorobenzyl, 3,4-difluorobenzyl and 3-trifluoromethoxy-4-fluorobenzyl.

33. The compound according to claim 23, wherein B is

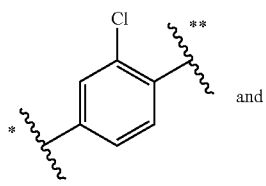 [SMILES: *c1ccc(*)c(Cl)c1]

Z is a member selected from 1,3-thiazol-2-yl, and (5-chloro)-1,3-thiazol-2-yl.

34. The compound according to claim 33, wherein $R^6$ is a member selected from 3-fluoro-4-trifluoromethoxybenzyl, 4-trifluoromethylbenzyl, 3-chloro-4-trifluoromethylbenzyl and 3,4 dichlorobenzyl.

35. The compound according to claim 33, wherein
when Z is 1,3-thiazol-2-yl, $R^6$ is a member selected from 3-fluoro-4-trifluoromethoxybenzyl and 4-trifluoromethylbenzyl and
when Z is 5-chloro-(1,3-thiazol-2-yl), $R^6$ is 3,4 dichlorobenzyl.

36. The compound according to claim 23, wherein B is

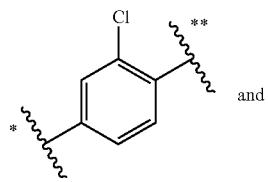 [SMILES: *c1ccc(*)c(Cl)c1]

Z is a member selected from 1,3-thiazol-2-yl, and, (5-chloro)1,3-thiazol-2-yl.

37. The compound according to claim 36, wherein $R^6$ is a member selected from 3-fluoro-4-trifluoromethoxybenzyl, 3-chloro-4-trifluoromethylbenzyl and 3-fluoro-4-trifluoromethylbenzyl.

38. A pharmaceutical formulation comprising a compound according to claim 1 in admixture with one or more pharmaceutically acceptable excipients.

39. The compound of claim 1 in which $R^5$ is H.

* * * * *